US011197925B2

(12) United States Patent
Kawaoka et al.

(10) Patent No.: US 11,197,925 B2
(45) Date of Patent: Dec. 14, 2021

(54) INFLUENZA B VIRUS REPLICATION FOR VACCINE DEVELOPMENT

(71) Applicant: Wisconsin Alumni Research Foundation (WARF), Madison, WI (US)

(72) Inventors: Yoshihiro Kawaoka, Middleton, WI (US); Gabriele Neumann, Madison, WI (US); Jihui Ping, Madison, WI (US)

(73) Assignee: Wisconsin Alumni Research Foundation (WARF), Madison, WI (US)

( * ) Notice: Subject to any disclaimer, the term of this patent is extended or adjusted under 35 U.S.C. 154(b) by 118 days.

(21) Appl. No.: 15/436,245

(22) Filed: Feb. 17, 2017

(65) Prior Publication Data

US 2017/0258888 A1 Sep. 14, 2017

Related U.S. Application Data

(60) Provisional application No. 62/297,400, filed on Feb. 19, 2016.

(51) Int. Cl.

| | |
|---|---|
| ***A61K 39/145*** | (2006.01) |
| ***C12N 7/00*** | (2006.01) |
| ***A61K 39/12*** | (2006.01) |
| ***C12N 15/86*** | (2006.01) |
| *A61K 39/00* | (2006.01) |

(52) U.S. Cl.

CPC ............ *A61K 39/145* (2013.01); *A61K 39/12* (2013.01); *C12N 7/00* (2013.01); *C12N 15/86* (2013.01); *A61K 2039/5258* (2013.01); *C12N 2760/16023* (2013.01); *C12N 2760/16071* (2013.01); *C12N 2760/16221* (2013.01); *C12N 2760/16222* (2013.01); *C12N 2760/16234* (2013.01); *C12N 2760/16251* (2013.01)

(58) Field of Classification Search

None

See application file for complete search history.

(56) References Cited

U.S. PATENT DOCUMENTS

| | | | |
|---|---|---|---|
| 4,071,618 | A | 1/1978 | Konobe et al. |
| 4,659,569 | A | 4/1987 | Mitsuhashi et al. |
| 5,166,057 | A | 11/1992 | Palese et al. |
| 5,716,821 | A | 2/1998 | Wertz et al. |
| 5,789,229 | A | 8/1998 | Wertz et al. |
| 5,820,871 | A | 10/1998 | Palese et al. |
| 5,840,520 | A | 11/1998 | Clarke et al. |
| 5,854,037 | A | 12/1998 | Palese et al. |
| 5,948,410 | A | 9/1999 | Van Scharrenburg et al. |
| 5,994,526 | A | 11/1999 | Meulewaeter et al. |
| 6,033,886 | A | 3/2000 | Conzelmann |
| 6,037,348 | A | 3/2000 | Colacino et al. |
| 6,146,642 | A | 11/2000 | Garcia-Sastre et al. |
| 6,169,175 | B1 | 1/2001 | Frace et al. |
| 6,194,546 | B1 | 2/2001 | Newton et al. |
| 6,455,298 | B1 | 9/2002 | Groner et al. |
| 6,544,785 | B1 | 4/2003 | Palese et al. |
| 6,656,720 | B2 | 12/2003 | Groner et al. |
| 6,825,036 | B2 | 11/2004 | Makizumi et al. |
| 6,872,395 | B2 | 3/2005 | Kawaoka |
| 6,951,752 | B2 | 10/2005 | Reiter et al. |
| 6,951,754 | B2 | 10/2005 | Hoffmann |
| 6,974,695 | B2 | 12/2005 | Vogels et al. |
| 7,037,707 | B2 | 5/2006 | Webster et al. |
| 7,176,021 | B2 | 2/2007 | Kawaoka |
| 7,226,774 | B2 | 6/2007 | Kawaoka |
| 7,312,064 | B2 | 12/2007 | Hoffmann |
| 7,507,411 | B2 | 3/2009 | Zhou et al. |
| 7,566,458 | B2 | 7/2009 | Yang et al. |
| 7,585,657 | B2 | 9/2009 | Kawaoka |
| 7,588,769 | B2 | 9/2009 | Kawaoka |
| 7,670,837 | B2 | 3/2010 | Schwartz |
| 7,833,788 | B2 | 11/2010 | Pau et al. |
| 7,883,844 | B2 | 2/2011 | Nouchi et al. |
| 7,955,833 | B2 | 6/2011 | Reiter et al. |
| 7,959,930 | B2 | 6/2011 | Wit et al. |
| 7,972,843 | B2 | 7/2011 | Hoffmann |
| 7,993,924 | B2 | 8/2011 | Billeter et al. |
| 8,012,736 | B2 | 9/2011 | Hoffman et al. |
| 8,048,430 | B2 | 11/2011 | Yang et al. |

(Continued)

FOREIGN PATENT DOCUMENTS

| | | |
|---|---|---|
| AU | 2012204138 B2 | 5/2014 |
| AU | 2014202470 | 11/2016 |

(Continued)

OTHER PUBLICATIONS

McCullers et al. Virology vol. 336, Issue 2, Jun. 5, 2005, pp. 318-326 (Year: 2005).*

U.S. Appl. No. 14/332,121, U.S. Pat. No. 9,950,057, filed Jul. 15, 2014, High Titer Recombinant Influenza Viruses With Enhanced Replication in MDCK or Vero Cells or Eggs.

U.S. Appl. No. 15/593,039, filed May 11, 2017, High Titer Recombinant Influenza Viruses With Enhanced Replication in MDCK or Vero Cells or Eggs.

U.S. Appl. No. 16/178,323, filed Nov. 1, 2018, High Titer Recombinant Influenza Viruses With Enchanced Replication in MDCK or Vero Cells or Eggs.

(Continued)

*Primary Examiner* — Shanon A. Foley
*Assistant Examiner* — Myron G Hill
(74) *Attorney, Agent, or Firm* — Schwegman Lundberg & Woessner, P.A.

(57) ABSTRACT

The invention provides a composition useful to prepare high titer influenza B viruses, e.g., in the absence of helper virus, which includes internal genes from an influenza B virus vaccine strain or isolate, e.g., one that is safe in humans, for instance, one that does not result in significant disease, that confer enhanced growth in cells in culture, such as MDCK cells, or in eggs.

20 Claims, 39 Drawing Sheets

Specification includes a Sequence Listing.

(56) References Cited

U.S. PATENT DOCUMENTS

| | | | |
|---|---|---|---|
| 8,057,806 | B2 | 11/2011 | Kawaoka et al. |
| 8,093,033 | B2 | 1/2012 | Kemble et al. |
| 8,114,415 | B2 | 2/2012 | Hoffmann et al. |
| 8,119,337 | B2 | 2/2012 | Gregersen |
| 8,119,388 | B2 | 2/2012 | Schwartz et al. |
| 8,309,099 | B2 | 11/2012 | Hoffmann |
| 8,354,114 | B2 | 1/2013 | Lu et al. |
| 8,357,376 | B2 | 1/2013 | Liu et al. |
| 8,409,843 | B2 | 4/2013 | Kemble et al. |
| 8,460,914 | B2 | 6/2013 | Gregersen |
| 8,475,806 | B2 | 7/2013 | Kawaoka |
| 8,524,497 | B2 | 9/2013 | Reiter et al. |
| 8,546,123 | B2 | 10/2013 | Lewis |
| 8,574,591 | B2 | 11/2013 | Hoffmann et al. |
| 8,574,593 | B2 | 11/2013 | Yang et al. |
| 8,580,277 | B2 | 11/2013 | Yang et al. |
| 8,591,914 | B2 | 11/2013 | Yang et al. |
| 9,109,013 | B2 | 8/2015 | Kawaoka et al. |
| 9,254,318 | B2 | 2/2016 | Kawaoka et al. |
| 9,474,798 | B2 | 10/2016 | Watanabe et al. |
| 9,890,363 | B2 | 2/2018 | Kawaoka |
| 9,926,535 | B2 | 3/2018 | Kawaoka et al. |
| 9,950,057 | B2 | 4/2018 | Kawaoka et al. |
| 10,053,671 | B2 | 8/2018 | Kawaoka et al. |
| 10,633,422 | B2 | 4/2020 | Kawaoka et al. |
| 2002/0164770 | A1 | 11/2002 | Hoffmann |
| 2002/0197705 | A1 | 12/2002 | Kawaoka |
| 2003/0035814 | A1 | 2/2003 | Kawaoka et al. |
| 2003/0044962 | A1 | 3/2003 | Makizumi et al. |
| 2003/0073223 | A1 | 4/2003 | Groner et al. |
| 2003/0119183 | A1 | 6/2003 | Groner |
| 2003/0194694 | A1 | 10/2003 | Kawaoka |
| 2004/0002061 | A1 | 1/2004 | Kawaoka |
| 2004/0063141 | A1 | 4/2004 | Lok |
| 2004/0077086 | A1 | 4/2004 | Reiter et al. |
| 2004/0219170 | A1 | 11/2004 | Kawaoka |
| 2005/0003349 | A1 | 1/2005 | Kawaoka |
| 2005/0037487 | A1 | 2/2005 | Kawaoka et al. |
| 2005/0118140 | A1 | 6/2005 | Vorlop et al. |
| 2005/0158342 | A1 | 7/2005 | Kemble et al. |
| 2005/0186563 | A1 | 8/2005 | Hoffmann |
| 2005/0202553 | A1 | 9/2005 | Groner et al. |
| 2005/0232950 | A1 | 10/2005 | Kawaoka |
| 2005/0266026 | A1 | 12/2005 | Hoffmann et al. |
| 2006/0057116 | A1 | 3/2006 | Kawaoka et al. |
| 2006/0166321 | A1 | 7/2006 | Kawaoka et al. |
| 2006/0188977 | A1 | 8/2006 | Schwartz et al. |
| 2006/0246092 | A1 | 11/2006 | Neirynck et al. |
| 2007/0231348 | A1 | 10/2007 | Kawaoka et al. |
| 2008/0233560 | A1 | 9/2008 | Hoffmann |
| 2008/0254067 | A1 | 10/2008 | Trepanier et al. |
| 2008/0274141 | A1 | 11/2008 | Groner et al. |
| 2008/0311148 | A1 | 12/2008 | Hoffmann |
| 2008/0311149 | A1 | 12/2008 | Hoffmann |
| 2009/0074812 | A1 | 3/2009 | Watanabe et al. |
| 2009/0081252 | A1 | 3/2009 | Gregersen |
| 2009/0181446 | A1 | 7/2009 | Nouchi et al. |
| 2010/0112000 | A1 | 5/2010 | Schwartz |
| 2010/0183671 | A1 | 7/2010 | Gregersen et al. |
| 2010/0247572 | A1 | 9/2010 | Kawaoka |
| 2011/0027314 | A1 | 2/2011 | Broeker |
| 2011/0045022 | A1 | 2/2011 | Tsai |
| 2011/0110978 | A1 | 5/2011 | Kawaoka et al. |
| 2011/0236417 | A1 | 9/2011 | Watanabe et al. |
| 2012/0020997 | A1 | 1/2012 | Hoffman et al. |
| 2012/0034600 | A1 | 2/2012 | Gregersen |
| 2012/0115206 | A1 | 5/2012 | Schwartz et al. |
| 2012/0156241 | A1 | 6/2012 | De Wit et al. |
| 2012/0207785 | A1 | 8/2012 | Fabry et al. |
| 2013/0095135 | A1 | 4/2013 | Collignon et al. |
| 2013/0183741 | A1 | 7/2013 | Park et al. |
| 2013/0316434 | A1 | 11/2013 | Reiter et al. |
| 2014/0022731 | A1 | 8/2014 | Li et al. |
| 2015/0017205 | A1 | 1/2015 | Kawaoka et al. |
| 2015/0368621 | A1 | 12/2015 | Kawaoka et al. |
| 2016/0024479 | A1 | 1/2016 | Kawaoka et al. |
| 2016/0208223 | A1 | 7/2016 | Kawaoka et al. |
| 2016/0355790 | A1 | 12/2016 | Kawaoka et al. |
| 2017/0067029 | A1 | 3/2017 | Kawaoka et al. |
| 2017/0096645 | A1 | 4/2017 | Watanabe et al. |
| 2017/0354730 | A1 | 12/2017 | Kawaoka et al. |
| 2018/0245054 | A1 | 8/2018 | Kawaoka et al. |

FOREIGN PATENT DOCUMENTS

| | | | |
|---|---|---|---|
| CN | 1826407 | B | 9/2013 |
| CN | 109477074 | A | 3/2019 |
| EP | 0702085 | A1 | 3/1996 |
| EP | 1201760 | A1 | 5/2002 |
| EP | 2010557 | B1 | 2/2014 |
| EP | 1631663 | B1 | 8/2016 |
| IL | 171831 | A | 5/2015 |
| JP | 2004-500842 | A | 1/2004 |
| JP | 2005-523698 | A | 8/2005 |
| JP | 2005-245302 | A | 9/2005 |
| JP | 2005-535288 | A | 11/2005 |
| JP | 2009-532352 | A | 9/2009 |
| JP | 2010-530248 | A | 9/2010 |
| JP | 4927290 | B2 | 2/2012 |
| JP | 4927290 | | 5/2012 |
| JP | 2014-039551 | A | 3/2014 |
| JP | 2014-131516 | A | 7/2014 |
| JP | 2016-144463 | A | 8/2016 |
| JP | 2016-524915 | A | 8/2016 |
| JP | 2016-169225 | A | 9/2016 |
| JP | 2019510481 | A | 4/2019 |
| MX | 285206 | | 3/2011 |
| NO | 341506 | | 11/2017 |
| WO | WO-96/10631 | A1 | 4/1996 |
| WO | WO-96/10632 | A1 | 4/1996 |
| WO | WO-96/40955 | A1 | 12/1996 |
| WO | WO-97/37000 | A1 | 10/1997 |
| WO | WO-98/02530 | A1 | 1/1998 |
| WO | WO-98/53078 | A1 | 11/1998 |
| WO | WO-99/28445 | A1 | 6/1999 |
| WO | WO-0053786 | A1 | 9/2000 |
| WO | WO-0060050 | A2 | 10/2000 |
| WO | WO-0060050 | A3 | 1/2001 |
| WO | WO-0179273 | A2 | 10/2001 |
| WO | WO-01/83794 | A2 | 11/2001 |
| WO | WO-0/3068923 | A2 | 8/2003 |
| WO | WO-03/076462 | A1 | 9/2003 |
| WO | WO-03/091401 | A2 | 11/2003 |
| WO | WO-04/094466 | A2 | 11/2004 |
| WO | WO-04/112831 | A2 | 12/2004 |
| WO | WO-200/5062820 | A2 | 7/2005 |
| WO | WO-2007/126810 | A2 | 11/2007 |
| WO | WO-2007/126810 | A3 | 11/2007 |
| WO | WO-2008/156778 | A2 | 12/2008 |
| WO | WO-2008/156778 | A3 | 12/2008 |
| WO | WO-2008/157583 | A1 | 12/2008 |
| WO | WO-2008/156778 | A9 | 2/2009 |
| WO | WO-2011/056591 | A1 | 5/2011 |
| WO | WO-2012/177924 | A2 | 12/2012 |
| WO | WO-2013/034069 | A1 | 3/2013 |
| WO | WO-2014/195920 | A2 | 12/2014 |
| WO | WO-2015/009743 | A1 | 1/2015 |
| WO | WO-2015/196150 | A2 | 12/2015 |
| WO | WO-2015/196150 | A3 | 12/2015 |
| WO | WO-2017/007839 | A1 | 1/2017 |
| WO | WO-2017/143236 | A1 | 8/2017 |

OTHER PUBLICATIONS

U.S. Appl. No. 14/745,236, U.S. Pat. No. 10/053,671, filed Jun. 19, 2015, Mutations That Confer Genetic Stability to Additional Genes in Influenza Viruses.

U.S. Appl. No. 15/170,556, filed Jun. 1, 2016, Influenza Virus Replication by Inhibiting Microrna LEC7C Binding to Influenza Viral CRNA and MRNA.

U.S. Appl. No. 15/966,092, filed Apr. 30, 2018, Mutations That Confer Genetic Stability to Additional Genes in Influenza Viruses.

(56) References Cited

OTHER PUBLICATIONS

"U.S. Appl. No. 15/170,556, Non Final Office Action dated Feb. 8, 2019", 11 pgs.
"Gen Bank Accession JX414012", Influenza A virus (A reassortant IVR-148(Brisbane 59 2007 x Texas 1 1977)(H1 N1)) segment 7 matrix protein 2 (M2) and matrix protein 1 (M1) genes, complete cds, (2012), 2 pgs.
"Gen Bank Accession AFP82914", matrix protein 1 [Influenza A virus (A reassortant IVR-148(Brisbane 59 2007 x Texas 1 1977) (H1N1))], (2012), 2 pgs.
Result 17, NCBI Blast nucleotide search of Seq ID No. 2, database "nr", (Jul. 18, 2006), 3 pgs.
Result 1, NCBI Blast nucleotide search of Seq ID No. 3, database "nr"; Result 4, NCBI Blast nucleotide search of Seq ID No. 4, database "nr", (Jul. 22, 2006), 11 pgs.
Result 2, NCBI Blast nucleotide search of Seq ID No. 5, database "nr"; Result 4, NCBI Blast nucleotide search of Seq ID No. 6, database "nr", (Jul. 22, 2006), 6 pgs.
Results 1, NCBI Blast nucleotide search of Seq ID No. 7, database "nr"; Result 1, NCBI Blast nucleotide search of Seq ID No. 8, database "nr", (Jul. 23, 2006), 8 pgs.
Result 7, NCBI Blast nucleotide search of Seq ID: 1, database "nr", (Jul. 18, 2006), 3 pgs.
"FLUMISTTM Package Insert Template", [Online], Retrieved from the Internet: http://www.fda.gov/downloads/BiologicsBioodVaccines!lVaccines/ApprovedProducts/UCM294307.pdf, (Mar. 1, 2012), 26 pgs.
"1.A.32 The Type B Influenza Virus NB Channel (NB-C) Family", Transport Protein Database, (University of California, San Diego, The Sailer Laboratory Bioinformatics Group) [online], http://www.web.archive.org/web/200301311055254/http://tcdb.ucsd.edu/tcdb/tcfamilybrowse.php?tcname=1.A.32, (Archived Jan. 31, 2003), 1 pg.
"U.S. Appl. No. 09/834,095, Advisory Action dated Jan. 8, 2004", 3 pgs.
"U.S. Appl. No. 09/834,095, Final Office Action dated Aug. 26, 2003", 12 pgs.
"U.S. Appl. No. 09/834,095, Non-Final Office Action dated Nov. 4, 2002", 12 pgs.
"U.S. Appl. No. 09/834,095, Notice of Allowance dated Sep. 27, 2004", 13 pgs.
"U.S. Appl. No. 09/834,095, Office Action dated Apr. 20, 2004", 11 pgs.
"U.S. Appl. No. 09/834,095, Response filed Feb. 4, 2003 to Office Action dated Nov. 4, 2002", 14 pgs.
"U.S. Appl. No. 09/834,095, Response filed Jun. 12, 2003 to Restriction Requirement dated Apr. 22, 2003", 2 pgs.
"U.S. Appl. No. 09/834,095, Response filed Jun. 18, 2004 to Office Action dated Apr. 20, 2004", 11 pgs.
"U.S. Appl. No. 09/834,095, Response filed Aug. 1, 2002 to Restriction Requirement dated Jul. 1, 2002", 3 pgs.
"U.S. Appl. No. 09/834,095, Response filed Nov. 26, 03 to Final Office Action dated Aug. 26, 2003", 10 pgs.
"U.S. Appl. No. 09/834,095, Restriction Requirement dated Apr. 22, 2003", 5 pgs.
"U.S. Appl. No. 09/834,095, Restriction Requirement dated Jul. 1, 2002", 9 pgs.
"U.S. Appl. No. 09/834,095, Supplemental Amendment filed Aug. 4, 2004", 7 pgs.
"U.S. Appl. No. 10/827,995, Final Office Action dated Nov. 15, 2006", 10 pgs.
"U.S. Appl. No. 10/827,995, Non-Final Office Action dated Jun. 2, 2006", 15 pgs.
"U.S. Appl. No. 10/827,995, Non-Final Office Action dated Oct. 25, 2007", 7 pgs.
"U.S. Appl. No. 10/827,995, Notice of Allowance dated Feb. 17, 2009", 9 pgs.
"U.S. Appl. No. 10/827,995, Notice of Allowance dated Jul. 2, 2008", 9 pgs.
"U.S. Appl. No. 10/827,995, Notice of Allowance dated Oct. 17, 2008", 7 pgs.
"U.S. Appl. No. 10/827,995, Notice of Non-Compliant Amendment Jul. 25, 2007", 4 pgs.
"U.S. Appl. No. 10/827,995, Proposed Examiner's Amendment dated Jun. 5, 2008", 6 pgs.
"U.S. Appl. No. 10/827,995, Response filed Mar. 3, 2008 to Office Action dated Oct. 25, 2007", 10 pgs.
"U.S. Appl. No. 10/827,995, Response filed May 14, 2007 Final Office Action dated Nov. 15, 2006", 16 pgs.
"U.S. Appl. No. 10/827,995, Response filed Aug. 13, 2007 to Notice of Non-Compliant Amendment dated Jul. 25, 2007", 16 pgs.
"U.S. Appl. No. 10/827,995, Response filed Aug. 17, 2006 Non-Final Office Action dated Jun. 2, 2006", 15 pgs.
"U.S. Appl. No. 10/855,875 , Response filed May 17, 2012 to Non Final Office Action dated Mar. 15, 2012", 15 pgs.
"U.S. Appl. No. 10/855,875, Final Office Action dated Mar. 11, 2008", 20 pgs.
"U.S. Appl. No. 10/855,875, Final Office Action dated Dec. 10, 2010", 15 pgs.
"U.S. Appl. No. 10/855,875, Final Office Action dated Aug. 2, 2006", 34 pgs.
"U.S. Appl. No. 10/855,875, Non-Final Office Action dated Mar. 15, 2012", 15 pgs.
"U.S. Appl. No. 10/855,875, Non-Final Office Action dated Feb. 19, 2010", 7 pgs.
"U.S. Appl. No. 10/855,875, Non-Final Office Action dated Aug. 7, 2009", 32 pgs.
"U.S. Appl. No. 10/855,875, Non-Final Office Action dated Nov. 6, 2008", 12 pgs.
"U.S. Appl. No. 10/855,875, Non-Final Office Action dated Nov. 30, 2005", 13 pgs.
"U.S. Appl. No. 10/855,875, Non-Final Office Action dated May 3, 2007", 13 pgs.
"U.S. Appl. No. 10/855,875, Notice of Allowance dated Mar. 4, 2013", 8 pgs.
"U.S. Appl. No. 10/855,875, Preliminary Amendment filed Feb. 2, 2007", 14 pgs.
"U.S. Appl. No. 10/855,875, Response filed Jan. 29, 2007 to Final Office Action dated Aug. 2, 2007", 14 pgs.
"U.S. Appl. No. 10/855,875, Response filed Mar. 18, 2011 to Final Office Action dated Dec. 10, 2010", 15 pgs.
"U.S. Appl. No. 10/855,875, Response filed Aug. 17, 2010 to Non-Final Office Action dated Feb. 19, 2010", 20 pgs.
"U.S. Appl. No. 10/855,875, Response filed Dec. 7, 2009 to NonFinal Office Action dated Aug. 7, 2009", 15 pgs.
"U.S. Appl. No. 10/855,875, Response filed Dec. 7, 2009 to Non-Final Office Action dated Aug. 7, 2009", 5 pgs.
"U.S. Appl. No. 10/855,875, Response filed Mar. 31, 2009 to Non-Final Office Action dated Nov. 6, 2008", 14 pgs.
"U.S. Appl. No. 10/855,875, Response filed May 1, 2006 Non-Final Office Action dated Nov. 30, 2005", 13 pgs.
"U.S. Appl. No. 10/855,875, Response filed Aug. 18, 2008 to final Office Action dated Mar. 11, 2008", 15 pgs.
"U.S. Appl. No. 10/855,875, Response filed Sep. 20, 2005 to Restriction Requirement dated Jul. 26, 2005", 4 pgs.
"U.S. Appl. No. 10/855,875, Restriction Requirement dated Dec. 23, 2011", 9 pgs.
"U.S. Appl. No. 10/855,875, Restriction Requirement dated Jul. 26, 2005", 9 pgs.
"U.S. Appl. No. 10/855,875, Response filed Nov. 2, 2007 to Office Action dated May 3, 2007", 16 pgs.
"U.S. Appl. No. 11/043,768, Non-Final Office Action dated Sep. 27, 2010", 8 pgs.
"U.S. Appl. No. 11/043,768, Final Office Action dated Jun. 27, 2008", 8 pgs.
"U.S. Appl. No. 11/043,768, Non-Final Office Action dated Feb. 23, 2010", 6 pgs.
"U.S. Appl. No. 11/043,768, Non-Final Office Action dated Feb. 23, 2009", 7 pgs.
"U.S. Appl. No. 11/043,768, Non-Final Office Action dated Nov. 28, 2007", 9 pgs.
"U.S. Appl. No. 11/043,768, Notice of Allowance dated Jun. 29, 2011", 12 pgs.

(56) References Cited

OTHER PUBLICATIONS

"U.S. Appl. No. 11/043,768, Response filed May 2, 2011 to Final Office Action dated Feb. 3, 2011", 11 pgs.
"U.S. Appl. No. 11/043,768, Response filed Jun. 15, 2010 to Non-Final Office Action dated Feb. 23, 2010", 9 pgs.
"U.S. Appl. No. 11/043,768, Response filed Jun. 23, 2009 to Non-Final Office Action dated Feb. 23, 2009", 9 pgs.
"U.S. Appl. No. 11/043,768, Response filed Sep. 13, 2007 to Restriction Requirement dated Mar. 13, 2007", 10 pgs.
"U.S. Appl. No. 11/043,768, Response filed Oct. 26, 2010 to Non-Final Office Action dated Sep. 27, 2010", 11 pgs.
"U.S. Appl. No. 11/043,768, Response filed Dec. 12, 2008 to Final Office Action dated Jun. 27, 2008", 9 pgs.
"U.S. Appl. No. 11/043,768, Response filed Mar. 10, 2008 to Office Action dated Nov. 28, 2007", 12 pgs.
"U.S. Appl. No. 11/043,768, Restriction Requirement dated Mar. 13, 2007", 9 pgs.
"U.S. Appl. No. 11/043,786, Final Office Action dated Feb. 3, 2011", 10 pgs.
"U.S. Appl. No. 11/729,557, Advisory Action dated May 9, 2011", 3 pgs.
"U.S. Appl. No. 11/729,557, Advisory Action dated Dec. 24, 2014", 3 pgs.
"U.S. Appl. No. 11/729,557, Final Office Action dated Feb. 2, 2011", 14 pgs.
"U.S. Appl. No. 11/729,557, Final Office Action dated Aug. 20, 2009", 13 Pgs.
"U.S. Appl. No. 11/729,557, Final Office Action dated Sep. 12, 2014", 14 pgs.
"U.S. Appl. No. 11/729,557, Non-Final Office Action dated Feb. 18, 2015", 13 pgs.
"U.S. Appl. No. 11/729,557, No-Final Office Action dated Feb. 26, 2014", 16 pgs.
"U.S. Appl. No. 11/729,557, Non-Final Office Action dated Jan. 30, 2009", 20 pgs.
"U.S. Appl. No. 11/729,557, Non-Final Office Action dated Feb. 22, 2010", 16 pgs.
"U.S. Appl. No. 11/729,557, Non-Final Office Action dated Aug. 23, 2010", 15 pgs.
"U.S. Appl. No. 11/729,557, Notice of Allowance dated Sep. 30, 2015", 11 pgs.
"U.S. Appl. No. 11/729,557, Response filed Jun. 22, 2010 to Non-Final Office Action dated Feb. 22, 2010", 33 pgs.
"U.S. Appl. No. 11/729,557, Response filed Apr. 27, 2011 to Final Office Action dated Feb. 2, 2011", 14 pgs.
"U.S. Appl. No. 11/729,557, Response filed Apr. 30, 2009 to Non-Final Office Action dated Jan. 30, 2009", 18 pgs.
"U.S. Appl. No. 11/729,557, Response filed May 22, 2014 to Non-Final Office Action dated Feb. 26, 2014", 13 pgs.
"U.S. Appl. No. 11/729,557, Response filed May 28, 2008 to Restriction Requirement dated Nov. 28, 2007", 13 pgs.
"U.S. Appl. No. 11/729,557, Response filed Jun. 22, 2010 to Non-Final Office Action dated Feb. 22, 2010", 16 pgs.
"U.S. Appl. No. 11/729,557, Response filed Jun. 22, 2015 to Non-Final Office Action dated Feb. 18, 2015", 13 pgs.
"U.S. Appl. No. 11/729,557, Response filed Oct. 28, 2010 to Non-Final Office Action dated Aug. 23, 2010", 13 pgs.
"U.S. Appl. No. 11/729,557, Response filed Dec. 1, 2009 to Final Office Action dated Aug. 26, 2009", 16 pgs.
"U.S. Appl. No. 11/729,557, Response filed Dec. 11, 14 to Final Office Action dated Sep. 12, 2014", 15 pgs.
"U.S. Appl. No. 11/729,557, Restriction Requirement dated Nov. 28, 2007", 9 pgs.
"U.S. Appl. No. 12/214,414, Advisory Action dated Feb. 2, 2016", 5 pgs.
"U.S. Appl. No. 12/214,414, Advisory Action dated Apr. 15, 2015", 6 pgs.
"U.S. Appl. No. 12/214,414, Advisory Action dated Oct. 21, 2011", 5 pgs.
"U.S. Appl. No. 12/214,414, Examiner Interview Summary dated Dec. 11, 2015", 3 pgs.
"U.S. Appl. No. 12/214,414, Final Office Action dated Jan. 20, 2015", 28 pgs.
"U.S. Appl. No. 12/214,414, Final Office Action dated Aug. 2, 2011", 7 pgs.
"U.S. Appl. No. 12/214,414, Final Office Action dated Nov. 18, 2015", 17 pgs.
"U.S. Appl. No. 12/214,414, Non-Final Office Action dated Jun. 12, 2014", 28 pgs.
"U.S. Appl. No. 12/214,414, Non-Final Office Action dated Dec. 10, 2010", 6 pgs.
"U.S. Appl. No. 12/214,414, Non-Final Office Action dated Mar. 2, 2010", 9 pgs.
"U.S. Appl. No. 12/214,414, Notice of Allowance dated Jun. 7, 2016", 18 pgs.
"U.S. Appl. No. 12/214,414, Response filed Jan. 19, 2016 to Final Office Action dated Nov. 18, 2015", 14 pgs.
"U.S. Appl. No. 12/214,414, Response filed Feb. 18, 2016 to Final Office Action dated Nov. 18, 2015", 14 pgs.
"U.S. Appl. No. 12/214,414, Response filed Mar. 26, 2015 to Final Office Action dated Jan. 20, 2015", 13 pgs.
"U.S. Appl. No. 12/214,414, Response filed May 3, 2011 to Non-Final Office Action dated Dec. 10, 2010", 12 pgs.
"U.S. Appl. No. 12/214,414, Response filed Jul. 20, 2015 to Advisory Action dated Apr. 15, 2015", 14 pgs.
"U.S. Appl. No. 12/214,414, Response filed Aug. 31, 2010 to Non-Final Office Action dated Mar. 2, 2010", 11 pgs.
"U.S. Appl. No. 12/214,414, Response filed Oct. 3, 2011 to No-Final Office Action dated Aug. 2, 2011", 9 pgs.
"U.S. Appl. No. 12/214,414, Response filed Dec. 21, 2011 to Advisory Action dated Oct. 21, 2011", 10 pgs.
"U.S. Appl. No. 12/467,492, Restriction Requirement dated Nov. 22, 2010", 6 pgs.
"U.S. Appl. No. 12/912,411, Advisory Action dated Feb. 5, 2014", 3 pgs.
"U.S. Appl. No. 12/912,411, Examiner Interview Summary dated Feb. 11, 2014", 2 pgs.
"U.S. Appl. No. 12/912,411, Final Office Action dated Jan. 14, 2015", 10 pgs.
"U.S. Appl. No. 12/912,411, Final Office Action dated Oct. 25, 2013", 11 pgs.
"U.S. Appl. No. 12/912,411, Non-Final Office Action dated Jun. 7, 2013", 8 pgs.
"U.S. Appl. No. 12/912,411, Non-Final Office Action dated Sep. 24, 2014", 11 pgs.
"U.S. Appl. No. 12/912,411, Notice of Allowability dated May 20, 2015", 7 pgs.
"U.S. Appl. No. 12/912,411, Notice of Allowance dated Apr. 8, 2015", 11 pgs.
"U.S. Appl. No. 12/912,411, Response filed Jan. 27, 2014 to Final Office Action dated Oct. 25, 2013", 11 pgs.
"U.S. Appl. No. 12/912,411, Response filed Feb. 18, 2013 to Restriction Requirement dated Oct. 17, 2012", 9 pgs.
"U.S. Appl. No. 12/912,411, Response filed Feb. 25, 2014 to Final Office Action dated Oct. 25, 2013", 11 pgs.
"U.S. Appl. No. 12/912,411, Response filed Mar. 16, 2015 to Final Office Action dated Jan. 14, 2015", 9 pgs.
"U.S. Appl. No. 12/912,411, Response filed Oct. 7, 2013 to Non-Final Office Action dated Jun. 7, 2013", 10 pgs.
"U.S. Appl. No. 12/912,411, Response filed Dec. 31, 2014 to Non-Final Office Action dated Sep. 24, 2014", 12 pgs.
"U.S. Appl. No. 12/912,411, Restriction Requirement dated Oct. 17, 2012", 9 pgs.
"U.S. Appl. No. 13/070,110, Advisory Action dated Mar. 3, 2017", 5 pgs.
"U.S. Appl. No. 13/070,110, Examiner Interview Summary dated Jan. 16, 2018", 3 pgs.
"U.S. Appl. No. 13/070,110, Final Office Action dated Apr. 3, 2015", 18 pgs.
"U.S. Appl. No. 13/070,110, Final Office Action dated Jun. 12, 2013", 7 pgs.

(56) References Cited

OTHER PUBLICATIONS

"U.S. Appl. No. 13/070,110, Final Office Action dated Sep. 14, 2016", 12 pgs.
"U.S. Appl. No. 13/070,110, Non-Final Office Action dated Jul. 21, 2017", 14 pgs.
"U.S. Appl. No. 13/070,110, Non-Final Office Action dated Oct. 2, 2014", 24 pgs.
"U.S. Appl. No. 13/070,110, Non-Final Office Action dated Dec. 11, 2015", 19 pgs.
"U.S. Appl. No. 13/070,110, Non-Final Office Action dated Dec. 21, 2012", 7 pgs.
"U.S. Appl. No. 13/070,110, Notice of Allowance dated Mar. 26, 2018", 6 pgs.
"U.S. Appl. No. 13/070,110, Preliminary Amendment filed Jun. 6, 2011", 4 pgs.
"U.S. Appl. No. 13/070,110, Response filed Jan. 22, 2018 to Non-Final Office Action dated Jul. 21, 2017", 10 pgs.
"U.S. Appl. No. 13/070,110, Response filed Feb. 14, 2017 to Final Office Action dated Sep. 14, 2016", 8 pgs.
"U.S. Appl. No. 13/070,110, Response filed Mar. 22, 2013 to Non-Final Office Action dated Dec. 21, 2012", 8 pgs.
"U.S. Appl. No. 13/070,110, Response filed May 27, 2016 to Non-Final Office Action dated Dec. 11, 2015", 13 pgs.
"U.S. Appl. No. 13/070,110, Response filed Jun. 20, 2017 to Advisory Action dated Mar. 3, 2017", 13 pgs.
"U.S. Appl. No. 13/070,110, Response filed 09-0314 to Restriction Requirement dated Jul. 8, 2014", 7 pgs.
"U.S. Appl. No. 13/070,110, Response filed Oct. 2, 2015 to Final Office Action dated Apr. 3, 2015", 11 pgs.
"U.S. Appl. No. 13/070,110, Response filed Nov. 12, 2013 to Final Office Action dated Jun. 12, 2013", 9 pgs.
"U.S. Appl. No. 13/070,110, Response filed Dec. 30, 2014 to Non-Final Office Action dated Oct. 2, 2014", 13 pgs.
"U.S. Appl. No. 13/070,110, Restriction Requirement dated Jul. 8, 2014", 7 pgs.
"U.S. Appl. No. 14/332,121, Non-Final Office Action dated May 16, 2016", 9 pgs.
"U.S. Appl. No. 14/332,121, Notice of Allowance dated Feb. 15, 2017", 10 pgs.
"U.S. Appl. No. 14/332,121, Notice of Allowance dated Jun. 15, 2017", 8 pgs.
"U.S. Appl. No. 14/332,121, Notice of Allowance dated Oct. 11, 2017", 8 pgs.
"U.S. Appl. No. 14/332,121, Preliminary Amendment filed Sep. 30, 2014", 5 pgs.
"U.S. Appl. No. 14/332,121, Response filed Jan. 29, 2016 to Restriction Requirement dated Jul. 30, 2015", 9 pgs.
"U.S. Appl. No. 14/332,121, Response filed Sep. 7, 2017 to Notice of Allowability dated Jun. 15, 2017", 8 pgs.
"U.S. Appl. No. 14/332,121, Response filed Oct. 11, 2016 to Non Final Office Action dated May 16, 2016", 9 pgs.
"U.S. Appl. No. 14/332,121, Restriction Requirement dated Jul. 30, 2015", 9 pgs.
"U.S. Appl. No. 14/332,121, Supplemental Amendment filed Jan. 23, 2017", 10 pgs.
"U.S. Appl. No. 14/745,236, Advisory Action dated Nov. 15, 2017", 2 pgs.
"U.S. Appl. No. 14/745,236, Final Office Action dated Aug. 25, 2017", 16 pgs.
"U.S. Appl. No. 14/745,236, Non-Final Office Action dated Feb. 2, 2017", 14 pgs.
"U.S. Appl. No. 14/745,236, Notice of Allowability dated Jul. 5, 2018", 4 pgs.
"U.S. Appl. No. 14/745,236, Notice of Allowance dated Feb. 5, 2018", 9 pgs.
"U.S. Appl. No. 14/745,236, PTO Response to Rule 312 Communication dated Jul. 10, 2018", 2 pgs.
"U.S. Appl. No. 14/745,236, Response filed May 2, 2017 to Non-Final Office Action dated Feb. 2, 2017", 10 pgs.
"U.S. Appl. No. 14/745,236, Response filed Nov. 6, 2017 to Final Office Action dated Aug. 25, 2017", 12 pgs.
"U.S. Appl. No. 14/745,236, Response filed Dec. 14, 2017 to Final Office Action dated Aug. 25, 2017", 12 pgs.
"U.S. Appl. No. 14/745,236, Response filed Dec. 23, 2016 to Restriction Requirement dated Sep. 23, 2016", 8 pgs.
"U.S. Appl. No. 14/745,236, Restriction Requirement dated Sep. 23, 2016", 8 pgs.
"U.S. Appl. No. 14/816,807, Non-Final Office Action dated Oct. 3, 2017", 7 pgs.
"U.S. Appl. No. 14/816,807, Notice of Allowance dated Apr. 20, 2018", 8 pgs.
"U.S. Appl. No. 14/816,807, Preliminary Amendment filed Aug. 11, 2015", 8 pgs.
"U.S. Appl. No. 14/816,807, Response filed Jan. 3, 2018 to Non-Final Office Action dated Oct. 3, 2017", 8 pgs.
"U.S. Appl. No. 14/816,807, Response filed May 1, 2017 to Restriction Requirement dated Nov. 1, 2016", 9 pgs.
"U.S. Appl. No. 14/816,807, Restriction Requirement dated Nov. 1, 2016", 8 pgs.
"U.S. Appl. No. 15/000,851, Non-Final Office Action dated Jan. 26, 2017", 15 pgs.
"U.S. Appl. No. 15/000,851, Notice of Allowance dated Nov. 8, 2017", 9 pgs.
"U.S. Appl. No. 15/000,851, Preliminary Amendment filed Feb. 3, 2016", 3 pgs.
"U.S. Appl. No. 15/000,851, Response filed Jul. 26, 2017 to Non-Final Office Action dated Jan. 26, 2017", 16 pgs.
"U.S. Appl. No. 15/000,851, Response filed Oct. 12, 2016 to Restriction Requirement dated May 12, 2016", 11 pgs.
"U.S. Appl. No. 15/000,851, Restriction Requirement dated May 12, 2016", 6 pgs.
"U.S. Appl. No. 15/000,851, Supplemental Amendment filed Apr. 4, 2016", 10 pgs.
"U.S. Appl. No. 15/170,556, Non-Final Office Action dated Jul. 27, 2018", 10 pgs.
"U.S. Appl. No. 15/170,556, Preliminary Amendment filed Aug. 22, 2016", 9 pgs.
"U.S. Appl. No. 15/170,556, Response filed Apr. 5, 2018 to Restriction Requirement dated Feb. 16, 2018", 8 pgs.
"U.S. Appl. No. 15/170,556, Response filed Oct. 29, 2018 to Non-Final Office Action dated Jul. 27, 2018", 9 pgs.
"U.S. Appl. No. 15/170,556, Restriction Requirement dated Feb. 16, 2018", 7 pgs.
"U.S. Appl. No. 15/203,581, Examiners Interview Summary dated Sep. 11, 2017", 1 pg.
"U.S. Appl. No. 15/203,581, Notice of Allowance dated Sep. 11, 2017", 12 pgs.
"U.S. Appl. No. 15/203,581, Preliminary Amendment filed Sep. 22, 2016", 4 pgs.
"U.S. Appl. No. 15/203,581, PTO Response to Rule 312 Communication dated Dec. 27, 2017", 2 pgs.
"U.S. Appl. No. 15/203,581, Response filed Aug. 15, 2017 to Restriction Requirement dated Jun. 16, 2017", 8 pgs.
"U.S. Appl. No. 15/203,581, Restriction Requirement dated Jun. 16, 2017", 8 pgs.
"U.S. Appl. No. 15/292,595, Non-Final Office Action dated Sep. 25, 2017", 13 pgs.
"U.S. Appl. No. 15/292,595, Notice of Allowance dated Feb. 28, 2018", 9 pgs.
"U.S. Appl. No. 15/292,595, Preliminary Amendment filed Dec. 27, 2016", 5 pgs.
"U.S. Appl. No. 15/292,595, Response filed Dec. 22, 2017 to Non-Final Office Action dated Sep. 25, 2017", 9 pgs.
"U.S. Appl. No. 15/593,039, Non-Final Office Action dated Feb. 6, 2018", 8 pgs.
"U.S. Appl. No. 15/593,039, Notice of Allowance dated Jul. 11, 2018", 5 pgs.
"U.S. Appl. No. 15/593,039, Preliminary Amendment filed Jul. 25, 2017", 7 pgs.
"U.S. Appl. No. 15/593,039, PTO Response to Rule 312 Communication dated Oct. 9, 2018", 2 pgs.

(56) References Cited

OTHER PUBLICATIONS

"U.S. Appl. No. 15/593,039, Response filed Apr. 30, 2018 to Non-Final Office Action dated Feb. 4, 2018", 8 pgs.
"U.S. Appl. No. 15/593,039, Response filed Dec. 18, 2017 to Restriction Requirement dated Oct. 18, 2017", 8 pgs.
"U.S. Appl. No. 15/593,039, Restriction Requirement dated Oct. 18, 2017", 6 pgs.
"U.S. Appl. No. 15/593,039, Supplemental Preliminary Amendment filed Jul. 26, 2017", 4 pgs.
"U.S. Appl. No. 15/865,364, Preliminary Amendment filed Apr. 10, 2018", 10 pgs.
"Application Serial No. 200480021259.9 Office Action dated Sep. 11, 2009", 7 pgs.
"Application Serial No. 200480021259.9 Office Action Response Filed Aug. 20, 2010", 26 pgs.
"Application Serial No. 2006-533439 Office Action dated Mar. 9, 2010", 20 pgs.
"U.S. Appl. No. 12/214,414, Response filed Oct. 14, 2014 to Non-Final Office Action dated Jun. 12, 2014", 16 pgs.
"Australian Application Serial No. 2001255336, Examiner's First Report dated Feb. 16, 2005", 2 pgs.
"Australian Application Serial No. 2001255336, Response filed Aug. 23, 2005 to Examiner's First Report dated Feb. 16, 2005", 10 pgs.
"Australian Application Serial No. 2004249133, First Examiner's Report dated May 5, 2008", 4 pgs.
"Australian Application Serial No. 2004249133, Response filed Mar. 30, 2009 to First Examiner's Report dated May 5, 2008", 30 pgs.
"Australian Application Serial No. 2007245192, Office Action dated Aug. 25, 2011", 2 pgs.
"Australian Application Serial No. 2007245192, Response filed Feb. 28, 2012 to Office Action dated Aug. 25, 2011", 22 pgs.
"Australian Application Serial No. 2012204138, First Examiner Report dated Jul. 16, 2013", 4 pgs.
"Australian Application Serial No. 2012204138, Response filed Dec. 24, 2013 to First Examiner Report dated Jul. 16, 2013", 21 pgs.
"Australian Application Serial No. 2014202470, First Examiner Report dated Jul. 20, 2015", 2 pgs.
"Australian Application Serial No. 2014202470, Respojnse filed Jul. 4, 2016 to Subsequent Examiners Report dated Feb. 1, 2016", 3 pgs.
"Australian Application Serial No. 2014202470, Response filed Jul. 20, 2016 to Subsequent Examiners Report dated Jul. 19, 2016", 15 pgs.
"Australian Application Serial No. 2014202470, Response filed Dec. 1, 2015 to First Examiner Report dated Jul. 20, 2015", 22 pgs.
"Australian Application Serial No. 2014202470, Subsequent Examiners Report dated Feb. 1, 2016", 2 pgs.
"Australian Application Serial No. 2014202470, Subsequent Examiners Report dated Jul. 19, 2016", 3 pgs.
"Brazilian Application Serial No. PI0410702-0, Office Action dated Feb. 23, 2012", (w/ English Translation), 4 pgs.
"Brazilian Application Serial No. PI0410702-0, Response filed May 7, 2012 to Office Action dated Feb. 23, 2012", (w/ English Translation of Claims), 11 pgs.
"Canadian Application Serial No. 2,406,180, Office Action dated Sep. 9, 2008", 5 pgs.
"Canadian Application Serial No. 2,406,180, Office Action dated Nov. 10, 2011", 3 pgs.
"Canadian Application Serial No. 2,406,180, Office action dated Nov. 23, 2009", 3 pgs.
"Canadian Application Serial No. 2,406,180, Office Action dated Dec. 10, 2010", 2 Pgs.
"Canadian Application Serial No. 2,406,180, Response filed Jan. 26, 2009 to Official Action dated Sep. 9, 2008", 22 pgs.
"Canadian Application Serial No. 2,406,180, Response filed May 21, 2010 to Office action dated Nov. 23, 2009", 13 pgs.
"Canadian Application Serial No. 2,406,180, Response filed Jun. 14, 2011 to Office Action dated Dec. 10, 2010", 10 pgs.
"Canadian Application Serial No. 2,522,081, Amendment After Allowance filed Aug. 10, 2012", 3 pgs.
"Canadian Application Serial No. 2,522,081, Office Action filed Nov. 18, 2011", 11 pgs.
"Canadian Application Serial No. 2,522,081, Office Action dated Jun. 6, 2011", 2 pgs.
"Canadian Application Serial No. 2,522,081, Office Action dated Aug. 30, 2010", 2 pgs.
"Canadian Application Serial No. 2,522,081, Office Action dated Oct. 8, 2009", 6 pgs.
"Canadian Application Serial No. 2,522,081, Response filed Feb. 28, 2011 to Office Action dated Aug. 30, 2010", 10 pgs.
"Canadian Application Serial No. 2,522,081, Response filed Apr. 8, 2010 to Office Action dated Oct. 8, 2009", 30 pgs.
"Canadian Application Serial No. 2,522,081, Response filed Nov. 18, 2011 to Office Action dated Jun. 6, 2011", 11 pgs.
"Canadian Application Serial No. 2,525,953, Amendment and Response filed Feb. 1, 2017 to Office Action dated Aug. 1, 2016", 28 pgs.
"Canadian Application Serial No. 2,525,953, Office Action dated Jan. 21, 2016", 6 pgs.
"Canadian Application Serial No. 2,525,953, Office Action dated Jul. 31, 2012", 4 pgs.
"Canadian Application Serial No. 2,525,953, Office Action dated Aug. 1, 2016", 6 pgs.
"Canadian Application Serial No. 2,525,953, Office Action dated Aug. 16, 2013", 3 pgs.
"Canadian Application Serial No. 2,525,953, Office Action dated Oct. 3, 2017", 4 pgs.
"Canadian Application Serial No. 2,525,953, Office Action dated Nov. 6, 2014", 3 pgs.
"Canadian Application Serial No. 2,525,953, Office Action dated Jun. 22, 2011", 4 pgs.
"Canadian Application Serial No. 2,525,953, Response filed Jan. 31, 2013 to Office Action dated Jul. 31, 2012", 11 pgs.
"Canadian Application Serial No. 2,525,953, Response filed Feb. 1, 2017 to Office Action dated Aug. 1, 2016", 28 pgs.
"Canadian Application Serial No. 2,525,953, Response filed Feb. 14, 2014 to Office Action dated Aug. 16, 2013", 16 pgs.
"Canadian Application Serial No. 2,525,953, Response filed Apr. 3, 2018 to Office Action dated Oct. 3, 2017", 46 pgs.
"Canadian Application Serial No. 2,525,953, Response filed May 1, 2015 to Office Action dated Nov. 6, 2014", 23 pgs.
"Canadian Application Serial No. 2,525,953, Response filed Jul. 11, 2016 to Office Action dated Jan. 21, 2016", 21 pgs.
"Canadian Application Serial No. 2,525,953, Response filed Dec. 22, 2011 to Office Action dated Jun. 22, 2011", 17 pgs.
"Canadian Application Serial No. 2,647,985, Office Action dated May 15, 2013", 3 pgs.
"Canadian Application Serial No. 2,647,985, Response filed Sep. 30, 13 to Office Action dated May 15, 2013", 20 pgs.
"Canadian Application Serial No. 2406180, Response filed May 7, 2012 to Office Action dated Nov. 10, 2011", 11 pgs.
"Chinese Application Serial No. 200480017037, First Office Action dated May 25, 2007", (w/ English Translation), 10 pgs.
"Chinese Application Serial No. 200480017037, Response filed Oct. 30, 2007 to First Office Action dated May 25, 2007", (w/ English Translation of Claims), 26 pgs.
"Chinese Application Serial No. 200480017037.X, Response filed May 14, 2010 to Third Office Action dated Mar. 1, 2010", (w/ English Translation of Claims), 16 pgs.
"Chinese Application Serial No. 200480017037.X, Response filed Aug. 4, 2009 to Second Office Action dated Mar. 20, 2009", (w/ English Translation of Amended Claims), 15 pgs.
"Chinese Application Serial No. 200480017037.X, Second Office Action dated Mar. 20, 2009", (English Translation), 7 pgs.
"Chinese Application Serial No. 200480017037.X, Third Office Action dated Mar. 1, 2010", (w/ English Translation), 9 pgs.
"Chinese Application Serial No. 200480021259.9, First Offiice Action dated Aug. 24, 2007", (w/ English Translation), 9 pgs.
"Chinese Application Serial No. 200480021259.9, Notice of Reexamination dated Jul. 3, 2012", (w/ English Translation), 10 pgs.
"Chinese Application Serial No. 200480021259.9, Office Action dated Jan. 11, 2011", (w/ English Translation), 15 pgs.

(56) References Cited

OTHER PUBLICATIONS

"Chinese Application Serial No. 200480021259.9, Office Action dated May 6, 2010", (w/ English Translation), 12 pgs.
"Chinese Application Serial No. 200480021259.9, Office Action dated Jul. 3, 2012", (w/ English Translation), 10 pgs.
"Chinese Application Serial No. 200480021259.9, Request for Reexamination filed Apr. 26, 2011", (w/ English Translation of Amended Claims), 23 pgs.
"Chinese Application Serial No. 200480021259.9, Response filed Mar. 7, 2008 to Offiice Action dated Aug. 24, 2007", (w/ English Translation of Claims), 13 pgs.
"Chinese Application Serial No. 200480021259.9, Response filed Oct. 16, 2012 to Office Action dated Jul. 3, 2012", (w/ English Translation of Claims), 13 pgs.
"Chinese Application Serial No. 200780020095.1, Decision on Rejection dated Jul. 22, 2013", (w/ English Translation), 11 pgs.
"Chinese Application Serial No. 200780020095.1, First Office Action dated Jun. 24, 2011", (w/ English Translation), 13 pgs.
"Chinese Application Serial No. 200780020095.1, Office Action dated Jan. 29, 2013", (w/ English Translation), 10 pgs.
"Chinese Application Serial No. 200780020095.1, Office Action dated Mar. 5, 2015", (w/ English Translation), 12 pgs.
"Chinese Application Serial No. 200780020095.1, Office Action dated Apr. 26, 2016", (w/ English Summary), 4 pgs.
"Chinese Application Serial No. 200780020095.1, Office Action dated May 3, 2012", (w/ English Translation), 10 pgs.
"Chinese Application Serial No. 200780020095.1, Office Action dated Nov. 2, 2016", (w/ English Translation), 11 pgs.
"Chinese Application Serial No. 200780020095.1, Response filed Jan. 6, 2017 to Office Action dated Nov. 2, 2016", (w/ English Translation of Claims), 15 pgs.
"Chinese Application Serial No. 200780020095.1, Response filed Jun. 9, 2013 to Office Action dated Jan. 29, 2013", (w/ English Translation of Claims), 10 pgs.
"Chinese Application Serial No. 200780020095.1, Response filed Jun. 23, 2015 to Office Action dated Mar. 5, 2015", (w/ English Translation of Claims), 16 pgs.
"Chinese Application Serial No. 200780020095.1, Response filed Jun. 30, 2016 to Office Action dated Apr. 26, 2016", (w/ English Translation of Claims), 22 pgs.
"Chinese Application Serial No. 200780020095.1, Response filed Sep. 17, 2012 to Office Action dated May 3, 2012", (w/ English Translation of Claims), 17 pgs.
"Chinese Application Serial No. 200780020095.1, Response filed Nov. 5, 2013 to to Decision on Rejection dated Jul. 22, 2013", (w/ English Translation of Claims), 12 pgs.
"Chinese Application Serial No. 200780020095.1, Response filed Nov. 8, 2011 to Office Action dated Jun. 24, 2011", (w/ English Translation of Amended Claims), 20 pgs.
"Chinese Application Serial No. 200480021259.9, Office Action dated May 8, 2009", (w/ English Translation), 6 pgs.
"Eurasian Application No. 200501890, Notice of Allowance dated Jun. 23, 2009", 1 pg.
"Eurasian Application Serial No. 200501890, Office Action dated Mar. 23, 2007", (w English Translation), 2 pgs.
"Eurasian Application Serial No. 200501890, Office Action dated Sep. 4, 2008", (English Translation), 1 pg.
"Eurasian Application Serial No. 200501890, Office Action dated Dec. 17, 2007", (w/ English Translation), 6 pgs.
"Eurasian Application Serial No. 200501890, Response filed Mar. 26, 2008 to Office Action dated Dec. 17, 2007", (w/ English Translation of Claims), 15 pgs.
"Eurasian Application Serial No. 200501890, Response filed Jun. 14, 2007 to Office Action dated Mar. 23, 2007", (w/ English Translation of Claims), 11 pgs.
"Eurasian Application Serial No. 200501890, Response filed Dec. 17, 2008 to Office Action", (w/ English Translation of Claims), 13 pgs.
"Eurasian Application Serial No. 200501890, Response filed Dec. 17, 2008 to Office Action dated Sep. 4, 2008", (w/ English Translation of Claims), 14 pgs.
"European Application 04750333.9, Communication dated Oct. 12, 2006", 6 pgs.
"European Application 04750333.9, Communication dated Dec. 8, 2006", 4 pgs.
"European Application 04750333.9, Communication dated Apr. 11, 2008", 6 pgs.
"European Application 04750333.9, Response filed Oct. 4, 2007 to Communication dated Dec. 8, 2006", 42 pgs.
"European Application 04750333.9, Response filed Nov. 21, 2006 to Communication Oct. 12, 2006", 4 pgs.
"European Application Serial No. 01928486.8 Office Action dated Oct. 1, 2009", 2 pgs.
"European Application Serial No. 01928486.8, Communication dated Aug. 10, 2007", 3 pgs.
"European Application Serial No. 01928486.8, Communication dated Sep. 20, 2005", 4 pgs.
"European Application Serial No. 01928486.8, Office Action dated Feb. 19, 2009", 3 pgs.
"European Application Serial No. 01928486.8, Response filed Jan. 30, 2006 to Communication dated Sep. 20, 2005", 9 pgs.
"European Application Serial No. 01928486.8, Response filed Aug. 28, 2009 to Communication dated Feb. 19, 2009", 5 pgs.
"European Application Serial No. 01928486.8, Response filed Jan. 21, 2008 to Communication dated Aug. 10, 2007", 11 pgs.
"European Application Serial No. 01928486.8, Response filed Dec. 9, 2009 to Office Action dated Oct. 1, 2009", 11 pgs.
"European Application Serial No. 04750333.9, Office Action dated Jan. 22, 2009", 5 pgs.
"European Application Serial No. 04750333.9, Response filed Oct. 21, 2008 to Communication dated Apr. 11, 2008", 15 pgs.
"European Application Serial No. 04750333.9, Response filed Nov. 17, 2009 to Communication dated Jan. 22, 2009", 17 pgs.
"European Application Serial No. 04750333.9, Summons to Attend Oral Proceedings dated Aug. 3, 2011", 13 pgs.
"European Application Serial No. 04776133.3, Communication dated Mar. 30, 2006", 3 pgs.
"European Application Serial No. 04776133.3, Examination Notification Art. 94(3) dated Jul. 28, 2015", 4 pgs.
"European Application Serial No. 04776133.3, Examination Notification Art. 94(3) dated Nov. 25, 2013", 5 pgs.
"European Application Serial No. 04776133.3, Office Action dated Jan. 5, 2010", 4 pgs.
"European Application Serial No. 04776133.3, Response filed Jan. 25, 2007 to Communication dated Mar. 30, 2006", 20 pgs.
"European Application Serial No. 04776133.3, Response filed Apr. 30, 2014 to Examination Notification Art. 94(3) dated Nov. 25, 2013", 12 pgs.
"European Application Serial No. 04776133.3, Response filed Jul. 15, 2010 to Office Action dated Jan. 5, 2010", 9 pgs.
"European Application Serial No. 04776133.3, Response filed Sep. 18, 2015 to Examination Notification Art. 94(3) dated Jul. 28, 2015", 47 pgs.
"European Application Serial No. 07754132.4, Office Action dated Apr. 28, 2009", 4 pgs.
"European Application Serial No. 07754132.4, Office Action dated Sep. 5, 2011", 5 pgs.
"European Application Serial No. 07754132.4, Office Action dated Nov. 2, 2012", 4 pgs.
"European Application Serial No. 07754132.4, Response filed Feb. 5, 2010 to Office Action dated Apr. 28, 2009", 15 pgs.
"European Application Serial No. 07754132.4, Response filed Mar. 15, 2012 to Office Action dated Sep. 5, 2011", 21 pgs.
"European Application Serial No. 07754132.4, Response filed May 10, 2013 to Office Action dated Nov. 2, 2012", 14 pgs.
"European Application Serial No. 07754132.4, Response filed Jun. 26, 2013", 8 pgs.
"European Application Serial No. 10777154.5, Communication Pursuant to Article 94(3) EPC dated Apr. 4, 2018", 7 pgs.
"European Application Serial No. 10777154.5, Communication Pursuant to Article 94(3) EPC dated Oct. 12, 2017", 7 pgs.

(56) References Cited

OTHER PUBLICATIONS

"European Application Serial No. 10777154.5, Examination Notification Art. 94(3) dated Oct. 6, 2014", 7 pgs.
"European Application Serial No. 10777154.5, Office Action dated May 2, 2016", 6 pgs.
"European Application Serial No. 10777154.5, Office Action dated Jul. 4, 2012", 2 pgs.
"European Application Serial No. 10777154.5, Response filed Jan. 14, 2013 to Office Action dated Jul. 4, 2012", 12 pgs.
"European Application Serial No. 10777154.5, Response filed Feb. 21, 2018 to Communication Pursuant to Article 94(3) EPC dated Oct. 12, 2017", 12 pgs.
"European Application Serial No. 10777154.5, Response filed Sep. 8, 2016 to Office Action dated May 2, 2016", 69 pgs.
"European Application Serial No. 14745060.5, Communication Pursuant to Article 94(3) EPC dated Feb. 6, 2018", 5 pgs.
"European Application Serial No. 14745060.5, Office Action dated Feb. 23, 2016", 2 pgs.
"European Application Serial No. 14745060.5, Response filed Dec. 22, 2016 to Communication pursuant to Rules 161(1) and 162 EPC dated Feb. 23, 2016", 6 pgs.
"Evaluation of Medicines for human Use", EMEA/CPMP/BWP/2289/01, London, The European Agency for the Evaluation of Medicinal Products, Committee for Proprietary Medicinal Products (CPMP), (Feb. 20, 2003), 14.
"FLUZONE® Influenza Virus Vaccine", Sanofi Aventis Pasteur, Swiftwater, (Jul. 2005), 12 pgs.
"Hemagglutinin [Influenza A virus (A/swine/France/WVL13/1995(H1N1))]", GenBank Accession# AC025026, (May 22, 2009), 1 pg.
"Hemagglutinin [Influenza B virus (B/Hong Kong/330/2001)]", GenBank ABL77178.1, (2006), 1 pg.
"Indian Application Serial No. 02082/KOLNP/2005, Examination Report dated Mar. 17, 2008", 1 pg.
"Indian Application Serial No. 02082/KOLNP/2005, Examination Report dated Dec. 28, 2007", 1 pg.
"Indian Application Serial No. 02082/KOLNP/2005, First Examination Report dated Jan. 25, 2007", 9 pgs.
"Indian Application Serial No. 02082/KOLNP/2005, Response filed Jan. 22, 2008 to Examination Report dated Dec. 28, 2007", 13 pgs.
"Indian Application Serial No. 02082/KOLNP/2005, Response filed Jun. 10, 2008 to Examination Report dated Mar. 17, 2008", 3 pgs.
"Indian Application Serial No. 02082/KOLNP/2005, Response filed Nov. 19, 2007 to First Examination Report dated Jan. 25, 2007", 26 pgs.
"Indian Application Serial No. 1026/KOLNP/2009, First Examiner Report dated Mar. 13, 2014", 2 pgs.
"Indian Application Serial No. 2272/KOLNP/2005, First Examination Report dated Mar. 17, 2008", 10 pgs.
"Indian Application Serial No. 2272/KOLNP/2005, Response filed Mar. 16, 2009 to Subsequent Examination Report dated Mar. 6, 2009", 12 pgs.
"Indian Application Serial No. 2272/KOLNP/2005, Response filed Oct. 11, 2008 to First Examination Report dated Mar. 17, 2008", 27 pgs.
"Indian Application Serial No. 2272/KOLNP/2005, Subsequent Examination Report dated Mar. 6, 2009", 1 pg.
"Influenza B/lee/40, neuraminidase & nb (seg 6) rna", Database EM_VI E.B.I. Hinxton U.K., (Jun. 13, 1985), 10 pgs.
"International Application No. PCT/US2004/016680, International Search Report", (dated Feb. 2, 2005), 7 pgs.
"International Application Serial No. PCT/US01/11963, Amendment filed Sep. 9, 2002 to Written Opinion dated Aug. 7, 2002", 12 pgs.
"International Application Serial No. PCT/US01/11963, International Preliminary Examination Report dated Oct. 15, 2002", 13 pgs.
"International Application Serial No. PCT/US01/11963, International Search Report dated May 7, 2002", 5 pgs.
"International Application Serial No. PCT/US01/11963, Response filed Sep. 9, 2002 to Written Opinion dated Aug. 7, 2002", 12 pgs.
"International Application Serial No. PCT/US01/11963, Written Opinion dated Jun. 14, 2002", 2 pgs.
"International Application Serial No. PCT/US01/11963, Written Opinion dated Aug. 7, 2002", 6 pgs.
"International Application Serial No. PCT/US2004/012050, International Search Report dated Feb. 2, 2005", 8 pgs.
"International Application Serial No. PCT/US2004/012050, Written Opinion dated Feb. 2, 2005", 12 pgs.
"International Application Serial No. PCT/US2004/016680, International Preliminary Report on Patentability dated Dec. 15, 2005", 11 pgs.
"International Application Serial No. PCT/US2007/007562, International Preliminary Report on Patentability dated Oct. 9, 2008", 5 pgs.
"International Application Serial No. PCT/US2007/007562, International Search Report dated Jan. 14, 2008", 8 pgs.
"International Application Serial No. PCT/US2007/007562, Written Opinion dated Jan. 14, 2008", 9 pgs.
"International Application Serial No. PCT/US2008/007582, International Preliminary Report on Patentability dated Jan. 7, 2010", 9 pgs.
"International Application Serial No. PCT/US2008/007582, International Search Report and Written Opinion dated Feb. 18, 2009", 16 pgs.
"International Application Serial No. PCT/US2010/054128, Preliminary Report on Patentability dated May 10, 2012", 10 pgs.
"International Application Serial No. PCT/US2010/054128, Search Report dated Feb. 23, 2011", 6 pgs.
"International Application Serial No. PCT/US2010/054128, Written Opinion dated Feb. 23, 2011", 8 pgs.
"International Application Serial No. PCT/US2014/046731, International Preliminary Report on Patentability dated Jan. 28, 2016", 12 pgs.
"International Application Serial No. PCT/US2014/046731, International Search Report dated Nov. 25, 2014", 9 pgs.
"International Application Serial No. PCT/US2014/046731, Written Opinion dated Nov. 25, 2014", 10 pgs.
"International Application Serial No. PCT/US2015/036803, International Preliminary Report on Patentability dated Dec. 29, 2016", 10 pgs.
"International Application Serial No. PCT/US2015/036803, International Search Report dated Dec. 11, 2015", 8 pgs.
"International Application Serial No. PCT/US2015/036803, Invitation to Pay Add'l Fees and Partial Search Rpt dated Oct. 2, 2015", 8 pgs.
"International Application Serial No. PCT/US2015/036803, Written Opinion dated Dec. 11, 2015", 8 pgs.
"International Application Serial No. PCT/US2016/041172, International Preliminary Report on Patentability dated Jan. 18, 2018", 10 pgs.
"International Application Serial No. PCT/US2016/041172, International Search Report dated Oct. 27, 2016", 6 pgs.
"International Application Serial No. PCT/US2016/041172, Written Opinion dated Oct. 27, 2016", 8 pgs.
"International Application Serial No. PCT/US2017/018443, International Preliminary Report on Patentability dated Aug. 30, 2018", 11 pgs.
"International Application Serial No. PCT/US2017/018443, International Search Report dated May 22, 2017", 9 pgs.
"International Application Serial No. PCT/US2017/018443, Written Opinion dated May 22, 2017", 9 pgs.
"Israeli Application Serial No. 238584, Office Action dated Jul. 24, 2017", 2 pgs.
"Israeli Application Serial No. 238584, Response filed Nov. 21, 2017 to Office Action dated Jul. 24, 2017", W/English Translation, 2 pgs.
"Israeli Application Serial No. 171831, Notification of Defects dated Nov. 10, 2008", (English Translation), 10 pgs.
"Israeli Application Serial No. 171372, Office Action dated dated Feb. 21, 2010", (Translation), 2 pgs.

(56) References Cited

OTHER PUBLICATIONS

"Israeli Application Serial No. 171372, Office Action dated Nov. 6, 2008", (Translation), 12 pgs.
"Israeli Application Serial No. 171372, Response filed Nov. 18, 2010 to Office Action dated Feb. 21, 2010", (Translation), 19 pgs.
"Israeli Application Serial No. 171831, Office Action dated Feb. 21, 2010", (English Translation), 2 pgs.
"Israeli Application Serial No. 171831, Office Action dated Apr. 18, 2012", (English Translation), 2 pgs.
"Israeli Application Serial No. 171831, Response filed Jan. 20, 2011 to Office Action dated Feb. 21, 2010", (English Translation), 18 pgs.
"Israeli Application Serial No. 171831, Response filed Jun. 24, 2009 to Notification of Defects dated Nov. 10, 2008", (w/English Translation of Claims), 10 pgs.
"Israeli Application Serial No. 171831, Response filed Nov. 6, 2012 to Office Action dated Apr. 18, 2012", (w/ English Translation of Amended Claims), 54 pgs.
"Israeli Application Serial No. 238584, Office Action dated Apr. 14, 2016", (English Translation), 3 pgs.
"Israeli Application Serial No. 238584, Office Action dated Jul. 24, 2017", (Translation), 2 pgs.
"Israeli Application Serial No. 238584, Response filed Aug. 3, 2016 to Office Action dated Apr. 14, 2016", (English Translation of Claims), 19 pgs.
"Israeli Application Serial No. 238584, Response filed Nov. 21, 2017 to Office Action dated Jul. 24, 2017", (Translation), 2 pgs.
"Israeli Application Serial No. 171372, Office Action dated Feb. 20, 2011", (Translation), 2 pgs.
"Japanese Application No. 2001-576868, Office Action dated May 31, 2011", (w/ English Translation), 5 pgs.
"Japanese Application No. 2001-576868, Response filed Apr. 26, 2011 to Office Action dated Nov. 2, 2010", (w/ Translation of Amended Claims), 14 pgs.
"Japanese Application Serial No. 2001-576868, Office Action dated Nov. 2, 2010", w/ English Translation), 10 pgs.
"Japanese Application Serial No. 2001-576868, Response filed Dec. 1, 2011 to Office Action dated May 3, 2011", (w/ English Translation of Amended Claims), 37 pgs.
"Japanese Application Serial No. 2006-513125, Office Action dated Mar. 9, 2010", (English Translation), 11 pgs.
"Japanese Application Serial No. 2006-513125, Response filed Aug. 30, 2010 to Office Action dated Mar. 9, 2010", (w/ English Translation of Amended Claims), 60 pgs.
"Japanese Application Serial No. 2006-533439, Decision of Final Rejection dated Aug. 14, 2012", (w/ English Translation), 5 pgs.
"Japanese Application Serial No. 2006-533439, Office Action dated Mar. 27, 2012", w/ English Translation, 8 pgs.
"Japanese Application Serial No. 2006-533439, Response filed May 21, 2012 to Office Action dated Mar. 27, 2012", (w/ English Translation of Amended Claims), 19 pgs.
"Japanese Application Serial No. 2006-533439, Response filed Aug. 3, 2011 to Office Action dated Feb. 15, 2011", (w/ English Translation of Amended Claims), 18 pgs.
"Japanese Application Serial No. 2006-533439, Office Action dated Feb. 15, 2011", (w/ English Translation), 13 pgs.
"Japanese Application Serial No. 2006-533439; Office Action Response filed Jul. 9, 2010", (w/ English Translation of Claims), 25 pgs.
"Japanese Application Serial No. 2009-502945, Examiners Decision of Final Refusal dated Nov. 12, 2013", (w/ English Translation), 8 pgs.
"Japanese Application Serial No. 2009-502945, Office Action dated Oct. 23, 2012", (w/ English Translation), 16 pgs.
"Japanese Application Serial No. 2009-502945, Response filed Apr. 10, 2013 to Office Action dated Oct. 23, 2012", (w/ English Translation of Claims), 18 pgs.
"Japanese Application Serial No. 2011-111048, Office Action dated Jun. 25, 2013", (w/ English Translation), 7 pgs.
"Japanese Application Serial No. 2011-111048, Office Action dated Sep. 18, 2012", (w/ English Translation), 10 pga.
"Japanese Application Serial No. 2011-111048, Response filed Sep. 25, 2012 to Office Action dated Jun. 25, 2013", (w/ English Translation of Amended Claims), 18 pgs.
"Japanese Application Serial No. 2011-111048. Response filed Mar. 15, 2013", (w/ Translation of Amended Claims), 14 pgs.
"Japanese Application Serial No. 2012-273898, Office Action dated Jun. 10, 2014", (w/ English Translation), 7 pgs.
"Japanese Application Serial No. 2012-273898, Response filed Sep. 4, 2014 to Office Action dated Jun. 10, 2014", W/ English Claims, 9 pgs.
"Japanese Application Serial No. 2012-536963, Amendment and Argument filed Jun. 26, 2015 to Office Action dated Jan. 6, 2015", (w/ English Translation of Amended Claims), 12 pgs.
"Japanese Application Serial No. 2012-536963, Examiners Decision of Final Refusal dated Nov. 17, 2015", (w/ English Translation), 8 pgs.
"Japanese Application Serial No. 2012-536963, Office Action dated Jan. 6, 2015", (w/ English Translation), 14 pgs.
"Japanese Application Serial No. 2012-536963, Voluntary Amendment filed Jun. 27, 2012", (w/ English Translation of Amended Claims), 17 pgs.
"Japanese Application Serial No. 2013-198377, Office Action dated Jan. 6, 2015", (w/ English Translation), 9 pgs.
"Japanese Application Serial No. 2014-049025 Response filed Sep. 4, 2015 to Office Action dated Jun. 16, 2015", (w/ Amended Claims), 12 pgs.
"Japanese Application Serial No. 2014-049025, Examiners Decision of Final Refusal dated Feb. 2, 2016", W/ English Translation, 5 pgs.
"Japanese Application Serial No. 2014-049025, Office Action dated Jun. 16, 2015", (w/ English Translation), 6 pgs.
"Japanese Application Serial No. 2016-053990, Office Action dated Jun. 6, 2017", (w/ English Translation), 4 pgs.
"Japanese Application Serial No. 2016-053990, Response filed Dec. 6, 2017 to Office Action dated Jun. 6, 2017", (w/ English Translation of Amended Claims), 14 pgs.
"Japanese Application Serial No. 2016-110879, Office Action dated May 30, 2017", (w/ English Translation), 7 pgs.
"Japanese Application Serial No. 2016-110879, Response filed Nov. 30, 2017 to Office Action dated May 30, 2017", (w/ English Translation of Claims), 25 pgs.
"Japanese Application Serial No. 2006-513125, Final Office Action dated Jan. 18, 2011", (English Translation), 4 pgs.
"Korean Application Serial No. 10-2005-7020077, Response filed Apr. 28, 2008 to Examination Report dated Dec. 28, 2007", (w/ English Translation of Revised Claims), 41 pgs.
"Korean Application Serial No. 10-2005-7020077, Examination Report dated Dec. 28, 2007", (w/ English Translation), 8 pgs.
"Korean Application Serial No. 10-2005-7020077, Notice of Preliminary Rejection dated Jun. 28, 2007", (w/ English Translation), 9 pgs.
"Korean Application Serial No. 10-2005-7020077, Response filed Aug. 28, 07 to Notice of Preliminary Rejection dated Jun. 28, 2007", (w/ EnglishTranslation), 40 pgs.
"Korean Application Serial No. 10-2005-7022564, Notice of Preliminary Rejection dated Jul. 25, 2007", W/ English Translation, 5 pgs.
"Korean Application Serial No. 10-2005-7022564, Office Action dated Aug. 6, 2008", (w/ English Translation, 4 pgs.
"Korean Application Serial No. 10-2005-7022564, Response and Amendment filed Dec. 29, 2008 to Office Action dated Aug. 6, 2008", (w/ English Translation), 16 pgs.
"Korean Application Serial No. 10-2005-7022564, Response filed Mar. 25, 2008 to Notice of Preliminary Rejection dated Jul. 25, 2007", (w/ English Translation of Claims), 35 pgs.
"Korean Application Serial No. 10-2005-7022564, Response filed Dec. 29, 2008 to Office Action dated Aug. 6, 2008", (w/ English Translation of Claims), 16 pgs.
"Mexican Application No. PA/a/2005/012712 Office Action dated Jul. 21, 2009", (w/ English Translation), 9 pgs.
"Mexican Application Serial No. MX/a/2009/006341, Office Action dated Mar. 29, 2012", (English Translation), 1 pg.

(56) References Cited

OTHER PUBLICATIONS

"Mexican Application Serial No. MX/a/2009/006341, Response filed Jun. 4, 2012 to Mar. 29, 2012", (w/ English Translation of Amended Claims), 16 pgs.
"Mexican Application Serial No. MX/a/2012/009249 Response filed Sep. 10, 2015 to Office Action dated May 19, 2015", (w/ English Translation of Claims), 21 pgs.
"Mexican Application Serial No. MX/a/2012/009249, Office Action dated Feb. 5, 2016", (w/ English Claims), 2 pgs.
"Mexican Application Serial No. MX/a/2012/009249, Office Action dated May 19, 2015", (English Translation), 1 pg.
"Mexican Application Serial No. MX/a/2012/009249, Response filed Mar. 29, 2016 to Office Action dated Feb. 5, 2016", (English Translation of Claims), 18 pgs.
"Mexican Application Serial No. PA/a/2005/011250, Office Action dated Aug. 23, 2010", (w/ English Translation), 4 pgs.
"Mexican Application Serial No. PA/a/2005/011250, Response Filed Dec. 20, 2010 to Office Action dated Aug. 23, 2010", (w/ English Translation of Claims), 14 pgs.
"Mexican Application Serial No. PA/a/2005/012712, Office Action dated Aug. 11, 2009", (English Translation), 5 pgs.
"Mexican Application Serial No. PA/a/2005/012712, Response filed Sep. 28, 2009 to Office Action dated Jul. 21, 2009", (w/ English Translation of Claims), 24 pgs.
"Mexican Application Serial No. PA/a/2005/012712, Office Action dated May 12, 2010", (w/English Translation), 19 pgs.
"Mexican Application Serial No. PA/a/2005/012712, Office Action dated Jun. 9, 2010", (w/English Translation), 11 pgs.
"Mexican Application Serial No. PA/a/2005/012712, Office Action dated Nov. 30, 2009", (w/ English Translation), 14 pgs.
"Mexican Application Serial No. PA/a/2005/012712, Official Action dated Mar. 5, 2009", (English Translation), 2 pgs.
"Mexican Application Serial No. PA/a/2005/012712, Response filed Feb. 3, 2010 to Office Action dated Nov. 30, 2009", (w/ English Translation of Amended Claims), 22 pgs.
"Mexican Application Serial No. PA/a/2005/012712, Response filed Sep. 27, 2010 to Office Action dated May 12, 2010", (w/ English Translation of Claims), 19 pgs.
"Mexico Application Serial No. PA/a/2005/012712, Response filed Jun. 12, 2009 to Official Action dated Mar. 5, 2009", (w/ English Translation of Claims), 11 pgs.
"Neuraminidase, partial [Influenza A virus (A/swine/France/WVL13/1995(H1N1))]", GenBank Accession# AC025028, (May 22, 2009), 2 pgs.
"New Zealand Application Serial No. 542935, Examination Report dated Feb. 25, 2008", 2 pgs.
"New Zealand Application Serial No. 542935, Examination Report dated Jun. 14, 2006", 2 pgs.
"New Zealand Application Serial No. 542935, Response filed Jun. 30, 2008 to Examination Report dated Feb. 25, 2008", 32 pgs.
"New Zealand Application Serial No. 542935, Response filed Aug. 7, 2007 to Examination Report dated Jun. 14, 2006", 18 pgs.
"New Zealand Application Serial No. 542935, Voluntary Amendments filed Sep. 12, 2007", 10 pgs.
"New Zealand Application Serial No. 543446, Examination Report dated Feb. 29, 2008", 2 pgs.
"New Zealand Application Serial No. 543446, Examination Report dated May 12, 2008", 2 pgs.
"New Zealand Application Serial No. 543446, Response dated Mar. 20, 2008 to Examination Report dated Feb. 29, 2008", 2 pgs.
"Nonstructural protein 1 [influenza B virus (B/Hong Kong/330/2001)]", GenBank AAT69443.1, (2006), 1 pg.
"Norwegan Application Serial No. 20056074, Office Action dated Jan. 17, 2017", (English Translation), 5 pgs.
"Norwegan Application Serial No. 20056074, Response filed Apr. 18, 2017", (w/ English Translation of Claims, 27 pgs.
"Norwegan Application Serial No. 20056074, Response filed Jul. 25, 2017 to Office Action dated Apr. 25, 2017", (w/ English Translation of Amended Claims), 111 pgs.
"Norwegan Application Serial No. 20056074, Office Action dated Apr. 25, 2017", (Translation), 3 pgs.
"Polymerase acidic [influenza A virus (A/swine/Shizuoka/120/97(H3N2))]", GenBank AAO15329.1,(2003), 1 pg.
"Polymerase PA [Influenza B virus (B/Hong Kong/330/2001)]", GenBank ABL7718 6 .1, (2006), 1 pg.
"Polymerase PB1 [Influenza B virus (B/Hong Kong/330/2001)]", GenBank ABL77187, (2006), 1 pg.
"Polymerase PB2 [Influenza B virus (B/Hong Kong/330/2001)] GenBank ABL77188.1", (2006), 1 pg.
"RecName: Full=Polymerase acidic protein {ECG: 0000256|RuleBase;RU361280, ECO: 0000256|SAAS: SAAS00262764}", XP002744257, retrieved from EBI accession No. UNIPR0T:A3R6C9 Database accession No. A3R6C9 the whole document, (Apr. 3, 2007), 1 pgs.
"RecName: Full=Polymerase acidic protein {ECO:0000256|RuleBase;RU361280, ECO: 0000256|SAAS: SAAS00262764}", XP002744258, retrieved from EBI accession No. UNIPROT:U3S198 Database accession No. U3S198 the whole document, (Dec. 11, 2013), 1 pg.
"Russian Federation Application No. 2005136233, Office Action dated Dec. 25, 2007", 2 pgs.
"Russian Federation Application No. 2005136233, Response filed May 29, 2008 to Office Action dated Dec. 25, 2007", (w/ Partial English Translation), 7 pgs.
"Russian Federation Application Serial No. 2005136233, First Office Action dated Feb. 27, 2007", (w/ English Translation), 5 pgs.
"Russian Federation Application Serial No. 2005136233, Response filed Jun. 14, 2007 to First Office Action dated Feb. 27, 2007", (English Translation of Claims), 6 pgs.
"Russian Federation Application Serial No. 2005136233, Response filed Nov. 20, 2007 to Office Action", (w/ English Translation of Amended Claims), 18 pgs.
"Singaporean Application Serial No. 200506858-0, Examination Report dated Feb. 9, 2007", 4 pgs.
"Singaporean Application Serial No. 200506858-0, Response filed Dec. 22, 2006 to Written Opinion dated Jul. 26, 2006", 18 pgs.
"Singaporean Application Serial No. 200506858-0, Written Opinion dated Jul. 26, 2006", 8 pgs.
"Singaporean Application Serial No. 200507468-7, Examination Report dated Mar. 19, 2008", 5 pgs.
"Singaporean Application Serial No. 200507468-7, Invitation to Respond to Written Opinion dated Jun. 12, 2007", 6 pgs.
"Singaporean Application Serial No. 200507468-7, Response filed Nov. 7, 2007 to Invitation to Respond to Written Opinion dated Jun. 12, 2007", 9 pgs.
"The Influenza Virus: Structure and Replication", Rapid Reference to Influenza. Elsevier Ltd, [Online], Retrieved from the Internet: http://www. rapidreferenceinfluenza.com/chapter/B978-0-7234-3433-7.50009-8/aim/influenza-virus-structure, (2006), 6 pgs.
"The Integral Membrane Proteins of Influenza A, B, and C Viruses", The Influenza Sequence Database, http://www.flu.lanl.gov/review/fluc.review2.html, (Observed Feb. 26, 2003), 1 pg.
"Ukrainese Application Serial No. 200512619, Response filed Jan. 21, 2010 to Office Action dated Jun. 17, 2009", W/ English Claims, 14 pgs.
"Ukrainian Application Serial No. 200512619, Office Action dated Feb. 27, 2009", (w/ English Translation), 21 pgs.
"Ukrainian Application Serial No. 200512619, Office Action dated Jun. 17, 2009", (w/ English Translation), 4 pgs.
"Ukrainian Application Serial No. 200512619, Response filed Apr. 8, 2009 to Office Action dated Feb. 27, 2009", (w/ English Translation of Claims), 9 pgs.
Air, Gillian M., et al., "Antigenic, Sequence, and Crystal Variation in Influenza B Neuraminidase", Virology, 177(2), (1990), 578-587.
Author Unknown, "New Approaches to Influenza Vaccine", Medscape—Infections in Medicine, http://www.medscape.com/viewarticle/417404_3, (Observed Feb. 26, 2003), 4 pgs.
Avetisyan, G, et al., "Cell-mediated immune responses to influenza vaccination in healthy volunteers and allogeneic stem cell transplant recipients", Bone Marrow Transplant, (2005), 411-415.

(56) References Cited

OTHER PUBLICATIONS

Avilov, Sergiy V., et al., "Influenza A virus progeny vRNP trafficking in live infected cells studied with the virus-encoded fluorescently tagged PB2 protein", Vaccine, 30, (2012), 7411-7417.
Avilov, Sergiy V., et al., "Replication-Competent Influenza A Virus That Encodes a Split-Green Fluorescent Protein-Tagged PB2 Polymerase Subunit Allows", Journal of Virology, 86, (2012), 1433-1448.
Baez, M., et al., "Complete nucleotide sequence of the influenza A/PR/8/34 virus NS gene and comparison with the NS genes of the A/Udorn/72 and A/FPV/Rostock/34 strains", Nucleic Acids Research, 23(8), (1980), 5845-5858.
Bancroft, C. T, et al., "Evidence for segment-nonspecific packaging of the influenza a virus genome", J Virol., 76(14), (Jul. 2002), 7133-9.
Banerjee, A. K., et al., "Gene Expression of Vesicular Stomatitis Virus Genome RNA.", Virology, 188(2), (1992), 417-428.
Baron, M. D., et al., "Rescue of Rinderpest Virus From Cloned cDNA", Journal of Virology, 71(2), (1997), 1265-1271.
Basler, C. F, et al., "Mutation of Neuraminidase Cysteine Residues Yields Temprature-Sensitive Influenza Viruses", Journal of Virology, 73(10), (Jun. 30, 1999), 8095-8103.
Beare, A. S., "Trials in Man With Live Recombinants Made From A/PR/8/34 (H0 N1) and Wild H3 N2 Influenza Viruses", The Lancet, 2(7938), (1975), 729-732.
Betakova, T., et al., "The NB protein is an integral component of the membrane of influenza B virus.", J Gen Virol., 77 ( Pt 11), (Nov. 1996), 2689-94.
Bourmakina, S. V, et al., "Reverse genetics studies on the Filamentous morphology of influenza A Virus", Journal of General Virology (2003) 84,, (2003), 517-527.
Bowie, J. U., et al., "Deciphering the Message in Protein Sequences: Tolerance to Amino Acid Substitutions", Science, 247(4948), (1990), 1306-1310.
Boyer, J. C., et al., "Infectious transcripts and cDNA clones of RNA viruses", Virology, 198(2), (Feb. 1994), 415-426.
Brassard, D.L., et al., "Influenza B virus NB glycoprotein is a component of the virion", Virol., 220(2), No Document, (1996), 350-360.
Bridgen, A., "Rescue of a Segmented Negative-Strand RNA Virus Entirely From Cloned Complementary DNAs", Proc. Natl. Acad. Sci. USA, 93, (1996), 15400-15404.
Brooke, C B, "Biological activities of 'noninfectious' influenza A virus particles", Future Virol 9(1), (Jan. 2014), 41-51.
Brown, E. G., et al., "Genetic analysis of mouse-adapted influenza A virus identifies roles for the NA, PB1, and PB2 genes in virulence", Virus Research, 61(1), (May 1999), 63-76.
Buchholz, U. J., et al., "Generation of Bovine Respiratory Syncytial Virus (BRSV) From cDNA: BRSV NS2 is Not Essentiial for Virus Replication in Tissue Culture, and the Human RSV Leader Region Acts as a Functional BRSV Genome Promoter", Journal of Virology, 73(1), (1999), 251-259.
Bukreyev, A., et al., "Recovery of infectious respiratory syncytial virus expressing an additional, foreign gene", Journal of Virology, 70(10), (Oct. 1996), 6634-6641.
Cao, S., et al., "Characterization of the Nucleocytoplasmic Shuttle of the Matrix Protein of Influenza B Virus", Journal of Virology., 88(13), (Jul. 2014), 7464-7473.
Castrucci, Maria R., et al., "Reverse genetics system for generation of an influenza A virus mutant containing a deletion of the carboxyl-terminal residue of M2 protein.", J Virol., 69(5), (May 1995), 2725-8.
Chan, Winnie, et al., "The cold adapted and temperature sensitive influenza A/Ann Arbor/6/60 virus, the master donor virus for live attenuated influenza vaccines, has multiple defects in replication at the restrictive temperature", Virology, 380(2), (2008), 304-311.
Chen, H, et al., "Generation and evaluation of a high-growth reassortant H9N2 influenza A virus as a pandemic vaccine candidate", Vaccine, 21(17-18), (May 16, 2003), 1974-9.
Chen, Z., et al., "Influenza A Virus NS1 Protein Targets Poly(A)-Binding Protein II of the Cellular 3'-End Processing Machinery", The EMBO Journal, 18(8), (1999), 2273-2283.
Chevalie, Christophe, et al., "PB1-F2 Influenza A Virus Protein Adopts a B-Sheet Conformation and Forms Amyloid Fibers in Membrane Environments", The of Biological Chemistry, 285(17), (2010), 13233-13243.
Clarke, D. K., et al., "Rescue of Mumps Virus From cDNA", Journal of Virology, 74(10), (2000), 4831-4838.
Collins, P. L., et al., "Chapter 41—Parainfluenza Viruses", In: Fields Virology, edited by Fields, B. N., et al. (3rd Edition, 1996, Lippincott—Raven Publishers, Philadelphia, PA, 1205-1241.
Collins, P. L., et al., "Production of Infectious Human Respiratory Syncytial Virus From Cloned cDNA Confirms an Essential Role for the Transcription Elongation Factor From the 5' Proximal Open Reading Frame of the M2 mRNA in Gene Expression and Provides a Capability for Vaccine D", Proc. Natl. Acad. Sci. USA, 92, (1995), 11563-11567.
Collins, P. L., "Rescue of Synthetic Analogs of Respiratory Syncytial Virus Genomic RNA and Effect of Truncations and Mutations on the Expression of a Foreign Reporter Gene", Proc. Natl. Acad. Sci. USA, 88, (1991), 9663-9667.
Conzelmann, K.-K., "Genetic Engineering of Animal RNA Viruses", Trends in Microbiology, 4(10), (1996), 386-393.
Conzelmann, K.-K., "Genetic manipulation of non-segmented negative-strand RNA viruses", Journal of General Virology, 77(Pt. 3), (Mar. 1996), 381-389.
Conzelmann, K.-K., "Nonsegmented Negative-Strand RNA Viruses: Genetics and Manipulation of Viral Genomes", Annu. Rev. Genet., 32, (1998), 123-162.
Conzelmann, K.-K., "Rescue of Synthetic Genomic RNA Analogs of Rabies Virus by Plasmid-Encoded Proteins", Journal of Virology, 68(2), (1994), 713-719.
De, B. P., et al., "Requirements and Functions of Vesicular Stomatitis Virus L and NS Proteins in the Transcription Process in Vitro", Biochemical and Biophysical Research Communications, 126(1), (1985), 40-49.
De, B. P., et al., "Rescue of synthetic analogs of genome RNA of human parainfluenza virus type 3", Virology, 196(1), (Sep. 1993), 344-348.
De, B. P., et al., "Reverse Genetics of Negative Strand RNA Viruses", Indian Journal of Biochemistry & Biophysics, 31, (1994), 367-375.
De Filette, Marina, et al., "An influenza A vaccine based on tetrameric ectodomain of matrix protein 2", J Biol Chem. 2008 ; 283 (17):, (Feb. 5, 2008), 11382-7.
De La Luna, S., et al., "Influenza virus naked RNA can be expressed upon transfection into cells co-expressing the three subunits of the polymerase and the nucleoprotein from simian virus 40 recombinant viruses", Journal of General Virology, 74(pt. 3), (Mar. 1993), 535-539.
De La Luna, S., et al., "Influenza Virus NS1 Protein Enhances the Rate of Translation Initiation of Viral mRNAs", Journal of Virology, 69(4), (1995), 2427-2435.
Desheva, J. A, et al., "Characterization of an influenza A H5N2 reassortant as a candidate for live-attenuated and inactivated vaccines against highly pathogenic H5N1 viruses with pandemic potential", Vaccine, (2006), 6859-6866.
Dimmock, Nigel J, et al., "In vivo antiviral activity: defective interfering virus protects better against virulent Influenza A virus than avirulent virus", Journal of General Virology 87, (Jan. 8, 2006), 1259-1265.
Dimock, K., et al., "Rescue of Synthetic Analogs of Genomic RNA and Replicative-Intermediate RNA of Human Parainfluenza Virus Type 3", Journal of Virology, 67(5), (1993), 2772-2778.
Dos Santos Afonso, Emmanuel, et al., "The generation of recombinant influenza A viruses expressing a PB2 fusion protein requires the conservation of a packaging signal overlapping the coding and noncoding regions at the 5V end of the PB2 segment", Virology, 341,(2005), 34-46.

(56) References Cited

OTHER PUBLICATIONS

Dreher, T. W., et al., "Mutational Analysis of the Sequence and Structural Requirements in Brome Mosaic Virus RNA for Minus Strand Promoter Activity", Journal of Molecular Biology, 201(1), (1988), 31-40.
Duff, K. C., et al., "The secondary structure of influenza A M2 transmembrane domain", FEBS Letters, 311 (3), (Oct. 1992), pp. 256-258.
Duff, K. C., et al., "The Transmembrane Domain of Influenza A M2 Protein Forms Amantadine-Sensitive Proton Channels in Planar Lipid Bilayers", Vilology, 190(1), (Sep. 1992), pp. 485-489.
Dunham, Eleca J., et al., "Different Evolutionary Trajectories of European Avian-Like and Classical Swine H1N1 Influenza A Viruses", Journal of Virology, 83(11), (Jun. 2009), 5485-5494.
Dunn, E. F., et al., "Transcription of a recombinant bunyavirus RNA template by transiently expressed bunyavirus proteins", Virology, 211(1), (1995), 133-143.
Durbin, A. P., et al., "Recovery of infectious human parainfluenza virus type 3 from cDNA", Virology, 235(2), (Sep. 1, 1997), 323-332.
Elhefnawi, M, et al., "Identification of novel conserved functional motifs across most Influenza A viral strains", Virol J. Jan. 27, 2011;8:44. doi: 10.1186/1743-422X-8-44, (2011), 2 pgs.
Elliott, R. M., et al., "Rescue of Infectious Bunyavirus Entirely From Cloned cDNA", 10th International Conference on Negative Strand Virus, (Abstract No. 96), (1997), 1 pg.
Elliott, R. M., et al., "Some Highlights of Virus Research in 1990", Journal of General Virology, 72(Part 8), (1991), 1761-1779.
Emerson, S. U., et al., "Both NS and L Proteins Are Required for In Vitro RNA Synthesis by Vesicular Stomatitis Virus", Journal of Virology, 15(6), (1975), 1348-1356.
Enami, M., "An Influenza Virus Containing Nine Different RNA Segments", Virology, 185(1), (1991), 291-298.
Enami, M., et al., "High-Efficiency Formation of Influenza Virus Transfectants", Journal of Virology, 65(5), (1991), 2711-2713.
Enami, M., et al., "Introduction of Site-Specific Mutations Into the Genome of Influenza Virus", Proc. Natl. Acad. Sci. USA, 87, (1990), 3802-3805.
Fahey, J. L., "Status of Immune-Based Therapies in HIV Infection and Aids", Clinincal and Experimental Immunology, 88(1), (1992), 1-5.
Fan, J, et al., "Preclinical study of influenza virus A M2 peptide conjugate vaccines in mice, ferrets, and rhesus monkeys", Vaccine, 22, (2004), 2993-3003.
Fischer, W. B, et al., "Viral ion channels: structure and function.", Biochim Biophys Acta., 1561(1), (Mar. 19, 2002), 27-45.
Fleming, D. M, et al., "Comparison of the efficacy and safety of live attenuated cold-adapted influenza vaccine, trivalent, with trivalent inactivated influenza virus vaccine in children and adolescents with asthma", Pediatr Infect Dis J., 25(10), (2006), 860-869.
Fodor, E., et al., "Rescue of Influenza A Virus from Recombinant DNA", Journal of Virology, 73(11), XP002151487; ISSN:0022-538X, (Nov. 1999), 9679-9682.
Forbes, Nicole E, et al., "Multifunctional Adaptive NS1 Mutations Are Selected upon Human Influenza Virus Evolution in the Mouse", Pios One, vol. 7, No. 2, (Feb. 21, 2012).
Fortes, P., et al., "Influenza Virus NS1 Protein Inhibits Pre-mRNA Splicing and Blocks mRNA Nucleocytoplasmic Transport", The EMBO Journal, 13(3), (1994), 704-712.
Fujii, Ken, et al., "Importance of both the Coding and the Segment-Specific Noncoding Regions of the Influenza A Virus NS Segment for Its Efficient Incorporation into Virions", Journal of Virology, 79(6), (Mar. 2005), 3766-3774.
Gao, Qinshan, et al., "A Nine-Segment Influenza A Virus Carrying Subtype H1 and H3 Hemagglutinins†", Journal of Virology, 84(16), (Aug. 2010), 8062-8071.
Gao, Qinshan, et al., "The Influenza A Virus PB2, PA, NP, and M Segments Play a Pivotal Role during Genome Packaging", Journal of Virology, 86(13), Chou, (Jul. 2011), 043-7051.
Garcia-Sastre, A., et al., "Genetic Manipulation of Negative-Strand RNA Virus Genomes", Annu. Rev. Microbiol., 47, (1993), 765-790.
Garcin, D., et al., "A Highly Recombinogenic System for the Recovery of Infectious Sendai Paramyxovirus From cDNA: Generation of a Novel Copy-Back Nondefective Interfering Virus", The EMBO Journal, 14(24), (1995), 6087-6094.
Giddings, A M, et al., "The matrix protein of HIV-1 is not sufficient for assembly and release of virus-like particles", Virology, 248(1), (1998), 108-116.
Gorman, O T, "Evolution of influenza A virus PB2 genes: implications for evolution of the ribonucleoprotein complex and origin of human influenza A virus", Department of Virology and Molecular Biology, St. Jude Children's Research Hospital, Memphis Tennessee 38101-0318, J. Virol. Oct. 1990; 64(10):4893-902, (1990), 2 pgs.
Gotea, V, et al., "The functional relevance of somatic synonymous mutations in melanoma and other cancers", Pigment Cell & Melanoma Research, vol. 28, Issue 6, (Nov. 1, 2015), 673-686.
Goto, H., "Mutations Affecting the Sensitivity of the Influenza Virus Neuraminidase to 4-Guanidino-2, 4-dideoxy 2, 3-dehydro-N-acetylneuraminic Acid", Virology, 238, (1997), 265-272.
Grambas, S., et al., "Influence of amantadine resistance mutations on the pH regulatory function of the M2 protein of influenza A viruses", Virology, 191(2), (Dec. 1992), 541-549.
Grosfeld, H., et al., "RNA Replication by Respiratory Syncytial Virus (RSV) Is Directed by the N, P, and L Proteins; Transcription Also Occurs Under These Conditions but Requires RSV Superinfection for Efficient Synthesis of Full-Length mRNA", Journal of Virology, 69(9), (1995), 5677-5686.
Hai, Rong, et al., "Influenza B Virus NS1-Truncated Mutants: Live-Attenuated Vaccine Approach", Journal of Virology, 82(21), (2008), 10580-10590.
Harty, Ronald N, "A Proline-Rich Motif within the Matrix Protein of Vesicular Stomatitis Virus and Rabies Virus Interacts with WW Domains of Cellular Proteins: Implications for Viral Budding", Journal of Virology, 73 (4), (1999), 2921-2929.
Hatada, E., et al., "Binding of Influenza A Virus NS1 Protein to dsRNA in vitro", Journal of General Virology, 73, (1992), 3325-3329.
Hatta, M., et al., "The NB protein of influenza B virus is not necessary for virus replication in vitro", Journal of Virology, 77(10), (May 2003), 6050-6054.
Hay, A. J., et al., "The role of the M2 protein in influenza A virus infection", Proceedings of the International Conference on Options for the Control of Influenza, Courchevel, (1992), 281-288.
He, B., et al., "Recovery of infectious SV5 from cloned DNA and expression of a foreign gene", Virology, 237(2), (1997), 249-260.
Helenius, A., "Unpacking the Incoming Influenza Virus", Cell, 69, (May 1992), pp. 577-578.
Hevey, Michael, et al., "Marburg virus vaccines based upon alphavirus replicons protect guinea pigs and nonhuman primates", Virology, 251(1), (Nov. 10, 1998), 28-37.
Hickman, Danielle, et al., "An avian live attenuated master backbone for potential use in epidemic and pandemic influenza vaccines", Journal of General Virology, 89(Part 11), (2008), 2682-2690.
Hiromoto, Y., et al., "Phylogenetic Analysis of the Three Polymerase Genes (PB1, PB2 and PA) of Influenza B Virus", Journal of General Virology, 81, (Apr. 2000), 929-937.
Hoffman, Lucas R, et al., "Structure-Based Identification of an Inducer of the Low-pH Conformational Change in the Influenza Virus Hemagglutinin: Irreversible Inhibition of Infectivity", Journal of Virology, vol. 71, No. 11, (Nov. 1997), 8808-8820.
Hoffman, M. A., et al., "An Infectious Clone of Human Parainfluenza Virus Type 3", Journal of Virology, 71(6), (1997), 4272-4277.
Hoffmann, E., et al., "A DNA transfection system for generation of influenza A virus from eight plasmids", Proc Natl Acad Sci U S A., 97(11), (May 23, 2000), 6108-13.
Hoffmann, E., et al., "Ambisense Approach for the Generation of Influenza A Virus: vRNA and mRNA Synthesis from One Template", Virology, 267, (2000), 310-317.
Hoffmann, E., et al., "Eight-plasmid System for Rapid Generation of Influenza Virus Vaccines", Vaccine, Butterworth Scientific Guildford, 20(25-56), (Aug. 19, 2002), 3165-3170.

(56) References Cited

OTHER PUBLICATIONS

Hoffmann, E., et al., "Rescue of Influenza B Virus from Eight Plasmids", Proceedings of the National Academy of Sciences of USA, National Academy of Science, 99(17), (Aug. 20, 2002), 11411-11416.
Holmes, E. C, et al., "Whole-Genome Analysis of Human Influenza A Virus Reveals Multiple Persistent Lineages and Reassortment Among Recent H3N2 Viruses", PLoS Biology, 3(9), (2005), 1579-1589.
Holsinger, L. J., et al., "Influenza A Virus M2 Ion Channel Protein: a Structure-Function Analysis", Journal of Virology, 68 (3), (1994), pp. 1551-1563.
Honda, Ayae, et al., "Differential Roles of Viral RNA and cRNA in Functional Modulation of the Influenza Virus RNA Polymerase", The Journal of Biological Chemistry, 276(33), (2001), 31179-31185.
Horimoto, "Designing Vaccines for Pandemic Influenza", Current Topics Microbiol Immunol 333, (2009), 165-176.
Horimoto, T., et al., "Enhanced growth of seed viruses for H5N1 influenza vaccines", Virology, 366(1), (Sep. 15, 2007), 23-27.
Horimoto, T., et al., "Generation of Influenza A Viruses with Chimeric (Type A/B) Hemagglutinins", Journal of Virology, 77(14), (2003), 8031-8038.
Horimoto, T., et al., "The Development and Characterization of H5 Influenza Virus Vaccines Derived from a 2003 Human Isolate", Vaccine, 24(17), (2006), 3669-3676.
Huang, T.-S., et al., "Determination of Influenza Virus Proteins Required for Genome Replication", Journal of Virology, 64(11), (1990), 5669-5673.
Hunt, R., "Virology—Chapter Eight—Vaccines: Past Successes and Future Prospects", Microbiology and Immunology On-Line, http://www.med.sc.edu:85/lecture/vaccines.htm, (Observed Feb. 26, 2003), 15 pgs.
Isakova-Sivak, Irina, et al., "Characterization of Reverse Genetics-Derived Cold-Adapted Master Donor Virus A/Leningrad/134/17/57 (H2N2) and Reassortants with H5N1 Surface Genes in a Mouse Model", Clinical and Vaccine Immunology, 21(5), (May 2014), 722-731.
Ives, J. A., et al., "The H274Y mutation in the influenza A/H1N1 neuraminidase active site following oseltamivir phosphate treatment leave virus severely compromised both in vitro and in vivo.", Antiviral Research, 55(2), (2002), 307-317.
Iwatsuki-Horimoto, K., et al., "The cytoplasmic tail of the influenza A virus M2 protein plays a role in viral assembly.", J Virol., 80(11), (Jun. 2006), 5233-40.
Jackson, D., et al., "A reverse genetics approach for recovery of recombinant influenza B viruses entirely from cDNA.", J Virol., 76(22), (Nov. 2002), 11744-7.
Jang, S.-W., et al., "Deoxygedunin, a Natural Product with Potent Neurotrophic Activity in Mice", PLoS ONE 5(7): e11528, (2010), 1-15.
Jasenosky, Luke D, et al., "Ebola Virus VP40-Induced Particle Formation and Association with the Lipid Bilayer", Journal of Virology, 75 (110, (Jun. 2001), 5205-5214.
Kaplan, G., et al., "In vitro Synthesis of Infectious Poliovirus RNA", Proc. Natl. Acad. Sci. USA, 82, (1985), 8824-8428.
Katinger, D., et al., "Attenuated Influenza Viruses as a Vector for Mucosal Immunization Against HIV-1", Vaccines, 97, Cold Spring Harbor, (1997), 315-319.
Kato, A., et al., "Initiation of Sendai Virus Multiplication From Transfected cDNA or RNA With Negative or Positive Sense", Genes to Cells, 1, (1996), 569-579.
Kawaoka, Y, et al., "Sequence requirements for cleavage activation of influenza virus hemagglutinin expressed in mammalian cells", Proc Natl Acad Sci., 85(2), (1988), 324-328.
Kawaoka, Y., "Mutant Cells With Altered Sialic Acid", U.S. Appl. No. 11/644,179, filed Dec. 22, 2006, 51 pgs.
Kilbourne, E. D, et al., "Related studies of a recombinant influenza-virus vaccine. I. Derivation and characterization of virus and vaccine", J Infect Dis., 124(5), (Nov. 1971), 449-62.
Kim, H., et al., "Cold adaptation generates mutations associated with the growth of influenza B vaccine viruses", Vaccine, 33(43), (2015), 5786-5793.
Kimura, N., et al., "An In Vivo Study of the Replication Origin in the Influenza Virus Complementary RNA", The Journal of Biochemistry, 113(1), (1993), 88-92.
Kimura, N., et al., "Transcription of a Recombinant Influenza Virus RNA in Cells That Can Express the Influenza Virus RNA Polymerase and Nucleoprotein Genes", Journal of General Virology, 73, (1992), 1321-1328.
Kiseleva, I., et al., "Role of individual genes of the A-Leningrad/134/17/57 (H2N2) cold-adapted donor strain in manifestation of the temperature-sensitive phenotype of reassortant influenza A viruses", International Congress Series, vol. 1263, (2004), 547-550.
Kiseleva, Irina V, et al., "PB2 and PA genes control the expression of the temperature-sensitive phenotype of cold-adapted B/USSR/60/69 influenza master donor virus", Journal of General Virology, 91(4), (2010), 931-937.
Kistner, Otfried, et al., "Cell culture (Vero) derived whole virus (H5N1) vaccine based on wild-type virus strain induces cross-protective immune responses", Vaccine, 25(32), (2007), 6028-6036.
Kittel, Christian, et al., "Generation of an Influenza A Virus Vector Expressing Biologically Active Human lnterleukin-2 from the NS Gene Segment", Journal of Virology, 79(16), (Aug. 2005), 10672-10677.
Kobayashi, M., et al., "Reconstitution of Influenza Virus RNA Polymerase From Three Subunits Expressed Using Recombinant Baculovirus System", Virus Research, 22, (1992), 235-245.
Kochendoerfer, G. G, et al., "Total Chemical Synthesis of the Integral Membrane Protein Influenza A Virus M2: Role of its C-Terminal Domain in Tetramer Assembly", Biochemistry 38, (1999), 11905-11913.
Konarska, M. M., et al., "Structure of RNAs Replicated by the DNA-Dependent T7 Rna Polymerase", Cell, 63(2), (1990), 609-618.
Kovacova, A., et al., "Sequence similarities and evolutionary relationships of influenza virus A hemagglutinins.", Virus Genes, 24(1), (2002), 57-63.
Kovacova, Andrea, et al., "Sequence Similarities and Evolutionary Relationships of Influenza Vrus A Hemagglutinins", Virus Genes, 24(1), (2002), 57-63.
Krystal, M., et al., "Expression of the Three Influenza Virus Polymerase Proteins in a Single Cell Allows Growth Complementation of Viral Mutants", Proc. Natl. Acad. Sci. USA, 83, (1986), 2709-2713.
Krystal, M., "Influenza B/Lee/40, hemagglutinin (seg 4), complete segment.", Database Em_ VI E.B.I. Hinxton U.K., (Apr. 25, 1990).
Kunkel, T. A., "Rapid and Efficient Site-Specific Mutagenesis Without Phenotypic Selection", Proc. Natl. Acad. Sci. USA, 82, (1985), 488-492.
Lamb, Robert A., et al., "Chapter 20—Paramyxoviridae: The Viruses and Their Replication", In: Fundamental Virology, Fields, B. N., et al., editors, Lippincott-Raven (2nd Edition), (1996), 577-647.
Lawson, N. D., "Recombinant Vesicular Stomatitis Viruses From DNA", Proc. Natl. Acad. Sci. USA, 92(10), (1995), 4477-4481.
Lazarovits, Janette, et al., "Endocytosis of Chimeric Influenza Virus Hemaggulutinin Proteins That Lack a Cytoplasmic Recognition Feature for Coated Pits", The Journal of Cell Biology, vol. 134, No. 2, (1996), 339-348.
Lee, C. W, et al., "Generation of reassortant influenza vaccines by reverse genetics that allows utilization of a DIVA (Differentiating Infected from Vaccinated Animals) strategy for the control of avian influenza", Vaccine, vol. 22, (2004), 3175-3181.
Lee, Dong-Hun, et al., "Progress and hurdles in development of influenza virus-like particle vaccines for veterinary use", Korean Vaccine Society, (2014), 133-139.
Lee, Jong-Soo, et al., "The Highly Conserved HA2 Protein of the Influenza A Virus Induces a Cross Protective Immune Response", Journal of Virological Methods, 194(1-2), (2013), 280-288.
Lee, M. S, et al., "Genetic and pathogenic characterization of H6NI avian influenza viruses isolated in Taiwan between 1972 and 2005", Avian Diseases, 50(4), (Dec. 2006), 561-571.

(56) References Cited

OTHER PUBLICATIONS

Levis, R., et al., "Deletion Mapping of Sindbis Virus DI RNAs Derived From cDNAs Defines the Sequences Essential for Replication and Packaging", Cell, 44, (1986), 137-145.
Li, et al., "Genesis of a highly pathogenic and potentially pandemic H5N1 influenza virus in eastern Asia", (2004), 209-213 pgs.
Li, K. S, et al., "Genesis of a highly pathogenic and potentially pandemic H5NI influenza virus in eastern Asia", Nature, 430(6996), (Jul. 8, 2004), 209-213.
Li, Y, et al., "Viral liposomes released from insect cells infected with recombinant baculovirus expressing the matrix protein of vesicular stomatitis virus", Journal of Virology, 67 (7), (1993), 4415-4420.
Lin, Y P, et al., "Adaptation of egg-grown and transfectant influenza viruses for growth in mammalian cells: selection of hemagglutinin mutants with elevated pH of membrane fusion", Virology, vol. 233, No. 2, (1997), 402-410.
Liu, Bo, et al., "[Comparison of three methods in construction fusion gene of influenza A virus Nucleoprotein].", (English Abstract), Zhonghua Shi Yan He Lin Chuang Bing Du Xue Za Zhi, 26(1), 70-74, (Feb. 2012), 1 pg.
Lu, Xiuhua, et al., "Cross-protective immunity in mice induced by live-attenuated or inactivated vaccines against highly pathogenic influenza A (H5N1) viruses", Vaccine, 24(44-46), (2006), 6588-6593.
Lugovtsev, V. Y., et al., "Genetic Composition and Mutational Pattern of Influenza B Viruses Adapted to Replication in Embryonated Eggs", GenBank: AAT69446.1, (2005), 1 pg.
Luo, M., "Inhibitors of Influenza Virus Neuraminidase", Abstract No. WO296, from a paper presented at the Annual Meeting of the American Crystallographic Association, http://www.hwi.buffalo.edu/ACA/ACA98/abstracts/text/WO296.html, (Observed Feb. 27, 2003), 1 pg.
Luytjes, W., "Amplification, Expression, and Packaging of a Foreign Gene by Influenza Virus", Cell, 59(6), (1989), 1107-1113.
Ma, Y.-J., et al., "Cellular micro RNA let-7c inhibits M1 protein expression of the H1N1 influenza A virus in infected human lung epithelial cells", J. Cell. Mol. Med., 16(10), (2012), 2539-2546.
Manicassamy, Balaji, et al., "Analysis of in vivo dynamics of influenza virus infection in mice using a GFP reporter virus", Proc Natl Acad Sci. USA, 107(25), (2010), 11531-11536.
Manz, Benjamin, et al., "Disruption of the Viral Polymerase Complex Assembly as a Novel Approach to Attenuate Influenza A Virus", The Journal of Biological Chemistry, 286(10), (2011), 8414-8424.
Mark, A, et al., "Effect of Mutations and Deletions in a Bicistronic mRNA on the Synthesis of Influenza B Virus NB and NA Glycoproteins", Journal of Virology, vol. 77, No. 10, (May 2003), 6050-6054.
Matsuoka, et al., "Neuraminidase Stalk Length and Additional Glycosylation of the Hemagglutinin Influence the Virulence of Influenza H5N1 Viruses for Mice", Journal of Virology, vol. 83, No. 9, (2009), pp. 4704-4708.
Matsuzaki, Y., et al., "Epitope Mapping of the Hemagglutinin Molecule of A/(H1N1)pdm09 Influenza Virus by Using Monoclonal Antibody Escape Mutants", Journal of Virology, 88(21), (2014), 12364-12373.
McCown, M F, et al., "The influenza A virus M2 cytoplasmic tail is required for infectious virus production and efficient genome packaging.", J Virol., 79(6), (Mar. 2005), 3595-605.
McCown, M. F, et al., "Distinct domains of the influenza a virus M2 protein cytoplasmic tail mediate binding to the M1 protein and facilitate infectious virus production.", J Virol., 80(16), (Aug. 2006), 8178-89.
McKimm, J. L., et al., "Mutations in a Conserved Residue in the Influenza Virus Neuraminidase Active Site Decreases Sensitivity to Neu5Ac2en-Derived Inhibitors", Journal of Virology, 72(3), (1998), 2456-2462.
Mebatsion, Teshome, et al., "Budding of Rabies Virus Particles in the Absence of the Spike Glycoprotein", Cell, 84(6), (1996), 941-951.
Mebatsion, Teshome, et al., "Matrix Protein of Rabies Virus Is Responsible for the Assembly and Budding of Bullet-Shaped Particles and Interacts with the Transmembrane Spike Glycoprotein G", Journal of Virology, 73 (1), (Jan. 1999), 242/250.
Mena, I., "Rescue of a Synthetic Choramphenicol Acetyltransferase RNA into influenza Virus-Like Particles obtained from recombinant plasmids", Journal of Virology, 70(8), (1996), 5016-5024.
Mena, I., et al., "Synthesis of Biologically Active Influenza Virus Core Proteins Using a Vaccinia Virus-T7 RNA Polymerase Expression System", Journal of General Virology, 75, (1994), 2109-2114.
Mitnaul, et al., "The Cytoplasmic Tail of Influenza a Virus Neuraminidase (NA) Affects NA Incorporation into Virons, Viron Morphology, and Virulence in Mice but is not essential for Virus Replication", Journal of Virology, 70 (2), (1996), 873-879.
Monto, Arnold S, et al., "Comparative efficacy of inactivated and live attenuated influenza vaccines.", N Engl J Med., 361(13), (Sep. 24, 2009), 1260-7.
Moyer, S. A., et al., "Assembly and Transcription of Synthetic Vesicular Stomatitis Virus Nucleocapsids", Journal of Virology, 65(5), (1991), 2170-2178.
Murakami, "Enhanced Growth of Influenza Vaccine Seed Viruses in Vero Cells Mediated by Broadening the Optimal pH Range for Virus Membrane Fusion", J Virol 86(3), (2012), 1405-1410.
Murakami, Shin, et al., "Growth Determinants for H5N1 Influenza Vaccine Seed Viruses in MDCK Cells", Journal of Virology, vol. 82, No. 21, (Nov. 2008), 10502-10509.
Murphy, Brian R, et al., "Virulence of Avian Influenza A Viruses for Squirrel Monkeys", Infection and Immunity 37 (3), (Sep. 1982), 1119-1126.
Muster, T., et al., "An Influenza A Virus Containing Influenza B Virus 5' and 3' Noncoding Regions on the Neuraminidase Gene is Attenuated in Mice", Proc. Natl. Acad. Sci. USA, 88, (1991), 5177-5181.
Naito, S., et al., "Function and Structure of RNA Polymerase From Vesicular Stomatitis Virus", The Journal of Biological Chemistry, 251(14), (1976), 4307-4314.
Nara, P. L., et al., "Simple, Rapid, Quantitative, Syncytium-Forming Microassay for the Detection of Human Immunodeficiency Virus Neutralizing Antibody", Aids Research and Human Retroviruses, 3(3), (1987), 283-302.
Neirynck, S., "A universal influenza A vaccine based on the extracellular domain of the M2 protein", Nature Medicine, 5 (10), (Oct. 1999), pp. 1157-1163.
Nemeroff, M. E., et al., "Influenza Virus NS1 Protein Interacts With the Cellular 30 kDa Subunit ofCPSF and Inhibits 3' End Formation of Cellular Pre-mRNAs", Molecular Cell, 1(7), (1998), 991-1000.
Neumann, G., et al., "An Improved Reverse Genetics System for Influenza A Virus Generation and Its Implications for Vaccine Production", Proc. Natl. Acad. Sci. USA, 102(46), (2005), 16825-16829.
Neumann, G., et al., "Emergence and pandemic potential of swine-origin HIN1 influenza virus", Nature (LONDON), 459(7249), (Jun. 2009), 931-939.
Neumann, G., et al., "Generation of influenza A virus from cloned cDNAs—historical perspective and outlook for the new millenium.". Rev Med Virol., 12(1), XP002314285, (Jan.-Feb. 2002), 13-30.
Neumann, G., et al., "Generation of influenza A viruses entirely from cloned cDNAs", Proc. Natl. Acad. Sci. USA., 96(16), (1999), 9345-9350.
Neumann, G., et al., "Plasmid-driven formation of influenza virus-like particles", J Virol., 74(1), [Online] Retrieved From Internet: <http://www.ncbi.nlm.nih.gov/pmc/articles/PMC111569/>, (Jan. 2000), 547-551.
Neumann, G., et al., "Reverse Genetics of Influenza Viruses—Applications in Research and Vaccine Design", Monographs in Virology, 27, (2008), 118-133.
Neumann, G., et al., "RNA Polymerase I-Mediated Expression of Influenza Viral RNA Molecules", Virology, 202(1), (1994), 477-479.
Neumann, Gabriele, et al., "Reverse Genetics Demonstrates that Proteolytic Processing of the Ebola Virus Glycoprotein Is Not Essential for Replication in Cell Culture", Journal of Virology, 76 (1), (Jan. 2002), 406-410.

(56) References Cited

OTHER PUBLICATIONS

Noda, Takeshi, et al., "Three-dimensional analysis of ribonucleoprotein complexes in influenza A virus", Nature Communications, 3, (2012), 1-6.
Odagiri, T et al., "Nucleotide Sequence of the PA Gene of Influenza A/WSN/33 (H1N1)", Nucleic Acids Research, 18 (3), Department of Virology, (Jan. 9, 1990).
Orkin, S. H, et al., "Report and Recommendations of the Panel to Assess the NIH Investment in Research on Gene Therapy", http://www.nih.gov/news/panelrep.html, (Dec. 7, 1995), 37 pgs.
Ozaki, "Generation of High-Yielding Influenza A Viruses in African Green Monkey Kidney (Vero) Cells by Reverse Genetics", J Virol 78(4), (2004), 1851-1857.
Palese, P., et al., "47. Orthomyxoviridae: The Viruses and Their Replication", In: Fields Virology (5th Edition), (2007), 90 pgs.
Palese, P., "Negative-Strand RNA Viruses: Genetic Engineering and Applications", Proc. Natl. Acad. Sci. USA, 93(21), (1996), 11354-11358.
Park, Eun K., et al., "The M2 Ectodomain is important for its incorporation into influenza A virions", J. of Virology, vol. 72, No. 3, XP002196797, (Mar. 1998), 2449-2455.
Park, K. H., et al., "Rescue of a Foreign Gene by Sendai Virus", Proc. Natl. Acad. Sci. USA, 88, (1991), 5537-5541.
Pattnaik, A. K., et al., "Cells That Express All Five Proteins of Vesicular Stomatitis Virus From Cloned cDNAs Support Replication, Assembly, and Budding of Defective Interfering Particles", Proc. Natl. Acad. Sci. USA, 88(4), (1991), 1379-1383.
Peeters, B. P. H., et al., "Rescue of Newcastle Disease Virus From Cloned cDNA: Evidence That Cleavability of the Fusion Protein Is a Major Determinant for Virulence", Journal of Virology, 73(6), (1999), 5001-5009.
Pekosz, A., "Commentary—Reverse Genetics of Negative-Strand RNA Viruses: Closing the Circle", Proc. Natl. Acad. Sci. USA, 96, (1999), 8804-8806.
Pekosz, A., et al., "Influenza C virus CM2 integral membrane glycoprotein is produced from a polypeptide precursor by cleavage of an internal signal sequence", Proc. Natl. Acad. Sci., vol. 95, (Oct. 1998), 13233-13238.
Percy, N., et al., "Expression of a Foreign Protein by Influenza A Virus", Journal of Virology, 68(7), (1994), 4486-4492.
Perez, Jasmine T., et al., "Unit 15G.4—Insertion of a GFP Reporter Gene in Influenza Virus", Curr Protoc Microbiol., (2013), 20 pgs.
Piller, S C., et al., "Vpr protein of human immunodeficiency virus type 1 forms cation-selective channels in planar lipid bilayers", Proc. Natl/Acad. Sci. USA, 93, (1996), 111-115.
Ping, J, et al., "Development of high-yield influenza A virus vaccine viruses", Nature Communications, [online]. Retrieved from the Internet: <http://www.nature.eom/article-assets/npg/ncomms/2015/150902/ncomms9148/extref/ncomms9148-sl.pdf>, (2015), 50 pgs.
Ping, J., et al., "Development of high-yield influenza B virus vaccine viruses", Proc. Natl. Acad. Sci. USA, 113(51), (2016), E8296-E8305, and 25 pgs of Supplemental Material.
Pinto, L. H., et al., "Influenza Virus M2 Protein Has Ion Channel Activity", Cell, 69, (May 1992), 517-528.
Plant, E P, et al., "Mutations to A/PuertoRico/8/34 PB1 gene improves seasonal reassortant influenza A virus growth kinetics", Vaccine, 31 (1), (2012), 207-212.
Pleschka, S., et al., "A Plasmid-Based Reverse Genetics System for Influenza A Virus", Journal of Virology, 70(6), (1996), 4188-4192.
Qiu, Y., et al., "The Influenza Virus NS1 Protein Binds to a Specific Region in Human U6 snRNA and Inhibits U6-U2 and U6-U4 snRNA Interactions During Splicing", RNA, 1, (1995), 304-316.
Qiu, Y., et al., "The Influenza Virus NS1 Protein Is a Poly(A)-Binding Protein That Inhibits Nuclear Export of mRNAs Containing Poly(A)", Journal of Virology, 68(4), (1994), 2425-2432.
Racaniello, V. R., et al., "Cloned Poliovirus Complimentary DNA Is Infectious in Mammalian Cells", Science, 214, (1981).
Radecke, F., et al., "Rescue of Measles Viruses From Cloned DNA", The EMBO Journal, 14(23), (1995), 5773-5784.
Radecke, F., et al., "Reverse Genetics Meets the Nonsegmented Negative-Strand RNA Viruses", Reviews in Medical Virology, 7, (1997), 49-63.
Reed, M. L, et al., "Amino Acid Residues in the Fusion peptide Pocket Regulate the pH of Activation of the H5N1 Influenza Virus Hemagglutinin Protein", . J. Virol., 83(8), (2009), 3568-3580.
Roberts, A., et al., "Minireview—Recovery of Negative-Strand RNA Viruses From Plasmid DNAs: A Positive Approach Revitalizes a Negative Field", Virology, 247(1), (1998), 1-6.
Romanova, J., et al., "Live cold-adapted influenza A vaccine produced in Vero cell line", Virus Research, 103, (2004), 187-193.
Rose, J. K., "Positive Strands to the Rescue Again: A Segmented Negative-Strand RNA Virus Derived From Cloned cDNAs", Proc. Natl. Acad. Sci. USA, 94, (1996), 14998-15000.
Ruigrok, R W, et al., "Characterization of three highly purified influenza virus strains by electron microscopy", J Gen Virol 65 (Pt 4), (Apr. 1984), 799-802.
Ruigrok, R W, et al., "Structural Characterization and Membrane Binding Properties of the Matrix Protein VP40 of Ebola Virus", Journal of Molecular Biology, 300(1), (2000), 103-112.
Sansom, M. S., et al., "Influenza virus M2 Protein: a molecular modelling study of the ion channel", Protein Engineering, 6 (1), (1993), 65-74.
Schickli, J. H, et al., "Plasmid-only Rescue of Influenza A Virus Vaccine Candidates", Philosophical Transactions of the Royal Society of London. Series B, Biological Sciences, 356(1416), (2001), 1965-1973.
Schlesinger, S., "RNA Viruses as Vectors for the Expression of Heterologous Proteins", Molecular Biotechnology, 3(2), (1995), 155-165.
Schnell, M. J., "Infectious Rabies Viruses From Cloned cDNA", The EMBO Journal, 13(18), (1994), 4195-4203.
Schnell, Matthias J, et al., "Requirement for a non-specific glycoprotein cytoplasmic domain sequence to drive efficient budding of vesicular stomatitis virus", EMBO Journal, 17(5), (1998), 1289-1296.
Schotsaert, M, et al., "Universal M2 ectodomain-based influenza A vaccines: preclinical and clinical developments", Expert Rev Vaccines. Apr. 2009;8(4), 499-508.
Seong, B. L., et al., "A New Method for Reconstituting Influenza Polymerase and RNA in Vitro: A Study of the Promoter Elements for cRNA AND vRNA Synthesis in Vitro and Viral Rescue in Vivo", Virology, 186(1), (1992), 247-260.
Shinya, Kyoko, et al., "Characterization of a Neuraminidase-Deficient Influenza A Virus as a Potential Gene Delivery Vector and a Live Vaccine", Journal of Virology, 78(6), (2004), 3083-3088.
Sidhu, M. S., et al., "Rescue of Synthetic Measles Virus Minireplicons: Measles Genomic Termini Direct Efficient Expression and Propagation of a Reporter Gene", Virology, 208, (1995), 800-807.
Skehel, J. J., et al., "On the Mechanism of Inhibition of Influenza Virus Replication by Amantadine Hydrochloride", The Journal of General Virology, 38 (1), (1977), 97-110.
Smeenk, et al., "Mutations in the Hemagglutinin and Matrix Genes of a Virulent Influenza Virus Variant, A/FM/1/47-MA, Control Different Stages in Pathogenesis", Virus Research 44, (1996), 79-95.
Subbarao, E. K., et al., "Sequential Addition of Temperature-Sensitive Missense Mutations into the PB2 Gene of Influenza A Transfectant Viruses Can Effect an Increase in Temperature Sensitivity and Attenuation and Permits the Rational Design of a Genetically Engineered Live Influen", Journal of Virology, 69(10), (1995), 5969-5977.
Subbarao, K., et al., "Evaluation of a Genetically Modified Reassortant H5N1 Influenza A Virus Vaccine Candidate Generated by Plasmid-based Reverse Genetics", Virology, vol. 305(1), (Jan. 5, 2003), 192-200.
Sugrue, R. J., et al., "Specific structural alteration of the influenza haemagglutinin by amantadine", The EMBO Journal, 9 (11), (1990), pp. 3469-3476.
Sugrue, R. J., et al., "Structural Characteristics of the M2 Protein of Influenza A Viruses: Evidence That It Forms a Tetrameric Channel", Virology, 180, (1991), pp. 617-624.

(56) References Cited

OTHER PUBLICATIONS

Suguitan, A. L, et al., "Live, Attenuated Influenza A H5N1 Candidate Vaccines Provide Broad Cross-Protection in Mice and Ferrets", PLoS Med., 3(9), (2006), 1541-1555.
Sunstrom, N. A., et al., "Ion Channels formed by NB, an influenza B virus Protein", J. of Membrane Biology, vol. 150, XP002196654, (Dec. 1996), 127-132.
Sweet, T. M., et al., "Creation of amantadine resistant clones of influenza type A virus using a new transfection procedure.", J Virol Methods., 69(1-2), (Dec. 1997), 103-11.
Szewczyk, B., "Purification, Thioredoxin Renaturation, and Reconstituted Activity of the Three Subunits of the Influenza A Virus RNA Polymerase", Proc. Natl. Acad. Sci. USA, 85, (1988), 7907-7911.
Takeda, M., et al., "Influenza a virus M2 ion channel activity is essential for efficient replication in tissue culture.", J Virol., 76(3), (Feb. 2002), 1391-9.
Takeuchi, K., et al., "Influenza Virus M2 Protein Ion Channel Activity Stabilizes the Native Form of Fowl Plague Virus Hemagglutinin during Intracellular Transport", Journal of Virology, 68 (2), (Feb. 1994), pp. 911-919.
Tannock, G. A, et al., "Relative immunogenicity of the cold-adapted influenza virus A/Ann Arbor/6/60 (A/AA/6/60-ca), recombinants of A/AA/6/60-ca, and parental strains with similar surface antigens.", Infect Immun., 43(2), (Feb. 1984), 457-62.
Taylor, J., et al., "Newcastle Disease Virus Fusion Protein Expressed in a Fowlpox Virus Recombinant Confers Protection in Chickens", Journal of Virology, 64(4), (1990), 1441-1450.
Tobler, K, "Effect of cytoplasmic tail truncations on the activity of the M(2) ion channel of influenza A virus", J Virol., (1999), 9695-701.
Uraki, R., et al., "A Novel Bivalent Vaccine Based on a PB2-Knockout Influenza Virus Protects Mice from Pandemic H1N1 and Highly Pathogenic H5N1 Virus Challenges", Journal of Virology, 87(14), (2013), 7874-7881.
Verma, I. M, et al., "Gene Therapy—Promises, Problems and Prospects", Nature, 389, (1997), 239-242.
Voeten, J. T, et al., "Characterization of high-growth reassortant influenza A viruses generated in MDCK cells cultured in serum-free medium", Vaccine, vol. 17, (1999), 1942-1950.
Volchkov, Viktor E, et al., "Recovery of Infectious Ebola Virus from Complementary DNA: RNA Editing of the GP Gene and Viral Cytotoxicity", Science Magazine, 291, (Mar. 2001), 1965-1969.
Wagner, R., et al., "Interdependence of hemagglutinin glycosylation and neuraminidase as regulators of influenza virus growth: a study by reverse genetics", Journal of Virology, 74(14), (Jul. 2000), 6316-6323.
Wang, C., et al., "Ion Channel Activity of Influenza A Virus M2 Protein: Characterization of the Amantadine Block", Journal of Virology, 67 (9), (Sep. 1993), pp. 5585-5594.
Wang, Wenlig, et al., "Robust Immunity and Heterologous Protection against Influenza in Mice Elicited by a Novel Recombinant NP-M2e Fusion Protein Expressed in *E. coli*", PLoS ONE 7(12): e52488, (Dec. 2012), 1-13.
Ward, C. D., et al., "Direct Measurement of the Poliovirus RNA Polymerase Error Frequency In Vitro", Journal of Virology, 62(2), (1988), 558-562.
Wareing, M. D, et al., "Immunogenic and isotype-specific responses to Russian and US cold-adapted influenza a vaccine donor strains A/Leningrad/134/17/57, A/Leningrad/134/47/57, and A/Ann Arbor/6/60 (H2N2) in mice.", J Med Virol., 65(1), (Sep. 2001), 171-7.
Watanabe, et al., "Novel Approach to the Development of Effective H5N1 Influenza A Virus Vaccines: Use of M2 Cytoplasmic Tail Mutants", Journal of Virology, 82(5), (2008), 2486-2492.
Watanabe, S., et al., "Influenza A Virus Lacking M2 Protein as a Live Attenuated Vaccine", Journal of Virology, 83(11), (2009), 5947-5950.
Watanabe, T., et al., "Influenza A virus can undergo multiple cycles of replication without M2 ion channel activity", J Virol., 75(12), (Jun. 2001), 5656-62.
Watanabe, T., et al., "Influenza A Virus with Defective M2 Ion Channel Activity as a Live Vaccine", Virology, 299(2), (Aug. 1, 2002), 266-270.
Watanabe, Tokiko, et al., "Exploitation of Nucleic Acid Packaging Signals to Generate a Novel Influenza Virus-Based Vector Stably Expressing Two Foreign Genes", Journal of Virology, 77(19), (Oct. 2003), 10575-10583.
Watanabe, Tokiko, et al., "Influenza A Virus Can Undergo Multiple Cycles of Replication without M2 Ion Channel Activity", Journal of Virology 75(12), (2001), 5656-5662.
Wei, Hung-Ju, et al., "Fabrication of influenza virus-like particles using M2 fusion proteins for imaging single viruses and designing vaccines", Vaccine, 29, (2011), 7163-7172.
Whelan, S. P. J., et al., "Efficient Recovery of Infectious Vesicular Stomatitis Virus Entirely from cDNA Clones", Proc. Natl. Acad. Sci. USA, 92, (1995), 8388-8392.
Williams, Mark A., et al., "Effect of Mutations and Deletions in a Bicistronic mRNA on the Synthesis of Influenza B Virus NB and NA Glycoproteins", Journal of Virology, 63(1), (1989), 28-35.
Wilson, Julie A, et al., "Epitopes Involved in Antibody-Mediated Protection from Ebola Virus", Science, 287, (Mar. 2000), 1664-1666.
Winter, G., et al., "The use of synthetic oligodeoxynucleotide primers in cloning and sequencing segment 8 of influenza virus (A/PR/8/34)", Nucleic Acids Res., 9(2), (1981), 237-245.
Wu, Rui, et al., "A live bivalent influenza vaccine based on a H9N2 virus strain", Vaccine, 28, (2010), 673-680.
Xu, X., et al., "Reassortment and evolution of current human influenza A and B viruses", Virus Research, 103, (2004), 55-60.
Yamanaka, K., et al., "In vivo Analysis of the Promoter Structure of the Influenza Virus RNA Genome Using a Transfection System With an Engineered RNA", Proc. Natl. Acad. Sci. USA, 88, (1991), 5369-5373.
Yannarell, Dean A., et al., "Factors affecting the yield of cold-adapted influenza virus vaccine", Journal of Virological Methods, vol. 64, 161-169, (1997), 1 pg.
Yi, Pu Lin, et al., "Adaptation of Egg-Grown and Transfectant Influenza Viruses for Growth in Mammalian Cells: Selection of Hemagglutinin Mutants with Elevated pH of Membrane Fusion", Virology, 233(2), (Jul. 7, 1997), 402-410.
Yu, Q., et al., "Functional cDNA Clones of the Human Respiratory Syncytial (RS) Virus N, P, and L Proteins Support Replication of RS Virus Genomic RNA Analogs and Define Minimal trans-Acting Requirements for RNA Replication", Journal of Virology, 69(4), (1995), 2412-2419.
Yusoff, K., et al., "Nucleotide Sequence Analysis of the L Gene of Newcastle Disease Virus: Homologies With Sendai and Vesicular Stomatitis Viruses", Nucleic Acids Research, 15(10), (1987), 3961-3976.
Zaghouani, H, et al., "Induction of Antibodies to the Envelope Protein of the Human Immunodeficiency Virus by Immunization With Monoclonal Anti-Idiotypes", Proc. Natl. Acad. Sci. USA, 88, (1991), 5645-5649.
Zaghouani, H., et al., "Cells Expressing an H Chain 1g Gene Carrying a Viral T Cell Epitope are Lysed by Specific Cytolytic T Cells", The Journal of Immunology, 148(11), (1992), 3604-3609.
Zebedee, S. L, et al., "Characterization of the Influenza Virus M2 Integral Membrane Protein and Expression at the Infected-Cell Surface from Cloned cDNA", Journal of Virology, 56(2), (Nov. 1985), 502-511.
Zhang, H., et al., "Expression of Functional Influenza Virus A Polymerase Proteins and Template From Cloned cDNAs in Recombinant Vaccinia Virus Infected Cells", Biochemical and Biophysical Research Communications, 200(1), (1994), 95-101.
Zobel, A., et al., "RNA Polymerase I Catalysed Transcription of Insert Viral cDNA", Nucleic Acids Research, 21(16), (1993), 3607-3614.
"U.S. Appl. No. 15/170,556, Response filed Apr. 15, 2019 to Non Final Office Action dated Feb. 8, 2019", 9 pgs.
"European Application Serial 17709236.8 , Response filed Apr. 26, 2019 to Communication Pursuant to Rules 161(1) and 162 EPC dated Oct. 19, 2018", 9 pgs.

(56) References Cited

OTHER PUBLICATIONS

"U.S. Appl. No. 15/170,556, Notice of Allowability dated Jan. 29, 2020", 4 pgs.
"U.S. Appl. No. 15/170,556. PTO Response to Rule 312 Communication dated Apr. 3, 2020", 2 pgs.
"Canadian Application Serial No. 3,014,435, Response filed Mar. 13, 2020 to Office Action dated Nov. 13, 2019", 18 pgs.
"Japanese Application Serial No. 2018-543688, Written Opinion and Written Amendment filed Apr. 28, 2020 in response to Notification of Reasons for Rejection dated Oct. 29, 2019", (w/ English Translation), 16 pgs.
"Canadian Application Serial No. 3,014,435, Office Action dated Nov. 13, 2019", 4 pgs.
"Japanese Application Serial No. 2018-543688, Notification of Reasons for Rejection dated Oct. 29, 2019", (w/ English Translation), 14 pgs.
"Australian Application Serial No. 2017221444, Subsequent Examiners Report dated Nov. 27, 2020", 4 pgs.
"U.S. Appl. No. 15/966,092, Non Final Office Action dated Jun. 26, 2020", 22 pgs.
"U.S. Appl. No. 15/966,092, Response filed Oct. 26, 2020 to Non Final Office Action dated Jun. 26, 2020", 9 pgs.
"Australian Application Serial No. 2017221444, First Examination Report dated Jul. 8, 2020", 6 pgs.
"Australian Application Serial No. 2017221444, Response filed Nov. 13, 2020 to First Examination Report dated Jul. 8, 2020", 13 pgs.
"Canadian Application Serial No. 3,014,435, Office Action dated Nov. 6, 2020", 5 pgs.
"Influenza B/Ann Arbor/1/66 (cold-adapted) nonstructural protein (seg 8) RNA, complete cds", GenBank Accession M20224, (Aug. 2, 1993).
"Japanese Application Serial No. 2018-543688, Office Action dated Jun. 30, 2020", w/ English translation, 11 pgs.
"RecName: Full=Non-structural protein 1; Short=NS1; AltName: Full=NS1 B", GenPept Accesion P08013, (Dec. 9, 2015).
"Australian Application Serial No. 2017221444, Fourth Examiners Report dated Jun. 29, 2021", 3 pgs.
"European Application Serial No. 17709236.8, Communication Pursuant to Article 94(3) EPC dated Jul. 6, 2021", 10 pgs.
"Canadian Application Serial No. 3,014,435, Office Action dated Oct. 26, 2021", 4 pgs.

* cited by examiner

B/Yamagata/1/1973 PB2:

AGCAGAAGCGGAGCGTTTTCAAGATGACATTGGCTAAAATTGAATTGTTAAAACAACTGTTAAGGGACAACGAAGCCAAA
ACAGTATTGAAACAAACAACGGTAGACCAATATAACATAATAAGAAAATTCAATACATCAAGAATTGAAAAGAACCCTTC
ATTAAGGATGAAGTGGGCCATGTGTTCTAATTTTCCCTTGGCTCTGACCAAGGGTGATATGGCAAATAGAATCCCCTTGG
AATACAAGGGAATACAACTTAAAACAAATGCTGAAGACATAGGAACCAAAGGCCAAATGTGCTCAATAGCAGCAGTTACC
TGGTGGAATACATATGGACCAATAGGAGACACTGAAGGTTTCGAAAAGGTCTACGAAAGCTTCTTTCTCAGAAAGATGAG
ACTTGACAATGCCACTTGGGGCCGAATAACTTTTGGCCCAGTTGAAAGAGTAAGAAAAAGGGTACTGCTAAACCCTCTCA
CCAAGGAAATGCCTCCAGATGAAGCGAGCAATGTGATAATGGAAATATTGTTCCCTAAGGAAGCAGGAATACCAAGAGAA
TCTACTTGGATACATAGGGAACTGATAAAAGAAAAAAGAGAAAAATTGAAAGGAACGATGATAACTCCCATTGTACTGGC
ATACATGCTTGAGAGAGAATTGGTTGCCCGAAGAAGGTTCCTGCCAGTGGCAGGAGCAACATCAGCTGAGTTCATAGAAA
TGCTACACTGCTTACAAGGTGAAAATTGGAGACAAATATATCACCCAGGAGGGAATAAACTAACTGAATCTAGGTCTCAA
TCAATGATTGTAGCTTGTAGAAAAATAATCAGAAGATCAATAGTCGCATCAAACCCACTAGAGCTAGCTGTAGAAATTGC
AAACAAGACTGTGATAGATACTGAACCTTTAAAATCATGTCTGGCAGCCATAGACGGAGGTGATGTAGCCTGTGACATAA
TGAGAGCTGCATTAGGACTAAAGATCAGACAAAGACAAAGATTTGGACGGCTTGAACTAAAGAGAATATCAGGAAGAGGA
TTCAAAAATGATGAAGAAATATTGATCGGGAACGGAACAATACAGAAGATTGGAATATGGGACGGAGAAGAGGAGTTCCA
TGTAAGATGTGGTGAATGCAGGGGAATATTAAAAAAGAGCAAAATGAGAATGGAAAAACTACTAATAAATTCAGCCAAAA
AGGAGGACATGAAAGATTTAATAATCTTGTGCATGGTATTTTCTCAAGACACTAGGATGTTCCAAGGAGTGAGAGGAGAA
ATAAATTTTCTTAATCGAGCAGGCCAACTTTTATCTCCAATGTACCAACTCCAAAGATATTTTTTGAATAGGAGCAACGA
TCTTTTTGATCAATGGGGGTATGAGGAATCACCCAAAGCAAGTGAACTACATGGGATAAATGAATTAATGAATGCATCTG
ATTATACGTTGAAAGGGGTTGTAGTAACAAAAAATGTGATTGATGACTTTAGTTCTACTGAAACAGAAAAAGTATCTATA
ACAAAAAATCTTAGTTTAATAAAAAGAACTGGGGAAGTCATAATGGGGGCTAATGACGTAAGTGAATTAGAATCACAAGC
TCAGCTAATGATAACATATGATACACCTAAGATGTGGGAGATGGGAACAACCAAAGAACTGGTGCAAAACACCTACCAAT
GGGTGCTAAAAAATTTGGTAACACTGAAGGCTCAGTTTCTTCTAGGAAAAGAAGACATGTTCCAATGGGATGCATTTGAA
GCATTTGAAAGCATAATCCCCCAGAAGATGGCTGGCCAGTACAGTGGATTTGCAAGGGCAGTGCTCAAACAAATGAGAGA
CCAAGAGGTTATGAAAACTGACCAGTTCATAAAGTTGTTGCCTTTCTGTTTCTCACCACCAAAATTAAGGAGCAATGGGG
AGCCTTATCAATTCTTGAGGCTTATATTGAAGGGAGGAGGAGAAAATTTCATCGAAGTAAGGAAAGGGTCCCCTCTATTC
TCCTACAATCCACAAACAGAAGTCCTAACTATATGCGGCAGAATGATGTCATTAAAAGGGAAAATTGAAGATGAAGAAAG
GAATAGATCAATGGGGAATGCAGTATTGGCAGGCTTTCTCGTTAGTGGCAAGTATGACCCAGATCTTGGAGATTTCAAAA
CTATTGAAGAACTTGAAAAGCTAAAACCGGGGGAGAAAGCAAACATCTTACTTTATCAAGGAAAGCCCGTTAAAGTAGTT
AAAAGGAAAAGATATAGTGCTTTATCCAATGACATTTCACAAGGAATTAAGAGACAAAGAATGACAGTTGAGTCCATGGG
GTGGGCCTTGAGCTAATATAAATTTATCCATTAATTCAATAAACACAATTGAGTGAAAAATGCTCGTGTTTCTACT (SEQ ID NO:1)

FIG. 1A

B/Yamagata/1/1973 PB1:

AGCAGAAGCGGAGCCTTTAAGATGAATATAAATCCTTATTTTCTCTTCATAGATGTACCCATACAGGCAGCAATTTCAAC
AACATTCCCATACACCGGTGTTCCCCCTTATTCCCATGGAACGGGAACAGGCTACACAATAGACACCGTGATCAGAACAC
ATGAGTACTCAAACAAGGGAAAACAGTACATTTCTGATGTTACAGGATGTACAATGGTAGATCCAACAAATGGGCCATTA
CCCGAAGACAATGAGCCGAGTGCCTATGCACAATTAGATTGCGTTCTGGAGGCTTTGGATAGAATGGATGAAGAACATCC
AGGTCTGTTTCAAGCAGCCTCACAGAATGCCATGGAGGCACTAATGGTCACAACTGTAGACAAATTAACCCAGGGGAGAC
AGACTTTTGATTGGACAGTATGCAGAAACCAACCTGCTGCAACGGCACTGAACACAACAATAACCTCTTTTAGGTTGAAT
GATTTGAATGGAGCCGACAAGGGTGGATTAGTACCCTTTTGCCAAGATATCATTGATTCATTGGACAGACCTGAAATGAC
TTTCTTCTCAGTAAAGAATATAAAGAAAAAATTGCCTGCTAAAAACAGAAAGGGTTTCCTCATAAAGAGAATACCAATGA
AGGTAAAAGACAGAATAACCAGAGTGGAATACATCAAAAGAGCATTATCATTAAACACAATGACAAAAGATGCTGAAAG
A
GGCAAACTAAAAAGAAGAGCGATTGCCACCGCTGGAATACAAATCAGAGGGTTTGTATTAGTAGTTGAAAACTTGGCTAA
AAATATCTGTGAAAATCTAGAACAAAGTGGTTTGCCAGTAGGTGGAAACGAGAAGAAGGCCAAACTGTCAAATGCAGTG
G
CCAAAATGCTCAGTAACTGCCCACCAGGAGGGATCAGCATGACAGTAACAGGAGACAATACCAAATGGAATGAATGCTTA
AATCCAAGAATCTTTTTGGCTATGACTGAAAGAATAACCAGAGACAGCCCAATTTGGTTCCGGGATTTTTGTAGTATAGC
ACCGGTCTTGTTCTCCAATAAAATAGCCAGATTGGGAAAAGGGTTTATGATAACAAGCAAAACAAAAAGACTGAAGGCTC
AAATACCTTGTCCTGATCTGTTTAGTATACCATTAGAAAGATATAATGAAGAAACAAGGGCAAAATTGAAAAAGCTGAAA
CCATTCTTCAATGAAGAAGGAACGGCATCTTTGTCGCCTGGGATGATGATGGGAATGTTTAATATGCTATCTACCGTGTT
GGGAGTAGCCGCACTAGGTATCAAAAACATTGGAAACAAAGAATACTTATGGGATGGACTGCAATCTTCTGATGATTTTG
CTCTGTTTGTTAATGCAAAAGATGAAGAGACATGTATGGAAGGAATAAACGACTTTTACCGAACATGTAAACTATTGGGA
ATAAACATGAGCAAAAAGAAAAGTTACTGTAATGAAACTGGAATGTTTGAATTTACAAGCATGTTCTACAGAGATGGATT
TGTATCTAATTTTGCAATGGAACTTCCTTCATTTGGAGTTGCTGGAGTAAATGAATCAGCAGATATGGCAATAGGAATGA
CAATAATAAAGAACAATATGATCAACAATGGGATGGGTCCAGCAACAGCACAAACAGCCATACAATTATTCATAGCTGAT
TATAGATACACCTACAAATGCCACAGGGGAGATTCCAAAGTGGAAGGAAAGAGAATGAAAATTATAAAGGAGCTATGGG
A
AAACACTAAAGGAAGAGATGGTCTGTTAGTAGCAGATGGTGGGCCTAACATTTACAATTTGAGAAACTTGCATATCCCAG
AAATAGTATTAAAGTACAACCTAATGGACCCTGAATACAAAGGGCGGTTACTTCATCCTCAAAATCCCTTTGTAGGACAT
TTGTCTATTGAGGGCATCAAAGAGGCAGATATAACCCCAGCACATGGTCCAGTAAAGAAAATGGACTATGATGCGGTGTC
TGGAACTCATAGTTGGAGAACCAAAAGGAACAGATCTATACTAAACACTGATCAGAGGAACATGATTCTTGAGGAACAAT
GCTACGCTAAGTGTTGCAACCTTTTTGAGGCCTGTTTTAACAGTGCATCATACAGGAAACCAGTAGGTCAGCACAGCATG
CTTGAGGCTATGGCCCACAGATTAAGAATGGATGCACGACTAGATTATGAATCAGGAAGAATGTCAAAGGATGATTTTGA
GAAAGCAATGGCTCACCTTGGTGAGATTGGGTACATATAAGCTTCGAAGATGTCTATGGGGTTATTGGTCATCATTGAAT
ACATGCGGTACACAAATGATTAAAATGAAAAAAGGCTCGTGTTTCTACT (SEQ ID NO:2)

FIG. 1B

B/Yamagata/1/1973 PA:

AGCAGAAGCGGTGCGTTTGATTTGCCATAATGGATACTTTTATTACAAGAAACTTCCAGACTACAATAATACAAAAGGCC
AAAAACACAATGGCAGAATTTAGTGAAGATCCTGAATTACAACCAGCAATGCTATTCAACATCTGCGTCCATCTGGAGGT
CTGCTATGTAATAAGTGATATGAATTTTCTTGATGAAGAAGGAAAAGCATATACAGCATTAGAAGGACAAGGAAAAGAAC
AAAACTTGAGACCACAATATGAAGTGATTGAGGGAATGCCAAGAAACATAGCATGGATGGTTCAAAGATCCTTAGCCCAA
GAGCATGGGATAGAGACTCCAAGGTATCTGGCTGATTTGTTCGATTATAAAACTAAGAGGTTTATAGAAGTTGGAATAAC
AAAGGGATTGGCTGATGATTACTTCTGGAAAAAGAAAGAAAAGCTGGGGAATAGCATGGAACTGATGATATTCAGCTACA
ATCAAGACTATTCGTTAAGTAATGAATCCTCATTGGATGAGGAAGGAAAAGGGAGAGTGCTAAGCAGACTCACAGAACTT
CAGGCTGAGTTAAGTCTGAAAAATCTATGGCAAGTTCTCATAGGAGAAGAAGATATTGAAAAAGGAATTGACTTCAAACT
TGGACAAACAATATCTAAACTAAGGGATATATCTGTTCCAGCTGGTTTCTCCAATTTTGAAGGAATGAGGAGCTACATAG
ACAATATAGATCCTAAAGGAGCAATAGAGAGAAATCTAGCAAGGATGTCTCCCTTAGTATCAGTTACACCTAAAAAGTTG
AAATGGGAGGACCTAAGACCAATAGGGCCTCACATTTACAACCATGAGCTACCAGAAGTTCCATATAATGCCTTTCTTCT
AATGTCTGATGAATTGGGGCTGGCTAATATGACTGAAGGGAAGTCCAAGAAACCGAAGACCTTAGCCAAAGAGTGCCTAG
AAAAGTACTCAACACTACGGGATCAAACTGACCCAATATTAATAATGAAAAGCGAAAAAGCTAATGAACACTTCCTATGG
AAACTGTGGAGGGACTGTGTAAATACAATAAGTAATGAGGAAACAAGTAACGAATTACAGAAAACCAATTATGCCAAGTG
GGCCACAGGAGATGGATTAACATATCAGAAAATAATGAAAGAAGTAGCAATAGATGACGAAACAATGTACCAAGAAGAGC
CCAAAATACCTAACAAATGTAGAGTGGCTGCTTGGGTTCAAACAGAGATGAATCTATTGAGCACTCTGACAAGTAAAAGG
GCCCTGGATCTGCCAGAAATAGGGCCAGACGTAGCACCCGTGGAGCATGTAGGGAGTGAAAGAAGGAAATACTTTGTTAA
TGAAATCAACTACTGTAAGGCCTCTACCGTTATGATGAAGTATGTACTTTTTCACACTTCATTATTAAATGAAAGCAATG
CCAGCATGGGAAAATATAAAGTAATACCAATAACCAACAGAGTAGTAAATGAAAAGGGAGAAAGTTTTGACATGCTTTAT
GGTCTAGCGGTTAAAGGGCAATCTCATCTGAGGGGAGATACTGATGTTGTAACAGTTGTGACTTTCGAATTTAGTAGTAC
AGATCCCAGAGTGGACTCAGGAAAGTGGCCAAAATATACTGTATTTAGAATTGGCTCCTTATTTGTGAGTGGGAGGGAAA
AATCTGTATACCTATATTGCCGAGTGAATGGTACAAATAAGATCCAAATGAAATGGGGAATGGAAGCTAGAAGATGTCTG
CTTCAATCAATGCAACAAATGGAAGCAATTGTTGAACAAGAATCATCGATACAAGGATATGACATGACCAAAGCTTGTTT
CAAGGGAGACAGAGTGAATAGTCCAAAAACTTTCAGTATTGGGACTCAAGAAGGAAAACTAGTGAAAGGATCCTTTGGGA
AAGCACTAAGAGTAATATTCACCAAATGTTTGATGCACTATGTATTTGGAAATGCCCAATTGGAGGGGTTTAGTGCCGAA
TCTAGGAGACTTCTACTGTTAATTCAGGCATTAAAAGACAGAAAGGGCCCTTGGGTATTCGACTTAGAGGGAATGTATTC
TGGAATAGAAGAATGTATTAGTAACAACCCTTGGGTAATACAGAGTGCATACTGGTTTAATGAATGGTTGGGCTTTGAAA
AAGAGGGGAGTAAAGTATTAGAATCAGTAGATGAAATAATGGATGAATGAAAGAAGGGCATAGTGCTCAATTTGGTACTA
TTTTGTTCATTATGTATCTAAACATCCAATAAAAAGAATTGAGAATTAAAAATGCACGTGTTTCTACT (SEQ ID NO:3)

FIG. 1C

B/Yamagata/1/1973 NP:
AGCAGAAGCACAGCATTTTCTTGTGAACTTCAAGTACCAACAAAAACTGAAAATCAAAATGTCCAACATGGACATTGAC
GGCATCAACACTGGAATAATTGACAAAACACCAGAAGAAATAACTTCCGGAACCAGTGGGGCAACCAGACCAATCATCAG
ACCAGCAACCCTTGCCCCACCAAGCAACAAACGAACCAGAAACCCATCCCCGGAAAGGGCAACCACAAGCAGTGAAGCTG
ATGTCGGAAGGAAAACCCAAAAGAAACAAACTCCGACAGAGATAAAGAAGAGCGTCTACAATATGGTAGTGAAACTGGGT
GAATTCTACAACCAGATGATGGTCAAAGCTGGACTCAACGATGACATGGAGAGAAACCTAATCCAAAATGCACATGCTGT
GGAAAGAATTCTATTGGCTGCTACTGATGACAAGAAAACTGAATTCCAAAAGAAAAAGAATGCCAGAGACGTCAAAGAAG
GGAAAGAAGAAATAGACCACAACAAAACAGGAGGCACCTTTTACAAGATGGTAAGAGATGATAAAACCATCTACTTCAGC
CCTATAAGAATTACCTTTTTAAAAGAAGAGGTGAAAACAATGTACAAAACCACCATGGGGAGTGACGGTTTCAGTGGACT
AAATCACATCATGATTGGGCATTCACAGATGAACGATGTCTGTTTCCAAAGATCAAAGGCACTAAAAAGAGTTGGACTTG
ACCCTTCATTAATCAGTACTTTTGCAGGAAGCACACTCCCCAGAAGATCAGGTACAACTGGTGTTGCGACCAAAGGAGGT
GGAACTTTAGTGGCAGAAGCCATTCGATTTATAGGAAGAGCAATGGCAGACAGAGGGCTATTGAGAGACATCAGAGCCAA
GACGGCCTATGAAAAGATTCTTCTGAATCTGAAAAACAAGTGCTCTGCGCCCCAACAAAAGGCTCTGGTTGATCAAGTGA
TCGGAAGTAGAAATCCAGGGATTGCAGACATAGAAGATCTCACCCTGCTTGCTCGAAGTATGGTCGTTGTTAGGCCCTCT
GTAGCAAGCAAAGTGGTGCTTCCCATAAGCATCTATGCTAAAATACCTCAACTGGGGTTCAACGTTGAAGAATACTCTAT
GGTTGGGTATGAAGCCATGGCTCTTTATAATATGGCAACACCTGTTTCCATATTAAGAATGGGAGACGATGCAAAAGATA
AATCACAATTATTCTTCATGTCTTGCTTTGGAGCTGCCTATGAAGACCTAAGAGTTCTGTCTGCACTAACAGGCACGGAA
TTCAAGCCTAGGTCAGCATTAAAGTGCAAAGGTTTCCACGTTCCAGCAAAGGAGCAAGTGGAAGGAATGGGGGCAGCTCT
GATGTCCATCAAGCTCCAGTTTTGGGCTCCAATGACCAGATCTGGGGGGAATGAAGTAGGTGGAGACGGAGGGTCTGGTC
AAATAAGTTGCAGCCCCGTGTTTGCAGTAGAAAGACCTATTGCTCTAAGCAAGCAAGCTGTAAGAAGAATGCTGTCAATG
AATATTGAGGGACGTGATGCAGATGTCAAAGGAAATCTACTCAAGATGATGAATGATTCAATGGCTAAGAAAACCAATGG
AAATGCTTTCATTGGGAAGAAAATGTTCCAAATATCAGACAAAAACAAAACCAATCCCGTTGAGATTCCAATTAAGCAGA
CCATCCCCAGTTTCTTCTTTGGGAGGGACACAGCAGAGGATTATGATGACCTCGATTATTAAAGCAACAAAATAGACACT
ATGGCTGTGATTGTTTCAGTACGTTTGGAATGTGGGTGTTTACTCTTATTGAAATAAATGTAAAAAATGCTGTTGTTTCT (SEQ ID NO:4)

B/Yamagata/1/1973 M:
AGCAGAAGCACGCACTTTCTTAAAATGTCGCTGTTTGGAGACACAATTGCCTACCTGCTTTCACTAACAGAAGATGGAGA
AGGCAAAGCAGAACTAGCGGAAAAATTACACTGTTGGTTCGGTGGGAAAGAATTCGATCTAGACTCTGCTTTGGAATGGA
TAAAAAACAAAAGATGCCTAACTGATATACAAAAAGCACTAATTGGTGCCTCTATCTGCTTTTTGAAACCCAAAGACCAA
GAAAGAAAAAGAAGATTCATCACAGAGCCCCTGTCAGGAATGGGAACAACAGCAACAAAAAAGAAAGGCCTGATTCTAGC
TGAAAGAAAAATGAGAAGATGTGTGAGTTTTCATGAGGCATTTGAAATAGCAGAAGGCCATGAAAGCTCAGCACTACTAT
ATTGTCTCATGGTCATGTACCTGAACCCTGGAAATTATTCAATGCAAGTAAAACTAGGAACGCTCTGTGCTTTATGCGAG
AAACAAGCATCACATTCACACAGAGCTCATAGCAGAGCAGCAAGATCTTCAGTGCCTGGAGTGAGGCGAGAAATGCAAAT
GGTTTCAGCTATGAACACAGCAAAAACAATGAATGGAATGGGGAAGGGAGAAGACGTCCAAAAACTGGCAGAAGAGCTGC
AAAGCAACATTGGAGTATTGAGATCTCTGGGGGCAAGTCAAAAGAATGGAGAAGGAATTGCAAAGGATGTAATGGAAGTG
CTAAAGCAGAGCTCCATGGGAAATTCAGCTCTTGTGAAGAAATACCTATAATGCTCGAGCCATTTCAGATTCTTTCAATT
TGCTCTTTCATTTTATCGGCTCTCCATTTCATGGGCTGGACAATAGGGCATTTAAATCAAATAAAAAGAGGAGTAAACCT
AAAAATACGAATAAGAAATCCAAATAAAGAGACAATAAATAGAGAGGTATCAATTTTGAGACACAGTTACCAAAAAGAAA
TCCAAGCCAAAGAAACAATAAAGGAAGTACTCTCTGACAACATGGAGAGATTGAGTGACCACATAGTAATTGAGGGGCTT
TCTGCTGAAGAGATAATAAAAATGGGTGAAACAGTTTTGGAGGTAGAAGAATTGCATTAAACCCAATTTTCACCGTATTT
CTTACTATGCATTTAAGCAAATTGTAATCAATGTCAGCAAATAAACTGGAAAAAGTGCGTTGTTTCTACT (SEQ ID NO:5)

FIG. 1D

B/Yamagata/1/1973 NS:

AGCAGAAGCAGAGGATTTGTTTAGTCACTGGCAAACGGAAAAAAATGGCGGACAACATGACCACAACACAAATTGAGGTG
GGTCCGGGAGCAACCAATGCCACTATAAACTTTGAAGCAGGAATTTTGGAGTGCTATGAAAGGCTTTCATGGCAAAGAGC
CCTTGACTACCCTGGTCAAGACCGCCTAAACAGACTAAAGAGAAAATTAGAATCAAGAATAAAGACTCACAACAAAAGTG
AGCCTGAAAGTAAAAGGATGTCTCTTGAAGAGAGAAAAGCAATTGGGGTAAAAATGATGAAAGTGCTCCTATTTATGAAC
CCATCTGCTGGAATTGAAGGGTTTGAGCCATACTGTATGAAAAATTCCTCCAATAGCAACTGCCCAAACTGCAATTGGGC
CGATTACCCTCCAACATCAGGAAAGTGCCTTGATGACATAGAAGAAGAACCGGAGAATGTTGATGACCCAACTGAAATAG
TATTAAGGGACATGAACAACAAAGATGCAAGGCAAAAGATAAAAGAGGAAGTAAACACTCAGAAAGAAGGGAAGTTCCGT
TTGACAATAAAAAGGGATATACGTAATGTGTTGTCCTTGAGAGTGTTGGTAAACGGAACATTCCTCAAGCACCCTAATGG
ATACAAGTCCTTATCAACTCTGCATAGATTGAATGCATATGACCAGAGTGGAAGGCTTGTTGCTAAACTTGTTGCTACTG
ATGATCTTACAGTGGAGGATGAAGAAGATGGCCATCGGATCCTCAACTCACTCTTCGAGCGTTTTAATGAAGGACATTCA
AAGCCAATTCGAGCAGCTGAAACTGCGGTGGGAGTCTTATCCCAATTTGGTCAAGAGCACCGATTATCACCAGAGGAGGG
AGACAATTAGACTGGTTACGGAAGAACTTTATCTTTTAAGTAAAAGAATTGATGATAACATATTGTTCCACAAAACAGTA
ATAGCTAACAGCTCCATAATAGCTGACATGATTGTATCATTATCATTATTGGAAACATTGTATGAGATGAAGGATGTGGT
TGAAGTGTACAGCAGGCAGTGCTTGTGAATTTAAAATAAAAATCCTCTTGTTACTACT (SEQ ID NO:6)

HA

MKAIIVLLMVVTSNADRICTGITSSNSPHVVKTATQGEVNVTGVIP
LTTTPTKSHFANLKGTKTRGKLCPNCLNCTDLDVALGRPMCMGTI
PSAKASILHEVRPVTSGCFPIMHDRTKIRQLPNLLRGYENIRLSTHN
VINAERAPGGPYRLGTSGSCPNVTSRNGFFATMAWAVPRDNKTA
TNPLTVEVPYICTKGEDQITVWGFHSDDKTQMKNLYGDSNPQKFT
SSANGVTTHYVSQIGDFPNQTEDGGLPQSGRIVVDYMVQKPGKT
GTIVYQRGVLLPQKVWCASGRSKVIKGSLPLIGEADCLHEKYGGLN
KSKPYYTGEHAKAIGNCPIWVKTPLKLANGTKYRPPAKLLKERGFF
GAIAGFLEGGWEGMIAGWHGYTSHGAHGVAVAADLKSTQEAINK
ITKNLNSLSELEVKNLQRLSGAMDELHNEILELDEKVDDLRADTISS
QIELAVLLSNEGIINSEDEHLLALERKLKKMLGPSAVDIGNGCFETK
HKCNQTCLDRIAAGTFNAGEFSLPTFDSLNITAASLNDDGLDNHTI
LLYYSTAASSLAVTLMIAIFIVYMVSRDNVSCSICL (SEQ ID NO:7)

Encoded by

```
  1 tttctaatat ccacaaaatg aaggcaataa ttgtactact catggtagta acatccaacg
 61 cagatcgaat ctgcactggg ataacatctt caaactcacc tcatgtggtc aaaacagcta
121 ctcaagggga agttaatgtg actggtgtga taccactgac aacaacacca acaaaatctc
181 attttgcaaa tctcaaagga acaaagacca gagggaaact atgcccaaac tgtctcaact
241 gcacagatct ggatgtggcc ttgggcagac caatgtgtat ggggaccata ccttcggcaa
301 aagcttcaat actccacgaa gtcagacctg ttacatccgg gtgctttcct ataatgcacg
361 acagaacaaa aatcagacag ctacccaatc ttctcagagg atatgaaaat atcagattat
421 caacccataa cgttatcaac gcagaaaggg caccaggagg accctacaga cttggaacct
481 caggatcttg ccctaacgtt accagtagaa acggattctt cgcaacaatg gcttgggctg
541 tcccaaggga caacaaaaca gcaacgaatc cactaacagt agaagtacca tacatttgca
601 caaaaggaga agaccaaatt actgtttggg ggttccattc tgatgacaaa acccaaatga
```

FIG. 1E

```
 661 aaaacctcta tggagactca aatcctcaaa agttcacctc atctgccaat ggagtaacca
 721 cacattatgt ttctcagatt ggtgacttcc caaatcaaac agaagacgga gggctaccac
 781 aaagcggcag aattgttgtt gattacatgg tgcaaaaacc tgggaaaaca ggaacaattg
 841 tctatcaaag aggtgttttg ttgcctcaaa aggtgtggtg cgcaagtggc aggagcaagg
 901 taataaaagg gtccttgcct ttaattggtg aagcagattg ccttcacgaa aaatacggtg
 961 gattaaacaa aagcaagcct tactacacag gagaacatgc aaaagccata ggaaattgcc
1021 caatatgggt gaaaacacct ttgaagcttg ccaatggaac caaatataga cctcctgcaa
1081 aactattaaa ggaaaggggt ttcttcggag ctattgctgg tttcttagag ggaggatggg
1141 aaggaatgat tgcaggttgg cacggataca catctcatgg agcacatgga gtggcagtgg
1201 cagcagacct taagagcacg caagaagcca taaacaagat aacaaaaaat ctcaattctt
1261 tgagtgagct agaagtaaag aatcttcaaa gactaagtgg tgccatggat gaactccaca
1321 acgaaatact cgagctggat gagaaagtgg atgatctcag agctgacaca ataagctcgc
1381 aaatagagct tgcagtcttg ctttccaacg aaggaataat aaacagtgaa gatgagcatc
1441 tattggcact tgagagaaaa ctaaagaaaa tgctgggtcc ctctgctgta gacataggga
1501 atggatgctt cgaaaccaaa cacaagtgca accagacctg cttagacagg atagctgctg
1561 gcacctttaa tgcaggagaa ttttctcttc ccacttttga ttcactgaat attactgctg
1621 catctttaaa tgatgatgga ttggataatc atactatact gctctactac tcaactgctg
1681 cttctagttt ggccgtaaca ttgatgatag ctatttttat tgtttatatg gtctccagag
1741 acaatgtttc ttgctccatc tgtctataag gaaaattaag ccctgtattt tcctttattg
1801 tagtgcttgt ttgcttgtta ccattacaaa gaaacgttat tga (SEQ ID NO:9)
```

NA

```
M L P S T I Q T L T L F L T S G G V L L S L Y V S A S L S
Y L L Y S D I L L K F S P T E I T A P K V P L D C A N A S
N V Q A V N R S A T K G M T L L L S E P E W T Y P R L S C
Q G S T F Q K A L L I S P H R F G E T R G N S A P L I I R
E P F I A C G P K E C K H F A L T H Y A A Q P G G Y Y N G
T R E D R N K L R H L I S V K L G K I P T V E N S I F H M
A A W S G S A C H D G R E W T Y I G V D G P D S N A L I K
I K Y G E A Y T D T Y H S Y A N N I L R T Q E S A C N C I
G G D C Y L M I T D G S A S G I S K C R F L K I R E G R I
I K E I F P T G R V E H T E E C T C G F A S N K T I E C A
C R D N S Y T A K R P F V K L N V E T D T A E I R L M C T
E T Y L D T P R P D D G S I T G P C E S N G D K G R G G I
K G G F V H Q R M A S K I G R W Y S R T M S K T E R M G M
E L Y V K Y D G D P W T D S D A L A P S G V M V S M K E P
G W Y S F G F E I K D K K C D V P C I G I E M V H D G G K
K T W H S A A T A I Y C L M G S G Q L L W D T V T G V D M
A L (SEQ ID NO:8)
```

FIG. 1F

Encoded by

```
   1 aaactgaggc aaataggcca aaaatgaaca atgctacctt caactataca aacgttaacc
  61 ctatttctca catcaggggg agtgttatta tcactatatg tgtcagcttc actgtcatac
 121 ttactgtatt cggatatatt gctaaaattt tcaccaacag aaataactgc accaaaagtg
 181 ccattggatt gtgcaaacgc atcaaatgtt caggctgtga accgttctgc aacaaaaggg
 241 atgacacttc ttctctcaga accggagtgg acataccctc gtttatcttg ccagggctca
 301 acctttcaga aagcactcct aattagccct catagattcg gagaaaccag aggaaactca
 361 gctcccttga taataaggga acctttttatt gcttgtggac caaaggaatg caaacacttt
 421 gctctaaccc attatgcagc tcaaccaggg ggatactaca atggaacaag agaggacaga
 481 aacaagctga ggcatctgat ttcagtcaaa ttgggcaaaa tcccaacagt agaaaactcc
 541 attttccaca tggcagcttg gagcgggtcc gcatgccatg atggtagaga atggacatat
 601 atcggagttg atggccctga cagtaatgca ttgatcaaaa taaaatatgg agaagcatat
 661 actgacacat accattccta tgcaaacaac atcctaagaa cacaagaaag tgcctgcaat
 721 tgcatcgggg gagattgtta tcttatgata actgatggct cagcttcagg aattagtaaa
 781 tgcagatttc ttaagattcg agagggtcga ataataaaag aaatatttcc aacaggaaga
 841 gtagaacata ctgaagaatg cacatgcgga tttgccagca ataaaaccat agaatgtgcc
 901 tgtagagata acagttacac agcaaaaaga ccctttgtca aattaaatgt ggagactgat
 961 acagctgaaa taagattgat gtgcacagag acttatttgg acacccccag accagatgat
1021 ggaagcataa cagggccttg cgaatctaat ggggacaaag ggcgtggagg catcaaggga
1081 ggatttgttc atcaaagaat ggcatccaag attggaagat ggtactctcg aacgatgtct
1141 aaaactgaaa gaatggggat ggaactgtat gtcaagtatg atggagaccc atggactgac
1201 agtgacgccc ttgctcctag tggagtaatg gtttcaatga aagaacctgg ttggtattcc
1261 tttggcttcg aaataaaaga taagaaatgt gatgtcccct gtattgggat agagatggta
1321 catgatggtg gaaaaaagac ttggcactca gcagcaacag ccatttactg tttaatgggc
1381 tcaggacaat tgctatggga cactgtcaca ggtgttgata tggctctgta atggaggaat
1441 ggttgagtct gttctaaacc ctttgttcct attttgtttg aacaattgtc cttactgaac
1501 ttaa(SEQ ID NO:10)
```

FIG. 1G

Figure 5
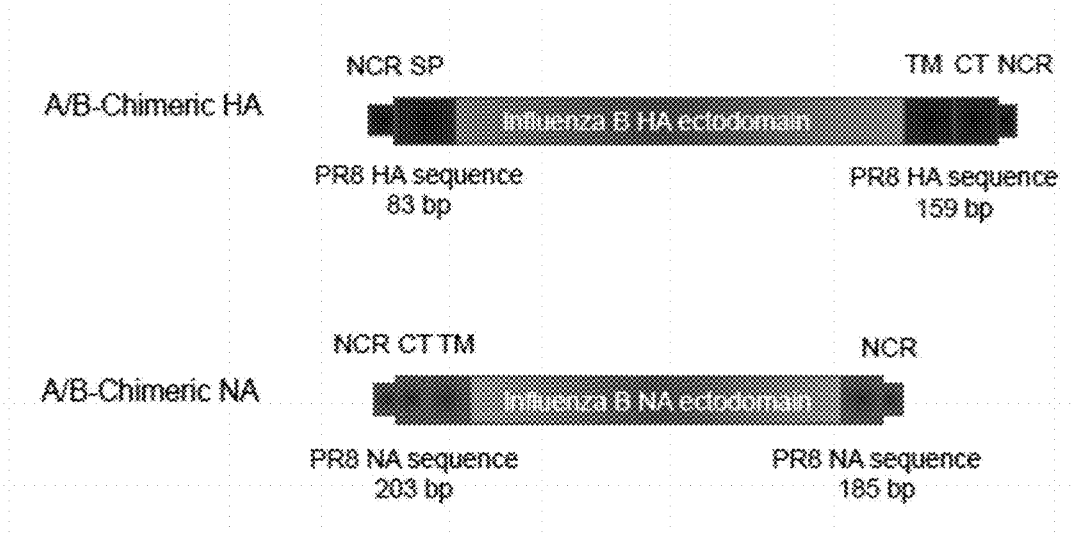
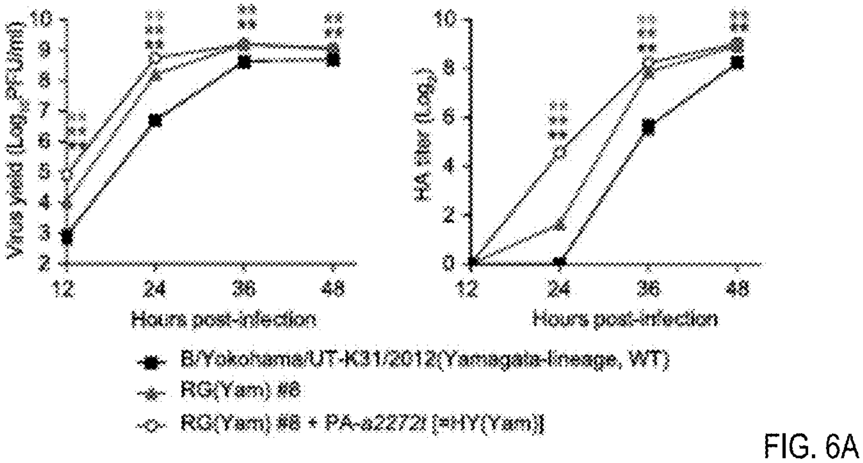
FIG. 6A
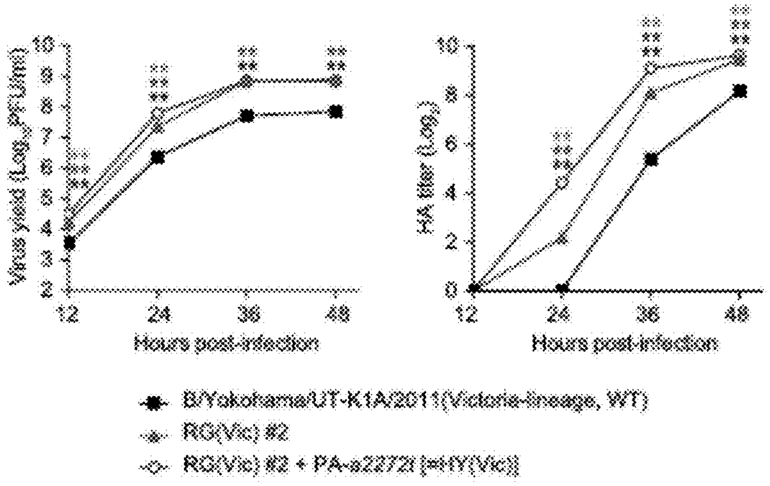
FIG. 6B
A/B-Chimeric HA
NCR SP — Influenza B HA ectodomain — TM CT NCR
PR8 HA sequence 83 bp | PR8 HA sequence 159 bp
A/B-Chimeric NA
NCR CT TM — Influenza B NA ectodomain — NCR
PR8 NA sequence 203 bp | PR8 NA sequence 185 bp
- B/Yokohama/UT-K31/2012 (Yamagata-lineage, WT)
- RG(Yam) #8
- RG(Yam) #8 + PA-a2272t [=HY(Yam)]
- B/Yokohama/UT-K1A/2011 (Victoria-lineage, WT)
- RG(Vic) #2
- RG(Vic) #2 + PA-a2272t [=HY(Vic)]

- ■ Yamagata/1/73 + B/Yokohama/UT-K31/2012(HA+NA)
- ● Yamagata/1/73 + PA-a2272t + B/Yokohama/UT-K31/2012(HA+NA)
- ✱ Yamagata/1/73 + NP-P40S + B/Yokohama/UT-K31/2012(HA+NA)
- ◇ Yamagata/1/73 + M1-R77K + B/Yokohama/UT-K31/2012(HA+NA)
- ◆ Yamagata/1/73 + NS-a39g + NS1-K176Q + B/Yokohama/UT-K31/2012(HA+NA)
- ◇ HY(Yam) + B/Yokohama/UT-K31/2012(HA+NA)

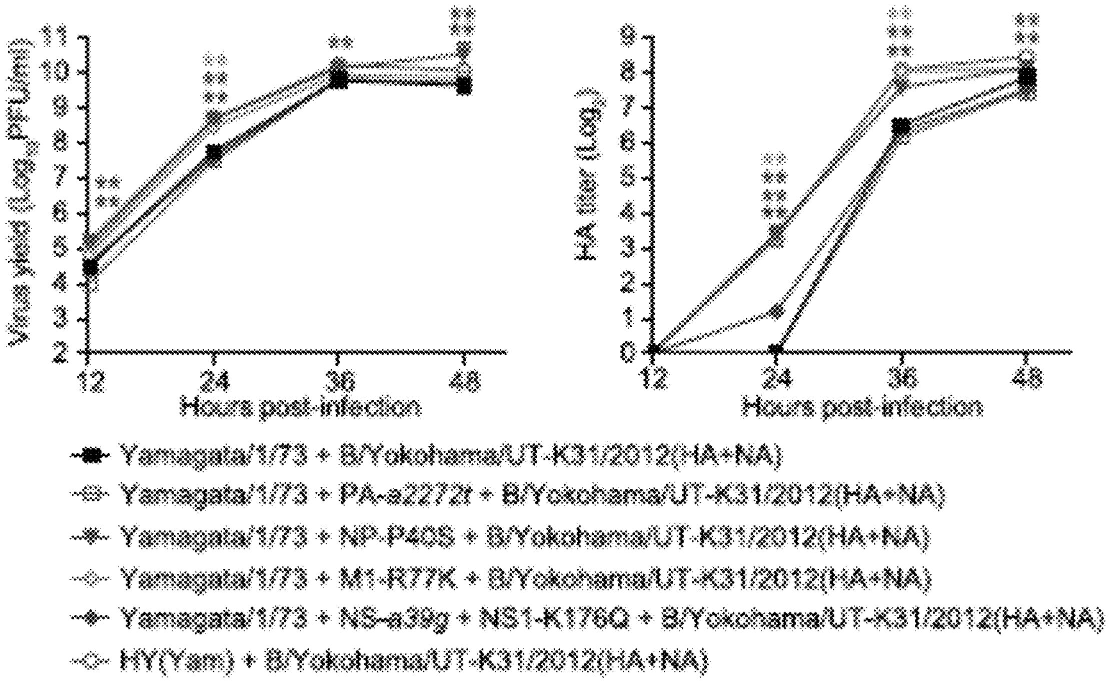

FIG. 12A

- ■ Yamagata/1/73 + B/Yokohama/UT-K1A/2011(HA+NA)
- ● Yamagata/1/73 + PA-a2272t + B/Yokohama/UT-K1A/2011(HA+NA)
- ✱ Yamagata/1/73 + NP-P40S/M204T + B/Yokohama/UT-K1A/2011(HA+NA)
- ◇ Yamagata/1/73 + M1-M86T + B/Yokohama/UT-K1A/2011(HA+NA)
- ◆ Yamagata/1/73 + NS-3S(+1)g + B/Yokohama/UT-K1A/2011(HA+NA)
- ◇ HY(Vic) + B/Yokohama/UT-K1A/2011(HA+NA)

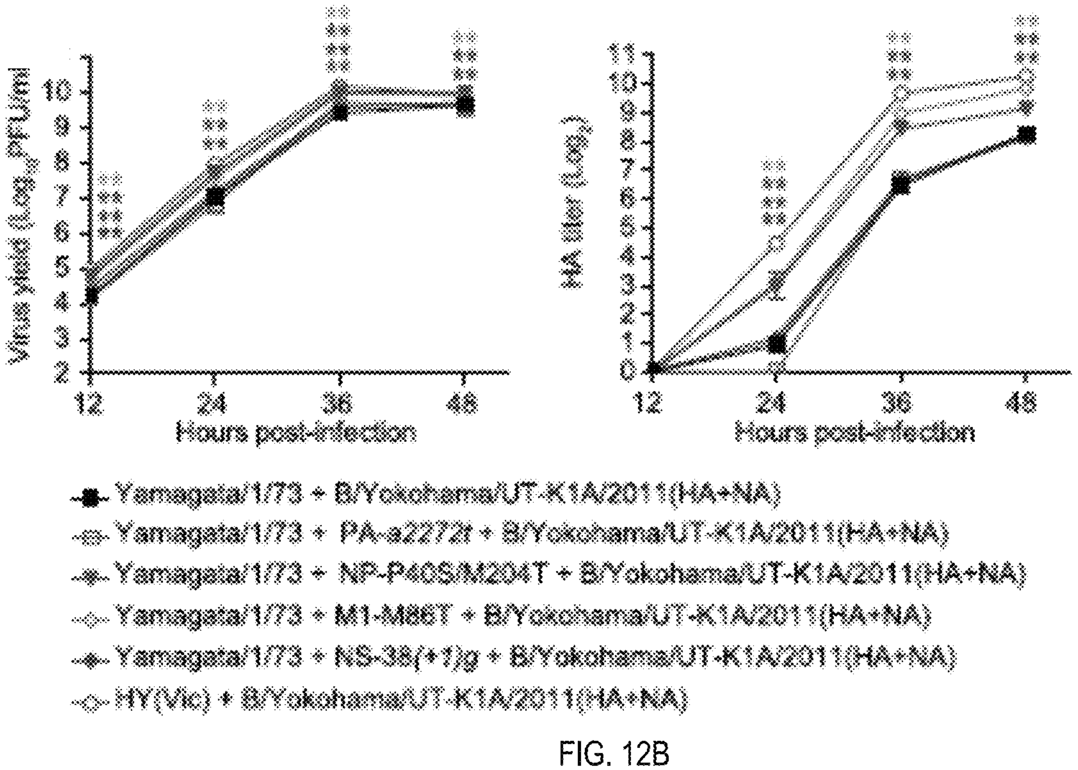

FIG. 12B

Yamagata/1/73 PB2:

AGCAGAAGCGGAGCGTTTTCAAGATGACATTGGCTAAAATTGAATTGTTAAAACAACTGTTAAGGGACAACGAAGCCAAA
ACAGTATTGAAACAAACAACGGTAGACCAATATAACATAATAAGAAAATTCAATACATCAAGAATTGAAAAGAACCCTTC
ATTAAGGATGAAGTGGGCCATGTGTTCTAATTTTCCCTTGGCTCTGACCAAGGGTGATATGGCAAATAGAATCCCCTTGG
AATACAAGGGAATACAACTTAAAACAAATGCTGAAGACATAGGAACCAAAGGCCAAATGTGCTCAATAGCAGCAGTTACC
TGGTGGAATACATATGGACCAATAGGAGACACTGAAGGTTTCGAAAAGGTCTACGAAAGCTTCTTTCTCAGAAAGATGAG
ACTTGACAATGCCACTTGGGGCCGAATAACTTTTGGCCCAGTTGAAAGAGTAAGAAAAAGGGTACTGCTAAACCCTCTCA
CCAAGGAAATGCCTCCAGATGAAGCGAGCAATGTGATAATGGAAATATTGTTCCCTAAGGAAGCAGGAATACCAAGAGAA
TCTACTTGGATACATAGGGAACTGATAAAAGAAAAAAGAGAAAAATTGAAAGGAACGATGATAACTCCCATTGTACTGGC
ATACATGCTTGAGAGAGAATTGGTTGCCCGAAGAAGGTTCCTGCCAGTGGCAGGAGCAACATCAGCTGAGTTCATAGAAA
TGCTACACTGCTTACAAGGTGAAAATTGGAGACAAATATATCACCCAGGAGGGAATAAACTAACTGAATCTAGGTCTCAA
TCAATGATTGTAGCTTGTAGAAAAATAATCAGAAGATCAATAGTCGCATCAAACCCACTAGAGCTAGCTGTAGAAATTGC
AAACAAGACTGTGATAGATACTGAACCTTTAAAATCATGTCTGGCAGCCATAGACGGAGGTGATGTAGCCTGTGACATAA
TGAGAGCTGCATTAGGACTAAAGATCAGACAAAGACAAAGATTTGGACGGCTTGAACTAAAGAGAATATCAGGAAGAGGA
TTCAAAAATGATGAAGAAATATTGATCGGGAACGGAACAATACAGAAGATTGGAATATGGGACGGAGAAGAGGAGTTCCA
TGTAAGATGTGGTGAATGCAGGGGAATATTAAAAAAGAGCAAAATGAGAATGGAAAAACTACTAATAAATTCAGCCAAAA
AGGAGGACATGAAAGATTTAATAATCTTGTGCATGGTATTTTCTCAAGACACTAGGATGTTCCAAGGAGTGAGAGGAGAA
ATAAATTTTCTTAATCGAGCAGGCCAACTTTTATCTCCAATGTACCAACTCCAAAGATATTTTTTGAATAGGAGCAACGA
TCTTTTTGATCAATGGGGGTATGAGGAATCACCCAAAGCAAGTGAACTACATGGGATAAATGAATTAATGAATGCATCTG
ATTATACGTTGAAAGGGGTTGTAGTAACAAAAAATGTGATTGATGACTTTAGTTCTACTGAAACAGAAAAAGTATCTATA
ACAAAAAATCTTAGTTTAATAAAAAGAACTGGGGAAGTCATAATGGGGGCTAATGACGTAAGTGAATTAGAATCACAAGC
TCAGCTAATGATAACATATGATACACCTAAGATGTGGGAGATGGGAACAACCAAAGAACTGGTGCAAAACACCTACCAAT
GGGTGCTAAAAAATTTGGTAACACTGAAGGCTCAGTTTCTTCTAGGAAAAGAAGACATGTTCCAATGGGATGCATTTGAA
GCATTTGAAAGCATAATCCCCCAGAAGATGGCTGGCCAGTACAGTGGATTTGCAAGGGCAGTGCTCAAACAAATGAGAGA
CCAAGAGGTTATGAAAACTGACCAGTTCATAAAGTTGTTGCCTTTCTGTTTCTCACCACCAAAATTAAGGAGCAATGGGG
AGCCTTATCAATTCTTGAGGCTTATATTGAAGGGAGGAGGAGAAAATTTCATCGAAGTAAGGAAAGGGTCCCCTCTATTC
TCCTACAATCCACAAACAGAAGTCCTAACTATATGCGGCAGAATGATGTCATTAAAAGGGAAAATTGAAGATGAAGAAAG
GAATAGATCAATGGGGAATGCAGTATTGGCAGGCTTTCTCGTTAGTGGCAAGTATGACCCAGATCTTGGAGATTTCAAAA
CTATTGAAGAACTTGAAAAGCTAAAACCGGGGGAGAAAGCAAACATCTTACTTTATCAAGGAAAGCCCGTTAAAGTAGTT
AAAAGGAAAAGATATAGTGCTTTATCCAATGACATTTCACAAGGAATTAAGAGACAAAGAATGACAGTTGAGTCCATGGG
GTGGGCCTTGAGCTAATATAAATTTATCCATTAATTCAATAAACACAATTGAGTGAAAAATGCTCGTGTTTCTACT (SEQ ID NO.11)

FIG. 16A

Yamagata/1/73 PB1:

AGCAGAAGCGGAGCCTTTAAGATGAATATAAATCCTTATTTTCTCTTCATAGATGTACCCATACAGGCAGCAATTTCAAC
AACATTCCCATACACCGGTGTTCCCCCTTATTCCCATGGAACGGGAACAGGCTACACAATAGACACCGTGATCAGAACAC
ATGAGTACTCAAACAAGGGAAAACAGTACATTTCTGATGTTACAGGATGTACAATGGTAGATCCAACAAATGGGCCATTA
CCCGAAGACAATGAGCCGAGTGCCTATGCACAATTAGATTGCGTTCTGGAGGCTTTGGATAGAATGGATGAAGAACATCC
AGGTCTGTTTCAAGCAGCCTCACAGAATGCCATGGAGGCACTAATGGTCACAACTGTAGACAAATTAACCCAGGGGAGAC
AGACTTTTGATTGGACAGTATGCAGAAACCAACCTGCTGCAACGGCACTGAACACAACAATAACCTCTTTTAGGTTGAAT
GATTTGAATGGAGCCGACAAGGGTGGATTAGTACCCTTTTGCCAAGATATCATTGATTCATTGGACAGACCTGAAATGAC
TTTCTTCTCAGTAAAGAATATAAAGAAAAAATTGCCTGCTAAAAACAGAAAGGGTTTCCTCATAAAGAGAATACCAATGA
AGGTAAAAGACAGAATAACCAGAGTGGAATACATCAAAAGAGCATTATCATTAAACACAATGACAAAAGATGCTGAAAGA
GGCAAACTAAAAAGAAGAGCGATTGCCACCGCTGGAATACAAATCAGAGGGTTTGTATTAGTAGTTGAAAACTTGGCTAA
AAATATCTGTGAAAATCTAGAACAAAGTGGTTTGCCAGTAGGTGGAAACGAGAAGAAGGCCAAACTGTCAAATGCAGTGG
CCAAAATGCTCAGTAACTGCCCACCAGGAGGGATCAGCATGACAGTAACAGGAGACAATACCAAATGGAATGAATGCTTA
AATCCAAGAATCTTTTTGGCTATGACTGAAAGAATAACCAGAGACAGCCCAATTTGGTTCCGGGATTTTTGTAGTATAGC
ACCGGTCTTGTTCTCCAATAAAATAGCCAGATTGGGAAAAGGGTTTATGATAACAAGCAAAACAAAAAGACTGAAGGCTC
AAATACCTTGTCCTGATCTGTTTAGTATACCATTAGAAAGATATAATGAAGAAACAAGGGCAAAATTGAAAAAGCTGAAA
CCATTCTTCAATGAAGAAGGAACGGCATCTTTGTCGCCTGGGATGATGATGGGAATGTTTAATATGCTATCTACCGTGTT
GGGAGTAGCCGCACTAGGTATCAAAAACATTGGAAACAAAGAATACTTATGGGATGGACTGCAATCTTCTGATGATTTTG
CTCTGTTTGTTAATGCAAAAGATGAAGAGACATGTATGGAAGGAATAAACGACTTTTACCGAACATGTAAACTATTGGGA
ATAAACATGAGCAAAAAGAAAAGTTACTGTAATGAAACTGGAATGTTTGAATTTACAAGCATGTTCTACAGAGATGGATT
TGTATCTAATTTTGCAATGGAACTTCCTTCATTTGGAGTTGCTGGAGTAAATGAATCAGCAGATATGGCAATAGGAATGA
CAATAATAAAGAACAATATGATCAACAATGGGATGGGTCCAGCAACAGCACAAACAGCCATACAATTATTCATAGCTGAT
TATAGATACACCTACAAATGCCACAGGGGAGATTCCAAAGTGGAAGGAAAGAGAATGAAAATTATAAAGGAGCTATGGGA
AAACACTAAAGGAAGAGATGGTCTGTTAGTAGCAGATGGTGGGCCTAACATTTACAATTTGAGAAACTTGCATATCCCAG
AAATAGTATTAAAGTACAACCTAATGGACCCTGAATACAAAGGGCGGTTACTTCATCCTCAAAATCCCTTTGTAGGACAT
TTGTCTATTGAGGGCATCAAAGAGGCAGATATAACCCCAGCACATGGTCCAGTAAAGAAAATGGACTATGATGCGGTGTC
TGGAACTCATAGTTGGAGAACCAAAAGGAACAGATCTATACTAAACACTGATCAGAGGAACATGATTCTTGAGGAACAAT
GCTACGCTAAGTGTTGCAACCTTTTTGAGGCCTGTTTTAACAGTGCATCATACAGGAAACCAGTAGGTCAGCACAGCATG
CTTGAGGCTATGGCCCACAGATTAAGAATGGATGCACGACTAGATTATGAATCAGGAAGAATGTCAAAGGATGATTTTGA
GAAAGCAATGGCTCACCTTGGTGAGATTGGGTACATATAAGCTTCGAAGATGTCTATGGGGTTATTGGTCATCATTGAAT
ACATGCGGTACACAAATGATTAAAATGAAAAAAGGCTCGTGTTTCTACT (SEQ ID NO:12)

FIG. 16B

**Yamagata/1/73 PA *a1406g/c1445t/a2272t*,:**

AGCAGAAGCGGTGCGTTTGATTTGCCATAATGGATACTTTTATTACAAGAAACTTCCAGACTACAATAATACAAAAGGCC
AAAAACACAATGGCAGAATTTAGTGAAGATCCTGAATTACAACCAGCAATGCTATTCAACATCTGCGTCCATCTGGAGGT
CTGCTATGTAATAAGTGATATGAATTTTCTTGATGAAGAAGGAAAAGCATATACAGCATTAGAAGGACAAGGAAAAGAAC
AAAACTTGAGACCACAATATGAAGTGATTGAGGGAATGCCAAGAAACATAGCATGGATGGTTCAAAGATCCTTAGCCCAA
GAGCATGGGATAGAGACTCCAAGGTATCTGGCTGATTTGTTCGATTATAAAACTAAGAGGTTTATAGAAGTTGGAATAAC
AAAGGGATTGGCTGATGATTACTTCTGGAAAAAGAAAGAAAAGCTGGGGAATAGCATGGAACTGATGATATTCAGCTACA
ATCAAGACTATTCGTTAAGTAATGAATCCTCATTGGATGAGGAAGGAAAAGGGAGAGTGCTAAGCAGACTCACAGAACTT
CAGGCTGAGTTAAGTCTGAAAAATCTATGGCAAGTTCTCATAGGAGAAGAAGATATTGAAAAAGGAATTGACTTCAAACT
TGGACAAACAATATCTAAACTAAGGGATATATCTGTTCCAGCTGGTTTCTCCAATTTTGAAGGAATGAGGAGCTACATAG
ACAATATAGATCCTAAAGGAGCAATAGAGAGAAATCTAGCAAGGATGTCTCCCTTAGTATCAGTTACACCTAAAAAGTTG
AAATGGGAGGACCTAAGACCAATAGGGCCTCACATTTACAACCATGAGCTACCAGAAGTTCCATATAATGCCTTTCTTCT
AATGTCTGATGAATTGGGGCTGGCTAATATGACTGAAGGGAAGTCCAAGAAACCGAAGACCTTAGCCAAAGAGTGCCTAG
AAAAGTACTCAACACTACGGGATCAAACTGACCCAATATTAATAATGAAAAGCGAAAAAGCTAATGAACACTTCCTATGG
AAACTGTGGAGGGACTGTGTAAATACAATAAGTAATGAGGAAACAAGTAACGAATTACAGAAAACCAATTATGCCAAGTG
GGCCACAGGAGATGGATTAACATATCAGAAAATAATGAAAGAAGTAGCAATAGATGACGAAACAATGTACCAAGAAGAGC
CCAAAATACCTAACAAATGTAGAGTGGCTGCTTGGGTTCAAACAGAGATGAATCTATTGAGCACTCTGACAAGTAAAAGG
GCCCTGGATCTGCCAGAAATAGGGCCAGACGTAGCACCCGTGGAGCATGTAGGGAGTGAAAGAAGGAAATACTTTGTTAA
TGAAATCAACTACTGTAAGGCCTCTACCGTTATGATGAAGTATGTGCTTTTTCACACTTCATTATTAAATGAAAGCAATG
CCAGTATGGGAAAATATAAAGTAATACCAATAACCAACAGAGTAGTAAATGAAAAGGGAGAAAGTTTTGACATGCTTTAT
GGTCTAGCGGTTAAAGGGCAATCTCATCTGAGGGGAGATACTGATGTTGTAACAGTTGTGACTTTCGAATTTAGTAGTAC
AGATCCCAGAGTGGACTCAGGAAAGTGGCCAAAATATACTGTATTTAGAATTGGCTCCTTATTTGTGAGTGGGAGGGAAA
AATCTGTATACCTATATTGCCGAGTGAATGGTACAAATAAGATCCAAATGAAATGGGGAATGGAAGCTAGAAGATGTCTG
CTTCAATCAATGCAACAAATGGAAGCAATTGTTGAACAAGAATCATCGATACAAGGATATGACATGACCAAAGCTTGTTT
CAAGGGAGACAGAGTGAATAGTCCAAAAACTTTCAGTATTGGGACTCAAGAAGGAAAACTAGTGAAAGGATCCTTTGGGA
AAGCACTAAGAGTAATATTCACCAAATGTTTGATGCACTATGTATTTGGAAATGCCCAATTGGAGGGGTTTAGTGCCGAA
TCTAGGAGACTTCTACTGTTAATTCAGGCATTAAAAGACAGAAAGGGCCCTTGGGTATTCGACTTAGAGGGAATGTATTC
TGGAATAGAAGAATGTATTAGTAACAACCCTTGGGTAATACAGAGTGCATACTGGTTTAATGAATGGTTGGGCTTTGAAA
AAGAGGGGAGTAAAGTATTAGAATCAGTAGATGAAATAATGGATGAATGAAAGAAGGGCATAGTGCTCAATTTGGTACTA
TTTTGTTCATTATGTATCTAAACATCCAATATAAAGAATTGAGAATTAAAAATGCACGTGTTTCTACT (SEQ ID NO:13)

FIG. 16C

**Yamagata/1/73 NP P40S, *c500t*:**

AGCAGAAGCACAGCATTTTCTTGTGAACTTCAAGTACCAACAAAAACTGAAAATCAAAATGTCCAACATGGACATTGAC

GGCATCAACACTGGAATAATTGACAAAACACCAGAAGAAATAACTTCCGGAACCAGTGGGGCAACCAGACCAATCATCAG

ACCAGCAACCCTTGCCTCACCAAGCAACAAACGAACCAGAAACCCATCCCCGGAAAGGGCAACCACAAGCAGTGAAGCTG

ATGTCGGAAGGAAAACCCAAAAGAAACAAACTCCGACAGAGATAAAGAAGAGCGTCTACAATATGGTAGTGAAACTGGGT

GAATTCTACAACCAGATGATGGTCAAAGCTGGACTCAACGATGACATGGAGAGAAACCTAATCCAAAATGCACATGCTGT

GGAAAGAATTCTATTGGCTGCTACTGATGACAAGAAAACTGAATTCCAAAAGAAAAAGAATGCCAGAGACGTCAAAGAAG

GGAAAGAAGAAATAGACCATAACAAAACAGGAGGCACCTTTTACAAGATGGTAAGAGATGATAAAACCATCTACTTCAGC

CCTATAAGAATTACCTTTTTAAAAGAAGAGGTGAAAACAATGTACAAAACCACCATGGGGAGTGACGGTTTCAGTGGACT

AAATCACATCATGATTGGGCATTCACAGATGAACGATGTCTGTTTCCAAAGATCAAAGGCACTAAAAAGAGTTGGACTTG

ACCCTTCATTAATCAGTACTTTTGCAGGAAGCACACTCCCCAGAAGATCAGGTACAACTGGTGTTGCGACCAAAGGAGGT

GGAACTTTAGTGGCAGAAGCCATTCGATTTATAGGAAGAGCAATGGCAGACAGAGGGCTATTGAGAGACATCAGAGCCAA

GACGGCCTATGAAAAGATTCTTCTGAATCTGAAAAACAAGTGCTCTGCGCCCCAACAAAAGGCTCTGGTTGATCAAGTGA

TCGGAAGTAGAAATCCAGGGATTGCAGACATAGAAGATCTCACCCTGCTTGCTCGAAGTATGGTCGTTGTTAGGCCCTCT

GTAGCAAGCAAAGTGGTGCTTCCCATAAGCATCTATGCTAAAATACCTCAACTGGGGTTCAACGTTGAAGAATACTCTAT

GGTTGGGTATGAAGCCATGGCTCTTTATAATATGGCAACACCTGTTTCCATATTAAGAATGGGAGACGATGCAAAAGATA

AATCACAATTATTCTTCATGTCTTGCTTTGGAGCTGCCTATGAAGACCTAAGAGTTCTGTCTGCACTAACAGGCACGGAA

TTCAAGCCTAGGTCAGCATTAAAGTGCAAAGGTTTCCACGTTCCAGCAAAGGAGCAAGTGGAAGGAATGGGGGCAGCTCT

GATGTCCATCAAGCTCCAGTTTTGGGCTCCAATGACCAGATCTGGGGGAATGAAGTAGGTGGAGACGGAGGGTCTGGTC

AAATAAGTTGCAGCCCCGTGTTTGCAGTAGAAAGACCTATTGCTCTAAGCAAGCAAGCTGTAAGAAGAATGCTGTCAATG

AATATTGAGGGACGTGATGCAGATGTCAAAGGAAATCTACTCAAGATGATGAATGATTCAATGGCTAAGAAAACCAATGG

AAATGCTTTCATTGGGAAGAAAATGTTCCAAATATCAGACAAAAACAAAACCAATCCCGTTGAGATTCCAATTAAGCAGA

CCATCCCCAGTTTCTTCTTTGGGAGGGACACAGCAGAGGATTATGATGACCTCGATTATTAAAGCAACAAAATAGACACT

ATGGCTGTGATTGTTTCAGTACGTTTGGAATGTGGGTGTTTACTCTTATTGAAATAAATGTAAAAAATGCTGTTGTTTCT

ACT (SEQ ID NO:14)

FIG. 16D

**Yamagata/1/73 NP P40S/M204T, *c500t*:**

AGCAGAAGCACAGCATTTTCTTGTGAACTTCAAGTACCAACAAAAACTGAAAATCAAAATGTCCAACATGGACATTGAC
GGCATCAACACTGGAATAATTGACAAAACACCAGAAGAAATAACTTCCGGAACCAGTGGGGCAACCAGACCAATCATCAG
ACCAGCAACCCTTGCCTCACCAAGCAACAAACGAACCAGAAACCCATCCCCGGAAAGGGCAACCACAAGCAGTGAAGCTG
ATGTCGGAAGGAAAACCCAAAAGAAACAAACTCCGACAGAGATAAAGAAGAGCGTCTACAATATGGTAGTGAAACTGGGT
GAATTCTACAACCAGATGATGGTCAAAGCTGGACTCAACGATGACATGGAGAGAAACCTAATCCAAAATGCACATGCTGT
GGAAAGAATTCTATTGGCTGCTACTGATGACAAGAAAACTGAATTCCAAAAGAAAAAGAATGCCAGAGACGTCAAAGAAG
GGAAAGAAGAAATAGACCATAACAAAACAGGAGGCACCTTTTACAAGATGGTAAGAGATGATAAAACCATCTACTTCAGC
CCTATAAGAATTACCTTTTTAAAAGAAGAGGTGAAAACAATGTACAAAACCACCATGGGGAGTGACGGTTTCAGTGGACT
AAATCACATCATGATTGGGCATTCACAGACGAACGATGTCTGTTTCCAAAGATCAAAGGCACTAAAAAGAGTTGGACTTG
ACCCTTCATTAATCAGTACTTTTGCAGGAAGCACACTCCCCAGAAGATCAGGTACAACTGGTGTTGCGACCAAAGGAGGT
GGAACTTTAGTGGCAGAAGCCATTCGATTTATAGGAAGAGCAATGGCAGACAGAGGGCTATTGAGAGACATCAGAGCCAA
GACGGCCTATGAAAAGATTCTTCTGAATCTGAAAAACAAGTGCTCTGCGCCCCAACAAAAGGCTCTGGTTGATCAAGTGA
TCGGAAGTAGAAATCCAGGGATTGCAGACATAGAAGATCTCACCCTGCTTGCTCGAAGTATGGTCGTTGTTAGGCCCTCT
GTAGCAAGCAAAGTGGTGCTTCCCATAAGCATCTATGCTAAAATACCTCAACTGGGGTTCAACGTTGAAGAATACTCTAT
GGTTGGGTATGAAGCCATGGCTCTTTATAATATGGCAACACCTGTTTCCATATTAAGAATGGGAGACGATGCAAAAGATA
AATCACAATTATTCTTCATGTCTTGCTTTGGAGCTGCCTATGAAGACCTAAGAGTTCTGTCTGCACTAACAGGCACGGAA
TTCAAGCCTAGGTCAGCATTAAAGTGCAAAGGTTTCCACGTTCCAGCAAAGGAGCAAGTGGAAGGAATGGGGGCAGCTCT
GATGTCCATCAAGCTCCAGTTTTGGGCTCCAATGACCAGATCTGGGGGGAATGAAGTAGGTGGAGACGGAGGGTCTGGTC
AAATAAGTTGCAGCCCCGTGTTTGCAGTAGAAAGACCTATTGCTCTAAGCAAGCAAGCTGTAAGAAGAATGCTGTCAATG
AATATTGAGGGACGTGATGCAGATGTCAAAGGAAATCTACTCAAGATGATGAATGATTCAATGGCTAAGAAAACCAATGG
AAATGCTTTCATTGGGAAGAAAATGTTCCAAATATCAGACAAAAACAAAACCAATCCCGTTGAGATTCCAATTAAGCAGA
CCATCCCCAGTTTCTTCTTTGGGAGGGACACAGCAGAGGATTATGATGACCTCGATTATTAAAGCAACAAAATAGACACT
ATGGCTGTGATTGTTTCAGTACGTTTGGAATGTGGGTGTTTACTCTTATTGAAATAAATGTAAAAAATGCTGTTGTTTCT
ACT (SEQ ID NO:15)

FIG. 16E

Yamagata/1/73 M R77K:

AGCAGAAGCACGCACTTTCTTAAAATGTCGCTGTTTGGAGACACAATTGCCTACCTGCTTTCACTAACAGAAGATGGAGA

AGGCAAAGCAGAACTAGCGGAAAAATTACACTGTTGGTTCGGTGGGAAAGAATTCGATCTAGACTCTGCTTTGGAATGGA

TAAAAAACAAAAGATGCCTAACTGATATACAAAAAGCACTAATTGGTGCCTCTATCTGCTTTTTGAAACCCAAAGACCAA

GAAAGAAAAAGAAAATTCATCACAGAGCCCCTGTCAGGAATGGGAACAACAGCAACAAAAAAGAAAGGCCTGATTCTAGC

TGAAAGAAAAATGAGAAGATGTGTGAGTTTTCATGAGGCATTTGAAATAGCAGAAGGCCATGAAAGCTCAGCACTACTAT

ATTGTCTCATGGTCATGTACCTGAACCCTGGAAATTATTCAATGCAAGTAAAACTAGGAACGCTCTGTGCTTTATGCGAG

AAACAAGCATCACATTCACACAGAGCTCATAGCAGAGCAGCAAGATCTTCAGTGCCTGGAGTGAGGCGAGAAATGCAAAT

GGTTTCAGCTATGAACACAGCAAAAACAATGAATGGAATGGGGAAGGGAGAAGACGTCCAAAAACTGGCAGAAGAGCTGC

AAAGCAACATTGGAGTATTGAGATCTCTGGGGGCAAGTCAAAAGAATGGAGAAGGAATTGCAAAGGATGTAATGGAAGTG

CTAAAGCAGAGCTCCATGGGAAATTCAGCTCTTGTGAAGAAATACCTATAATGCTCGAGCCATTTCAGATTCTTTCAATT

TGCTCTTTCATTTTATCGGCTCTCCATTTCATGGGCTGGACAATAGGGCATTTAAATCAAATAAAAAGAGGAGTAAACCT

AAAAATACGAATAAGAAATCCAAATAAAGAGACAATAAATAGAGAGGTATCAATTTTGAGACACAGTTACCAAAAAGAAA

TCCAAGCCAAAGAAACAATAAAGGAAGTACTCTCTGACAACATGGAGAGATTGAGTGACCACATAGTAATTGAGGGGCTT

TCTGCTGAAGAGATAATAAAAATGGGTGAAACAGTTTTGGAGGTAGAAGAATTGCATTAAACCCAATTTTCACCGTATTT

CTTACTATGCATTTAAGCAAATTGTAATCAATGTCAGCAAATAAACTGGAAAAAGTGCGTTGTTTCTACT (SEQ ID NO:16)

FIG. 16F

Yamagata/1/73 M M86T:

AGCAGAAGCACGCACTTTCTTAAAATGTCGCTGTTTGGAGACACAATTGCCTACCTGCTTTCACTAACAGAAGATGGAGA

AGGCAAAGCAGAACTAGCGGAAAAATTACACTGTTGGTTCGGTGGGAAAGAATTCGATCTAGACTCTGCTTTGGAATGGA

TAAAAAACAAAAGATGCCTAACTGATATACAAAAAGCACTAATTGGTGCCTCTATCTGCTTTTTGAAACCCAAAGACCAA

GAAAGAAAAAGAAGATTCATCACAGAGCCCCTGTCAGGAACGGGAACAACAGCAACAAAAAAGAAAGGCCTGATTCTAGC

TGAAAGAAAAATGAGAAGATGTGTGAGTTTTCATGAGGCATTTGAAATAGCAGAAGGCCATGAAAGCTCAGCACTACTAT

ATTGTCTCATGGTCATGTACCTGAACCCTGGAAATTATTCAATGCAAGTAAAACTAGGAACGCTCTGTGCTTTATGCGAG

AAACAAGCATCACATTCACACAGAGCTCATAGCAGAGCAGCAAGATCTTCAGTGCCTGGAGTGAGGCGAGAAATGCAAAT

GGTTTCAGCTATGAACACAGCAAAAACAATGAATGGAATGGGGAAGGGAGAAGACGTCCAAAAACTGGCAGAAGAGCTGC

AAAGCAACATTGGAGTATTGAGATCTCTGGGGGCAAGTCAAAAGAATGGAGAAGGAATTGCAAAGGATGTAATGGAAGTG

CTAAAGCAGAGCTCCATGGGAAATTCAGCTCTTGTGAAGAAATACCTATAATGCTCGAGCCATTTCAGATTCTTTCAATT

TGCTCTTTCATTTTATCGGCTCTCCATTTCATGGGCTGGACAATAGGGCATTTAAATCAAATAAAAAGAGGAGTAAACCT

AAAAATACGAATAAGAAATCCAAATAAAGAGACAATAAATAGAGAGGTATCAATTTTGAGACACAGTTACCAAAAAGAAA

TCCAAGCCAAAGAAACAATAAAGGAAGTACTCTCTGACAACATGGAGAGATTGAGTGACCACATAGTAATTGAGGGGCTT

TCTGCTGAAGAGATAATAAAAATGGGTGAAACAGTTTTGGAGGTAGAAGAATTGCATTAAACCCAATTTTCACCGTATTT

CTTACTATGCATTTAAGCAAATTGTAATCAATGTCAGCAAATAAACTGGAAAAAGTGCGTTGTTTCTACT (SEQ ID NO:17)

FIG. 16G

**Yamagata/1/73 NS *a39g* K176Q :**

AGCAGAAGCAGAGGATTTGTTTAGTCACTGGCAAACGGGAAAAAATGGCGGACAACATGACCACAACACAAATTGAGGTG

GGTCCGGGAGCAACCAATGCCACTATAAACTTTGAAGCAGGAATTTTGGAGTGCTATGAAAGGCTTTCATGGCAAAGAGC

CCTTGACTACCCTGGTCAAGACCGCCTAAACAGACTAAAGAGAAAATTAGAATCAAGAATAAAGACTCACAACAAAAGTG

AGCCTGAAAGTAAAAGGATGTCTCTTGAAGAGAGAAAAGCAATTGGGGTAAAAATGATGAAAGTGCTCCTATTTATGAAC

CCATCTGCTGGAATTGAAGGGTTTGAGCCATACTGTATGAAAAATTCCTCCAATAGCAACTGCCCAAACTGCAATTGGGC

CGATTACCCTCCAACATCAGGAAAGTGCCTTGATGACATAGAAGAAGAACCGGAGAATGTTGATGACCCAACTGAAATAG

TATTAAGGGACATGAACAACAAAGATGCAAGGCAAAAGATAAAAGAGGAAGTAAACACTCAGAAAGAAGGGAAGTTCCGT

TTGACAATACAAAGGGATATACGTAATGTGTTGTCCTTGAGAGTGTTGGTAAACGGAACATTCCTCAAGCACCCTAATGG

ATACAAGTCCTTATCAACTCTGCATAGATTGAATGCATATGACCAGAGTGGAAGGCTTGTTGCTAAACTTGTTGCTACTG

ATGATCTTACAGTGGAGGATGAAGAAGATGGCCATCGGATCCTCAACTCACTCTTCGAGCGTTTTAATGAAGGACATTCA

AAGCCAATTCGAGCAGCTGAAACTGCGGTGGGAGTCTTATCCCAATTTGGTCAAGAGCACCGATTATCACCAGAGGAGGG

AGACAATTAGACTGGTTACGGAAGAACTTTATCTTTTAAGTAAAAGAATTGATGATAACATATTGTTCCACAAAACAGTA

ATAGCTAACAGCTCCATAATAGCTGACATGATTGTATCATTATCATTATTGGAAACATTGTATGAGATGAAGGATGTGGT

TGAAGTGTACAGCAGGCAGTGCTTGTGAATTTAAAATAAAAATCCTCTTGTTACTACT (SEQ ID NO:18)

FIG. 16H

**Yamagata/1/73 NS *38(+1)g*:**

AGCAGAAGCAGAGGATTTGTTTAGTCACTGGCAAACGGGAAAAAAATGGCGGACAACATGACCACAACACAAATTGAGGT
GGGTCCGGGAGCAACCAATGCCACTATAAACTTTGAAGCAGGAATTTTGGAGTGCTATGAAAGGCTTTCATGGCAAAGAG
CCCTTGACTACCCTGGTCAAGACCGCCTAAACAGACTAAAGAGAAAATTAGAATCAAGAATAAAGACTCACAACAAAAGT
GAGCCTGAAAGTAAAAGGATGTCTCTTGAAGAGAGAAAAGCAATTGGGGTAAAAATGATGAAAGTGCTCCTATTTATGAA
CCCATCTGCTGGAATTGAAGGGTTTGAGCCATACTGTATGAAAAATTCCTCCAATAGCAACTGCCCAAACTGCAATTGGG
CCGATTACCCTCCAACATCAGGAAAGTGCCTTGATGACATAGAAGAAGAACCGGAGAATGTTGATGACCCAACTGAAATA
GTATTAAGGGACATGAACAACAAAGATGCAAGGCAAAAGATAAAAGAGGAAGTAAACACTCAGAAAGAAGGGAAGTTCCG
TTTGACAATAAAAAGGGATATACGTAATGTGTTGTCCTTGAGAGTGTTGGTAAACGGAACATTCCTCAAGCACCCTAATG
GATACAAGTCCTTATCAACTCTGCATAGATTGAATGCATATGACCAGAGTGGAAGGCTTGTTGCTAAACTTGTTGCTACT
GATGATCTTACAGTGGAGGATGAAGAAGATGGCCATCGGATCCTCAACTCACTCTTCGAGCGTTTTAATGAAGGACATTC
AAAGCCAATTCGAGCAGCTGAAACTGCGGTGGGAGTCTTATCCCAATTTGGTCAAGAGCACCGATTATCACCAGAGGAGG
GAGACAATTAGACTGGTTACGGAAGAACTTTATCTTTTAAGTAAAAGAATTGATGATAACATATTGTTCCACAAAACAGT
AATAGCTAACAGCTCCATAATAGCTGACATGATTGTATCATTATCATTATTGGAAACATTGTATGAGATGAAGGATGTGG
TTGAAGTGTACAGCAGGCAGTGCTTGTGAATTTAAAATAAAAATCCTCTTGTTACTACT (SEQ ID NO:19)

FIG. 16I

INFLUENZA B VIRUS REPLICATION FOR VACCINE DEVELOPMENT

CROSS-REFERENCE TO RELATED APPLICATIONS

This application claims the benefit of the filing date of U.S. application Ser. No. 62/297,400, flied on Feb. 19, 2016, the disclosure of which is incorporated by reference herein.

STATEMENT OF GOVERNMENT RIGHTS

This invention was made with government support under HHSN272201400008C awarded by the National Institutes of Health. The government has certain rights in the invention.

BACKGROUND

Influenza B viruses are a major cause of respiratory disease in humans. The segmented nature of the influenza virus genome allows for reassortment of segments during virus replication in cells infected with two or more influenza viruses. The reassortment of segments, combined with genetic mutation and drift, can give rise to a myriad of divergent strains of influenza virus over time. The new strains exhibit antigenic variation in their hemagglutinin (HA) and/or neuraminidase (NA) proteins, and in particular the gene coding for the HA protein has a high rate of variability. The predominant current practice for the prevention of flu is vaccination. As the influenza HA protein is the major target antigen for the protective immune responses of a host to the virus and is highly variable, the isolation of influenza virus and the identification and characterization of the HA antigen in viruses associated with recent outbreaks is important for vaccine production. Based on prevalence and prediction, a vaccine is designed to stimulate a protective immune response against the predominant and expected influenza virus strains (Park at al., 2004).

There are three general types of influenza viruses, Type A, Type B and Type C, which are defined by the absence of serological crossreactivity between their internal proteins. Influenza Type B viruses are further classified into two lineages based on antigenic and genetic differences of the glycoprotein HA.

The burden of human infections with influenza A and B viruses is substantial, and the impact of influenza B virus infections can exceed that of influenza A virus infections in some seasons. Over the past few decades, viruses of two influenza B virus lineages (Victoria and Yamagata) have circulated in humans, and both lineages are now represented in influenza vaccines, as recommended by the World Health Organization. Influenza B virus vaccines for humans have been available for more than half a century, yet no systematic efforts have been undertaken to develop high-yield candidates. On the basis of their antigenic properties, influenza viruses are divided into three types (influenza A, B, and C); however, only type A and B influenza viruses cause human health concerns. Influenza A viruses are further divided into 18 hemagglutinin (HA, the major viral antigen) and 11 neuraminidase (NA, the second viral antigen) subtypes that are referred to as H1-H18 and N1-N11, respectively. Influenza A viruses are responsible for annual epidemics (caused by antigenic escape variants possessing point mutations in the antigenic epitopes of HA) and occasional pandemics. Pandemics are caused by avian or avian/human/swine reassortant influenza viruses that encode an HA protein to which humans lack protective immune responses. The epidemiology of influenza B viruses differs from that of influenza A viruses. Influenza B viruses primarily circulate in humans and do not cause pandemics. Nevertheless, the impact of influenza B virus infections on influenza-related morbidity and mortality is substantial and has exceeded that of influenza A viruses in some seasons (Paul-Glezen et al., 2013; Tafalla et al., 2016; van de Sandt et al., 2015). Until 1983, only one influenza B virus lineage was circulating in humans. Since then, two lineages (Victoria, named after B/Victoria/2/1987, and Yamagata, named after B/Yamagata/16/1988) can be distinguished genetically and antigenically on the basis of their HA (Paul-Glezen at al., 2013; van de Sandt at al., 2015; Rota et al., 1990). Until 2000, one of these two lineages tended to dominate each season; however, since 2001 both influenza B virus lineages have been cocirculating in human populations each year (Belshe, 2010; Belshe et al., 2010).

Until recently, most influenza vaccines were trivalent: that is, they were comprised of influenza A strains of the H1N1 and H3N2 subtypes, and an influenza B virus strain. Two studies demonstrated that the recommended influenza B vaccine strain matched the dominant strain of the particular influenza season only half the time (Belshe, 2010; Ambrose et al., 2010). On the basis of these findings and the continuing cocirculation of Yamagata- and Victoria-lineage viruses, in 2012 the World Health Organization (WHO) recommended including influenza B viruses of both lineages in human influenza vaccines. Accordingly, most seasonal influenza vaccines are now quadrivalent.

Many influenza vaccines are generated by combining the HA and NA viral RNA (vRNA) segments of WHO-recommended vaccine strains with the remaining six vRNA segments of a "backbone" strain. For live attenuated influenza A and B vaccine viruses, virus backbones were developed in the 1960s (Maassab, 1969). Many inactivated influenza A virus vaccines are based on the A/Puerto Rico/8/34 (H1N1; PR8) virus backbone, which was selected because of its efficient replication in embryonated chicken eggs. For inactivated influenza B vaccines, the B/Lee/40, B/Panama/45/90, or wild-type strains have been used as backbones (www.who.int/influenza/vaccines/virus/recommendations/summary_b_vic_cvv_nh1516.pdf).

SUMMARY

The present invention relates to several mutations in the 'internal' genes of influenza B virus, as well as several mutations in the viral glycoproteins HA and NA of influenza B viruses, that enhance viral titers and/or HA yields in cultured cells and may also enhance viral titers and/or HA yields in embryonated chicken eggs. The exemplary reassortant or recombinant parental influenza B viruses represent the two major influenza B virus lineages (i.e., the 'B/Victoria' and 'B/Yamagata' lineages). Virus libraries were generated for each lineage, which libraries were then passaged in selected cells, and mutations were identified that enhanced viral growth. The use of one or more of these mutations in vaccine virus master strains (where the internal viral genes, the "backbone," are used with selected HA and NA, e.g., those of circulating strains or predicted to be circulating strains), result in higher virus titers in virus cultured in cells in vitro and/or embryonated chicken eggs, allowing more efficient influenza B virus growth, and more rapid and cost-effective vaccine production.

Several strategies may be employed (including random mutagenesis and the comprehensive testing of growth-enhancing mutations) to develop influenza B viruses, e.g., based on reassortant or recombinant B/Yamagata- and B/Victoria-viruses, with enhanced properties, e.g., viruses that replicate to high titers, e.g., $10^8$ PFU/mL or more, e.g., $5\times10^9$, $10^9$, $5\times10^0$ or $10^{10}$ PFU/mL in cultured cells and/or embryonated chicken eggs. As discussed herein, a number of growth-enhancing mutations (both amino acid and non-coding nucleotide substitutions) were identified that increase the yield of influenza B viruses. Individual growth-enhancing amino acid residues in an influenza B virus polypeptide or in non-coding nucleotide sequence(s) in an influenza B virus segment, may be combined with one or more other growth-enhancing residues in the same influenza virus polypeptide or non-coding nucleotides in the same viral segment(s), or with one or more other growth-enhancing residues and/or nucleotide substitution(s) in other influenza virus polypeptide(s) or viral segment(s), respectively, e.g., growth-enhancing nucleotides in promoter sequences or in nucleotides between promoter sequences and an open reading frame. In particular, virus libraries possessing random mutations in the six "internal" influenza B viral RNA segments (those not encoding the major viral antigens, hemagglutinin (HA) and neuraminidase NA)) were screened for mutants that confer efficient replication. Candidate viruses that supported high yield in cell culture were tested with the HA and NA genes of eight different viruses of the Victoria and Yamagata lineages. Combinations of mutations that increased the titers of candidate vaccine viruses in mammalian cells used for human influenza vaccine virus propagation were identified and used in embryonated chicken eggs, the most common propagation system for influenza viruses, were identified. These influenza B virus vaccine backbones can be used for improved vaccine virus production.

For example, one or more growth-enhancing residues in a NP protein, for instance, 1, 2, 3, or 4 or more, growth-enhancing residues in NP, 1, 2, 3, or 4 or more, growth-enhancing residues in a M protein (such as 1, 2, 3, or 4 growth-enhancing residues in BM2 or 1, 2, 3, or 4 growth-enhancing residues in M1), 1, 2, 3, or 4 or more growth-enhancing residues in PA, or 1, 2, 3, or 4 growth-enhancing residues in NS1, or growth-enhancing nucleotides in viral non-coding sequences of NP, PA, NS, or in other viral segments, may be combined when preparing influenza B viruses, e.g., for a vaccine, to enhance viral titers. In one embodiment, growth-enhancing nucleotides in non-coding sequences may be introduced to a viral segment, or when present in a viral segment may be selected for inclusion in an influenza B virus. In one embodiment, one or more, e.g., 1, 2, 3, 4 or 5 or more growth-enhancing residues in HA and/or in NA may be introduced into, or when present in a HA or NA selected for inclusion in, a HA viral segment or a NA viral segment in an influenza virus. In one embodiment, the one or more growth-enhancing residues may enhance viral growth by at least 1.2, 2, 2.8, 4, 3, 5, 6, 8, 10, 100, or 200 fold or more.

In one embodiment, this disclosure provides isolated recombinant, e.g., reassortant, influenza B viruses with selected amino acid residues at one or more specified positions (including those described herein) in one or more viral segments for PA, PB1, PB2, NP, M (encoding M1 and BM2 proteins), and/or NS (encoding NS1 and NS2 proteins), e.g., in selected amino acid residues at specified positions of, for example, M1 and BM2; M1, BM2, and NS1; NP; M1 and NS1; NP, M1 and BM2; NP and M1; NP, M1 and NS1; BM2 and NS1; BM2, NS1 and PA; M1, BM2 and PA; M1, BM2, NP and PA; and optionally also including growth-enhancing non-coding nucleotide substitution(s), and in one embodiment, including HA and NA genes/proteins of interest, e.g., from annual and pandemic strains, or HA and NA viral segments with selected amino acid residues described herein, which viruses are produced more efficiently and cost-effectively via cell culture (in MDCK or Vero cells) or in embryonated chicken eggs.

In one embodiment, the reassortant or recombinant influenza B virus has an amino acid residue at position 28, 40, 51, 52, 57, 204, and/or 343, in NP, and/or a nucleotide other than c at position 500 in NP vRNA, or any combination thereof, that results in enhanced growth in cells including MDCK cells, Vero cells and/or eggs relative to a corresponding virus with, for instance, an alanine, proline, proline, glutamic acid, serine, methionine or proline at position 28, 40, 51, 52, 57, 204 and 343, respectively, in NP, i.e., the residue at position 28, 40, 51, 52, 57, 204 or 343, respectively, in the NP segment in the recombinant influenza B virus is not an alanine, proline, proline, glutamic acid, serine, methionine or proline but is a residue that is correlated with enhanced replication in MDCK cells, Vero cells or eggs. The recombinant virus may also optionally include other selected amino acid residues at one or more specified positions in one or more of M1, BM2, PA, PB2, and/or NS1, such as those described herein, and optionally PB1. In one embodiment, the recombinant influenza B virus has an amino acid residue at position 28, 40, 51, 52, 57, 204, and/or 343 in NP that results in enhanced interaction with one or more host proteins in MDCK cells, Vero cells or eggs relative to a corresponding virus with, for instance, alanine, proline, proline, glutamic acid, seine, methionine or proline at position 28, 40, 51, 52, 57, 204, and/or 343, respectively, in NP. In one embodiment, the recombinant influenza B virus has growth-enhancing residues in NP including but not limited to a residue other than alanine at position 28, other than proline at position 40, other than proline at position 51, other than glutamic acid at position 52, other than serine at position 57, other than methionine at position 204, and/or other than proline at position 343, and/or a nucleotide other than g at nucleotide position 1795 (italics indicates a nucleotide; position is relative to positive sense cRNA), or any combination thereof. In one embodiment, the recombinant influenza B virus has threonine at position 28, serine at position 40, glutamine at position 51, lysine at position 52, glycine at position 57, threonine at position 214, and/or threonine at position 343 in NP, nucleotide a at nucleotide position 1795, and/or nucleotide t at nucleotide position 500 in NP vRNA, or any combination thereof, as well as optionally selected amino acid residues at one or more specified positions in M, PA, PB1, PB2, and/or NS viral segments.

In one embodiment, the reassortant or recombinant influenza B virus has an amino acid residue at position 34, 54, 77, 86, and/or 97 in M1 that results in enhanced growth in cells including MDCK cells, Vero cells or eggs relative to a corresponding virus with, for instance, glycine, aspartic acid, arginine, methionine or isoleucine at position 34, 54, 77, 86, or 97, respectively, in M1, i.e., the residue at position 34, 54, 77, 86, or 97, respectively, in M1 in the M segment in the recombinant influenza virus is not glycine, aspartic acid, arginine, methionine or isoleucine but is a residue that is correlated with enhanced replication in MDCK cells, Vero cells or eggs. The recombinant virus may also optionally include selected amino acid residues at one or more specified positions PA, BM2, PB2, NP, and/or NS1, such as those described herein, and optionally PB1. in one embodiment, the recombinant influenza B virus has an amino acid residue at position 34, 54, 77, 86, and/or 97 in M1 that results in enhanced interaction with one or more host proteins in MDCK cells, Vero cells or eggs relative to a corresponding virus with, for instance, glycine, aspartic acid, arginine, methionine or isoleucine at position 34, 54, 77, 86, or 97, respectively, in M1. In one embodiment, the recombinant influenza B virus has a valine or asparagine, glycine, lysine, threonine or asparagine at position 34, 54, 77, 86, or 97, respectively, in M1 as well as optionally selected amino acid residues at one or more specified positions NP, PA, PB1, PB2, and/or NS.

In one embodiment, the reassortant or recombinant influenza B virus has an amino acid residue at position 26, position 27, position 58, or position 80 in BM2 that results in enhanced growth in cells including MDCK cells, Vero cells or eggs relative to a corresponding virus with, for instance, glycine, histidine, histidine or arginine, at residue 26, 27, 58 or 80, respectively, in BM2. The recombinant virus may also optionally include as selected amino acid residues at one or more specified positions NS1, PA, NP, PB2, and/or M1 which are described herein. In one embodiment, the residue in BM2 at position 26 is arginine, at position 27 is arginine, position 58 is arginine, or position 80 is glycine.

In one embodiment, the reassortant or recombinant influenza B virus has an amino acid residue other than tyrosine at position 42, other than methionine at position 117, other than lysine at position 176, and/or other than serine at position 252, a nucleotide other than a at position 39, a nucleotide insertion after position 38, or any combination thereof, in NS1 that results in enhanced growth in cells including MDCK cells, Vero cells or eggs relative to a corresponding virus with, for instance, tyrosine at position 42, methionine at position 117, lysine at position 176, serine at position 252, or an a at position 39. The recombinant virus may also optionally include selected amino acid residues at one or more specified positions PA, PB2, BM2, NP, and/or M1, e.g., those which are described herein, and optionally PB1. In one embodiment, the recombinant influenza virus has asparagine at position 42, tyrosine at position 117, glutamine at position 176, threonine at position 252, a g at nucleotide position 39, an additional g after nucleotide position 38, or any combination thereof, in NS1, and optionally selected amino acid residues at one or more specified positions PA, PB2, BM2, NP, and/or M1 which are described herein.

In one embodiment, the reassortant or recombinant influenza B virus has an amino acid residue in PA other than tyrosine at position 387, other than valine at position 434, other than aspartic acid at position 494, other than threonine at position 524, and/or a nucleotide other than a at position 2272, a nucleotide other than g at position 2213, a nucleotide other than a at position 1406, and/or a nucleotide other than c at position 1445 in PA vRNA, or any combination thereof, that results in enhanced growth in cells including MDCK cells, Vero cells or eggs relative to a corresponding virus with, for instance, tyrosine at position 387, valine at position 434, aspartic acid at position 494, threonine at position 524, and/or a nucleotide a at position 2272, g at position 2213, a at position 1406, or c at position 1445, or any combination thereof. The recombinant virus may also optionally include selected amino acid residues at one or more specified positions NS1, BM2, NP, PB2, and/or M1, e.g., those which are described herein, and optionally PB1. In one embodiment, the recombinant influenza virus has histidine at position 387, alanine at position 434, or asparagine at position 494, alanine at position 534 in PA, and/or t at position 2272, a at position 2213, g at position 1406, and/or t at position 1445 in PA vRNA, or any combination thereof.

In one embodiment, the reassortant or recombinant influenza B virus has an amino acid residue in PB2 other than asparagine at position 16 that results in enhanced growth in cells including MDCK cells, Vero cells or eggs relative to a corresponding virus with, for instance, asparagine at position 16. The recombinant virus may also optionally include selected amino acid residues at one or more specified positions PA, NS1, BM2, NP, and/or M1, e.g., those which are described herein, and optionally PB1. In one embodiment, the recombinant influenza virus has serine at position 16 in PB2.

In one embodiment, the reassortant or recombinant influenza B virus has an amino acid residue in HA1 other than threonine at position 34, other than arginine at position 98, other than lysine at position 129, other than asparagine at position 168, other than asparagine at position 194, and/or other than threonine at position 196, and/or in HA2 a residue other than lysine at position 39, other than serine at position 56, other than lysine at position 61, or other than aspartic acid at position 112, or any combination thereof, that results in enhanced growth in cells including MDCK cells, Vero cells or eggs relative to a corresponding virus with, for instance, in HA1 threonine at position 34, arginine at position 98, lysine at position 129, asparagine at position 168, asparagine at position 194, and/or threonine at position 196, and/or in HA2 lysine at position 39, serine at position 56, lysine at position 61, aspartic acid at position 112. The recombinant virus may also include selected amino acid residues at one or more specified positions PA, BM2, PB2, NS1, NP, and/or M1, e.g., those which are described herein, and/or PB1. In one embodiment, the recombinant influenza virus has isoleucine at position, 34, glutamic acid at position 129, glutamic acid or aspartic acid at position 168, proline, alanine, isoleucine or asparagine at position 196, lysine at position 98, aspartic acid at position 194, glycine at position 39 (in HA2), glycine at position 56 (in HA2), asparagine at position 51 (in HA2), or glutamic acid at position 112 (in HA2), or any combination thereof.

In one embodiment, the reassortant or recombinant influenza B virus has an amino acid residue other than threonine (T) at position 76, other than arginine (R) at position 102, other than glutamic acid (E) at position 105, other than proline (P) at position 139, other than asparagine (N) at position 169, other than glycine (G) at position 434, other than threonine at position 436, and/or other than aspartic acid (D) at position 457, or any combination thereof, in NA that results in enhanced growth in cells including MDCK cells, Vero cells or eggs relative to a corresponding virus with, for instance, T at position 76, R at position 102, E at position 105, P at position 139, N at position 169, G at position 434, T at position 436, and/or D at position 457 in NA, which recombinant virus may also optionally include selected amino acid residues at one or more specified positions PA, PB2, BM2, NP, NS1, and/or M1, e.g., those which are described herein, PB1. In one embodiment, the recombinant influenza B virus has methionine (M) at position 76, lysine (K) at position 102, lysine (K) at position 105, serine (S) at position 139, threonine (T) at position 169, glutamic acid (E) at position 434, methionine (M) at position 436, and/or asparagine (N) at position 457, or any combination thereof.

In one embodiment, the invention provides an isolated recombinant reassortant influenza virus having six “internal” gene segments from a vaccine influenza virus with two or more of the selected amino acid residues at specified positions described herein, and a NA gene segment selected from a first influenza virus isolate, and a HA gene segment from the same isolate or a different isolate.

In one embodiment, the influenza virus of the invention is a recombinant influenza B virus having a particular amino acid residue at specified positions in one, two, three or more of PA, PB1, PB2, NP, M1 and/or NS1 and having an amino acid sequence with at least 80%, e.g., 90%, 92%, 95%, 97%, 98%, or 99%, including any integer between 80 and 99, contiguous amino acid sequence identity to a corresponding polypeptide encoded by one of SEQ ID Nos. 1-6 (the internal genes of B/Yamagata/1/73), such as a polypeptide with other than A at position 28, other than P at position 40, other than P at position 51, other than E at position 52, other than S at position 57, other than M at position 204, and/or other than P at position 343, in NP and/or g at position 1795 or t at position 500 in NP vRNA, or any combination thereof; residue other than G at position 34, other than D at position 54, other than R at position 77, other than M at position 86, other than I at position 97, or any combination thereof, in M1; other than H at position 58, other than R at position 80, other than H at position 27, other than G at position 26, in BM2, e.g. R at position 58, G at position 80, R at position 27, and/or R at position 26 in BM2; other than Y at position 42, other than M at position 117, other than K at position 176, and/or other than S at position 252, in SN1 and/or a39g, an additional g after 38, in NS1 vRNA, or any combination thereof; other than N at position 16 in PB2; and/or other than Y at position 387, other than V at position 434, other than D at position 494, other than T at position 524, in PA and/or a2272t, g2213a, a1406g, and/or c1445t, in PA vRNA, or any combination thereof. The residue other than the specified residue may be a conservative substitution. Conservative amino acid substitutions refer to the interchangeability of residues having similar side chains. For example, a group of amino acids having aliphatic side chains is glycine, alanine, valine, leucine, and isoleucine; a group of amino acids having aliphatic-hydroxyl side chains is serine and threonine; a group of amino acids having amide-containing side chains is asparagine and glutamine; a group of amino acids having aromatic side chains is phenylalanine, tyrosine and tryptophan; a group of amino acids having basic side chains is lysine, arginine and histidine; and a group of amino acids having sulfur-containing side chain is cysteine and methionine. In one embodiment, conservative amino acid substitution groups are: threonine-valine-leucine-isoleucine-alanine; phenylalanine-tyrosine; lysine-arginine; alanine-valine; glutamic-aspartic; and asparagine-glutamine. Non-conservative substitutions are also envisioned.

In one embodiment, the influenza B virus of the invention is a recombinant influenza B virus having a particular amino acid residue at specified positions in one, two, three or more of PA, NS1, M or NP which polypeptides have an amino acid sequence with at least 80%, e.g., 90%, 92%, 95%, 97%, 98%, or 99%, including any integer between 80 and 99, contiguous amino acid sequence identity to a corresponding polypeptide encoded by one of SEQ ID Nos. 1 or 4-6, respectively. In one embodiment, the influenza B virus of the invention is a recombinant influenza B virus having a particular amino acid residue at specified positions in one or more of PA, P61, PB2, NP, M1 and/or NS1 and an amino acid sequence with at least 80%, e.g., 90%, 92%, 95%, 97%, 98%, or 99%, including any integer between 80 and 99, contiguous amino acid sequence identity to a corresponding polypeptide encoded by one of SEQ ID Nos. 1-6, such as a polypeptide with a residue that is a conservative substitution.

Also included are any combination of the selected amino acid residues at specified positions described herein.

Viral segments for PA, NP, M and/or NS that have the residues at the specified positions may be combined with viral segment for PB1, a viral segment for PB2, a viral segment for HA, and a viral segment for NA, to provide the reassortant vaccine viruses of the invention. In one embodiment, the HA viral segment in the reassortant virus is heterologous to the viral segments for PA, P81, PB2, NP, M and NS. In one embodiment, the NA gene segment in the reassortant virus is heterologous to the viral segments for PA, P81, PB2, NP, M and NS. In one embodiment, the HA viral segment in the reassortant virus has viral segments for PA, PB1, PB2, NP, M and NS from one influenza virus isolate or strain ("parent"), or a variant thereof, e.g., one with viral segments encoding influenza virus proteins with at least 95%, 96%, 97%, 98%, 99%, or 99.5% amino acid sequence identity, or having 1, 2, 5, 10, or 20 substitutions relative, to sequences in a parent influenza virus isolate or strain. In one embodiment, the parent strain has viral segments with sequences corresponding to at least one of SEQ ID Nos. 1-6, and the recombinant virus has at least one of the viral segments with at least one of the substitutions in PA, NS, NP or M described herein, and at least one of the parental viral segments. In one embodiment, the HA gene segment in the reassortant virus is a chimeric HA gene segment, e.g., a chimera of heterologous HA ectodomain sequences linked to HA signal peptide sequences and/or HA transmembrane domain sequences from the HA gene segment of the parent isolate or strain, or variant thereof. In one embodiment, the NA gene segment in the isolated recombinant virus is a chimeric NA gene segment e.g., a chimera of heterologous NA ectodomain sequences linked to NA transmembrane domain sequences from the NA gene segment of the parent isolate or strain, or variant thereof, and/or stalk sequences from the parent isolate or strain, or variant thereof, for instance, chimeras of influenza B virus NA and influenza A virus NA. In one embodiment, the NA gene segment in the isolated recombinant virus is a chimeric NA gene segment e.g., a chimera of heterologous NA ectodomain sequences inked to NA transmembrane domain sequences from the NA gene segment of the parent isolate or strain, or variant thereof, and/or stalk sequences from a second isolate or strain, or variant thereof. In one embodiment, the isolated recombinant virus has a heterologous HA gene segment, a heterologous NA gene segment, a chimeric HA gene segment, a chimeric NA gene segment, or any combination thereof. The nucleic acid sequences employed to prepare vRNA or cRNA may be ones that introduce the residues at the specified positions via recombinant methodology or may be selected as having the residues at the specified positions.

As described herein, an influenza virus isolate useful as a vaccine virus (e.g., reassortants of B/Yamagata/1/73 with viruses of the B/Yamagata- or B/Victoria-lineage) to carry heterologous gene segments for NA and/or HA, was serially passaged in MDCK cells, e.g., about 10-12-times although fewer passages may be employed, to obtain virus with enhanced replication in those cells. In one embodiment, viruses obtained after serial passage which have enhanced replication, have titers that are at least 0.5 to 1 or 2 logs higher than viruses that were not serially passaged. In one embodiment, viruses obtained after serial passage had substitutions in two or more internal gene segments relative to the parent virus.

Thus, for vaccine viruses that are to be grown or passaged in cells in culture, e.g., MDCK or Vero cells or eggs, selection of sequences with, or replacement of, the disclosed residues at the specified positions in one or more of PA, BM2, NP, M1 and/or NS1, that confer enhanced growth of the virus in cultured cells when employed with HA and NA sequences of interest, can result in significantly higher viral titers. Thus, the invention provides a method to select for influenza viruses with enhanced replication in cell culture. The method includes providing cells suitable for influenza vaccine production; serially culturing one or more influenza virus isolates in the cells; and isolating serially cultured virus with enhanced growth relative to the one or more isolates prior to serial culture. In one embodiment, the cells are canine or primate, e.g., human or monkey, cells.

The invention provides a plurality of influenza virus vectors of the invention, e.g., those useful to prepare reassortant viruses including 6:1:1 reassortants, 6:2 reassortants and 7:1 reassortants. A 6:1:1 reassortant within the scope of the present invention is an influenza virus with 6 internal gene segments from a vaccine virus, a NA gene segment from a different (second) viral isolate, and a HA gene segment from a third isolate; a 6:2 reassortant within the scope of the present invention is an influenza virus with 6 internal gene segments from a vaccine virus, and a NA gene segment and a HA gene segment from a different (second) viral isolate; and a 7:1 reassortant within the scope of the present invention is an influenza virus with 6 internal gene segments and a NA gene segment from a vaccine virus, and a HA gene segment from a different viral source than the vaccine virus, or an influenza virus with 6 internal gene segments and a HA gene segment from the vaccine virus, and a NA gene segment is from a different viral source than the vaccine virus.

In one embodiment of the invention, the plurality includes vectors for vRNA or cRNA production selected from a vector comprising a promoter operably linked to an influenza virus PA DNA, e.g., cDNA, inked to a transcription termination sequence, a vector comprising a promoter operably linked to an influenza virus PB1 DNA, e.g., cDNA, linked to a transcription termination sequence, a vector comprising a promoter operably linked to an influenza virus PB2 DNA, e.g., cDNA, linked to a transcription termination sequence, a vector comprising a promoter operably linked to an influenza virus HA DNA, e.g., cDNA, inked to a transcription termination sequence, a vector comprising a promoter operably linked to an influenza virus NP DNA, e.g., cDNA, linked to a transcription termination sequence, a vector comprising a promoter operably linked to an influenza virus NA DNA, e.g., cDNA, linked to a transcription termination sequence, a vector comprising a promoter operably inked to an influenza virus M DNA, e.g., cDNA, linked to a transcription termination sequence, and a vector comprising a operably inked to an influenza virus NS DNA linked to a transcription termination sequence. In one embodiment, the DNAs for vRNA or cRNA production of PB1, P82, PA, NP, M, and NS, have sequences from an influenza virus that replicates to high titers in cultured mammalian cells such as MDCK cells, Vero cells or PER.C6® cells and also optionally embryonated eggs, and/or from a vaccine virus, e.g., one that does not cause significant disease in humans. The DNA, e.g., cDNA, for vRNA or cRNA production of NA may be from any NA, and the DNA for vRNA or cRNA production of HA may be from any HA. In one embodiment, the DNAs for vRNA or cRNA production may be for an influenza A or C virus. The DNAs for vRNA or cRNA production of NA and HA may be from different strains or isolates (6:1:1 reassortants) or from the same strain or isolate (6:2 reassortants), or the NA may be from the same strain or isolate as that for the internal genes (7:1 reassortant). The plurality also includes vectors for mRNA production selected from a vector encoding influenza virus PA, a vector encoding influenza virus PB1, a vector encoding influenza virus P82, and a vector encoding influenza virus NP, and optionally one or more vectors encoding NP, NS, M, e.g., M1 and BM2, HA or NA. The vectors encoding viral proteins may further include a transcription termination sequence.

Viruses that may provide the internal genes for reassortants within the scope of the invention include viruses that have high titers in MDCK cells, e.g., titers of at least about $10^5$ PFU/mL, e.g., at least $10^6$ PFU/mL, $10^7$ PFU/mL or $10^8$PFU/mL; high titers in embryonated eggs, e.g., titers of at least about $10^7$ $EID_{50}$/mL, e.g., at least $10^8$ $EID_{50}$/mL, $10^8$ $EID_{50}$/mL or $10^{10}$ $EID_{50}$/mL; high titers in cells such as MDCK cells, e.g., titers of at least about $10^7$ PFU/mL, e.g., at least $10^9$ PFU/mL, or high titers in two of more of those host cells.

In one embodiment, the titers of the reassortant viruses of the invention in cells such as MDCK cells or Vero cells may be over 1 log, 2 logs, 3 logs, or greater, than titers of the corresponding virus without particular residues at the specified positions.

In one embodiment, the DNAs for the internal genes for PB1, PB2, PA, NP, M, and NS encode proteins with substantially the same activity as a corresponding polypeptide encoded by one of SEQ ID NOs:1-6. As used herein, “substantially the same activity” includes an activity that is about 0.1%, 1%, 10%, 30%, 50%, 90%, e.g., up to 100% or more, or detectable protein level that is about 80%, 90% or more, the activity or protein level, respectively, of the corresponding full-length polypeptide. In one embodiment, the nucleic acid a sequence encoding a polypeptide which is substantially the same as, e.g., having at least 80%, e.g., 90%, 92%, 95%, 97%, 98%, or 99%, including any integer between 80 and 99, contiguous amino acid sequence identity to, a polypeptide encoded by one of SEQ ID NOs:1-6. In one embodiment, the isolated and/or purified nucleic acid molecule comprises a nucleotide sequence which is substantially the same as, e.g., having at least 50%, e.g., 60%, 70%, 80% or 90%, including any integer between 50 and 100, or more contiguous nucleic acid sequence identity to one of SEQ ID NOs:1-6 and, in one embodiment, also encodes a polypeptide having at least 80%, e.g., 90%, 92%, 95%, 97%, 98%, or 99%, including any integer between 80 and 99, contiguous amino acid sequence identity to a polypeptide encoded by one of SEQ ID NOs:1-6. In one embodiment, the influenza virus polypeptide has one or more, for instance, 2, 5, 10, 15, 20 or more, conservative amino acids substitutions, e.g., conservative substitutions of up to 10% or 20% of 2, 5, 10, 15, 20 or more, of a combination of conservative and non-conservative amino acids substitutions, e.g., conservative substitutions of up to 10% or 20% of the residues, or relative to a polypeptide encoded by one of SEQ ID NOs:1-6, and has a characteristic residue in one or more of PA, PB2, BM2, NP, M1, and/or NS1, relative to a polypeptide encoded by one of SEQ ID NOs:1-6. In one embodiment, the influenza virus polypeptide has one or more, for instance, 2, 3, 4, 5, 6, 7 or 8 conservative and/or nonconservative amino acid substitutions, relative to a polypeptide encoded by one of SEQ ID NOs:1-6.

The invention thus includes the use of isolated and purified vectors or plasmids, which express or encode influenza virus proteins, or express or encode influenza vRNA or cRNA, both native and recombinant vRNA or cRNA. The vectors may comprise influenza cDNA, e.g., influenza A. B or C DNA (see Fields *Virology* (Fields at al. (eds.), Lippincott, Williams and Wickens (2006), which is specifically incorporated by reference herein). Any suitable promoter or transcription termination sequence may be employed to express a protein or peptide, e.g., a viral protein or peptide, a protein or peptide of a nonviral pathogen, or a therapeutic protein or peptide.

A composition or plurality of vectors of the invention may also comprise a heterologous gene or open reading frame of interest, e.g., a foreign gene encoding an immunogenic peptide or protein useful as a vaccine or in gene replacement, for instance, may encode an epitope useful in a cancer therapy or vaccine, or a peptide or polypeptide useful in gene therapy. When preparing virus, the vector or plasmid comprising the gene or cDNA of interest may substitute for a vector or plasmid for an influenza viral gene or may be in addition to vectors or plasmids for all influenza viral genes. Thus, another embodiment of the invention comprises a composition or plurality of vectors as described above in which one of the vectors is replaced with, or further comprises, 5' influenza virus sequences optionally including 5' influenza virus coding sequences or a portion thereof, linked to a desired nucleic acid sequence, e.g., a desired cDNA, linked to 3' influenza virus sequences optionally including 3' influenza virus coding sequences or a portion thereof. In one embodiment, the desired nucleic acid sequence such as a cDNA is in an antisense (antigenomic) orientation. The introduction of such a vector in conjunction with the other vectors described above to a host cell permissive for influenza virus replication results in recombinant virus comprising vRNA or cRNA corresponding to the heterologous sequences of the vector.

The promoter in a vector for vRNA or cRNA production may be a RNA polymerase I promoter, a RNA polymerase II promoter, a RNA polymerase III promoter, a T7 promoter, or a T3 promoter, and optionally the vector comprises a transcription termination sequence such as a RNA polymerase I transcription termination sequence, a RNA polymerase ii transcription termination sequence, a RNA polymerase III transcription termination sequence, or a ribozyme. Ribozymes within the scope of the invention include, but are not limited to, tetrahymena ribozymes, RNase P, hammerhead ribozymes, hairpin ribozymes, hepatitis ribozyme, as well as synthetic ribozymes. In one embodiment, the RNA polymerase I promoter is a human RNA polymerase I promoter.

The promoter or transcription termination sequence in a vRNA, cRNA or virus protein expression vector may be the same or different relative to the promoter or any other vector. In one embodiment, the vector or plasmid which expresses influenza vRNA or cRNA comprises a promoter suitable for expression in at least one particular host cell, e.g., avian or mammalian host cells such as canine, feline, equine, bovine, ovine, or primate cells including human cells, or for expression in more than one host.

In one embodiment, at least one vector for vRNA or cRNA comprises a RNA polymerase II promoter linked to a ribozyme sequence linked to viral coding sequences linked to another ribozyme sequences, optionally linked to a RNA polymerase II transcription termination sequence. In one embodiment, at least 2, e.g., 3, 4, 5, 6, 7 or 8, vectors for vRNA or cRNA production comprise a RNA polymerase II promoter, a first ribozyme sequence, which is 5' to a sequence corresponding to viral sequences including viral coding sequences, which is 5' to a second ribozyme sequence, which is 5' to a transcription termination sequence. Each RNA polymerase II promoter in each vRNA or cRNA vector may be the same or different as the RNA polymerase II promoter in any other vRNA or cRNA vector. Similarly, each ribozyme sequence in each vRNA or cRNA vector may be the same or different as the ribozyme sequences in any other vRNA or cRNA vector. In one embodiment, the ribozyme sequences in a single vector are not the same.

In one embodiment, the invention provides a plurality of influenza virus vectors for a reassortant, comprising a vector for vRNA or cRNA production comprising a promoter operably linked to an influenza virus PA DNA, e.g., cDNA, linked to a transcription termination sequence, a vector for vRNA or cRNA production comprising a promoter operably inked to an influenza virus PB1 DNA, e.g., cDNA, linked to a transcription termination sequence, a vector for vRNA or cRNA production comprising a promoter operably linked to an influenza virus PB2 DNA, e.g., cDNA, linked to a transcription termination sequence, a vector for vRNA or cRNA production comprising a promoter operably linked to an influenza virus HA DNA, e.g., cDNA, linked to a transcription termination sequence, a vector for vRNA or cRNA production comprising a promoter operably linked to an influenza virus NP DNA, e.g., cDNA, inked to a transcription termination sequence, a vector for vRNA or cRNA production comprising a promoter operably inked to an influenza virus NA DNA, e.g., cDNA, linked to a transcription termination sequence, a vector for vRNA or cRNA production comprising a promoter operably linked to an influenza virus M DNA, e.g., cDNA, linked to a transcription termination sequence, and a vector for vRNA or cRNA production comprising a promoter operably inked to an influenza virus NS DNA, e.g., cDNA, linked to a transcription termination sequence, wherein the DNAs for PB1, PB2, PA, NP, NS, and M are from one or more influenza vaccine seed viruses and contain two or more of the characteristic residues at the specified position(s); and a vector for mRNA production comprising a promoter operably linked to a DNA segment encoding influenza virus PA, a vector for mRNA production comprising a promoter operably linked to a DNA segment encoding influenza virus PB1, a vector for mRNA production comprising a promoter operably linked to a DNA segment encoding influenza virus PB2, and a vector for mRNA production comprising a promoter operably linked to a DNA segment encoding influenza virus NP, and optionally a vector for mRNA production comprising a promoter operably linked to a DNA segment encoding influenza virus HA, a vector for mRNA production comprising a promoter operably linked to a DNA segment encoding influenza virus NA, a vector for mRNA production comprising a promoter operably linked to a DNA segment encoding influenza virus M1, a vector for mRNA production comprising a promoter operably linked to a DNA segment encoding influenza virus BM2, or a vector for mRNA production comprising a promoter operably linked to a DNA segment encoding influenza virus NS2. In one embodiment, at least one vector comprises sequences corresponding to those encoding PB1, PB2, PA, NP, M, or NS, or a portion thereof, having substantially the same activity as a corresponding polypeptide encoded by one of SEQ ID NOs:1-6, e.g., a sequence encoding a polypeptide with at least 80%, e.g., 85%, 90%, 92%, 95%, 98%, 99% or 100%, including any integer between 80 and 100, amino acid identity to a polypeptide encoded by one of SEQ ID NOs:1-6. Optionally, two vectors may be employed in place of the vector comprising a promoter operably linked to an influenza virus M cDNA linked to a transcription termination sequence, e.g., a vector comprising a promoter operably linked to an influenza virus M1 cDNA linked to a transcription termination sequence and a vector comprising a promoter operably linked to an influenza virus BM2 cDNA linked to a transcription termination sequence.

A plurality of the vectors of the invention may be physically linked or each vector may be present on an individual plasmid or other, e.g., linear, nucleic acid delivery vehicle. In one embodiment, each vRNA or cRNA production vector is on a separate plasmid. In one embodiment, each mRNA production vector is on a separate plasmid.

The invention also provides a method to prepare influenza virus. The method comprises contacting a cell with a plurality of the vectors of the invention, e.g., sequentially or simultaneously, in an amount effective to yield infectious influenza virus. The invention also includes isolating virus from a cell contacted with the plurality of vectors. Thus, the invention further provides isolated virus, as well as a host cell contacted with the plurality of vectors or virus of the invention. In another embodiment, the invention includes contacting the cell with one or more vectors, either vRNA or cRNA or protein production vectors, prior to other vectors, either vRNA or protein production vectors. In one embodiment, the promoter for vRNA or cRNA vectors employed in the method is a RNA polymerase I promoter, a RNA polymerase II promoter, a RNA polymerase III promoter, a T3 promoter or a T7 promoter. In one embodiment, the RNA polymerase I promoter is a human RNA polymerase I promoter. In one embodiment, each vRNA or cRNA vector employed in the method is on a separate plasmid. In one embodiment, the vRNA or cRNA vectors employed in the method are on one plasmid or on two or three different plasmids. In one embodiment, each mRNA vector employed in the method is on a separate plasmid. In one embodiment, the mRNA vectors for PA, PB1, PB2 and NP employed in the method are on one plasmid or on two or three different plasmids.

In one embodiment, the invention provides a method to select for influenza viruses with enhanced replication in cell culture. The method includes providing cells suitable for influenza vaccine production; serially culturing one or more influenza virus isolates in the cells; and isolating serially cultured virus with enhanced growth relative to the one or more isolates prior to serial culture. In one embodiment, the cells are rodent or primate cells.

The methods of producing virus described herein, which do not require helper virus infection, are useful in viral mutagenesis studies, and in the production of vaccines (e.g., for AIDS, influenza, hepatitis B, hepatitis C, rhinovirus, filoviruses, malaria, herpes, and foot and mouth disease) and gene therapy vectors (e.g., for cancer, AIDS, adenosine deaminase, muscular dystrophy, omithine transcarbamylase deficiency and central nervous system tumors). Thus, a virus for use in medical therapy (e.g., for a vaccine or gene therapy) is provided.

The invention also provides isolated viral polypeptides, and methods of preparing and using recombinant virus of the invention. The methods include administering to a host organism, e.g., a mammal, an effective amount of the influenza virus of the invention, e.g., an inactivated virus preparation, optionally in combination with an adjuvant and/or a carrier, e.g., in an amount effective to prevent or ameliorate infection of an animal such as a mammal by that virus or an antigenically closely related virus. In one embodiment, the virus is administered intramuscularly while in another embodiment, the virus is administered intranasally. In some dosing protocols, all doses may be administered intramuscularly or intranasally, while in others a combination of intramuscular and intranasal administration is employed. The vaccine may further contain other isolates of influenza virus including recombinant influenza virus, other pathogen(s), additional biological agents or microbial components, e.g., to form a multivalent vaccine. In one embodiment, intranasal vaccination, for instance containing with inactivated influenza virus, and a mucosal adjuvant may induce virus-specific IgA and neutralizing antibody in the nasopharynx as well as serum IgG.

The influenza virus of the invention may employed with other anti-virals, e.g., amantadine, rimantadine, and/or neuraminidase inhibitors, e.g., the virus may be administered separately, for instance, administered before and/or after, or in conjunction with, those anti-virals.

BRIEF DESCRIPTION OF THE FIGURES

FIG. 1A-G. Nucleotide sequences for B/Yamagata/1/1973 (SEQ ID NOs: 1-6,9, and 10) and amino acid sequences for HA (SEQ ID NO: 7) and NA (SEQ ID NO: 8).

FIGS. 2A-8. Overview of library passages in MDCK cells and the identification of high-yield (HY) candidates (HY (Yam) and HY(Vic)). Yamagata- and Victoria-lineage virus libraries with random mutations in the indicated vRNAs were passaged twelve times in MDCK cells, or passaged twice, mixed, and passaged ten more times. More than 700 virus plaques were picked for each virus lineage. Based on hemagglutination and virus titers, the top eight candidates for each lineage were identified in a step-wise selection process. Testing of combinatorial mutations led to the selection of RG(Yam) #8 and RG(Vic) #2. The introduction of additional mutations (identified in virus library screens in Vero cells) resulted in the high-yield vaccine backbones HY(Yam) and HY(Vic). HA titer, hemagglutination titer.

FIG. 5. Chimeric HA and NA constructs. The ectodomains of the influenza B virus HA (green) and NA (blue) proteins were inserted between the remaining sequences of the influenza A virus PR8 HA (purple) and NA (dark orange)

Figure 2A:
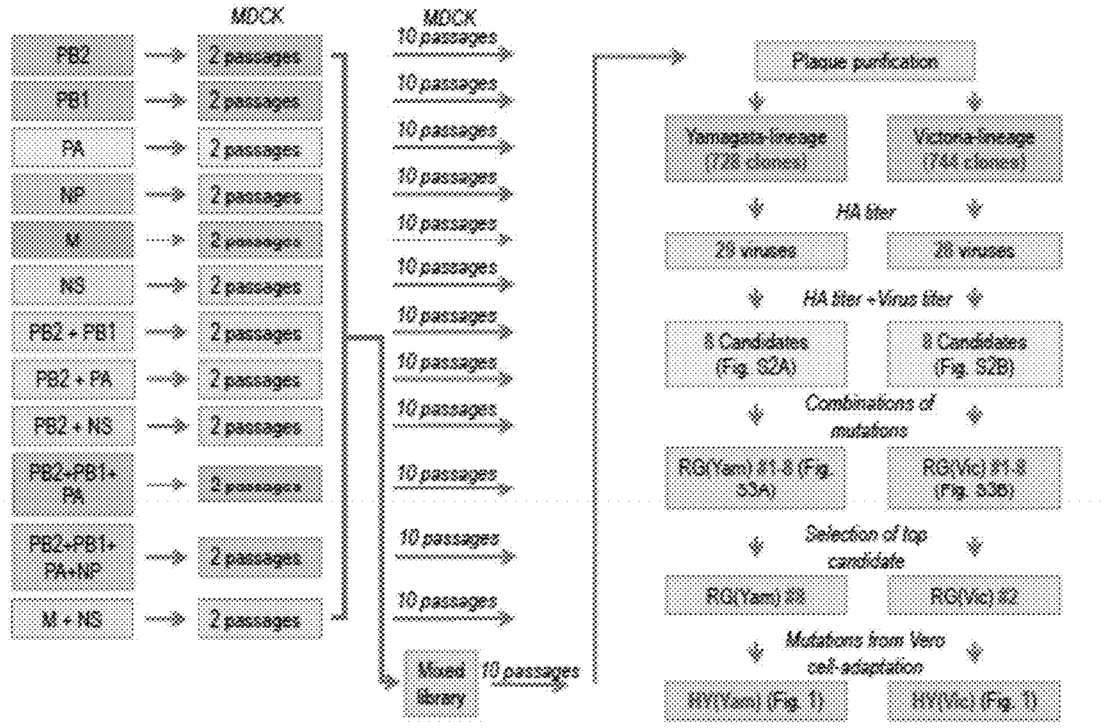

vRNAs. Wide bars indicate coding regions; small bars indicate non-coding regions (NCRs). SP, signal peptide; TM, transmembrane domain; CT, cytoplasmic tall.

FIG. 6A-B. Growth kinetics and HA titers of high-yield Yamagata- and Victoria-lineage viruses. (A) The indicated Yamagata-lineage wild-type virus was compared with the Yamagata-lineage high-yield candidate RG(Yam) #8 (Table 3) and with RG(Yam) #8 possessing the PA-a2272t mutation; the latter virus was selected as lead candidate HY(Yam). (B) The indicated Victoria-lineage wild-type virus was compared with the Victoria-lineage high-yield candidate RG(Vic) #2 (Table 4) and with RG(Vic) #2 possessing the PA-a2272t mutation; the latter virus was selected as lead candidate HY(Vic). In both sets of experiments, MDCK cells were infected in triplicate with the indicated viruses at an MOI of 0.001 and incubated at 35° C. At the indicated time points, virus and hemagglutination titers were determined by performing plaque or hemagglutination assays, respectively. The values presented are the average of three independent experiments±SD. P values were calculated by using the linear mixed model (*$P<0.05$; **$P<0.01$). Red and blue asterisks indicate the comparison of the respective virus with WT virus; beige asterisks indicate the comparison between the viruses depicted in red and blue.

FIGS. 7A-F. Comparison of wild-type and high-yield viruses possessing different HA and NA vRNAs. Viruses possessing the HA and NA vRNAs of the indicated viruses in combination with the internal vRNA segments of the respective natural wild-type isolate (WT), or of HY(Yam) (A-C) or HY(Vic) (D-F) (the viruses indicated by the black graphs possess the eight wild-type vRNA segments of a human influenza B virus isolate). The values presented are the average of three independent experiments±SD. P values were calculated by using the linear mixed model described in the Methods section (*$P<0.05$; **$P<0.01$). Red asterisks indicate the comparison of the respective virus with WT virus.

FIGS. 8A-D. Exchange of HY(Yam) and HY(Vic) backbones. (A and B) Comparison of the virus and hemagglutination titers of two wild-type Yamagata-lineage viruses with viruses possessing the same HA and NA vRNAs in combination with the internal genes of HY(Yam) or HY(Vic). (C and D) Comparison of the virus and hemagglutination titers of two wild-type Victoria-lineage viruses with viruses possessing the same HA and NA vRNAs in combination with the internal genes of HY(Yam) or HY(Vic). The values presented are the average of three independent experiments±SD. P values were calculated by using the linear mixed model (*$P<0.05$; **$P<0.01$). Red and blue asterisks indicate the comparison of the respective virus with WT virus; beige asterisks indicate the comparison between the viruses depicted in red and blue.

FIGS. 9A-F. Comparison of high-yield influenza A and B vaccine virus backbones. (A and B). The virus yield and hemagglutination titers of (I) the indicated wild-type viruses; (II) viruses possessing the indicated HA and NA vRNAs in combination with the internal genes of HY(Yam); and (II) viruses possessing the indicated type A/B chimeric HA and NA vRNAs in combination with the internal genes of high-yield influenza A virus. (C and D), were compared. Similar experiments were carried out for viruses of the Victoria lineage. (E and F) Comparison of the indicated wild-type and hybrid viruses in embryonated chicken eggs. The values presented are the average of three independent experiments±SD. The statistical significance was determined by using the linear mixed model (A-D), or by two-way ANOVA, followed by Tukey's post hoc test (E and F) (*$P<0.05$; **$P<0.01$); P values are not shown if the titer of the high-yield vaccine candidate was lower than that of wild-type virus. Red and blue asterisks indicate the comparison of the respective virus with WT virus; beige asterisks indicate the comparison between the viruses depicted in red and blue.

Figure 10A:
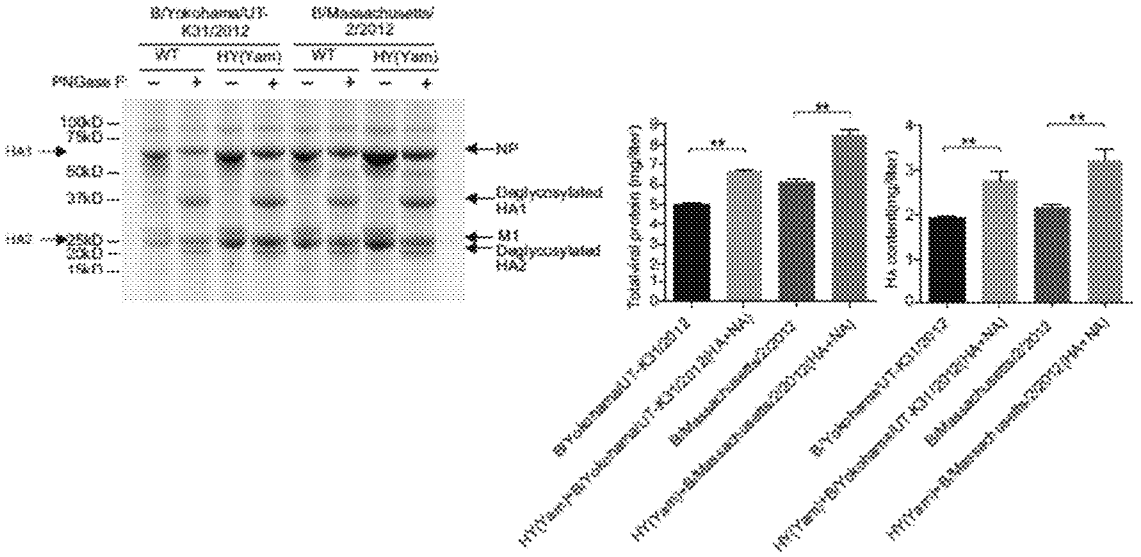
Figure 10B:
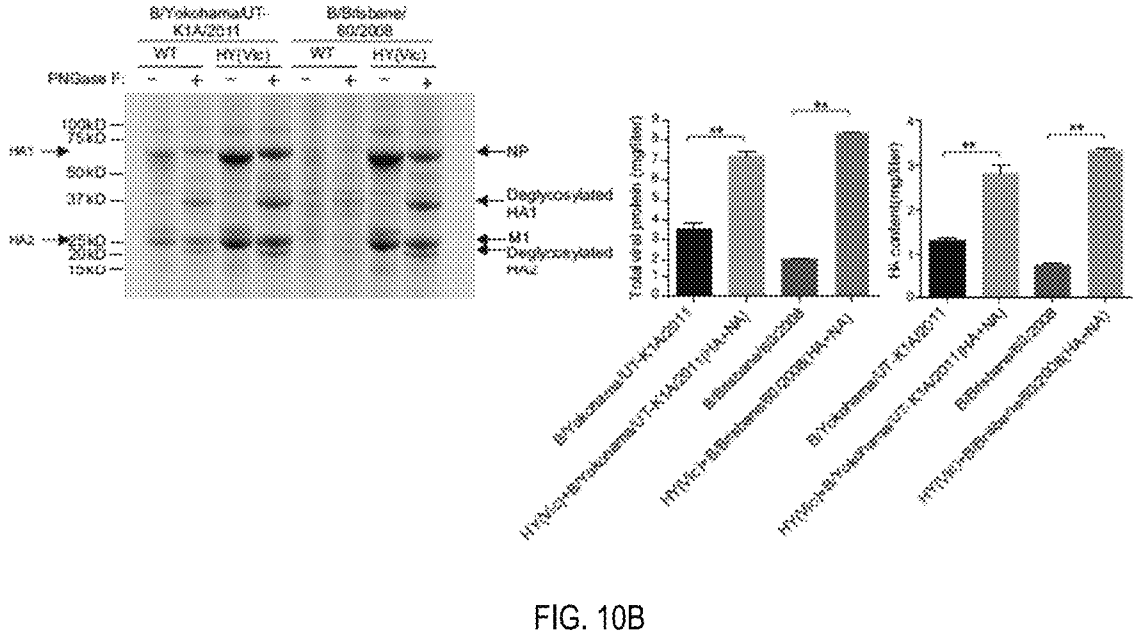

FIGS. 10A-B. Evaluation of the total viral protein yield and HA content of HY(Yam) and HY(Vic) viruses. A) Comparison of viruses possessing the HA and NA vRNAs of the indicated Yamagata-lineage viruses in combination with the internal vRNAs of the same natural wild-type virus (WT) or of HY(Yam). B) Comparison of viruses possessing the HA and NA vRNAs of the indicated Victoria-lineage viruses in combination with the internal vRNAs of the same wild-type virus (WT) or of HY(Vic). The total viral protein yield of MDCK cell-grown, sucrose gradient-purified virus samples is shown (Left and Center). PNGaseF treatment deglycosylates HA1 and HA2; this treatment was carried out because glycosylated HA2 migrates at a similar molecular weight asM1. The HA contents (Right) were calculated based on the total viral protein amounts and the relative amounts of HA. The values presented are the average of three independent experiments±SD. The statistical significance was assessed by using one-way ANOVA followed by Dunnett's test, comparing the total viral protein yield and HA content of wild-type viruses with that of recombinant high-yield vaccine viruses (*$P<0.05$; **$P<0.01$).

FIGS. 11A-F. Virulence of HY(Yam) and HY(Vic) viruses in mice. A-C) Comparison of a wild-type Yamagata-lineage virus (B/Massachusetts/2/2012), a virus possessing the B/Massachusetts/2/2012 HA and NA vRNAs in combination with the remaining vRNAs of B/Yamagata/1/73 (used for virus library generation), and a virus possessing the B/Massachusetts/2/2012 HA and NA vRNAs in combination with the remaining vRNAs of HY(Yam). D-F) Comparison of a wild-type Victoria-lineage virus (B/Brisbane/60/2008), a virus possessing the B/Brisbane/60/2008 HA and NA vRNAs in combination with the remaining vRNAs of B/Yamagata/1/73 (used for virus library generation), and a virus possessing the B/Brisbane/60/2008 HA and NA vRNAs in combination with the remaining vRNAs of HY(Vic). BALB/c mice (five per group) were inoculated intranasally with $10^6$ pfu of the indicated viruses and monitored daily for body weight changes (A and D) and survival (B and E). To assess virus replication in mice, $10^6$ pfu of the indicated viruses were used to infect 10 additional mice. On days 3 and 6 post-infection, five mice in each group were killed, and lung virus titers were determined by use of plaque assays in MDCK cells (C and F). Statistical significance was assessed by using one-way ANOVA followed by Dunnett's test (*$P<0.05$; **$P<0.01$).

FIGS. 12A-B. Growth kinetics and hemagglutination titers of single reassortant viruses. A) Comparison of the parental virus used for Yamagata-lineage virus library generation (B/Yamagata/1/73 with the HA and NA vRNAs of B/Yokohama/UT-K31/2012) with viruses that also possess an individual vRNA of HY(Yam). B) Comparison of the parental virus used for Victoria-lineage virus library generation (i.e., B/Yamagata/1/73 with the HA and NA vRNAs of B/Yokohama/UT-K1A/2011) with viruses that also possess an individual vRNA of HY(Vic). Data were obtained from three independent experiments; shown are average titers±SD. The values presented are the average of three independent experiments±SD. Statistical significance was determined by using the linear mixed model (*$P<0.05$;

**P<0.01). The color of the asterisks indicates the comparison of the respective virus with the comparator virus (depicted in black).

FIGS. 13A-D. Luciferase activity in mini-replicon assay at 35° C. Effect of mutations in the NP protein or PA and NS vRNAs on viral polymerase activity. 293T (A) or MDCK (B) cells were transfected with protein expression plasmids for the polymerase proteins and wild-type or mutant NP, and with a plasmid transcribing a virus-like RNA that encodes luciferase. Luciferase activity was measured 48 hours later. In parallel, MDCK cells were transfected with the protein expression plasmids described above, and with wild-type or mutant virus-like RNA encoding luciferase and possessing the indicated mutations in the non-coding regions of the PA vRNA (C) or NS vRNA (D). Luciferase activity was measured 48 hours later. Data were obtained from three independent experiments; shown are average titers±s.d. Statistical significance was determined by using one-way ANOVA, followed by Dunnett's test (*p<0.05; **p<0.01).

Figure 14A:
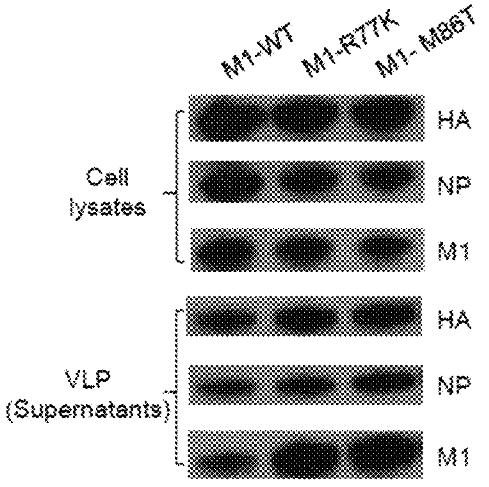
Figure 14B:
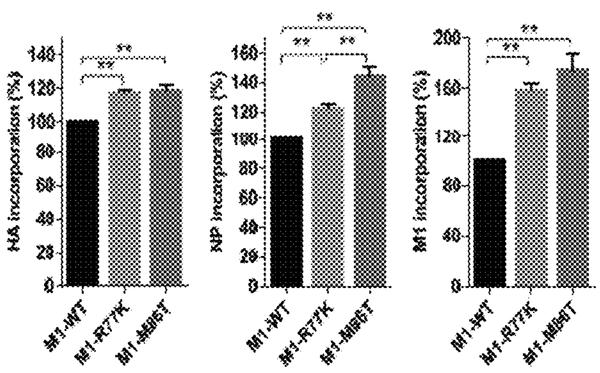

FIGS. 14A-B. Contribution of M1 mutations in HY backbones to HA, NP and M1 VLP incorporation and composition. 293T cells were transfected with protein expression plasmids for HA, NA, NP, BM2, NS2, and wild-type or mutant M1. At 48 hours post-transfection, cell lysates and VLPs in cell culture supernatants were Western blotted with anti-HA, anti-NP, and anti-M1 monoclonal antibodies (A). The intensity of the bands for HA, NP, and M1 was quantified by using ImageJ software (NIH), and the relative percentages of HA, NP, and M1 in VLPs are shown in (B). Data were obtained from three independent experiments; shown are average titers±s.d. Statistical significance was determined by using one-way ANOVA, followed by Tukey's post hoc test (*p<0.05; **p<0.01).

Figure 15A:
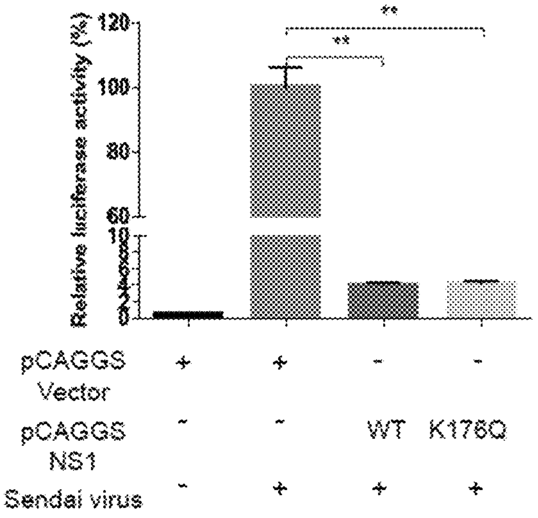
Figure 15B:
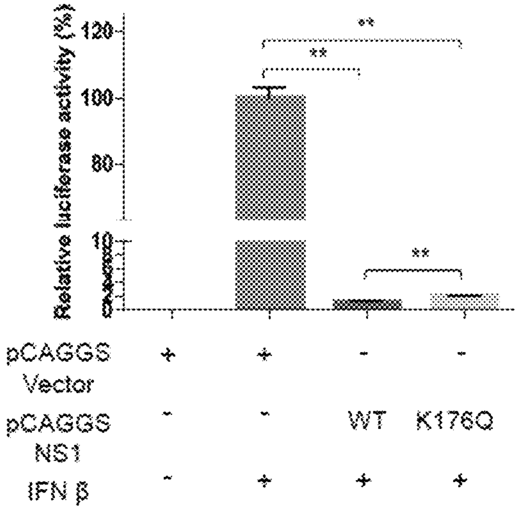

FIGS. 15A-B. Effect of NS1 mutation on IFN activity. A) To compare the ability of wild-type and mutant NS1 to interfere with IFN-β synthesis, 293T cells were transfected with a wild-type or NS1 protein expression plasmid and with the reporter plasmid pGL-IFN-β, which encodes the firefly luciferase protein under the control of the IFN-β promoter. Cells were incubated for 24 hours, infected with Sendai virus at an MOI of 5, again incubated for 24 hours, and then lysed to measure firefly luciferase. B) To determine the ability of wild-type and mutant NS1 to interfere with the synthesis of IFN-β-stimulated genes, 293T cells were transfected with a wild-type or mutant NS1 protein expression plasmid and with the reporter plasmid pISRE-Luc (which encodes the firefly luciferase protein under the control of an interferon-regulated promoter). Twenty-four hours later, cells were stimulated with human IFN-β. Forty-eight hours after transfection, we measured luciferase activity. Data were obtained from three independent experiments; shown are average titers±s.d. Statistical significance was determined by using one-way ANOVA, followed by Tukey's post hoc test (*p<0.05; **p<0.01).

FIG. 16A-I. Nucleotide sequences for viral segments in select HY clones (PB2 and PB1 from Yamagata/1/73; SEQ ID Nos. 11-12); PA from Yamagata/1/73 having a1406g/c1445t/a2272t (SEQ ID NO:13); NP from Yamagata/1/73 having P40S, c500t (SEQ ID NO:14) or P40S/M204T, c500t (SEQ ID NO:15); M from Yamagata/1/73 having R77K (SEQ ID NO:16) or M86T (SEQ ID NO:17); and NS from Yamagata/1/73 having a39g K176Q (SEQ ID NO:18) or 38(+1)g. (SEQ ID NO:19).

DETAILED DESCRIPTION

Definitions

As used herein, the term "isolated" refers to in vitro preparation and/or isolation of a nucleic acid molecule, e.g., vector or plasmid, peptide or polypeptide (protein), or virus of the invention, so that it is not associated with in vivo substances, or is substantially purified from in vitro substances. An isolated virus preparation is generally obtained by in vitro culture and propagation, and/or via passage in eggs, and is substantially free from other infectious agents.

As used herein, "substantially purified" means the object species is the predominant species, e.g., on a molar basis it is more abundant than any other individual species in a composition, and preferably is at least about 80% of the species present, and optionally 90% or greater, e.g., 95%, 98%, 99% or more, of the species present in the composition.

As used herein, "substantially free" means below the level of detection for a particular infectious agent using standard detection methods for that agent.

A "recombinant" virus is one which has been manipulated in vitro, e.g., using recombinant DNA techniques, to introduce changes to the viral genome. Reassortant viruses can be prepared by recombinant or nonrecombinant techniques.

As used herein, the term "recombinant nucleic acid" or "recombinant DNA sequence or segment" refers to a nucleic acid, e.g., to DNA, that has been derived or isolated from a source, that may be subsequently chemically altered in vitro, so that its sequence is not naturally occurring, or corresponds to naturally occurring sequences that are not positioned as they would be positioned in the native genome. An example of DNA "derived" from a source, would be a DNA sequence that is identified as a useful fragment, and which is then chemically synthesized in essentially pure form. An example of such DNA "isolated" from a source would be a useful DNA sequence that is excised or removed from said source by chemical means, e.g., by the use of restriction endonucleases, so that it can be further manipulated, e.g., amplified, for use in the invention, by the methodology of genetic engineering.

As used herein, a "heterologous" influenza virus gene or gene segment is from an influenza virus source that is different than a majority of the other influenza viral genes or gene segments in a recombinant, e.g., reassortant, influenza virus.

The terms "isolated polypeptide", "isolated peptide" or "isolated protein" include a polypeptide, peptide or protein encoded by cDNA or recombinant RNA including one of synthetic origin, or some combination thereof.

The term "recombinant protein" or "recombinant polypeptide" as used herein refers to a protein molecule expressed from a recombinant DNA molecule. In contrast, the term "native protein" is used herein to indicate a protein isolated from a naturally occurring (i.e., a nonrecombinant) source. Molecular biological techniques may be used to produce a recombinant form of a protein with identical properties as compared to the native form of the protein.

Methods of alignment of sequences for comparison are well known in the art. Thus, the determination of percent identity between any two sequences can be accomplished using a mathematical algorithm.

Computer implementations of these mathematical algorithms can be utilized for comparison of sequences to determine sequence identity. Alignments using these programs can be performed using the default parameters. Software for performing BLAST analyses is publicly available through the National Center for Biotechnology information (http://www.ncbl.nlm.nih.gov/). The algorithm may involve first identifying high scoring sequence pairs (HSPs) by identifying short words of length W in the query sequence, which either match or satisfy some positive-valued threshold score T when aligned with a word of the same length in a database sequence. T is referred to as the neighborhood word score threshold. These initial neighborhood word hits act as seeds for initiating searches to find longer HSPs containing them. The word hits are then extended in both directions along each sequence for as far as the cumulative alignment score can be increased. Cumulative scores are calculated using, for nucleotide sequences, the parameters M (reward score for a pair of matching residues; always >0) and N (penalty score for mismatching residues; always <0). For amino acid sequences, a scoring matrix is used to calculate the cumulative score. Extension of the word hits in each direction are halted when the cumulative alignment score falls off by the quantity X from its maximum achieved value, the cumulative score goes to zero or below due to the accumulation of one or more negative-scoring residue alignments, or the end of either sequence is reached.

In addition to calculating percent sequence identity, the BLAST algorithm may also perform a statistical analysis of the similarity between two sequences. One measure of similarity provided by the BLAST algorithm may be the smallest sum probability (P(N)), which provides an indication of the probability by which a match between two nucleotide or amino acid sequences would occur by chance. For example, a test nucleic acid sequence is considered similar to a reference sequence if the smallest sum probability in a comparison of the test nucleic acid sequence to the reference nucleic acid sequence is less than about 0.1, more preferably less than about 0.01, and most preferably less than about 0.001.

The BLASTN program (for nucleotide sequences) may use as defaults a wordlength (W) of 11, an expectation (E) of 10, a cutoff of 100, M=5, N=−4, and a comparison of both strands. For amino acid sequences, the BLASTP program may use as defaults a wordlength (W) of 3, an expectation (E) of 10, and the BLOSUM62 scoring matrix. See http://www.ncbi.n1m.nih.gov. Alignment may also be performed manually by inspection.

For sequence comparison, typically one sequence acts as a reference sequence to which test sequences are compared. When using a sequence comparison algorithm, test and reference sequences are input into a computer, subsequence coordinates are designated if necessary, and sequence algorithm program parameters are designated. The sequence comparison algorithm then calculates the percent sequence identity for the test sequence(s) relative to the reference sequence, based on the designated program parameters.

Influenza B Virus Structure and Propagation

Influenza B viruses possess a genome of eight single-stranded negative-sense viral RNAs (vRNAs) that encode at least ten proteins. The influenza virus life cycle begins with binding of the hemagglutinin (HA) to sialic acid-containing receptors on the surface of the host cell, followed by receptor-mediated endocytosis. The low pH in late endosomes triggers a conformational shift in the HA, thereby exposing the N-terminus of the HA2 subunit (the so-called fusion peptide). The fusion peptide initiates the fusion of the viral and endosomal membrane, and the matrix protein (M1) and RNP complexes are released into the cytoplasm. RNPs consist of the nucleoprotein (NP), which encapsidates vRNA, and the viral polymerase complex, which is formed by the PA, PB1, and PB2 proteins. RNPs are transported into the nucleus, where transcription and replication take place. The RNA polymerase complex catalyzes three different reactions: synthesis of an mRNA with a 5' cap and 3' polyA structure, of a full-length complementary RNA (cRNA), and of genomic vRNA using the cRNA as a template. Newly synthesized vRNAs, NP, and polymerase proteins are then assembled into RNPs, exported from the nucleus, and transported to the plasma membrane, where budding of progeny virus particles occurs. The neuraminidase (NA) protein plays a crucial role late in infection by removing sialic acid from sialyloligosaccharides, thus releasing newly assembled virions from the cell surface and preventing the self aggregation of virus particles. Although virus assembly involves protein-protein and protein-vRNA interactions, the nature of these interactions is largely unknown.

Influenza B Viruses of the Invention

Mutations that increase the replicative ability of viruses in cell culture and/or embryonated chicken eggs are useful to amplify influenza viruses and to establish robust influenza vaccine platforms. Currently, most influenza B vaccines are generated in embryonated chicken eggs. Influenza vaccines generated in MDCK cells are now approved for human use in the U.S. and in Europe, and influenza vaccines derived from Vero cells are approved for human use in Europe. As described herein, virus libraries possessing random mutations in the 'internal' viral genes (viral genes except those encoding the viral surface glycoproteins HA and NA) of a vaccine virus isolate, e.g., internal genes of B/Yamagata/1/73 with NA and HA genes from B/Yokohama/UT-K31/2012 (representing Yamagata-lineage) or NA and HA genes from B/Yokohama/UT-K1A/2011 (representing Victoria-lineage), were generated and passaged in cells, e.g., MDCK or Vero cells. The identified mutations result in higher virus titers in cells (that may also increase virus titers in heterologous cells and/or embryonated chicken eggs), allowing more efficient influenza B virus growth and more cost-effective vaccine production. In addition to mutations in the coding regions of the internal viral segments and viral glycoproteins, mutations in non-coding regions were observed to increase viral titers, e.g., g1795a in the NP segment, a39g in the NS segment, an additional g after position 38 in the NS segment, or g2213a or a2272t in the PA segment. The resulting coding sequences conferring enhanced growth may be also codon-usage optimized, e.g., optimized for expression in mammalian cells such as canine cells or primate cells, or avian cells, e.g., chicken embryos. The mutations can be used in various combinations, with results influenced by the cell line (or egg) in use and the desired level of improvement in the replication of the virus. One or more selected mutations may be introduced into one or more internal viral genes of a vaccine virus isolate, or one or more internal viral genes having one or more of the mutations may be selected for inclusion in a reassortant useful as a vaccine virus. That virus may then be combined with other viruses, e.g., one or more influenza A viruses and/or one or more other influenza B viruses, to form a multivalent vaccine.

Cell Lines that can be Used in the Present INVENTION

Any cell, e.g., any avian or mammalian cell, such as a human, e.g., 293T or PER.C64 cells, or canine, e.g., MDCK, bovine, equine, feline, swine, ovine, rodent, for instance mink, e.g., MvLu1 cells, or hamster, e.g., CHO cells, or non-human primate, e.g., Vero cells, including mutant cells, which supports efficient replication of influenza virus can be employed to isolate and/or propagate influenza viruses. Isolated viruses can be used to prepare a reassortant virus. In one embodiment, host cells for vaccine production are continuous mammalian or avian cell lines or cell strains. A complete characterization of the cells to be used, may be conducted so that appropriate tests for purity of the final product can be included. Data that can be used for the characterization of a cell includes (a) information on its origin, derivation, and passage history; (b) information on its growth and morphological characteristics; (c) results of tests of adventitious agents; (d) distinguishing features, such as biochemical, immunological, and cytogenetic patterns which allow the cells to be clearly recognized among other cell lines; and (e) results of tests for tumorigenicity. In one embodiment, the passage level, or population doubling, of the host cell used is as low as possible.

In one embodiment, the cells are WHO certified, or certifiable, continuous cell lines. The requirements for certifying such cell lines include characterization with respect to at least one of genealogy, growth characteristics, immunological markers, virus susceptibility tumorigenicity and storage conditions, as well as by testing in animals, eggs, and cell culture. Such characterization is used to confirm that the cells are free from detectable adventitious agents. In some countries, karyology may also be required. In addition, tumorigenicity may be tested in cells that are at the same passage level as those used for vaccine production. The virus may be purified by a process that has been shown to give consistent results, before vaccine production (see, e.g., World Health Organization, 1982).

Virus produced by the host cell may be highly purified prior to vaccine or gene therapy formulation. Generally, the purification procedures result in extensive removal of cellular DNA and other cellular components, and adventitious agents. Procedures that extensively degrade or denature DNA may also be used.

Influenza Vaccines

A vaccine of the invention includes an isolated recombinant influenza virus of the invention, and optionally one or more other isolated viruses including other isolated influenza viruses, one or more immunogenic proteins or glycoproteins of one or more isolated influenza viruses or one or more other pathogens, e.g., an immunogenic protein from one or more bacteria, non-influenza viruses, yeast or fungi, or isolated nucleic acid encoding one or more viral proteins (e.g., DNA vaccines) including one or more immunogenic proteins of the isolated influenza virus of the invention. In one embodiment, the influenza viruses of the invention may be vaccine vectors for influenza virus or other pathogens.

A complete virion vaccine may be concentrated by ultrafiltration and then purified by zonal centrifugation or by chromatography. Viruses other than the virus of the invention, such as those included in a multivalent vaccine, may be inactivated before or after purification using formalin or beta-propiolactone, for instance.

A subunit vaccine comprises purified glycoproteins. Such a vaccine may be prepared as follows: using viral suspensions fragmented by treatment with detergent, the surface antigens are purified, by ultracentrifugation for example. The subunit vaccines thus contain mainly HA protein, and also NA The detergent used may be cationic detergent for example, such as hexadecyl trimethyl ammonium bromide (Bachmeyer, 1975), an anionic detergent such as ammonium deoxycholate (Laver & Webster, 1976); or a nonionic detergent such as that commercialized under the name TRITON X100. The hemagglutinin may also be isolated after treatment of the virions with a protease such as bromelin, and then purified. The subunit vaccine may be combined with an attenuated virus of the invention in a multivalent vaccine.

A split vaccine comprises virions which have been subjected to treatment with agents that dissolve lipids. A spilt vaccine can be prepared as follows: an aqueous suspension of the purified virus obtained as above, inactivated or not, is treated, under stirring, by lipid solvents such as ethyl ether or chloroform, associated with detergents. The dissolution of the viral envelope lipids results in fragmentation of the viral particles. The aqueous phase is recuperated containing the split vaccine, constituted mainly of hemagglutinin and neuraminidase with their original lipid environment removed, and the core or its degradation products. Then the residual infectious particles are inactivated if this has not already been done. The split vaccine may be combined with an attenuated virus of the invention in a multivalent vaccine.

Inactivated Vaccines. Inactivated influenza virus vaccines are provided by inactivating replicated virus using known methods, such as, but not limited to, formalin or P-propiolactone treatment. Inactivated vaccine types that can be used in the invention can include whole-virus (WV) vaccines or subvirion (SV) (split) vaccines. The WV vaccine contains intact, inactivated virus, while the SV vaccine contains purified virus disrupted with detergents that solubilize the lipid-containing viral envelope, followed by chemical inactivation of residual virus.

In addition, vaccines that can be used include those containing the isolated HA and NA surface proteins, which are referred to as surface antigen or subunit vaccines.

Live Attenuated Virus Vaccines. Live, attenuated influenza virus vaccines, such as those including a recombinant virus of the invention can be used for preventing or treating influenza virus infection. Attenuation may be achieved in a single step by transfer of attenuated genes from an attenuated donor virus to a replicated isolate or reassorted virus according to known methods. Since resistance to influenza A virus is mediated primarily by the development of an immune response to the HA and/or NA glycoproteins, the genes coding for these surface antigens come from the reassorted viruses or clinical isolates. The attenuated genes are derived from an attenuated parent. In this approach, genes that confer attenuation generally do not code for the HA and NA glycoproteins.

Viruses (donor influenza viruses) are available that are capable of reproducibly attenuating influenza viruses, e.g., a cold adapted (ca) donor virus can be used for attenuated vaccine production. Live, attenuated reassortant virus vaccines can be generated by mating the ca donor virus with a virulent replicated virus. Reassortant progeny are then selected at 25° C. (restrictive for replication of virulent virus), in the presence of an appropriate antiserum, which inhibits replication of the viruses bearing the surface antigens of the attenuated ca donor virus. Useful reassortants are: (a) infectious, (b) attenuated for seronegative non-adult mammals and immunologically primed adult mammals, (c) immunogenic and (d) genetically stable. The immunogenicity of the ca reassortants parallels their level of replication. Thus, the acquisition of the six transferable genes of the ca donor virus by new wild-type viruses has reproducibly attenuated these viruses for use in vaccinating susceptible mammals both adults and non-adult.

Other attenuating mutations can be introduced into influenza virus genes by site-directed mutagenesis to rescue infectious viruses bearing these mutant genes. Attenuating mutations can be introduced into non-coding regions of the genome, as well as into coding regions. Such attenuating mutations can also be introduced into genes other than the HA or NA, e.g., the PB2 polymerase gene. Thus, new donor viruses can also be generated bearing attenuating mutations introduced by site-directed mutagenesis, and such new donor viruses can be used in the production of live attenuated reassortants vaccine candidates in a manner analogous to that described above for the ca donor virus. Similarly, other known and suitable attenuated donor strains can be reassorted with influenza virus to obtain attenuated vaccines suitable for use in the vaccination of mammals.

In one embodiment, such attenuated viruses maintain the genes from the virus that encode antigenic determinants substantially similar to those of the original clinical isolates. This is because the purpose of the attenuated vaccine is to provide substantially the same antigenicity as the original clinical isolate of the virus, while at the same time lacking pathogenicity to the degree that the vaccine causes minimal chance of inducing a serious disease condition in the vaccinated mammal.

The viruses in a multivalent vaccine can thus be attenuated or inactivated, formulated and administered, according to known methods, as a vaccine to induce an immune response in an animal, e.g., a mammal. Methods are well-known in the art for determining whether such attenuated or inactivated vaccines have maintained similar antigenicity to that of the clinical isolate or high growth strain derived therefrom. Such known methods include the use of antisera or antibodies to eliminate viruses expressing antigenic determinants of the donor virus; chemical selection (e.g., amantadine or rimantidine); HA and NA activity and inhibition; and nucleic acid screening (such as probe hybridization or PCR) to confirm that donor genes encoding the antigenic determinants (e.g., HA or NA genes) are not present in the attenuated viruses.

Pharmaceutical Compositions

Pharmaceutical compositions of the present invention, suitable for inoculation, e.g., nasal, parenteral or oral administration, comprise one or more influenza virus isolates, e.g., one or more attenuated or inactivated influenza viruses, a subunit thereof, isolated protein(s) thereof, and/or isolated nucleic acid encoding one or more proteins thereof, optionally further comprising sterile aqueous or non-aqueous solutions, suspensions, and emulsions. The compositions can further comprise auxiliary agents or excipients, as known in the art. The composition of the invention is generally presented in the form of individual doses (unit doses).

Conventional vaccines generally contain about 0.1 to 200 μg, e.g., 30 to 100 μg, of HA from each of the strains entering into their composition. The vaccine forming the main constituent of the vaccine composition of the invention may comprise a single influenza virus, or a combination of influenza viruses, for example, at least two or three influenza viruses, including one or more reassortant(s).

Preparations for parenteral administration include sterile aqueous or non-aqueous solutions, suspensions, and/or emulsions, which may contain auxiliary agents or excipients known in the art. Examples of non-aqueous solvents are propylene glycol, polyethylene glycol, vegetable oils such as olive oil, and injectable organic esters such as ethyl oleate. Carriers or occlusive dressings can be used to increase skin permeability and enhance antigen absorption. Liquid dosage forms for oral administration may generally comprise a liposome solution containing the liquid dosage form. Suitable forms for suspending liposomes include emulsions, suspensions, solutions, syrups, and elixirs containing inert diluents commonly used in the art, such as purified water. Besides the inert diluents, such compositions can also include adjuvants, wetting agents, emulsifying and suspending agents, or sweetening, flavoring, or perfuming agents.

When a composition of the present invention is used for administration to an individual, it can further comprise salts, buffers, adjuvants, or other substances which are desirable for improving the efficacy of the composition. For vaccines, adjuvants, substances which can augment a specific immune response, can be used. Normally, the adjuvant and the composition are mixed prior to presentation to the immune system, or presented separately, but into the same site of the organism being immunized.

Heterogeneity in a vaccine may be provided by mixing replicated influenza viruses for at least two influenza virus strains, such as 2-20 strains or any range or value therein. Vaccines can be provided for variations in a single strain of an influenza virus, using techniques known in the art.

A pharmaceutical composition according to the present invention may further or additionally comprise at least one chemotherapeutic compound, for example, for gene therapy, immunosuppressants, anti-inflammatory agents or immune enhancers, and for vaccines, chemotherapeutics including, but not limited to, gamma globulin, amantadine, guanidine, hydroxybenzimidazole, interferon-α, interferon-β, interferon-γ, tumor necrosis factor-alpha, thiosemicarbarzones, methisazone, rifampin, ribavirin, a pyrimidine analog, a purine analog, foscarnet, phosphonoacetic acid, acyclovir, dideoxynucleosides, a protease inhibitor, or ganciclovir.

The composition can also contain variable but small quantities of endotoxin-free formaldehyde, and preservatives, which have been found safe and not contributing to undesirable effects in the organism to which the composition is administered.

Pharmaceutical Purpose

The administration of the composition (or the antisera that it elicits) may be for either a "prophylactic" or "therapeutic" purpose. When provided prophylactically, the compositions of the invention which are vaccines are provided before any symptom or clinical sign of a pathogen infection becomes manifest. The prophylactic administration of the composition serves to prevent or attenuate any subsequent infection. When provided prophylactically, the gene therapy compositions of the invention, are provided before any symptom or clinical sign of a disease becomes manifest. The prophylactic administration of the composition serves to prevent or attenuate one or more symptoms or clinical signs associated with the disease.

When provided therapeutically, a viral vaccine is provided upon the detection of a symptom or clinical sign of actual infection. The therapeutic administration of the compound(s) serves to attenuate any actual infection. When provided therapeutically, a gene therapy composition is provided upon the detection of a symptom or clinical sign of the disease. The therapeutic administration of the compound(s) serves to attenuate a symptom or clinical sign of that disease.

Thus, a vaccine composition of the present invention may be provided either before the onset of infection (so as to prevent or attenuate an anticipated infection) or after the initiation of an actual infection. Similarly, for gene therapy, the composition may be provided before any symptom or clinical sign of a disorder or disease is manifested or after one or more symptoms are detected.

A composition is said to be "pharmacologically acceptable if its administration can be tolerated by a recipient mammal. Such an agent is said to be administered in a therapeutically effective amount" if the amount administered is physiologically significant. A composition of the present invention is physiologically significant if its presence results in a detectable change in the physiology of a recipient patient, e.g., enhances at least one primary or secondary humoral or cellular immune response against at least one strain of an infectious influenza virus.

The "protection" provided need not be absolute, i.e., the influenza infection need not be totally prevented or eradicated, if there is a statistically significant improvement compared with a control population or set of mammals. Protection may be limited to mitigating the severity or rapidity of onset of symptoms or clinical signs of the influenza virus infection.

Pharmaceutical Administration

A composition of the present invention may confer resistance to one or more pathogens, e.g., one or more influenza virus strains, by either passive immunization or active immunization. In active immunization, an attenuated live vaccine composition is administered prophylactically to a host (e.g., a mammal), and the hosts immune response to the administration protects against infection and/or disease. For passive immunization, the elicited antisera can be recovered and administered to a recipient suspected of having an infection caused by at least one influenza virus strain. A gene therapy composition of the present invention may yield prophylactic or therapeutic levels of the desired gene product by active immunization.

In one embodiment, the vaccine is provided to a mammalian female (at or prior to pregnancy or parturition), under conditions of time and amount sufficient to cause the production of an immune response which serves to protect both the female and the fetus or newborn (via passive incorporation of the antibodies across the placenta or in the mother's milk).

The present invention thus includes methods for preventing or attenuating a disorder or disease, e.g., an infection by at least one strain of pathogen. As used herein, a vaccine is said to prevent or attenuate a disease if its administration results either in the total or partial attenuation (i.e., suppression) of a clinical sign or condition of the disease, or in the total or partial immunity of the individual to the disease. As used herein, a gene therapy composition is said to prevent or attenuate a disease if its administration results either in the total or partial attenuation (i.e., suppression) of a clinical sign or condition of the disease, or in the total or partial immunity of the individual to the disease.

A composition having at least one influenza virus of the present invention, including one which is attenuated and one or more other isolated viruses, one or more isolated viral proteins thereof, one or more isolated nucleic acid molecules encoding one or more viral proteins thereof, or a combination thereof, may be administered by any means that achieve the intended purposes.

For example, administration of such a composition may be by various parenteral routes such as subcutaneous, intravenous, intradermal, intramuscular, intraperitoneal, intranasal, oral or transdermal routes. Parenteral administration can be accomplished by bolus injection or by gradual perfusion over time.

A typical regimen for preventing, suppressing, or treating an influenza virus related pathology, comprises administration of an effective amount of a vaccine composition as described herein, administered as a single treatment, or repeated as enhancing or booster dosages, over a period up to and including between one week and about 24 months, or any range or value therein.

According to the present invention, an "effective amount" of a composition is one that is sufficient to achieve a desired effect. It is understood that the effective dosage may be dependent upon the species, age, sex, health, and weight of the recipient, kind of concurrent treatment, if any, frequency of treatment, and the nature of the effect wanted. The ranges of effective doses provided below are not intended to limit the invention and represent dose ranges.

The dosage of a live, attenuated or killed virus vaccine for an animal such as a mammalian adult organism may be from about $10^2$-$10^{15}$, e.g., $10^3$-$10^{12}$, plaque forming units (PFU), or any range or value therein. The dose of inactivated vaccine may range from about 0.1 to 1000, e.g., 30 to 100 μg, of HA protein. However, the dosage should be a safe and effective amount as determined by conventional methods, using existing vaccines as a starting point.

The dosage of immunoreactive HA in each dose of replicated virus vaccine may be standardized to contain a suitable amount, e.g., 30 to 100 μg or any range or value therein, or the amount recommended by government agencies or recognized professional organizations. The quantity of NA can also be standardized, however, this glycoprotein may be labile during purification and storage.

The dosage of immunoreactive HA in each dose of replicated virus vaccine can be standardized to contain a suitable amount, e.g., 1-50 μg or any range or value therein, or the amount recommended by the U.S. Public Health Service (PHS), which is usually 15 μg per component for older children (greater than or equal to 3 years of age), and 7.5 μg per component for children less than 3 years of age. The quantity of NA can also be standardized, however, this glycoprotein can be labile during the processor purification and storage (Kendal et al., 1980; Kerr at al., 1975). Each 0.5-ml dose of vaccine may contains approximately 1-50 billion virus particles, and preferably 10 billion particles.

EXEMPLARY EMBODIMENTS

In one embodiment, the recombinant or reassortant influenza B virus has an amino acid that results in enhanced replication in MDCK cells, e.g., residues in HA including but not limited to a residue other than T at position 34, other than K at position 129, other than N at position 168, other than T at position 196, or any combination thereof; residues in NA including but not limited to a residue other than residue N at position 169, and/or other than G at position 434; residues in NP including but are not limited to a residue other than alanine (A) at position 28, other than P at position 40, other than P a position 51, other than E at position 52, other than S at position 57, other than M at position 204, other than g at nucleotide position 1795, or any combination thereof; residues in M1 including but not limited to a residue other than G at position 34, other than aspartic acid (D) at position 54, other than R at position 77, other than M at position 86; residues in BM2 including but not limited to a residue other than H at position 58 and/or other than R at position 80; residues in NS1 including but not limited to other than M at position 117, other than K at position 176, and/or other than S at position 252, a nucleotide other than a at position 39, or any combination thereof. In one embodiment, the recombinant influenza B virus has an amino acid that results in enhanced replication in MDCK cells, e.g., in HA1, residue I at position, 34, residue E at position 129, E, D at position 168, P, isoleucine (I), A or N at position 196, or any combination thereof; in NA, residue T at position 169 and/or residue E at position 434; in NP, residue T at position 28, residue S at position 40, residue 0 at position 51, residue K at position 52, residue G at position 57, residue T at position 214, g at nucleotide position 1795, or any combination thereof; in M1 residue valine (V) or N at position 34, residue G at position 54, residue K at position 77, residue T at position 86, residue N at position 97, or any combination thereof; in BM2 include residue R at position 58 and/or residue G at position 80; in NS1 include residue tyrosine (Y) at position 117, residue glutamine (Q) at position 176, residue T at position 252, a g at nucleotide position 39, additional g after nucleotide position 38, or any combination thereof.

In one embodiment, the recombinant or reassortant influenza B virus has an amino acid that results in enhanced replication in Vero cells, e.g., residues in HA1 including but not limited to a residue other than R at position 98, other than N at position 194, and/or other than T at position 196, and/or in HA2 including but not limited to a residue other than K at position 39, other than S at position 56, other than K at position 61, or other than D at position 112, or any combination thereof; residues in NA including but not limited to a residue other than residue T at position 76, other than residue R at position 102, other than residue E at position 105, other than residue P at position 139, other than residue T at position 436, other than D at position 457, or any combination thereof; residues in NP including but not limited to a residue other than P at position 343; residues in M1 other than G at position 34, other than I at position 97, or any combination thereof; residues in BM2 other than H at position 58, other than R at position 80, other than H at position 27, other than G at position 26, or any combination thereof; residues in NS1 including but not limited to a residue other than Y at position 42; residues in PA other than Y at position 387, other than V at position 434, other than D at position 494, other than T at position 524, a nucleotide other than a at nucleotide position 2272, a nucleotide other than g at nucleotide position 2213, a residue in PB2 other than N at position 16; or any combination thereof. In one embodiment, the recombinant influenza B virus has an amino acid that results in enhanced replication in Vero cells, e.g., in HA, P, I, A or N at position 196 (in HA1), residue K at position 98 (in HA1), residue D at position 194 (in HA1), residue G at position 39 (in HA2) residue G at position 56 (in HA2), residue N at position 51(in HA2), or residue E at position 112 (in HA2), or any combination thereof; in NA residue M at position 76, residue K at position 102, residue K at position 105, residue S at position 139, residue M at position 436, and/or residue N at position 457, or any combination thereof; in NP residue T at position 343; in M1 include residue V or N at position 34 and/or residue N at position 97; in BM2 residue R at position 58, residue G at position 80, residue R at position 27, residue R at position 26, or any combination thereof; in NS1 residue N at position; in PA residue H at position 387, residue A at position 434, residue N at position 494, residue A at position 534, g at nucleotide position 2272, a t at nucleotide position 2213; residue S at position 16 in PB2; or any combination thereof.

In one embodiment, for viruses related to B/Yamagata-lineage, the recombinant or reassortant influenza B virus has an amino acid in HA1 other than K at position 129, other than N at position 168, other than N at position 194, other than T at position 196, other than D at position 112, or any combination thereof; in NA other than T at position 76, other than R at position 102, other than E at position 105, other than P at position 139, other than G at position 434, other than T at position 436, other than D at position 457, or any combination thereof; in NP other than E at position 52, other than S at position 57, other than P at position 343, or any combination thereof; in M1 other than G at position 34, other than R at position 77, other than I at position 97, or in NP vRNA, a nucleotide other than c a position 500, or any combination thereof; in BM2 other than H at position 58, other than R at position 80, other than H at position 27, other than G at position 26, or any combination thereof; in NS1 other than M at position 117, other than S at position 252, and/or other than D at position 494 in PA, and/or a nucleotide other than a at position 2272, other than g at nucleotide position 2213, other than a at position 1406, and/or other than c at position 1445 in PA vRNA, or any combination thereof; in PB2 a residue other than N at position 16; or any combination thereof. In one embodiment, the recombinant influenza B virus has in HA1 E at position 129, D at position 168; P at position 196, D at position 194, in HA2 at position 112, or any combination thereof; in NA M at position 76, K at position 102, K at position 105, S at position 139, E at position 434, M at position 436, and/or N at position 457, or any combination thereof; in NP K at position 52, G at position 57, T at position 343, or any combination thereof; in M1 V or N at position 34, K at position 77, N at position 97, or any combination thereof; in BM2 R at position 58, G at position 80, R at position 27, R at position 26, or any combination thereof; in NS1 Y at position 117, T at position 252, or any combination thereof; in PA in N at position 494, t at position 2272, a at position 2213; in PB2 S at position 16; or any combination thereof.

In one embodiment, for influenza B viruses that are related to B/Victoria-lineage, the recombinant or reassortant influenza B virus has an amino acid in HA1 other than T at position 34, other than R at position 98, other than T at position 196, and/or in HA2 a residue other than K at position 39, other than S at position 56, other than K at position 61, or any combination thereof; in NA other than N at position 169 and/or other than D at position 457; in NP other than A at position 28, than P at position 40, other than P at position 51, other than M at position 204, or in NP vRNA a nucleotide other than g at position 1795 or other than c at position 500, or any combination thereof; in M1 other than D at position 54 and/or other than M at position 86; in BM2 other R at position 80; in NS1 other than Y at position 42, other than K at position 176, nucleotide other than a at position 39; in PA other than Y at position 387, other than V at position 434, other than T at position 524, or in PA vRNA a nucleotide other than a at nucleotide position 2272, a nucleotide other than g at nucleotide position 2213, a nucleotide other than a at position 1406, a nucleotide other than c at position 1445, or any combination thereof. In one embodiment, the recombinant influenza B virus has an amino acid has in HA I at position 34, P, I, A or N at position 196, K at position 98, and in HA2 G at position 39, residue G at position 56, residue N at position 61, or any combination thereof; in NA T at position 169 and/or N at position 457; in NP T at position 28, S at position 40, Q at position 51, T at position 204, a at position 1795, or any combination thereof; in M1 G at position 54 and/or T at position 86; in BM2 G at position 80; in NS1 N at position 42, Q at position 176, g at position 39, an additional g after position 38; in PA H at position 387, A at position 434, A at position 534, t at position 2272, a at position 2213, or any combination thereof.

In one embodiment, the recombinant or reassortant influenza B virus has one or more, e.g., 2, 3, 4, 5, 6, 7, 8, 9, 10 or more of the following: a residue other than Y at position 387, other than V at position 434, other than D at position 494, other than T at position 524, a nucleotide other than a2272, g2213, a1406, c1445, or any combination thereof, in PA or PA vRNA, e.g., 2272t, 2213a, 1406g, 1445t, 387H, 434A, 494N, 524A, or any combination thereof (e.g., residue H at position 387, residue A at position 434, residue N at position 494, residue A at position 524, or any combination thereof); a residue other than T at position 34, other than R at position 98, other than K at position 129, other than N at position 168, other than N at position 194, and/or other than T at position 196, in HA1, other than K at position 39, other than S at position 56, other than K at position 61, or other than D at position 112, in HA2, e.g., in HA1 34I, K129E, 168D, 196P/I/A/N, 98K, or 194D, and in HA2 including 39G, 56G, 61N, or 112E, or any combination thereof; a residue other than residue T at position 76, other than residue R at position 102, other than residue E at position 105, other than residue P at position 139, other than residue N at position 169, other than G at position 434, other than residue T at position 436, and/or residue D at position 457 in NA, e.g., 169T, 434E, 76M, 102K, 105K, 139S, 436M, 457N, or any combination thereof; a residue other than H at position 58, other than R at position 80, other than H at position 27, other than G at position 26 in BM2, such as residue R at position 58, residue G at position 80, residue R at position 27, and/or residue R at position 26; other than A at position 28; other than P at position 40, other than P at position 51, other than E at position 52, other than S at position 57, other than M at position 204, and/or other than P at position 343, and/or g at position 1795, or any combination thereof, in NP, e.g., residue T at position 28, residue S at position 40, residue Q at position 51, residue K at position 52, residue G at position 57, residue T at position 214, residue T at position 343, or any combination thereof; residue other than G at position 34, other than D at position 54, other than R at position 77, other than M at position 86, other than I at position 97, or any combination thereof in M1, e.g., residue V or N at position 34, residue G at position 54, residue K at position 77, residue T at position 86, and/or residue N at position 97; in PB2 other than N at position 16. In one embodiment, the recombinant virus has M1 34V/I97N, BM2 58R/80G, NP 40S, NS1 86T.

In one embodiment, the influenza virus of the invention is a recombinant or reassortant influenza virus having two or more of selected amino acid residues at specified positions in one or more segments for PA, NP, M (M1 and BM2), and/or NS, which can be employed with HA and NA genes of interest. In one embodiment, the recombinant reassortant influenza virus has two or more of in NP, A28T, P40S, P51Q, E52K, S57G, M204T, and/or P343T, and/or g1795a; in M1, G34V/N, D54G, R77K, M86T, I97N; in BM2, H58R, R80G, H27R, G26R; in NS1, M117Y, K176Q, S252T, a39g, an additional g after 38, Y42N, in PA, a2272t, g2213g, Y387H, V434A, D494N, T524A; in PB2 N16S.

In one embodiment, the influenza virus of the invention is a recombinant or reassortant influenza virus having two or more of selected amino acid residues at specified positions in one or more of PA, BM2, NP, M1, and/or NS1, which can be employed with HA and NA genes of interest. For example, in one embodiment, the recombinant influenza B virus has M1 34V/I97N, BM2 58R/80G, NP 40S, M1 M86T, or has NP P40S or has NP E52K, or has a substitution in NP, M1, and optionally NS1 and BM2, as in clones 1-8 in Table 3 and substitutions in NP, M1, and optionally NS1, as in clones 1-8 in Table 4.

In one embodiment, the influenza virus of the invention is a recombinant or reassortant influenza virus having two or more of a1406g, c1445t, a2272t in PA vRNA, P40S or P40S/M204T in NP, c500t in NP vRNA, M77K or M86T, and a39g or 38(+1)g in NS vRNA, or K176 Q in NS, e.g., an influenza virus having PA a1406g/c1445t/a2272t, NP P40S, c500t, M R77K and NS a39g K1760, or having PA a1406g/c1445W/a2272, NP P40S/M204T, c500t, M M86T and NS 38(+1)g.

The invention will be described by the following nonlimiting examples.

Example 1

The yield of vaccine viruses is important from an economic point of view. Even more important, the ability to produce high numbers of vaccine doses under tight timelines may save many lives during a virus outbreak. Mutations that increase the replicative ability of viruses in cell culture and/or embryonated chicken eggs are useful to amplify influenza viruses, and to establish robust influenza vaccine platforms. Currently, most influenza vaccines are generated in embryonated chicken eggs. Influenza vaccines generated in MDCK cells are now approved for human use in the U.S. and in Europe, and influenza vaccines derived from Vero cells are approved for human use in Europe.

To develop a high-yield influenza B virus backbone for growth of vaccine virus in these specific host cells, random mutagenesis of the internal genes of B/Yamagata/1/73 was conducted; the HA and NA genes of the mutant virus libraries were derived from B/Yokohama/UT-K31/2012 (Yamagata-lineage) or B/Yokohama/UT-K1A/2011 (Victoria-lineage), representing the two major influenza B virus lineages. The virus libraries that were generated possessed random mutations in the 'internal' viral genes as well as those encoding the viral surface glycoproteins hemagglutinin (HA) and neuraminidase (NA), as well as non-coding mutation. Those that conferred improved growth, and this are vaccine virus candidates, were further evaluated. In particular, these vaccine virus candidates confer higher yield in commonly used propagation systems for influenza vaccine virus production: that is, embryonated chicken eggs, Madin-Darby canine kidney cells, and African green monkey (Vero) cells. These vaccine candidates could be used to improve the influenza B virus vaccine production process.

Materials and Methods

Cells. MDCK cells were grown in MEM containing 5% (vol/vol) newborn calf serum. Vero cells were maintained in MEM containing 10% (vol/vol) FBS. 293T human embryonic kidney cells were grown in DMEM supplemented with 10% (vol/vol) FBS.

Construction of Plasmids. The sequences of the eight viral RNAs of B/Yamagata/1/73 virus were used to design gBlocks Gene Fragments (integrated DNA Technologies), which were amplified and joined by PCR; the resulting viral cDNAs were inserted into the RNA polymerase I vector pHH21 (Neumann at al., 1999). The vRNAs of the B/Yokohama/UT-K31/2012, B/Yokohama/UT-K1A/2011, B/Yokohama/P-2922/2005, B/Tokyo/UTE2/2008, B/Tochigi/UT-T1/2011, B/Massachusetts/2/2012, and B/Brisbane/60/2008 viruses were extracted from virus stocks by using the RNeasy Kit (Qiagen). The viral HA and NA genes were amplified with gene-specific oligonucleotides by using the One-Step RT-PCR Kit (Invitrogen), and the PCR-products were cloned into the pHH21 vector. The HA and NA genes of B/Yamagata/16/1988 were synthesized by PCR-amplification of joined gBlocks Gene Fragments, followed by cloning into pHH21. The type A/B chimeric HA and NA genes of B/Yokohama/UT-K31/2012, B/Yokohama/UT-K1A/2011, B/Massachusetts/2/2012 and B/Brisbane/60/2008 viruses were generated by overlapping PCRs.

Construction of Plasmid Libraries. One to four random mutations were introduced into each of the six internal genes of B/Yamagata/1/73 virus by error-prone PCR using the GeneMorph II Random Mutagenesis Kit. The randomly mutated PCR products were inserted into the pHH21 vector, and the diversity of the resulting plasmid libraries was confirmed by sequence analysis of at least 24 *Escherichia coli* colonies for each viral gene.

Virus Rescue and Virus Library Generation. Wild-type viruses and virus libraries possessing random mutations in the internal genes were generated with the help of reverse-genetics approaches (Neumann et al., 1999). Virus libraries were generated by transfecting 293T cells with a mutant plasmid library instead of the wild-type construct. Forty-eight hours later, supernatants from plasmid-transfected 293T cells were collected and amplified in MDCK cells to generate virus stock; the titers of the virus stocks were determined by using plaque assays in MDCK cells.

Evaluation of Viral Growth Kinetics. Wild-type or recombinant viruses were inoculated in triplicate into MDCK cells at a multiplicity of infection (MOI) of 0.001. After infection, cells were incubated with MEM/BSA medium with 0.6 μg/mL TPCK-trypsin. Supernatants were collected at the indicated time points and the virus titers were assessed by means of plaque assays in MDCK cells.

To analyze viral replication in embryonated chicken eggs, 10-day-old embryonated chicken eggs (four per virus) were inoculated with $1\times10^4$ pfu of virus and incubated them at 35° C. The allantoic fluids were collected at the indicated time points and virus titers were determined by use of plaque assays in MDCK cells.

The hemagglutination titers of viruses amplified in MDCK cells or embryonated chicken eggs were determined by using a hemagglutination assay. Briefly, 50 μL of virus sample was serially diluted twofold in 96-well U-bottom microtiter plates (Thermo Scientific) containing 50 μL of PBS per well. Next, 50 μL of 0.5% turkey red blood cells were added to each well, plates were incubated for 45 minutes at room temperature, and hemagglutination titers were calculated as the reciprocal value of the highest dilution at which agglutination occurred.

Virus Concentration and Purification. MDCK cells were grown in two 4-Layers Easy-Fill Cell Factories (Thermo Scientific) and infected with wild-type or high yield influenza B viruses at an MOI of 0.001 when the cells reached about 95% confluency. Cell-culture supernatants were harvested 48 hours later and clarified by centrifugation (3,500 rpm in a Beckman SX4750 rotor, 15 minutes, 4° C.). Viruses were pelleted by ultracentrtfugation (18,500 rpm, 90 minutes at 4° C. In a Beckman Type 19 rotor), resuspended in 5 mL of PBS, and loaded onto 20-50% (wt/vol) continuous sucrose gradients which were centrifuged at 25,000 rpm for 90 minutes at 4° C. in a Beckman SW32 rotor. The virus-containing band was collected, diluted in PBS, and pelleted again by centrifugation (25.000 rpm, 90 minutes, 4° C., Beckman SW32 rotor). The virus pellet was resuspended in 400 μL of PBS, aliquoted, and stored at −80° C.

Total Protein Assay. Total protein yield of virus concentrates was determined by using the Pierce BCA protein assay kit (Thermo Scientific) according to the manufacturer's instructions.

Deglycosylation of Viral Proteins Using PNGase F. To remove sugar moieties, 10 μL of virus concentrate was denatured. The sample was then incubated at 37° C. for 20 hours with 2 μL of a one-tenth dilution of PNGase F enzyme (New England Biolabs) in the buffer provided by the manufacturer and with Nonidet P-40 at a final concentration of 1%.

SDS/PAGE. 2 μL of virus concentrate was mixed with PBS to a total volume of 10 μL and 2.5 μL of loading dye with 2% (vol/vol) β-mercaptoethanol (as reducing agent) was added, which mixture was heated to 95° C. for 5 minutes. Samples were then loaded onto NuPage 4-12% (wt/vol) Bris-Tris precast gels (Life technology), which were run at 150 V for 120 minutes using 1×Mes buffer (Bio-Rad), and then stained with SYPRO-Ruby (Sigma). Quantitation of protein amounts was carried out by using ImageJ software (NIH). The HA content was calculated by dividing the HA amount (calculated by summing the amounts of HA1 and HA2) by the sum of the amounts of HA1, HA2, NP, and M1, and multiplying this value by the amount of total viral protein.

Virulence Studies in Mice. Six-week-old female BALB/c mice (Jackson Laboratory) were anesthetized with isoflurane and inoculated intranasally with $10^6$ pfu of influenza B viruses in a volume of 50 μL. Five mice were infected per group; this sample size is adequate to detect large effects between groups. Mice were randomized and investigators were not blinded. Body weight changes and survival were monitored daily for 14 days. To assess virus replication in mice, 10 mice per virus were infected with $10^6$ pfu; on days 3 and 6 post-infection, five mice in each group were killed and virus titers in the lungs were determined by use of plaque assays in MDCK cells.

Genetic Stability Testing. To evaluate the genetic stability of the high-yield vaccine backbones, viruses possessing the HY(Yam) and HY(Vic) backbones combined with the HA and NA vRNAs of B/Yokohama/UT-K31/2012 and B/Yokohama/UT-K1A/2011, respectively, were passaged 10 times in MDCK cells at an MOI of 0.01. Viruses collected after each passage were sequenced by means of Sanger sequencing.

Minireplicon Assay. For the minireplicon assay, 293T ceps and MDCK cells were transfected with 0.25 μg each of plasmids expressing the B/Yamagata/1/73 PB2, PB1, PA and NP proteins, together with 0.05 μg of pPolI-B/Yamagata/1/73-NS-Luc (which encodes the firefly luciferase gene under the control of the human RNA polymerase I promoter) or pPolIC250-B/Yamagata/1/73-NS-Luc (which encodes the firefly luciferase gene under the control of the canine RNA polymerase I promoter), respectively. Cells were cotransfected with 0.025 μg of pGL4.74 (hRluc/TK) (an internal control to monitor transfection efficiency; Promega). The transfected cells were incubated at 35° C. for 48 hours, lysed, and assayed for luciferase activity by using the dual-luciferase system detector kit according to the manufacturer's protocol (Promega). The firefly luciferase expression levels were normalized to the Renilla luciferase activity. The data presented are the averages of three independent experiments±SD.

To investigate the significance of the mutations in the noncoding regions of the B/Yamagata/1/73 PA and NS1 vRNAs, cells were transfected as described above; however, pPolIC250-NP(0)Fluc(0) was replaced with a reporter construct in which the firefly luciferase gene was flanked by the wild-type or mutant noncoding regions of the PA or NS vRNAs, respectively. At 48 hours post-transfection, luciferase activity was measured as described above.

VLP Budding Assay. For the VLP budding assay, 293T cells were transfected with 2 μg each of protein expression plasmids for wild-type or mutant B/Yamagata/1/73 M1, HA, NA, NP, BM2, and NS2. At 48 hours post-transfection, culture supernatant was harvested, clarified, loaded on a 20% (wt/vol) sucrose cushion, and ultracentrifuged at 60,000 rpm for 2 hours in a Beckman SW 60 Ti rotor; the pelleted VLPs were then resuspended in PBS overnight at 4° C. In parallel, we lysed the transfected cells with RIPA buffer.

Purified VLPs and cell lysates were separately mixed with 5× loading dye buffer and fractionated on NuPage 4-12% (wt/vol) Bris-Tris precast gels (Life Technology). The proteins were transferred to nitrocellulose membranes by using an Blot dry blotting system (Invitrogen). The membranes were then blocked for 3 hours at room temperature with PBS with 0.05% Tween 20 (PBS-T) containing 5% (wt/vol) skimmed milk. Then, the membranes were incubated with monoclonal antibodies to B/Brisbane/60/2008 HA (1:1,000; my BioSource, MBS430175), or to influenza B virus NP (1:1,000; Abcam, ab47876) or M1 (1:2,000; Abcam, ab82608) protein overnight at 4° C. After four washes with PBS-T for 10 minutes each, the membranes were incubated with goat antimouse secondary antibodies conjugated with horseradish peroxidase (1:2,000; Life Technology) for 1 hour at room temperature. After four washes with PBS-T for 10 minutes each, the blots were developed by using lumi-light Western blotting substrate (Roche Applied Science) and visualized following autoradiography. Quantitation of protein amounts was carried out by using ImageJ software (NIH). To calculate the percentages of HA, NP, and M1 protein incorporation into VLPs, the following formula was used: (ratio of the amount of protein in the mutant VLP to the total amount of mutant protein (VLP+cell lysate)ratio of the amount of protein in the wild-type VLP to the total amount of wild-type protein (VLP+cell lysate))×100.

IFN Antagonist Assays. To assess the IFN-antagonist activity of wild-type and mutant NS1 proteins, 293T cells were transfected with the NS1 protein expression plasmid and the reporter plasmid pGL-IFN-β, which encodes the firefly luciferase protein under the control of the IFN-β promoter (Bale at al., 2012). Twenty-four hours posttransfection, cells were infected with Sendai virus at an MOI of 5 for 1 hour. Cells were incubated for 24 hours and lysed with Go lysis buffer (Promega); then, Steady-Glo assay buffer (Promega) was added and luciferase expression measured. In another set of experiments, 293T cells were transfected with wild-type or mutant NS1 protein expression plasmids and the reporter plasmid pISRE-Luc (Promega), which encodes the firefly luciferase protein under the control of an IFN-regulated promoter. Twenty-four hours later, cells were treated with 104 U/mL of human IFN-0 for another 24 hours, followed by lysis and measurement of luciferase expression levels.

Statistical Analysis. Statistical analyses of the data were accomplished using the R software (www.r-project.org), v3.1. To compare multiple groups with measurements collected independently at several time points, a two-way ANOVA followed by Tukey's post hoc test was used. To compare measurements from multiple groups collected at a single time point, a one-way ANOVA followed by either Tukey's or Dunnett's post hoc test was used. To compare multiple groups with dependent measurements (e.g., viral growth curves in cell culture for which aliquots were collected from the same culture at different time points), a linear mixed-effects model to the data by using the R package NLME; the time, virus strains, and interaction between these two factors were considered. The R package PHIA was used to build a contrast matrix for comparing strains in a pairwise fashion at the same time point (e.g., group_1 vs. group_2 at 24 hours postinfection, group_1 vs. group_3 at 24 hours postinfection, group_2 vs. group_3 at 24 hours postinfection). Comparisons were performed individually; therefore, the final P values were adjusted by using Holm's method to account for multiple comparisons.

Raw data from growth curves were converted to the logarithmical scale before being analyzed; results were considered statistically significant for P (or adjusted P values)$<0.05$. Variance between groups was assessed by using Levene's test (which was similar for the groups being compared, with $P>0.05$).

Ethics and Biosafety. The experiments in mice followed the University of Wisconsin-Madison's Animal Care and Use Protocol. All experiments were approved by the Animal Care and Use Committee of the University of Wisconsin-Madison (protocol number V00806), which acknowledged and accepted both the legal and ethical responsibility for the animals, as specified in the Fundamental Guidelines for Proper Conduct of Animal Experiment and Related Activities in the Animal Welfare Act and associated Animal Welfare Regulations and Public Health Service Policy.

Results

Figure 2B:
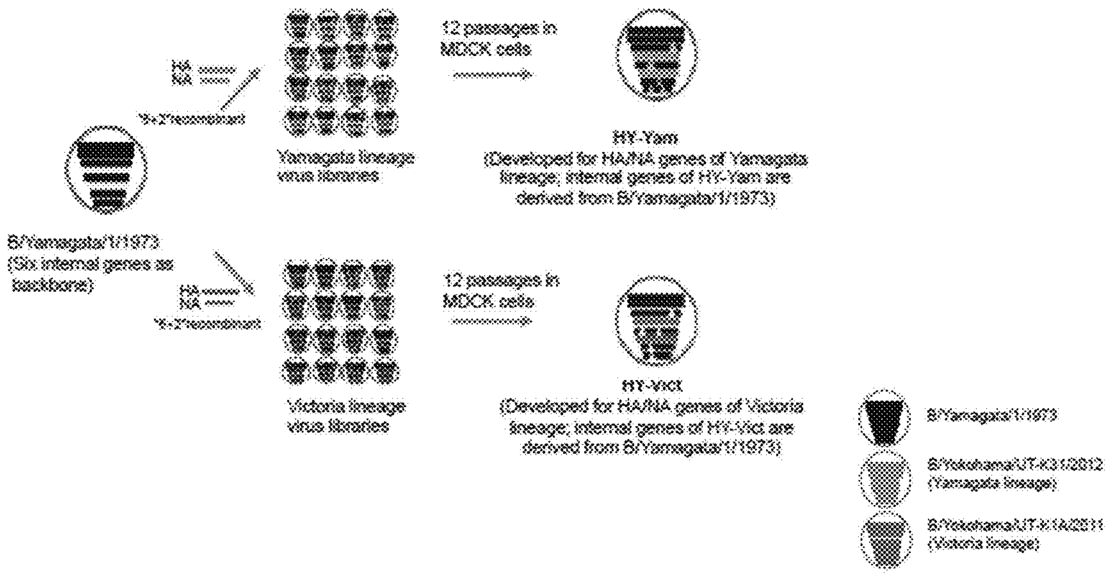

Virus Library Screens for High-Yield Variants in MDCK Cells. Comparable to a strategy to develop a high-yield influenza A virus PR8 vaccine backbone, mutagenesis and screening approaches were used to identify mutations associated with high yield of an influenza B virus. The six internal vRNA segments were from the B/Yamagata/1/73 virus, which grows efficiently in MDCK cells and was isolated before the Victoria and Yamagata lineages separated. A mutagenesis approach based on error-prone PCR was then used to generate libraries of cDNAs possessing one to four random amino acid changes in the viral proteins (FIG. 2). These cDNA libraries were then used to generate virus libraries. Six separate libraries representing each of the internal vRNAs (i.e., PB2, PB1, PA, NP, M, and NS) were generated (FIG. 2); three libraries for combinations of the polymerase vRNAs (i.e., PB2+PB1, PB2+PA, PB2+PB1+PA); one library for the polymerase and nucleoprotein (NP) vRNAs (i.e., PB2+PB1+PA+NP) because the PB2, PB1, PA, and NP proteins form the viral replication complex; one library for the PB2 and NS vRNAs (PB2+NS) because the PB2 and NS1 proteins (encoded by the NS vRNA) of influenza A viruses are important determinants of host virulence (Wright et al., 2013); and one library for the M and NS vRNAs because the M1 protein (encoded by the M vRNA) of influenza A viruses is associated with high-growth properties (Ramanunninair at al., 2013). Each of these 12 virus libraries was generated with the HA and NA vRNAs of a representative virus of the Victoria (B/Yokohama/UT-K1A/2011) or Yamagata (B/Yokohama/UTK31/2012) lineage, respectively, resulting in a total of 24 virus libraries. Libraries generated with the HA and NA vRNAs of the Victoria-lineage or Yamagata-lineage viruses will be referred to as "Victoria-lineage" or "Yamagata-lineage" libraries, respectively.

Figure 3A:
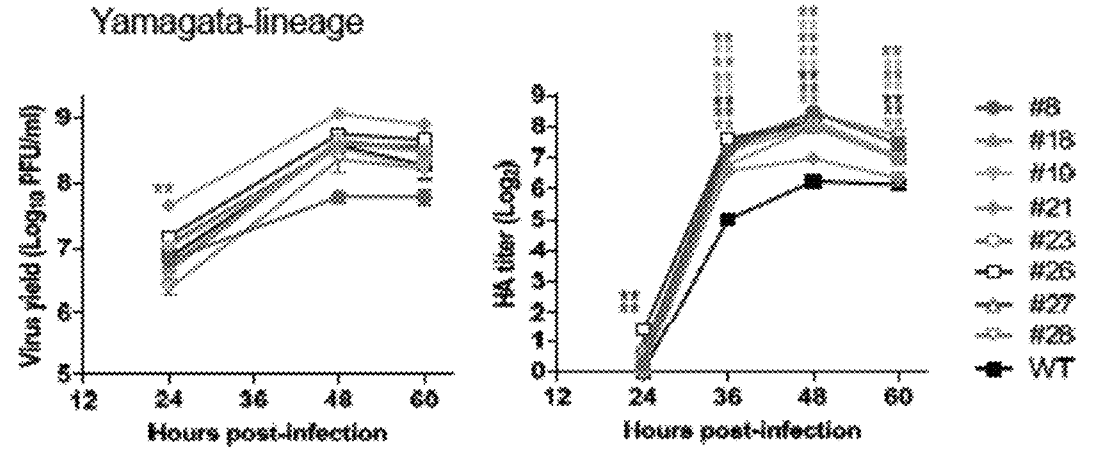
FIGS. 3A-B. Viral titers (growth kinetics) and hemagglutination (HA) titers for select high-yield candidates for the B/Yamagata-(A) and B/Victoria-(B) lineages. Viruses possessing high-yield vaccine backbones of the Yamagata-(A) and Victoria-lineages (B). Mutations detected in the candidate viruses are shown in Tables 1 and 2, respectively. Data were obtained from three independent experiments; shown are average titers±s.d. Statistical significance was determined by using the linear mixed model (*$p<0.05$; **$p<0.01$); P values are not shown if the titer of the high-yield vaccine candidate was lower than that of wild-type virus. The color of the asterisks indicates the comparison of the respective virus with WT virus.
Figure 3B:
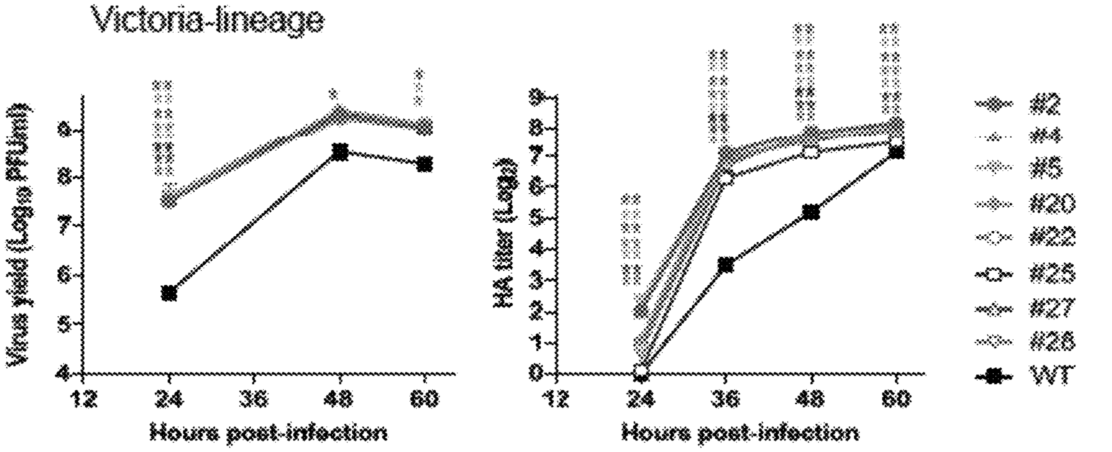

To select variants with enhanced growth properties, each library was passaged 12 times in MDCK cells. In parallel, virus libraries were combined after two passages in MDCK cells, and then 10 additional passages were performed in MDCK cells (FIG. 2). More than 700 viral plaques were randomly selected each from the Victoria- and Yamagata-lineage libraries, respectively, resulting in a total of 1,472 individual, plaque-purified viruses (FIG. 2). The plaque-purified viruses were then amplified in MDCK cells, and their yields were assessed in hemagglutination assays (as a surrogate for high HA yield) and compared with those of the parental Victoria- and Yamagata-lineage viruses (which possess the Victoria- or Yamagata-lineage lineage HA and NA vRNAs in combination with the six remaining vRNAs of B/Yamagata/1/73 virus). 29 Yamagata- and 28 Victoria-lineage viruses were identified with hemagglutination titers that were at least twofold higher than those of the respective control virus. These candidate viruses were reamplified in MDCK cells, and their high-yield properties were confirmed by assessing hemagglutination titers and replication kinetics in MDCK cells (used as another surrogate for high HA yield) (FIG. 3).

Next, the entire viral genomes of the top eight candidates of each lineage were sequenced and different sets of mutations were found for high-yield candidates of the Yamagata- and Victoria-lineages (amino acid changes and changes in the noncoding regions were evaluated) (Tables 1 and 2). Seven of the eight high-yield candidates isolated from the Yamagata-lineage libraries possessed G34V and I97N mutations in the M1 matrix protein, and H58R and R80G mutations in the BM2 ion channel protein (also encoded by the M gene) (Table 1), suggesting that these amino acid substitutions may confer efficient replication in MDCK cells.

All eight high-yield candidates obtained from the Victoria-lineage libraries encoded a P40S mutation in NP and an M86T mutation in M1 (Table 2). In addition, six of these eight high-yield candidates encoded nucleotide changes in the noncoding region of the NS vRNA: an additional nucleotide after position 38 was detected in five viruses (NS-38(+1)g; al nucleotide changes in noncoding regions are shown in italicized lowercase letters), and an a39g nucleotide replacement was detected in one virus (Table 2). A g1795a mutation was identified in the noncoding region of the NP segment in three high-yield candidates (Table 2).

Although the HA and NA vRNAs were not targeted by PCR-mediated random mutagenesis, several mutations were detected in the HA and NA proteins (Tables 1 and 2). Specifically, threonine at position 196 of HA was replaced with various other amino acids (e.g., alanine, isoleucine, proline, or asparagine) in seven of eight high-yield candidates derived from the Victoria-lineage libraries (Table 2), suggesting strong selective pressure at this position.

Figure 4A:
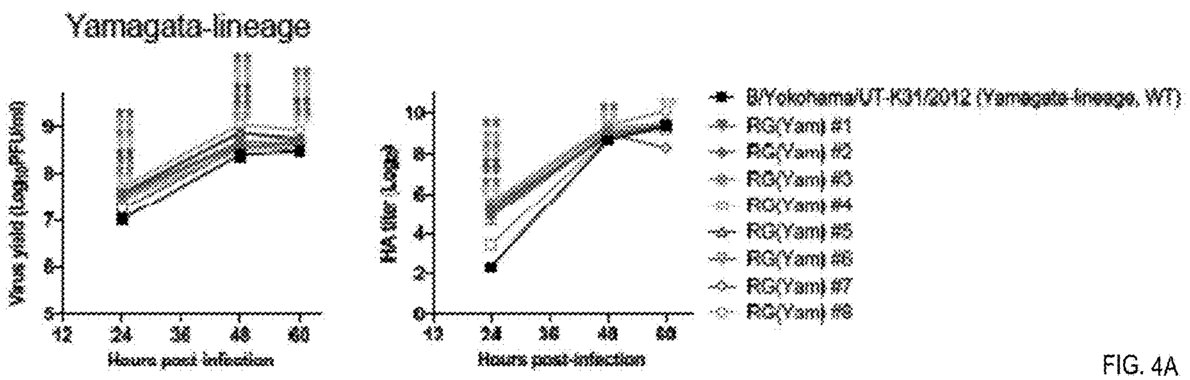
FIGS. 4A-B. Viral titers and HA titers for regenerated high-yield candidates for the B/Yamagata-(A) and B/Victoria-(B) lineages. Mutations introduced into the Yamagata-(A) and Victoria-lineage (B) viruses are shown in Tables 3 and 4, respectively. Data were obtained from three independent experiments; shown are average titers±s.d. P values were calculated by using the linear mixed model (*$p<0.05$; **$p<0.01$); P values are not shown if the titer of the high-yield vaccine candidate was lower than that of wild-type virus. The color of the asterisks indicates the comparison of the respective virus with WT virus.
Figure 4B:
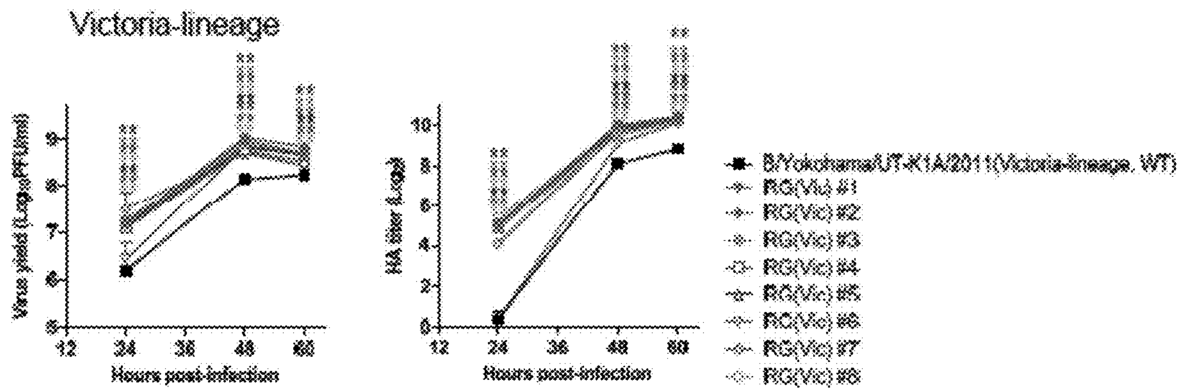
Figure 7A:
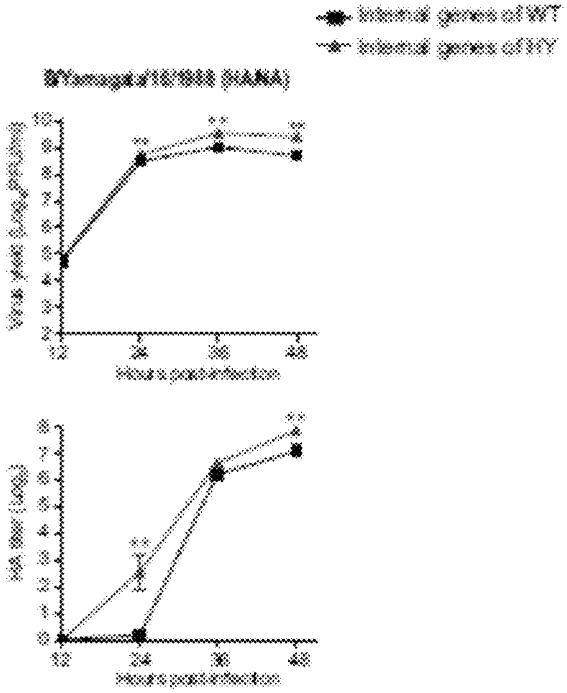
Figure 7B:
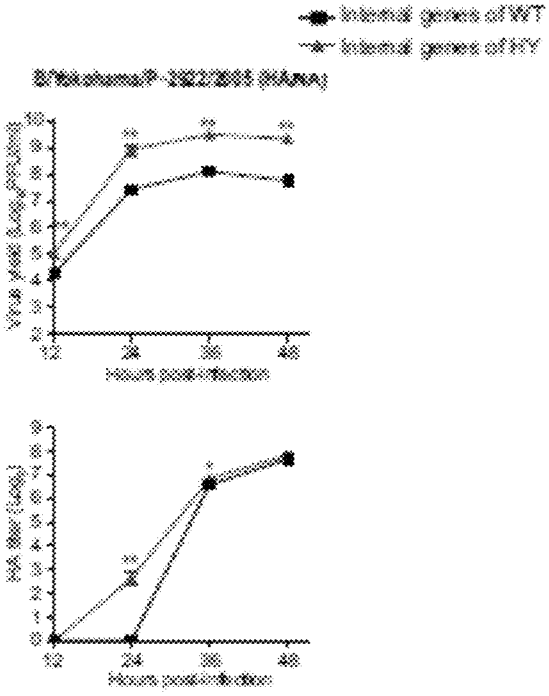
Figure 7C:
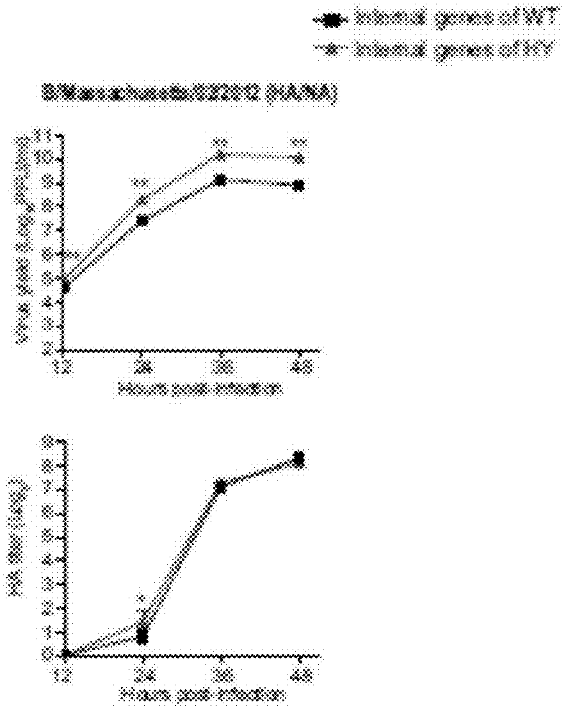
Figure 7D:
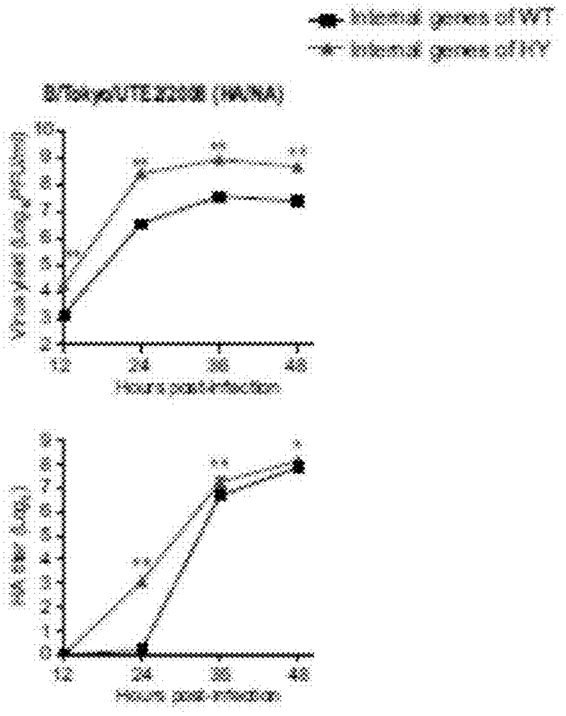
Figure 7E:
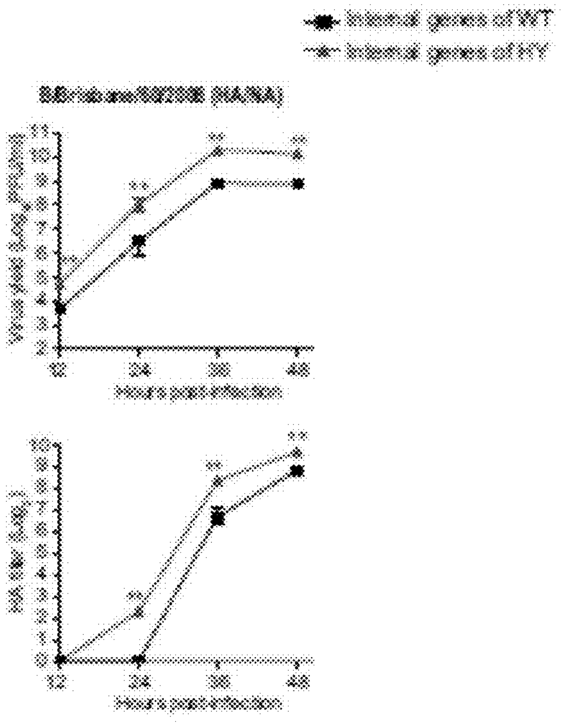
Figure 7F:
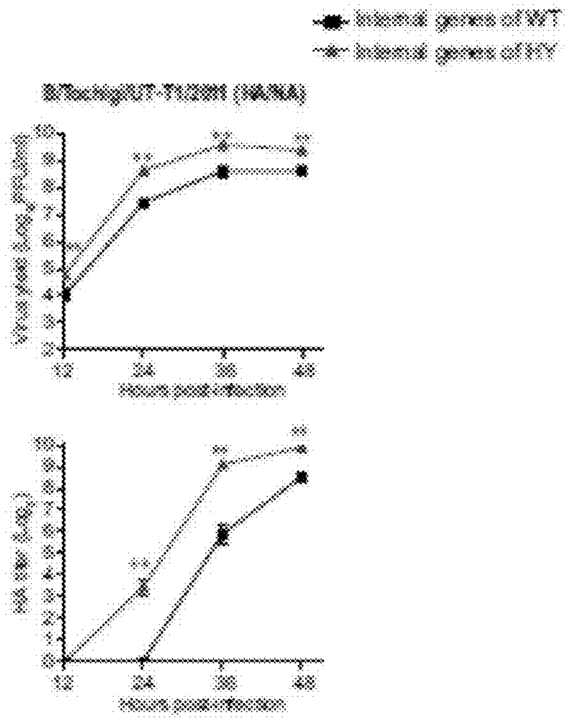
Figure 8A:
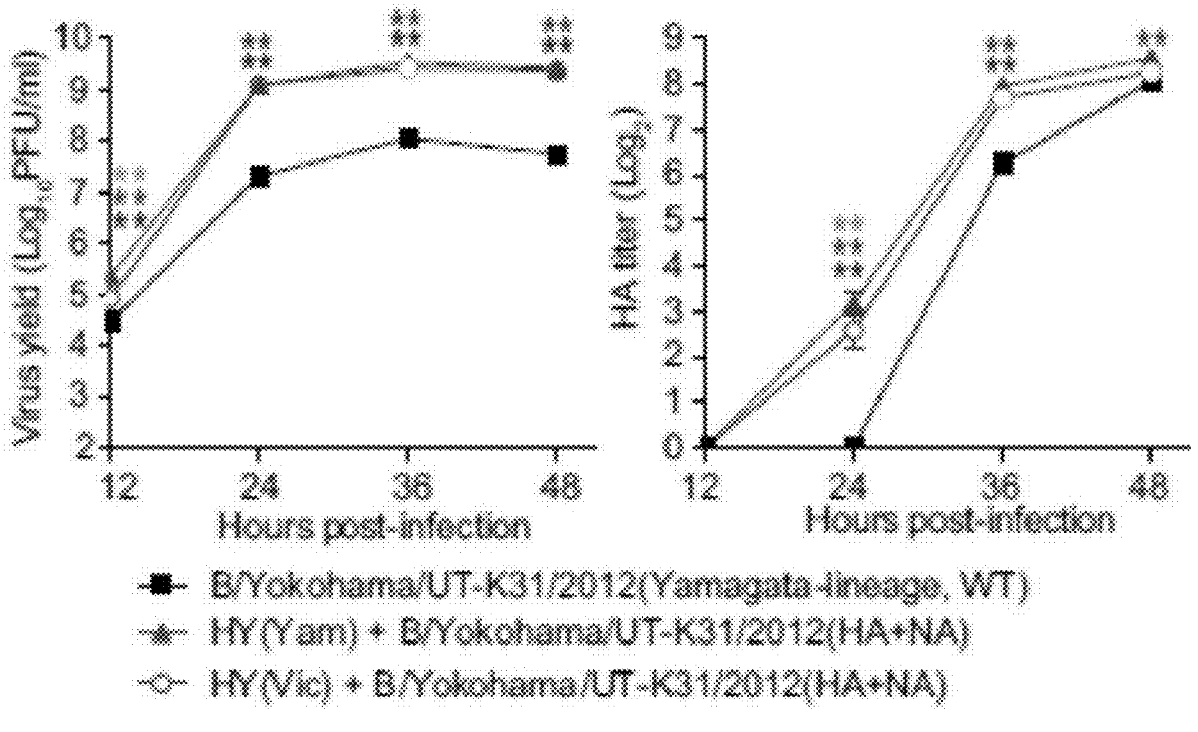
Figure 8B:
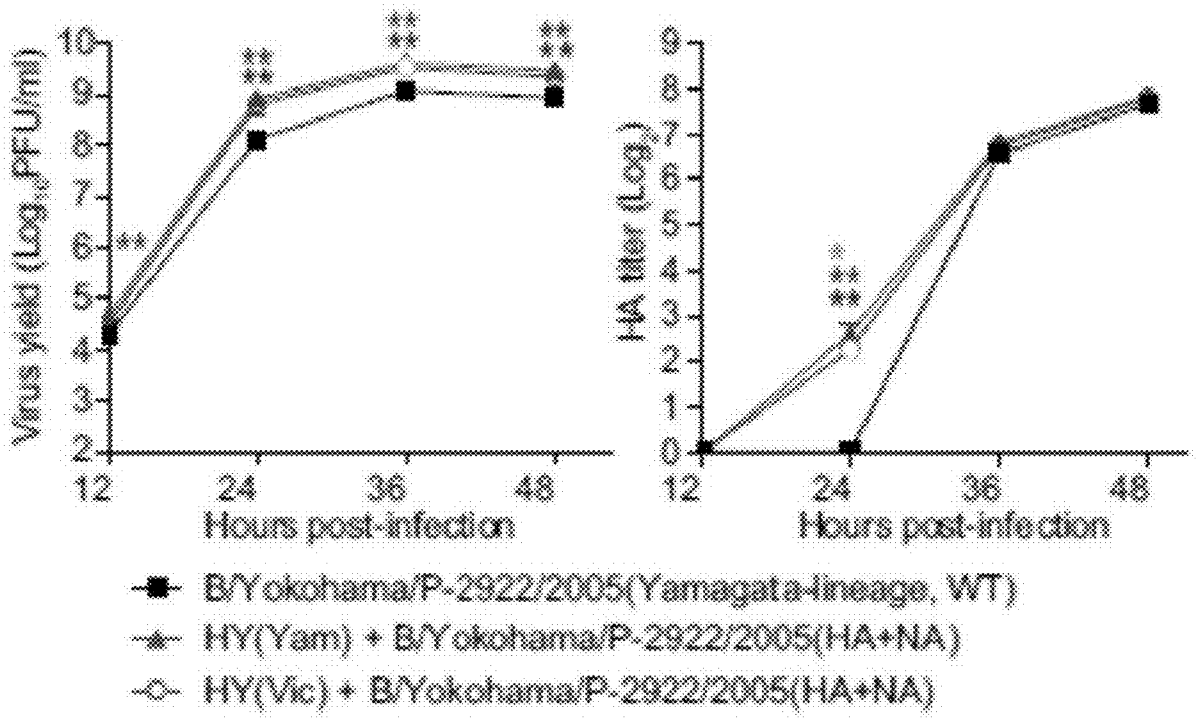
Figure 8C:
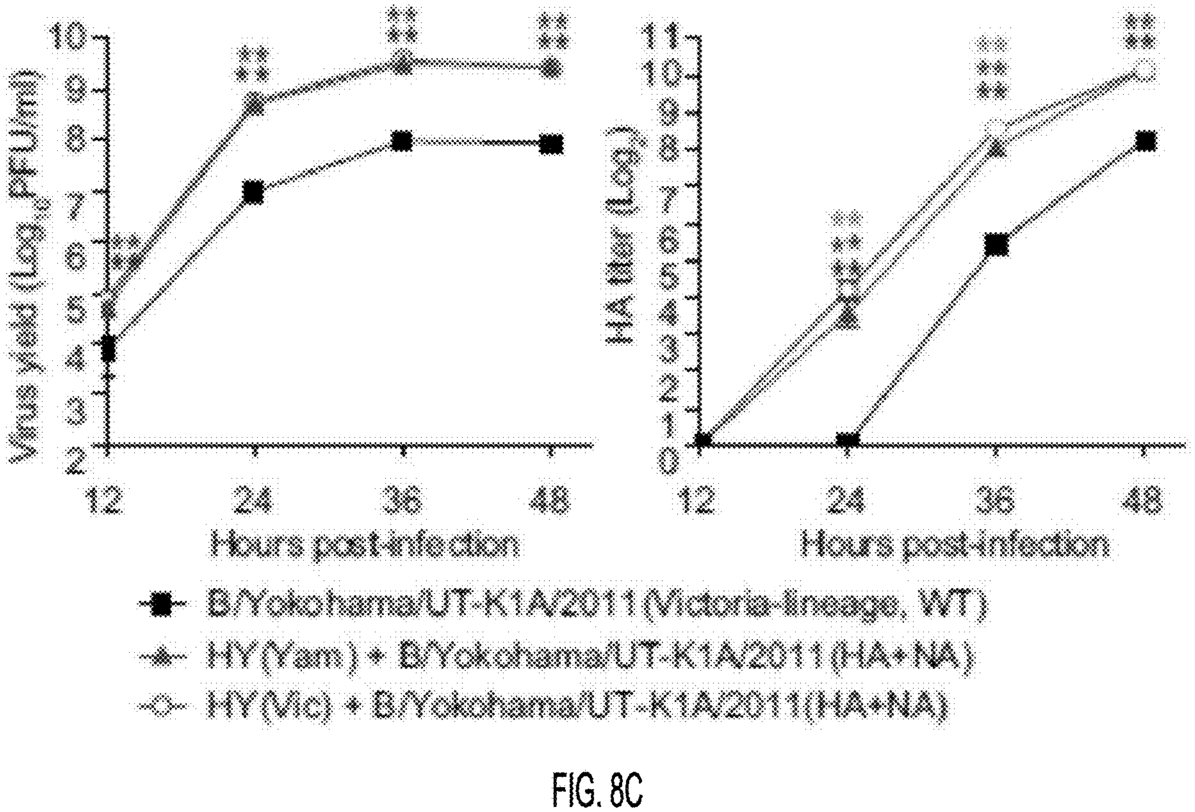
Figure 8D:
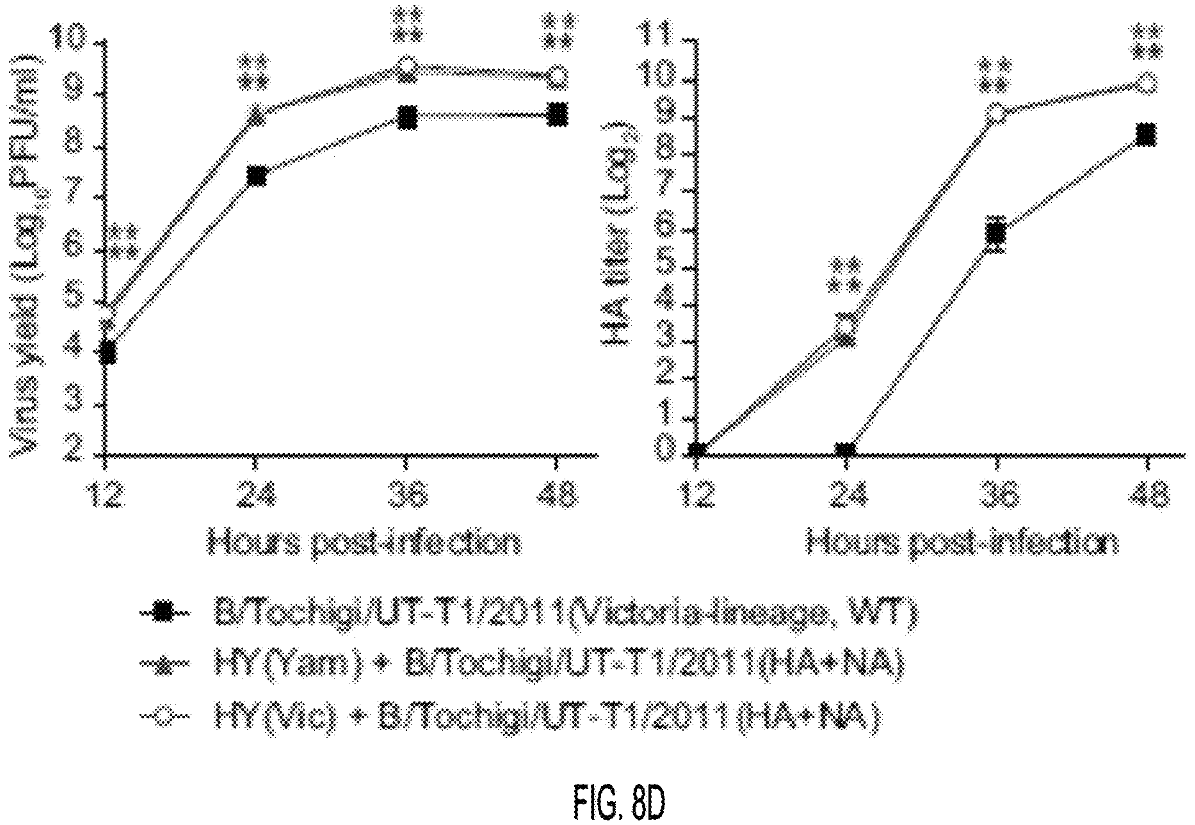

Potential Combinatorial Effects of Mutations. Next, reverse-genetics approaches were used to generate viruses possessing various combinations of the mutations found in the top eight high-yield Yamagata- or Victoria-lineage candidates (Tables 3 and 4). For example, the NP-E52K and M1-R77K mutations found in high-yield candidate #21 (which replicated to the highest titers in MDCK cells) (FIG. 3) were combined with the NS1-M117Y/S252T mutations found in high-yield candidates #23 and #26 (FIG. 3). Because the internal vRNAs of the Yamagata- and Victoria-lineage libraries are derived from the same virus, mutations found in high-yield Yamagata- and Victoria-lineage candidates were also combined (Tables 3 and 4). The resulting viruses were tested for their hemagglutination titers and viral titers in MDCK cells (FIG. 4). All high-yield Yamagata- and Victoria-lineage candidates replicated in MDCK cells more efficiently and had higher hemagglutination titers than the wild-type viruses at one or more time points, and most of these differences were statistically significant (FIG. 4).

Yamagata-lineage RG(Yam) #8 (encoding NP-P40S, M1-R77K, NS1-K176Q, and NS-a39g mutations) and Victoria-lineage RG(Vic) #2 (encoding NP-P40S/M204T, M1-M86T, and NS-38 (+1)g mutations) were selected as lead candidate vaccine backbones because they had the highest titers in their respective groups.

Virus Library Screens for High-Yield Variants in Vero Cells. The ideal vaccine virus backbone should confer a high yield in all three propagation systems currently used in the commercial production of human influenza vaccines: that is. MDCK cells, Vero cells, and embryonated chicken eggs. In parallel to the development of a high-yield influenza B vaccine backbone in MDCK cells, all 24 virus libraries (FIG. 2) were passaged in Vero cells. Because the titers of influenza B virus libraries were low in Vero cells, first the libraries were passaged in cocultured MDCK and Vero cells five times, followed by five passages in Vero cells. In parallel, virus libraries were combined after two passages in cocultured MDCK and Vero cells, passaged three more times in cocultured cells, and then passaged five times in Vero cells. A total of 382 individual virus plaques were randomly picked from the various virus libraries and amplified in Vero cells. Based on the results of hemagglutination assays, the top six candidates were picked from the Yamagata and Victoria lineage, Vero cell-passaged libraries and determined their fun genomic sequences (Tables 5 and 6).

The high-yield candidates possessed several of the mutations that were identified after the MDCK cell passages, which may have been selected in the MDCK cells during the passages in cocultured cells. These mutations include amino acid changes at positions M1-34/97, BM2-58 or -80, and HA1-196 (compare Tables 1 and 2 with Tables 5 and 6). The mutations at positions M1-34197 and BM2-58 were only detected in the Yamagata-lineages libraries, whereas mutations at position BM2-80 occurred in both the Yamagata- and Victoria-lineage viruses. The mutation at position HA1-196 predominated among viruses of the Victoria lineage, but also occurred in one virus of the Yamagata lineage. In addition, mutations not previously found after passages in MDCK cells were observed, most notably an a2272t nucleotide replacement in the noncoding region of PA, which was found in high-yield candidates of both virus lineages (Tables 5 and 6).

Selection of High-Yield Yamagata- and Victoria-Lineage Vaccine Virus Candidates. Next, it was tested whether the PA-a2272t mutation found after the Vero cell passages would enhance the growth properties of RG(Yam) #8 and/or RG(Vic) #2. The resulting viruses (HY(Yam) and HY(Vic), respectively) displayed higher hemagglutination and virus titers in MDCK cells compared with RG(Yam) #8 and RG(Vic) #2, and compared with the parental Yamagata- and Victoria-lineage viruses; some of these differences were small (although statistically significant). Therefore, HY(Yam) (encoding NP-P40S, M1-R77K, NS1-K1760, NS-a39g, PA-a2272t) and HY(Vic) (encoding NP-P40S/M204T, M1-M86T, NS-(38+1)g, PA-a2272t) were selected as lead high-yield candidates.

Evaluation of High-Yield Vaccine Virus Backbones with Different influenza B Virus HA and NA Genes. HY(Yam) and HY(Vic) were developed with the HA and NA genes of B/Yamagata/UT-K31/2012 and B/Yokohama/UT-K1A/2011, respectively. Because high-yield vaccine virus backbones should have a general growth-enhancing effect, the HY(Yam) and HY(Vic) vaccine virus backbones with the HA and NA genes of six influenza B viruses isolated over several decades, including WHO-recommended vaccine viruses, were tested (FIG. 7). At one or more time points tested, the HY(Yam) and HY(Vic) vaccine virus backbones conferred higher viral or hemagglutination titers compared with the parental viruses, although not al of the differences were statistically significant. For the viruses tested, HY(Vic) had a greater growth-enhancing effect than HY(Yam).

Exchange of HY(Yam) and HY(Vic) Backbones. Next, it was tested whether the HY(Yam) and HY(Vic) backbones supported efficient replication of viruses possessing HA and NA genes derived from the other influenza B virus lineage (FIG. 8). High viral and hemagglutination titers were detected for HY(Yam) viruses encoding Victoria-lineage HA and NA genes, and for HY(Vic) viruses encoding Yamagata-lineage HA and NA genes. Overall, the HY(Yam) vaccine backbone resulted in slightly higher virus or hemagglutination titers than the HY(Vic) vaccine backbone at several time points, but most of these differences were not statistically significant. These data indicate that the HY(Yam) and HY(Vic) vaccine backbones confer efficient replication to viruses of both lineages.

Figure 9A:
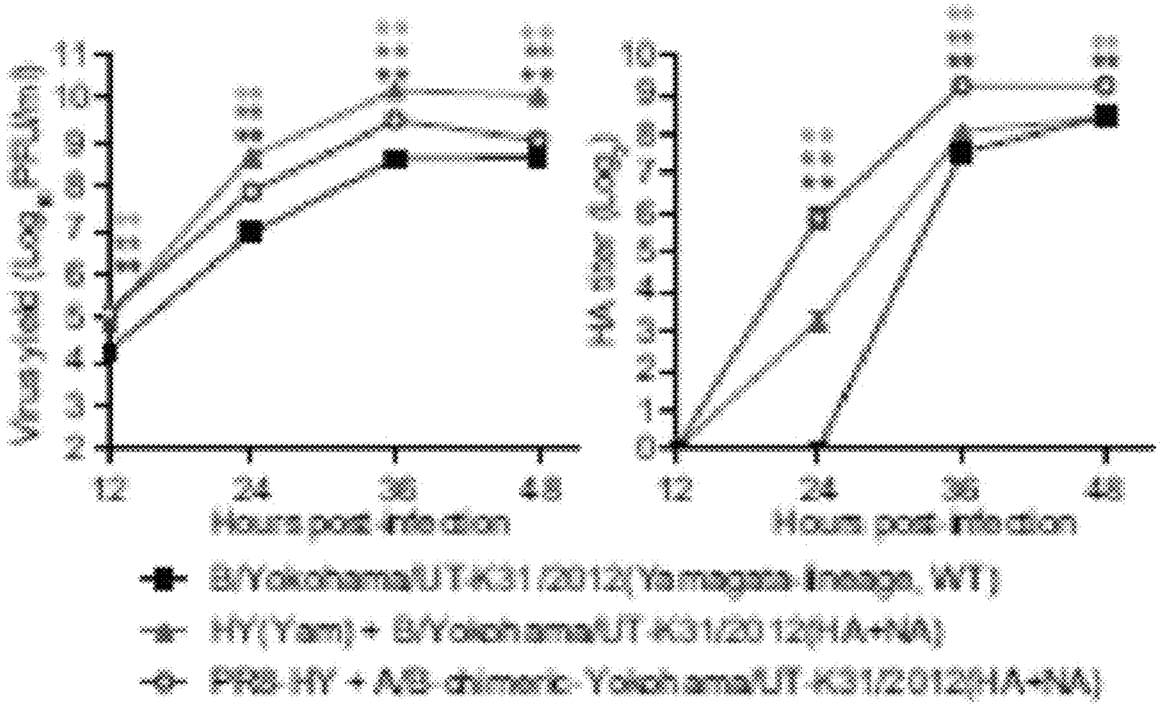
Figure 9B:
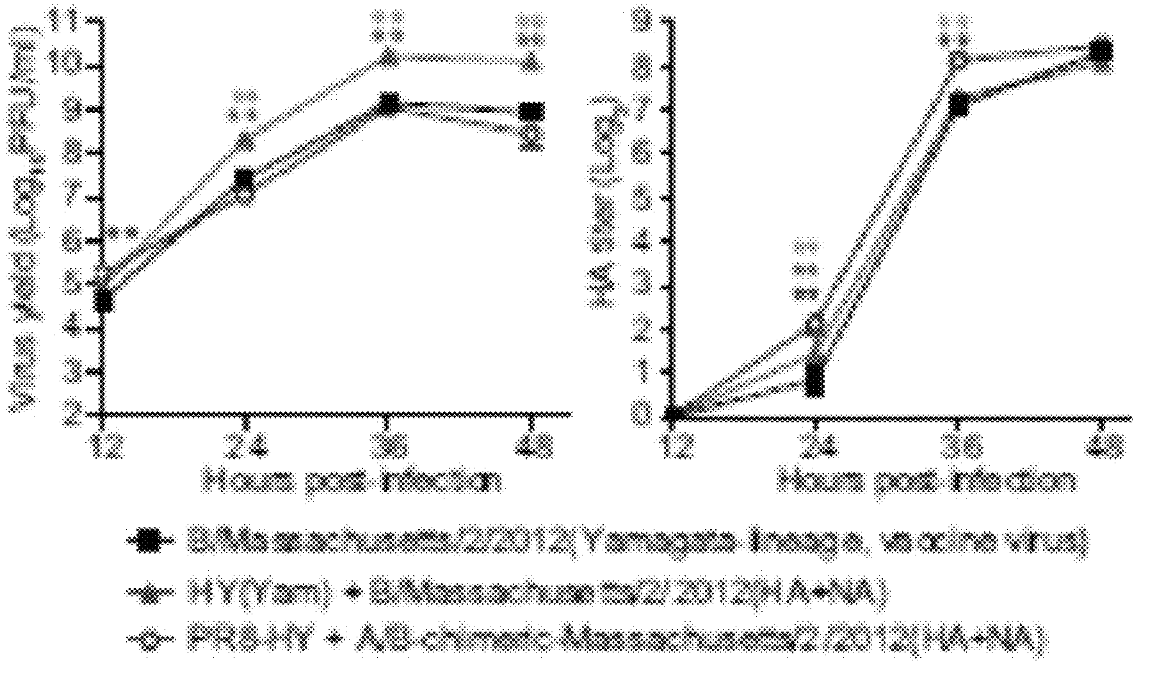
Figure 9C:
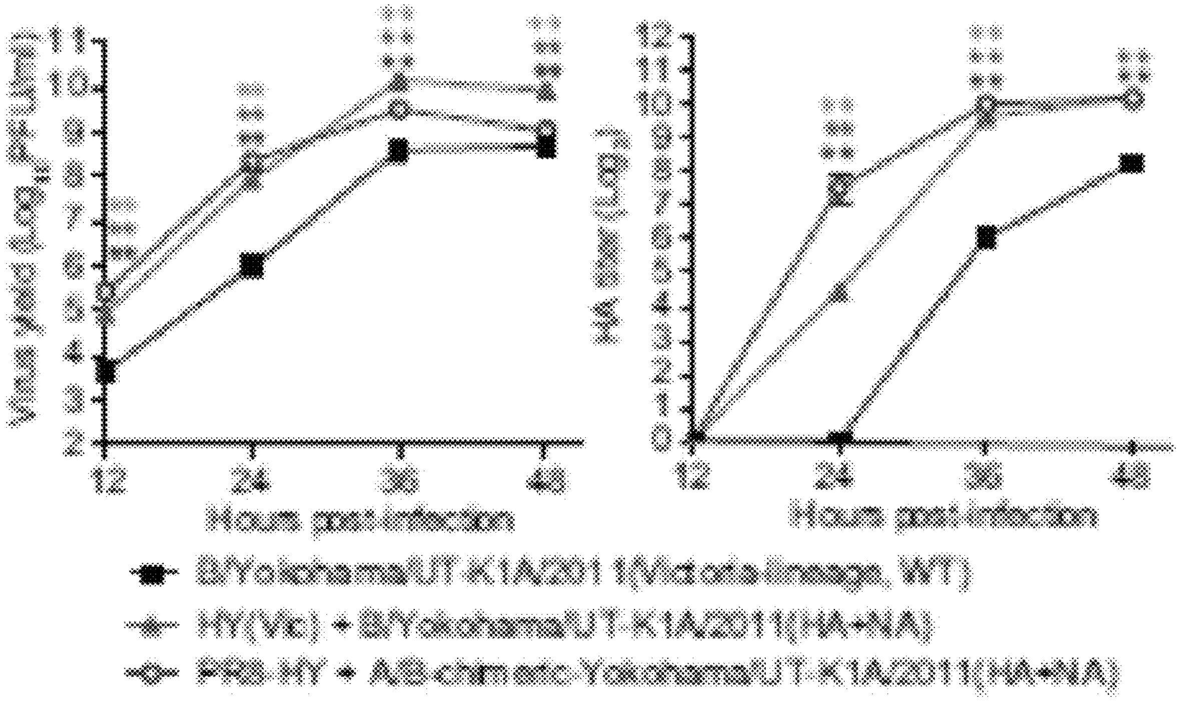
Figure 9D:
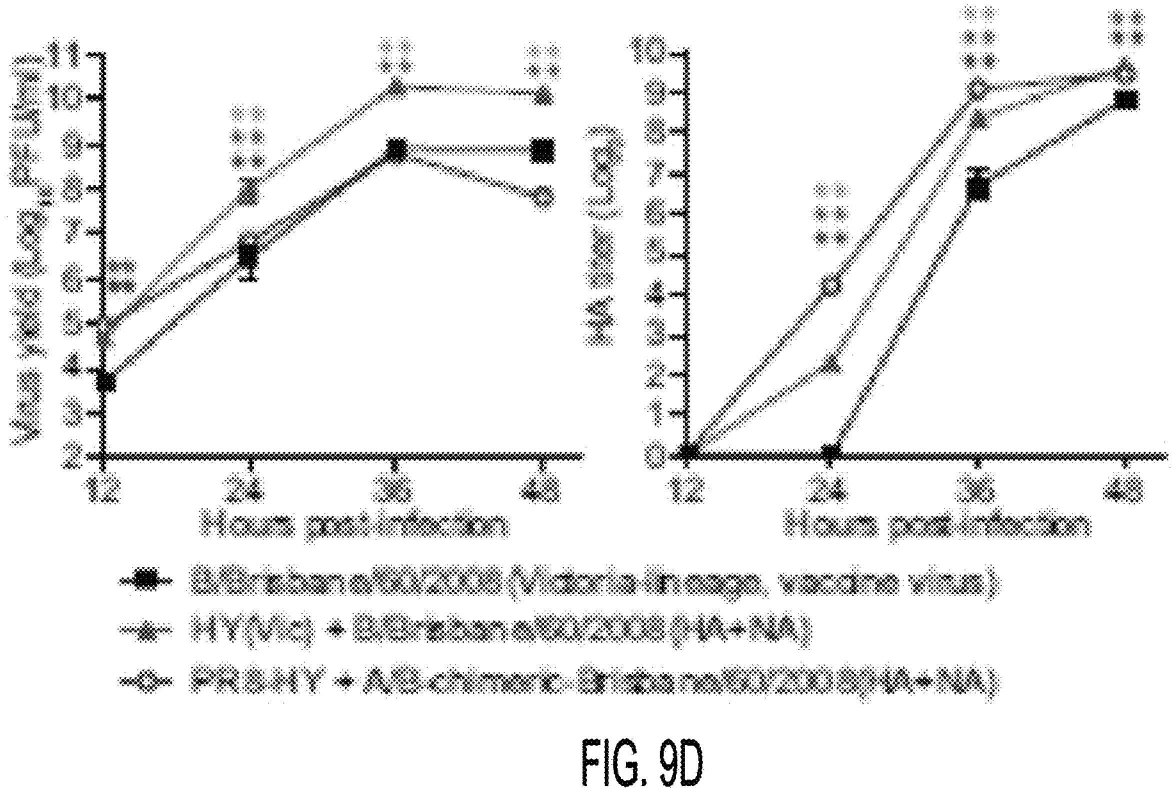
Figure 9E:
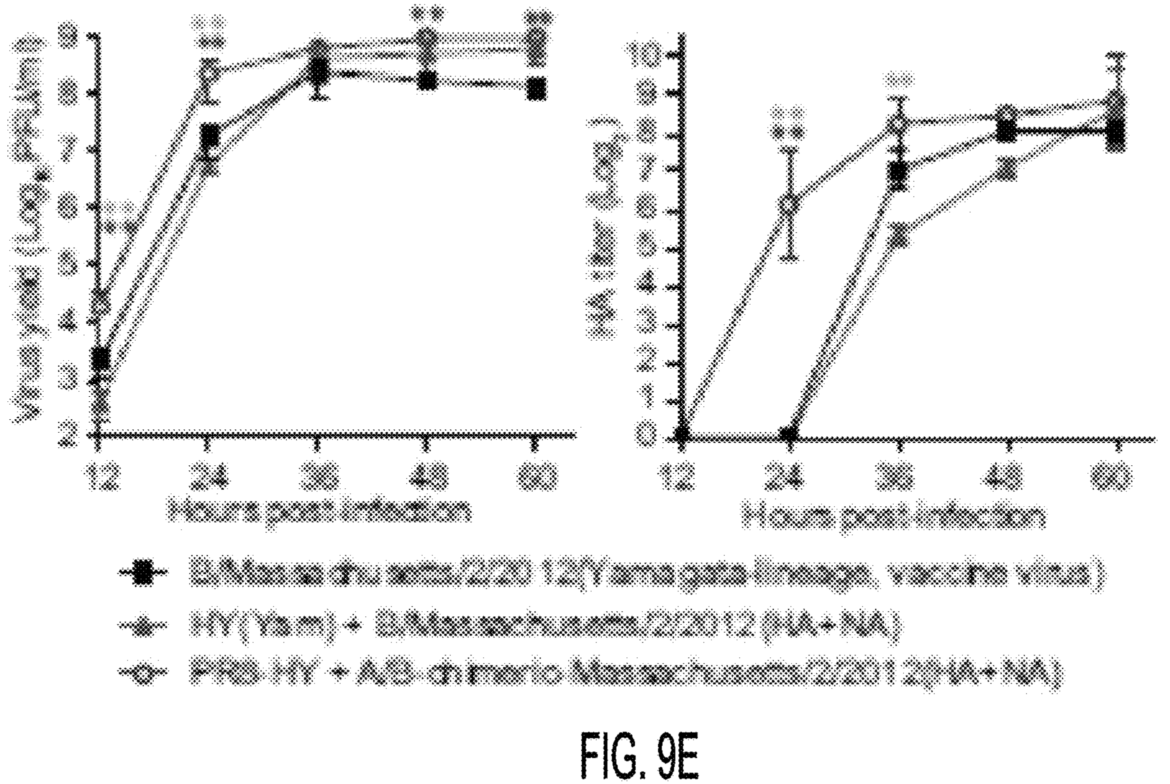
Figure 9F:
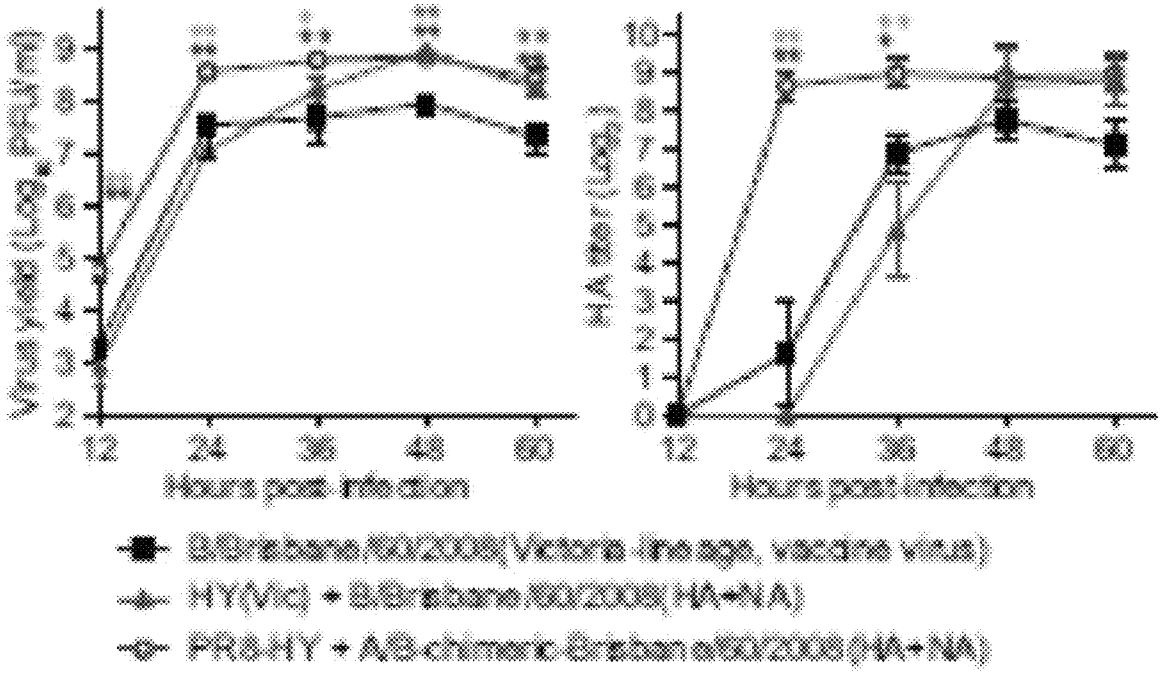

Comparison of influenza A and B Virus Vaccine Backbones. Chimeric influenza A viruses possessing the HA and NA genes of an influenza B virus have been generated previously (Horimoto et al., 2004 and Flandorfer et al., 2003). The use of a universal backbone for both influenza A and B viruses would simplify the vaccine production process. Reassortants between influenza A and B viruses do not occur naturally, likely because of type-specific viral packaging signals located in the 5 and 3 terminal regions of influenza vRNA segments (Fujil et al., 2003; Baker et al., 2014). Therefore, vRNA segments were generated in which the ectodomains of the influenza A PR8 virus HA and NA proteins were replaced with influenza B virus counterparts (FIG. 5). Then the hemagglutination and viral titers of the following three viruses were compared: a wild-type Yamagata-lineage influenza B virus; HY(Yam) with the HA and NA genes of a Yamagata-lineage virus; and high-yield PR8 virus with type A/B chimeric HA and NA genes of a Yamagata-lineage virus (FIGS. 9A-B). Similar experiments were carried out for viruses of the Victoria-lineage (FIGS. 9C-D). At most time points tested, the high-yield influenza A or B vaccine virus backbones conferred significantly increased hemagglutination and viral titers compared with wild-type viruses. Comparison of the influenza A and B vaccine backbones revealed higher virus titers with the influenza B vaccine backbone but, interestingly, higher hemagglutination titers with the influenza A vaccine backbone. Moreover, for two influenza B viruses representing both lineages, the influenza A vaccine backbone was superior to the influenza B vaccine backbones with respect to hemagglutination and viral titers in embryonated chicken eggs (FIGS. 4E-F). Other influenza B viruses containing the HA and NA from B/Yokohama/UT-K1A/2011, B/Yokohama/P-2922/2005, B/Tokyo/UTE2/2008, or B/Tochigi/UT-T1/2014 did not grow well in embryonated chicken eggs regardless of the backbone (wild-type or high-yield), suggesting that the HA and NA genes of these human viruses may restrict efficient growth in embryonated chicken eggs.

Evaluation of Total Viral Protein Yield and HA Content. Most preparations of inactivated influenza vaccines contain 15 µg each of H1 HA, H3 HA, and type B HA proteins. For vaccine optimization, total viral protein yield and HA content are therefore important parameters, prompting us to compare the total viral protein yield and HA content of different HY(Yam) and HY(Vic) viruses with their respective wild-type viruses in MDCK cells. Cell-culture supernatants were collected from infected cells, and viruses were concentrated and purified by use of sucrose gradient centrifugation. The total viral protein yield was then determined by using the Pierce BCA Protein Assay Kit (Thermo Scientific). In parallel, purified virus samples were treated with PNGase F, resulting in HA deglycosylation, which allows easier detection of HA2 (which in its glycosylated form is similar in size to M1). Samples were separated by using SDS/PAGE (FIGS. 10A-B) and the amounts of HA1, HA2, NP, and M1 were determined based on densitometric analysis. The HA content was calculated by dividing the HA amount (calculated by summing the amounts of HA1 and HA2) by the sum of the amounts of HA1, HA2, NP, and M1, and multiplying this value by the amount of total viral protein in the samples analyzed via gel electrophoresis (FIGS. 10A-B). For all viruses tested, total viral protein yield and HA content were significantly higher with the HY(Yam) and HY(Vic) vaccine backbones compared with the wild-type viruses from which the HA and NA vRNAs were derived.

Figure 11A:
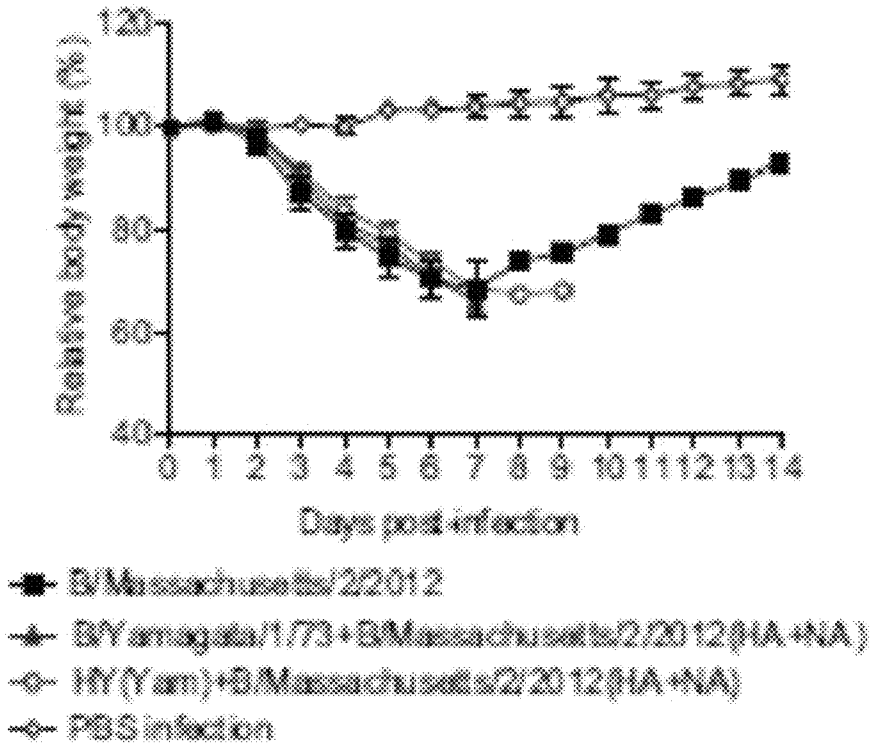
Figure 11B:
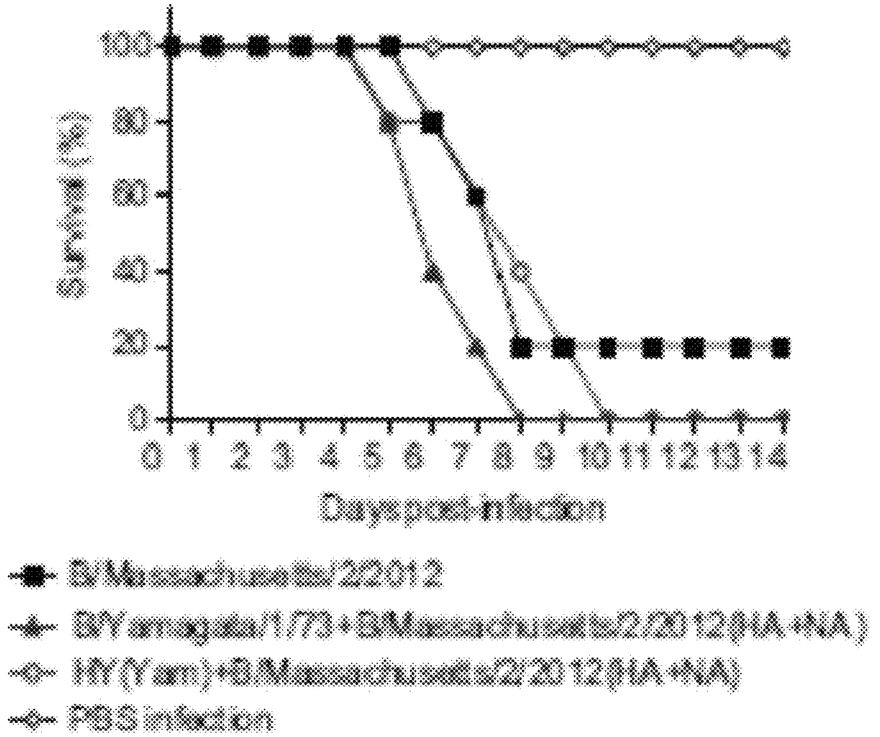
Figure 11C:
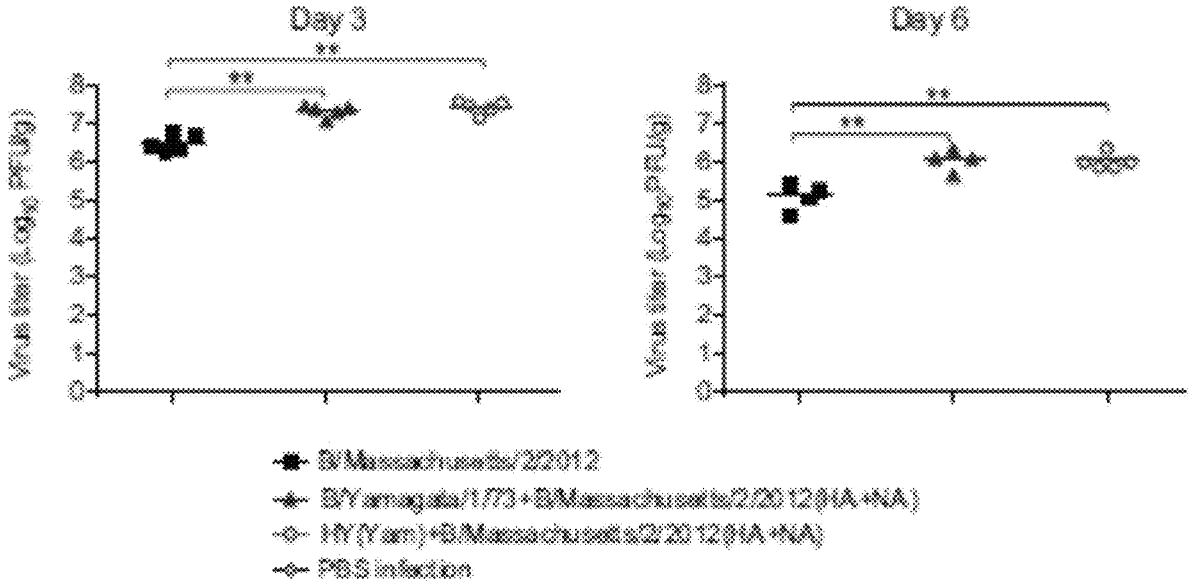
Figure 11D:
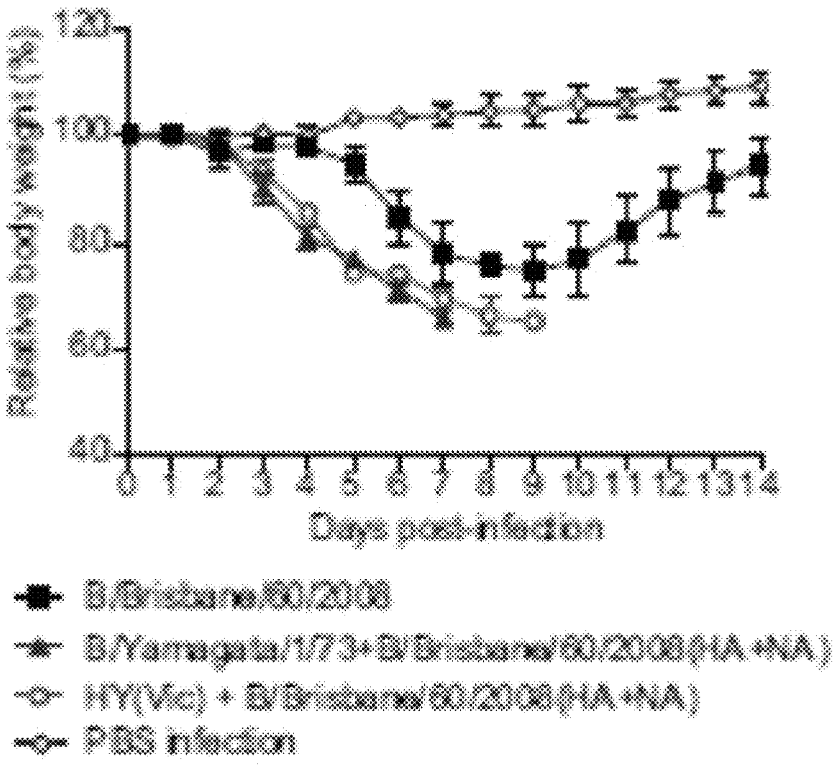
Figure 11E:
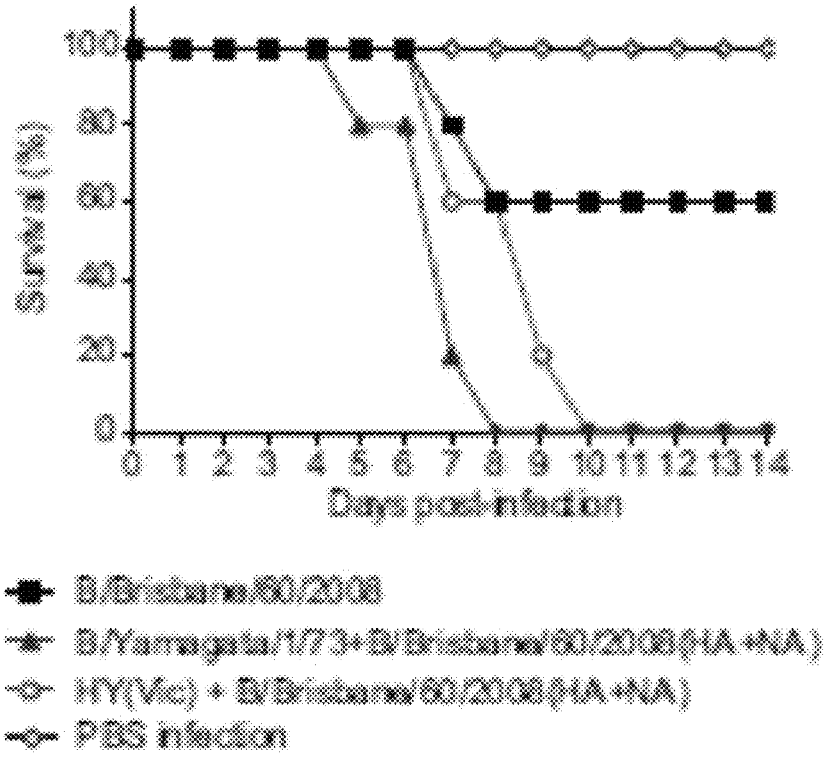
Figure 11F:
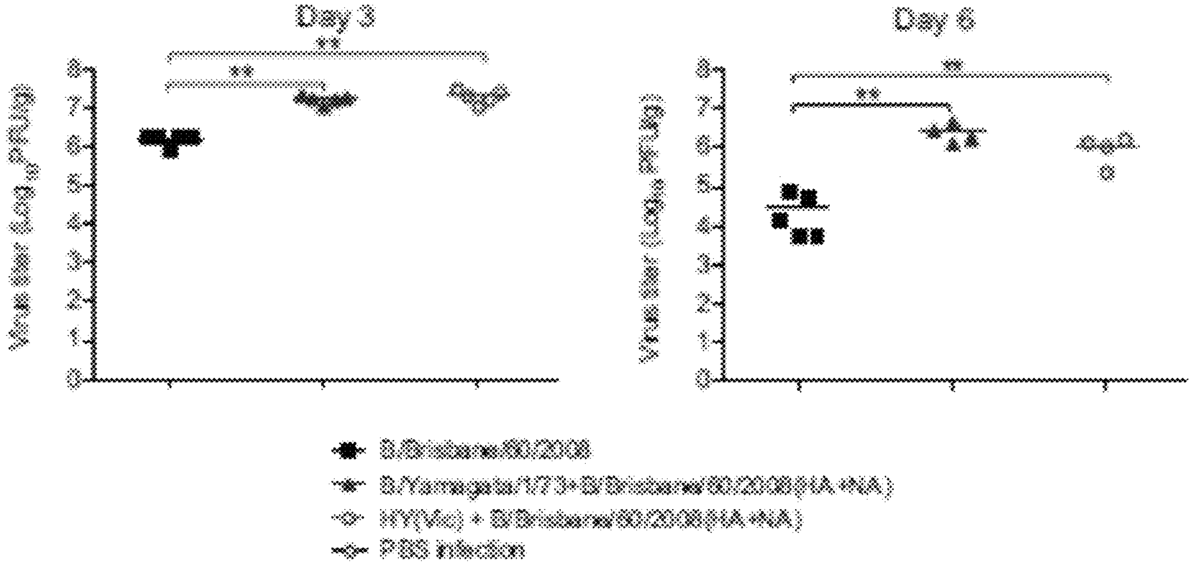

Virulence of PR8-HY-Based Vaccine Viruses in Mice. An experimental approach was designed to select mutants with increased replicative ability, which may also increase their virulence in mammals. To address this question, five mice per group were infected with $10^6$ pfu of a wild-type Yamagata-lineage virus, a virus possessing the HA and NA vRNAs of the Yamagata-lineage virus in combination with the remaining six genes of wild-type B/Yamagata/1/73 virus (which was used to generate the virus libraries), and a virus possessing the HA and NA vRNAs of the Yamagata-lineage virus in combination with the HY(Yam) vaccine virus backbone (FIGS. 11A-B). In parallel, groups of 10 mice were infected with $10^6$ pfu of the viruses described above, and five animals each were killed on days 3 and 6 post-infection to assess lung virus titers (FIG. 11C). Similarly, experiments were carried out with a Victoria-lineage viruses and the HY(Vic) vaccine backbone (FIGS. 11D-F). The wild-type B/Yamagata/1/73 virus backbone conferred higher pathogenicity than the B/Massachusetts/2/2012 and B/Brisbane/60/2008 backbones, respectively. However, the yield-enhancing mutations of HY(Yam) and HY(Vic) did not increase mouse virulence further; in fact, they had slightly attenuating effects compared with the B/Yamagata/1/73 backbone.

Genetic Stability of the HY(Yam) and HY(Vic) Vaccine Backbones. Vaccine viruses should be genetically stable so that their desired properties are maintained. To test the genetic stabilities of the high-yield candidates, 10 serial passages of a HY(Yam) virus were performed with the HA and NA vRNAs of B/Yokohama/UTK31/2012, and of a HY(Vic) virus with the HA and NA vRNAs of B/Yokohama/UT-K1A/2011 in MDCK cells. After each passage, the genomic sequences of the viruses were determined by Sanger sequencing. For the Yamagata-lineage virus, no mutations were detected. For the Victoria-lineage virus, mutations in the internal genes that define the high-yield properties of HY(Vic) were not detected. However, a mixed population encoding HA1-196T and -1961 was detected after passage 5; after passage 10, only the HA1-1961 mutant was detected.

Similarly, several wild-type and high-yield influenza B viruses of both lineages were passaged in embryonated chicken eggs (Table 7). After 5-10 consecutive passages, no egg-adapting mutations were detected in the internal genes. However, for viruses that possessed a glycosylation site at amino acids 194-196 of HA, mutations arose that resulted in the loss of that glycosylation site. This finding is consistent with the earlier finding of mutations at this glycosylation site in viruses of the Victoria-lineage (Table 2). Collectively, the data indicate that the yield-enhancing mutations in HY(Yam) and HY(Vic) were genetically stable for at least 5-10 consecutive passages in MDCK cells and embryonated chicken eggs.

Contribution of individual vRNAs to High-Yield Properties of HY(Yam) and HY(Vic). The HY(Yam) and HY(Vic) vaccine backbones possess mutations in several vRNA. To better understand the contributions of these mutations to the HY(Yam) and HY(Vic) phenotypes, reverse genetics was used to generate viruses possessing individual mutant vRNA segments of HY(Yam) or HY(Vic): for example, viruses were generated in which the HA and NA vRNAs of a Yamagata-lineage virus were combined with the six remaining vRNAs of wild-type B/Yamagata/1/73 (used to generate virus libraries), of wild-type B/Yamagata/1/73 (also encoding the NP-P40S mutation found in HY(Yam)), or of HY(Yam) (FIG. 12). The resulting viruses were tested for their replicative abilities and hemagglutination titers in MDCK cells (FIG. 12). When tested individually, the NP-P40S, M1-R77K, and NS-a39g+NS1-K176Q mutations significantly increased the viral and hemagglutination titers of Yamagata-linage viruses at one or more time points compared with the reference virus. For Victoria-lineage viruses, each of the mutations tested had a statistically significant growth-enhancing effect at one or more time points. Most of the viruses possessing individual mutations found in HY(Yam) or HY(Vic) did not replicate as efficiently as the high-yield vaccine candidates, demonstrating that combinations of several mutations are important for the high-yield properties of HY(Yam) and HY(Vic).

Figure 13A:
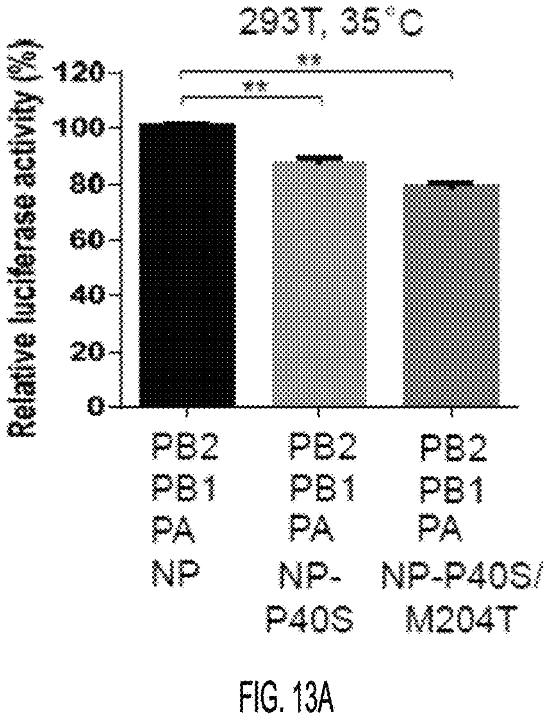
Figure 13B:
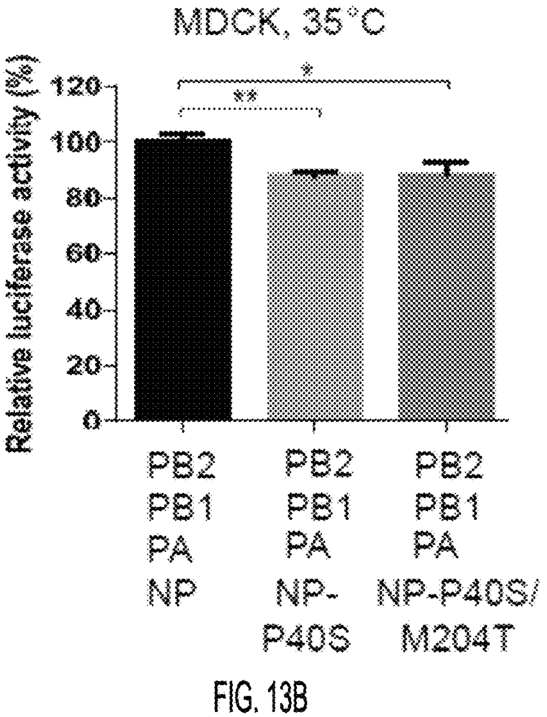
Figure 13C:
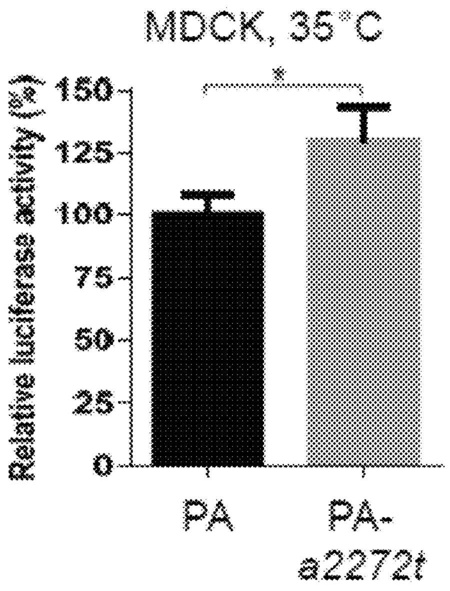
Figure 13D:
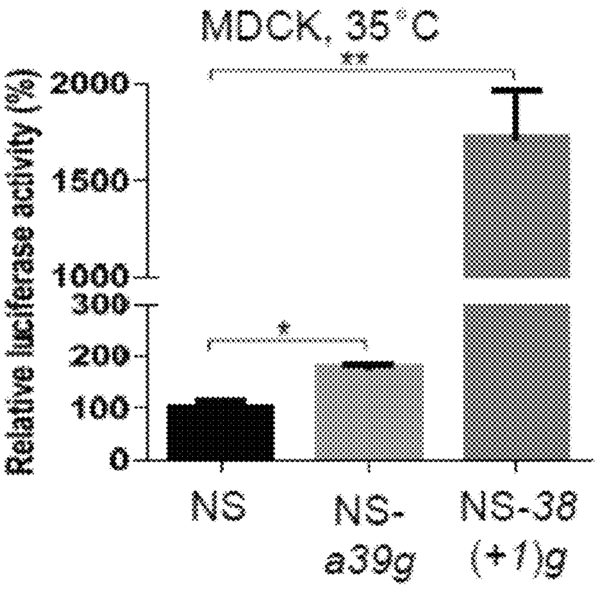

Effect of individual Mutations in HY(Yam) and HY(Vic) on the Activity of the Viral Replication Complex. The NP-P40S mutation was selected individually and in combination with NP-M204T from the Yamagata- and Victoria-lineage libraries, respectively. Moreover, these mutations increased viral and hemagglutination titers when tested without the other growth-enhancing mutations (FIG. 12). To assess whether these mutations affect the activity of the viral replication complex, 293T and MDCK cells were transfected with plasmids expressing the three polymerase subunits of B/Yamagata/1/73 virus, wild-type or mutant B/Yamagata/1/73 NP, and an influenza B virus-like RNA expressing the luciferase reporter protein (the NP-M204T mutant was not tested separately because it was selected from the virus libraries only in combination with NP-P40S). Interestingly, the NP-P40S and -P40S/M204T mutations significantly reduced the replicative activity of the viral replication complex (FIG. 13A-8).

The PA-a2272t mutation emerged during passages of virus libraries in Vero cells (Tables 5 and 6) and significantly increased the viral and hemagglutination titers of a Victoria-lineage vaccine candidate (FIG. 6). This mutation was found to significantly increase the replication of a virus-like RNA in minireplicon assays (FIG. 105C). HY(Yam) and HY(Vic) possess NS-a39g and NS-38(+1)g mutations, respectively. These mutations were introduced into a virus-like RNA that expresses luciferase. Both mutations conferred significantly increased expression of the reporter protein from the virus-like RNA (FIG. 13D); this effect was substantially greater for the NS-38(+1)g mutation compared with the NS-a39g mutation.

Effect of individual Mutations in HY(Yam) and HY(Vic) on the Composition of Virus-Like Particles. The M1-R77K and M1-M86T mutations in HY(Yam) and HY(Vic) affected viral and hemagglutination titers when tested individually (FIG. 12). M1 is the major structural component of virions and mutations in this protein could affect the composition of virions. 293T cells were transfected with plasmids for the expression of the B/Yamagata/1/73 HA, NA, NP, BM2, NS2, and wild-type or mutant M1 proteins; expression of this set of viral protein results in efficient virus-like particle (VLP) formation and release (Gomez-Puertas at al., 1999). Cell culture supernatant was collected and the VLP incorporation efficiency of viral proteins assessed (FIG. 14). Both mutations in M1 significantly increased the amount of viral HA, NP, and M1 proteins in the culture supernatant, which presumably resulted in the increased viral and hemagglutination titers conferred by the M1-R77K and -86T mutations.

Effect of a Mutation in the HY(Yam) NS1 Protein on IFN Antagonist Activity. The NS1 protein is the major influenza viral IFN antagonist (Yuan at al., 2001; Dauber at al., 2004). To assess the effect of the HY(Yam) NS1-K1760 mutation on NS1's ability to interfere with IFN-β synthesis, 293T cells were transfected with wild-type or mutant NS1 protein expression plasmids and with the reporter plasmid pGL-IFN-β, which encodes the firefly luciferase protein under the control of the IFN-β promoter (Bale at al., 2012). Cells were then infected with Sandal virus to stimulate IFN-β synthesis, resulting in increased reporter gene expression. Wild-type and mutant NS1 were comparable in their ability to down-regulate IFN-β synthesis (FIG. 12A). To determine the ability of wild-type and mutant NS1 to interfere with the expression of IFN-β-stimulated genes, 293T cells were transfected with wild-type or mutant NS1 protein expression plasmids and the reporter plasmid pISRE-Luc (Promega), which encodes the firefly luciferase protein under the control of an IFN-regulated promoter. Cells were stimulated with IFN-β 24 hours later, incubated again for 24 hours, and then assayed for luciferase expression. The NS1-K1760 protein was slightly less efficient than wild-type NS1 in suppressing gene synthesis from an IFN-regulated promoter (FIG. 12B), suggesting that other mechanisms account for its growth-enhancing effect.

Discussion

To date, no systematic efforts have been carried out to develop a high-yield influenza B vaccine backbone. Vodeiko et al. (Vodeiko at al., 2003) compared two influenza B viruses that differed in their replicative ability in embryonated chicken eggs. Reassortment experiments revealed several vRNAs that contributed to the phenotypic differences (Vodeiko at al., 2003); however, the specific amino acids that determined the growth properties were not identified. Kim at al. (Kim et al., 2015) found that coldadaptation of influenza B viruses enhanced their growth properties. Several amino acid changes in HA, NA, and NP (not the mutations reported here) were responsible for the increased virus titers (Kim at al., 2015). Le at al. (2015) tested reassortants between B/Lee/40 and Yamagata- and Victoria-lineage influenza B viruses isolated in 2002-2007; al 14 high-yield candidates possessed the NP vRNA of B/Lee/40 virus, suggesting that this vRNA confers efficient replicative ability. Ping at al. (2015) published a more comprehensive strategy to develop high-yield influenza A vaccine backbones, which was applied here to influenza B viruses: from virus libraries possessing random mutations in the internal genes, candidates were selected that improved influenza B virus replication in MDCK and Vero cells. Combinations of mutations resulted in Yamagata- and Victoria-lineage vaccine candidates (encoding the NP-P40S, M1-R77K, NS1-K1760, NS-a39g, and PA-a2272t mutations for the Yamagata-lineage vaccine and the NP-P40S/M204T, M1-M86T, NS-(38+1)g, and PA-a2272t mutations for the Victoria-lineage vaccine) with high yield in MDCK and Vero cells, and also in embryonated chicken eggs. Further studies in (semi)industrial settings would be necessary to determine whether lineage-specific vaccine backbones provide an advantage over a single backbone used for viruses of both lineages.

The total viral protein yield and HA content obtained from HY(Yam) and HY(Vic) were substantially higher than those from wild-type viruses (FIG. 10). High virus and HA yields are important for cost-effective vaccine production. More importantly, increases in vaccine virus yield may be imperative in years with high-vaccine demand and in years with shortened Virus yield vaccine production times. However, some of the observed differences in virus titers or HA yield were small (although statistically significant), and we currently do not know the extent by which HY(Yam) and HY(Vic) would increase vaccine virus yield in industrial vaccine production.

Evaluation of influenza B virus sequences revealed that the amino acid changes in HY(Yam) and HY(Vic) are rare among natural influenza B viruses (the NP-P40S, NP-M204T, and M1-M86T mutations have each been found in one isolate; the M1-R77K mutation has been reported in 14 isolates; and the NS1-K1760 mutation has not been detected). The 3D structure of an influenza B virus NP protein has been resolved (Ng at al., 2012), but position 40 (at which P-to-S mutations were selected from the Yamagata- and Victoria-lineage libraries) is part of the N-terminal 71 amino acids for which no structural data could be obtained, suggesting that this region is highly flexible. Sequence analysis of influenza B virus NP proteins revealed that the proline at position 40 is highly conserved: only 1 in 3,234 sequences does not encode NP-40P (the only exception, B/Tennessee/01/2015, encodes NP-40S, as found in this study). Interestingly, the NP P40S mutation reduced the activity of the viral replication complex in minireplicon assays, suggesting that the yield-enhancing effect of this mutation is mediated by functions other than replication and transcription. For example, this region in NP could interact with viral or cellular proteins during the export of viral ribonucleoprotein complexes from the nucleus to the cytoplasm, or during virion assembly.

Several mutations were also identified in the noncoding regions of vRNA segments that increased virus yield; some of these mutations conferred increased levels of replication and transcription, as measured in minireplicon assays. These mutations may, for example, increase the stability of the vRNA or affect its interaction with the viral polymerase complex. Further studies are needed to decipher the exact mechanistic functions of these mutations.

Collectively, influenza B vaccine virus backbones were developed that could increase the titers of seasonal influenza B vaccines in the propagation systems currently used for human influenza vaccine virus production.

TABLE 1

Amino acid changes of selected Yamagata lineage high yield clones.

| Yamagata lineage HY clones # | HA | NA | PB2 | PB1 | PA | NP | M1 | BM2 | NS1 |
|---|---|---|---|---|---|---|---|---|---|
| #18, #19 | | | | | | | G34V, I97N | H58R, R80G | |
| #28 | K129E | | | | | | G34V, I97N | H58R, R80G | |
| #23 | N168D | | | | | | G34V, I97N | H58R, R80G | M117Y, S252T |
| #26 | | G434E | | | | | G34V, I97N | H58R, R80G | M117Y, S252T |
| #8 | | G434E | | | | | G34V, I97N | H58R, R80G | |
| #27 | | | | | | S57G | G34V, I97N | H58R, R80G | |
| #21 | | | | | | E52K | R77K | | |

TABLE 2

Amino acid changes of selected Victoria lineage high yield clones.

| Victoria lineage HY clones # | HA | NA | PB2 | PB1 | PA | NP | M1 | NS1 |
|---|---|---|---|---|---|---|---|---|
| #2 | T196P | | | | | P40S, M240T | M86T | |
| #4 | T196I | | | | | P40S | M86T | |
| #27 | T196I | | | | | P40S | M86T | a39g, K176Q |
| #20 | T196A | | | | | P40S | D54G, M86T | Additional g insert after position 38* |
| #5 | T196P | | | | | P40S, P51Q | M86T | Additional g insert after position 38 |
| #25 | T34I, T196N | | | | | A28T, P40S, g1795a | M86T | Additional g insert after position 38 |
| #22 | T196P | N169T | | | | P40S, g1795a | M86T | Additional g insert after position 38 |
| #28 | | | | | | P40S, g1795a | M86T | Additional g insert after position 38 |

*Also referred to as 38(+1) g
Mutations in lowercase and italics in this and the following tables indicate nucleotide changes in the non-coding region

TABLE 3

Amino acid changes of Yamagata lineage HY vaccine virus candidates generated by using reverse genetics.

| Yamagata lineage candidates | HA & NA | P62 | PBI | PA | NP | M1 | BM2 | NSI |
|---|---|---|---|---|---|---|---|---|
| RG(Yam)#1 | | | | | E52K | R77K | | |
| RG(Yam)#2 | | | | | E52K | R77K | | M117Y, S252T |
| RG(Yam)#3 | | | | | E52K | G34V, I97N | H58R, R80G | |
| RG(Yam)#4 | | | | | S57G | R77K | | M117Y, S252T |
| RG(Yam)#5 | B/Yokohama/UT-K31/2012 (Yamagata lineage) | | | | P40S, g1795a | M86T | | Additional g insert after position 38 |
| RG(Yam)#6 | | | | | P40S | D54G, M86T | | Additional g insert after position 38 |
| RG(Yam)#7 | | | | | E52K | D54G, M86T | | M117Y, S252T |
| RG(Yam)#8 | | | | | P40S | R77K | | a39g, K176Q |

TABLE 4

Amino acid changes of Victoria lineage HY vaccine virus candidates generated by using reverse genetics.

| Victoria lineage candidates | HA & NA | PB2 | PBI | PA | NP | M1 | BM2 | NSI |
|---|---|---|---|---|---|---|---|---|
| RG(Vic)#1 | | | | | P40S | D54G, M86T | | Additional g insert after position 38 |
| RG(Vic)#2 | | | | | P40S, M204T | M86T | | Additional g insert after position 38 |
| RG(Vic)#3 | | | | | P40S, g1795a | M86T | | Additional g insert after position 38 |
| RG(Vic)#4 | B/Yokohama/UT-K1A/2011 (Victoria lineage) | | | | P40S, P51Q | M86T | | Additional g insert after position 38 |
| RG(Vic)#5 | | | | | P40S | M86T | | a39g, K176Q |
| RG(Vic)#6 | | | | | E52K | R77K | | |
| RG(Vic)#7 | | | | | E52K | D54G, M86T | | M117Y, S252T |
| RG(Vic)#8 | | | | | P40S | D54G, M86T | | Additional ga insert after position 38 |

Virus libraries were passaged for a total of 12 times in MDCK cells, e.g., 2 passages after which the libraries may be mixed and then 10 more passages were carried out (FIG. 2). After passages in MDCK cells, plaque assays were performed and over 1,400 individual plaques were picked. High-yield candidates are shown in Tables 1-4.

Tables 5 and 6 show changes that resulted in enhanced growth in Vero cells using a similar protocol.

TABLE 5

Amino acid changes of Vero cell adapted HY Yamagata lineage viruses.

| Yamagata lineage clone | HA1 | HA2** | NA | PB2 | PB1 | PA | NP | M1 | BM2 | NS1 |
|---|---|---|---|---|---|---|---|---|---|---|
| 1 | N194D | D112E | T436M | | | | | G34N, I97N | H58R | |
| 2 | T196P | D112E | E105K | N16S | | D494N | | G34N, I97N | H27R, H58R | |
| 3 | | D112E | T76M, P139S, D457N | N16S | | D494N | | G34N, I97N | H27R, H58R | |
| 4 | | D112E | R102K, T436M | | | a2272t | | G34N I97N | H58R | |

TABLE 5-continued

Amino acid changes of Vero cell adapted HY Yamagata lineage viruses.

| Yamagata lineage clone | HA1 | HA2** | NA | PB2 | PB1 | PA | NP | M1 | BM2 | NS1 |
|---|---|---|---|---|---|---|---|---|---|---|
| 5 | | D112E | T436M | | | a2272t | P343T | G34N, I97N | H58R | |
| 6 | | D112E | | | | g2213a, a2272t | P343T | G34N, I97N | G26R, H581R | |

**numbering begins at cleavage site

TABLE 6

Amino acid changes of Vero cell adapted HY Victoria lineage viruses.

| Victoria lineage clone | HA1 | HA2** | NA | PB2 | PB1 | PA | NP | M1 | BM2 | NS1 |
|---|---|---|---|---|---|---|---|---|---|---|
| 1 | T196A, | S56G, K61N | D457N | | | Y387H, V434A, T524A, a2272t | | | R80G | Y42N |
| 2 | T196A, | K39G, S56G | D457N | | | Y387H, V434A, a2272t | | | R80G | Y42N |
| 3 | T196A | S56G, K61N | D457N | | | Y387H, V434A, a2272t | | | R80G | Y42N |
| 4 | R98K, T196A | S56G | D457N | | | Y387H, V434A, a2272t | | | R80G | Y42N |
| 5 | T196A | K39G S56G | D457N | | | Y387H, V434A, a2272t | | | R80G | Y42N |
| 6 | T196A | S56G | D457N | | | Y387H, V434A, a2272t | | | R80G | Y42N |

**numbering begins at cleavage site

TABLE 7

Amino acid changes detected after serial virus passages in embryonated chicken eggs

| Virus | Egg passage | Amino acid changes in HA |
|---|---|---|
| B/Massachusetts/2/2012 | P1 | None |
| | P2 | None |
| | P3 | None |
| | P4 | None |
| | P5 | None |
| | P6 | None |
| | P7 | None |
| | P8 | None |
| | P9 | None |
| | P10 | None |
| HY(Yam) + B/Massachusetts/2/2012 (HA + NA) | P1 | None |
| | P2 | None |
| | P3 | None |
| | P4 | None |
| | P5 | None |
| | P6 | None |
| | P7 | None |
| | P8 | None |
| | P9 | None |
| | P10 | None |
| B/Brisbane/60/2008 | P1 | None |
| | P2 | None |
| | P3 | None |
| | P4 | None |

TABLE 7-continued

Amino acid changes detected after serial virus passages in embryonated chicken eggs

| Virus | Egg passage | Amino acid changes in HA |
|---|---|---|
| | P5 | None |
| | P6 | None |
| | P7 | None |
| | P8 | None |
| | P9 | None |
| | P10 | None |
| HY(Vic) + B/Brisbane/60/2008 (HA + NA) | P1 | None |
| | P2 | None |
| | P3 | None |
| | P4 | None |
| | P5 | None |
| | P6 | None |
| | P7 | None |
| | P8 | None |
| | P9 | None |
| | P10 | None |
| B/Yokohama/UT-K31/2012 | P1 | None |
| | P2 | N194K (loss of glycosylation site) |
| | P3 | N194K (loss of glycosylation site) |

TABLE 7-continued

Amino acid changes detected after serial virus passages in embryonated chicken eggs

| Virus | Egg passage | Amino acid changes in HA |
|---|---|---|
| | P4 | N194K (loss of glycosylation site) |
| | P5 | N194K (loss of glycosylation site) |
| HY(Yam) + B/Yokohama/UT-K31/2012(HA + NA) | P1 | None |
| | P2 | N194N/S (N194S results in loss of glycosylation site) |
| | P3 | N194S (loss of glycosylation site) |
| | P4 | N194S (loss of glycosylation site) |
| | P5 | N194S (loss of glycosylation site) |
| B/Yokohama/UT-K1A/2011 | P1 | None |
| | P2 | T196I (loss of glycosylation site) |
| | P3 | T196I (loss of glycosylation site) |
| | P4 | T196I (loss of glycosylation site) |
| | P5 | T196I (loss of glycosylation site) |
| Hy(Vic) + B/Yokohama/UT-K1A/2011(HA + NA) | P1 | None |
| | P2 | T196T/I (T196I results in loss of glycosylation site) |
| | P3 | T196T/I (T196I results in loss of glycosylation site) |
| | P4 | T196I (loss of glycosylation site) |
| | P5 | T196I (loss of glycosylation site) |
| Hy(Vic) + B/Yokohama/UT-K1A/2011(HA + NA) (10 sequential passages in MDCK cells) | P1 | None (MDCK passages already resulted in loss of glycosylation site at positions 194-196) |
| | P2 | None (MDCK passages already resulted in loss of glycosylation site at positions 194-196) |
| | P3 | None (MDCK passages already resulted in loss of glycosylation site at positions 194-196) |
| | P4 | None (MDCK passages already resulted in loss of glycosylation site at positions 194-196) |
| | P5 | None (MDCK passages already resulted in loss of glycosylation site at positions 194-196) |
| B/Yokohama/P-2922/2005 | P1 | None |
| | P2 | N194D (loss of glycosylation site) |
| | P3 | N194D (loss of glycosylation site) |
| | P4 | N194D (loss of glycosylation site) |
| | P5 | N194D (loss of glycosylation site) |
| HY(Yam) + B/Yokohama/P-2922/2005 | P1 | None |
| | P2 | N194D (loss of glycosylation site) |
| | P3 | N194D (loss of glycosylation site) |
| | P4 | N194D (loss of glycosylation site) |
| | P5 | N194D (loss of glycosylation site) |
| B/Tokyo/UTE2/2008 | P1 | T196I (loss of glycosylation site) |
| | P2 | T196I (loss of glycosylation site) |
| | P3 | T196I (loss of glycosylation site) |
| | P4 | T196I (loss of glycosylation site) |
| | P5 | T196I (loss of glycosylation site) |
| HY(Vic) + B/Tokyo/UTE2/2008 (HA + NA) | P1 | None |
| | P2 | N194S (loss of glycosylation site) |
| | P3 | N194S (loss of glycosylation site) |
| | P4 | N194S (loss of glycosylation site) |
| | P5 | N194S (loss of glycosylation site) |

REFERENCES

Ambrose and Levin, *Hum. Vaccin. Immunother.,* 8:81 (2012).

*Avery's Drug Treatment: Principles and Practice of Clinical Pharmacology and Therapeutics,* 3rd edition, ADIS Press, Ltd., Williams and Wilkins, Baltimore, Md. (1987).

Aymard-Henry et al., *Virology: A Practical Approach, Oxford IRL Press, Oxford,* 119-150 (1985).

Bachmeyer, *Intervirology,* 5:260 (1975).

Baker at al., *J. Virol.,* 88:10778 (2014).

Bale et al., *PLoS Pathog.,* 8:e1002916 (2012).

Belshe et al., *Influenza Other Respi. Viruses.* 4:141 (2010).

Belshe, *Vaccine.* 28:D45 (2010).

Berkow et al., eds., *The Merck Manual,* 16th edition, Merck & Co., Rahway, N.J. (1992).

Dauber et al., *J. Virol.,* 78:1865 (2004).

Flandorfer et al., *J. Virol.,* 77:9116 (2003).

Fujii et al., *Proc. Natl. Acad. Sci. U.S.A.,* 100:2002 (2003).

Glezen at al., *Am. J. Public Health,* 103:e43 (2013).

Gómez-Puertas et al., *J. Gen. Virol.,* 80:1635 (1999).

Hatta et al., *Science,* 293:1840 (2001).

Horimoto et al., *J. Virol.,* 68:3120 (1994).

Horimoto et al., *Microbes Infect.,* 6:579 (2004).

Horimoto et al., *Vaccine,* 24:3669 (2006).

Keitel et al., in Textbook of Influenza, eds. Nickolson, K. G., Webster, R. G., and Hay, A. (Blackwell, Oxford), pp. 373-390 (1998).

Kim et al., *Vaccine,* 33:5786 (2015).

Knipe et al., (Lippincott Williams & Wilkins, Philadelphia, Pa.), 6th Ed, vol 1, pp 1186-1243.

Lever & Webster, *Virology,* 69:511 (1976).

Le et al., *Vaccine.* 33:879 (2015).

Maassab, *J. Immunol.,* 102:728 (1969).

Neumann et al., *Adv. Virus Res.,* 53:265 (1999).

Neumann et al., *J. Gen. Virol.,* 83:2635 (2002).

Neumann et al., *J. Virol.,* 71:9690 (1997).

Neumann et al., *Proc. Natl. Acad. Sd. USA.* 96:9345 (1999).

Neumann et al., *Virology.* 287:243 (2001).

Ng, et al., *J. Virol.,* 86:6758 (2012).

Osol (ed.), *Remington's Pharmaceutical Sciences*, Mack Publishing Co., Easton, Pa. 1324-1341 (1980).

Ping et al., *Nat. Commun.,* 6:8148 (2015).

Ramanunninair, et al. *PLoS One,* 8:e65955 (2013).

Rota, et al., *Virology,* 175:59 (1990).

Sugawara et al., *Biologicals,* 30:303 (2002).

Tafalla et al., *Hum. Vaccin. Immunother.,* 12:993002 (2016).

van de Sandt et al., *Future Microbiol.,* 10:1447 (2015).

Vodeiko et al., *Vaccine,* 21:3867 (2003).

Webby & Webster et al., *Science,* 302:1519 (2003).

Wood & Robertson, *Nat. Rev. Microbiol.,* 2:842 (2004).

World Health Organization TSR No. 673 (1982).

World Health Organization. Confirmed human cases of avian Influenza A (H5N1). http://www.who.int/csr/disease/avian_influenza/country/en/Andex.html Wright at al., *Fields Virology*, eds (2013). Orthomyxoviruses.

Yuan and Krug, *EMBO J.,* 20:362 (2001).

All publications, patents and patent applications are incorporated herein by reference. While in the foregoing specification this invention has been described in relation to certain preferred embodiments thereof, and many details have been set forth for purposes of illustration, it will be apparent to those skilled in the art that the invention is susceptible to additional embodiments and that certain of the details described herein may be varied considerably without departing from the basic principles of the invention.

What is claimed is:

1. An isolated recombinant influenza B virus having PA, PB1, PB2, NP, NS, and M viral segments, a heterologous or chimeric influenza virus NA viral segment, and a heterologous or chimeric HA viral segment, wherein the NP viral segment encodes a NP polypeptide having serine at position 40, or a serine at position 40 and a threonine at position 204, and optionally the NS viral segment encodes a NS1 polypeptide having a residue other than Y at position 42, other than M at position 117, other than K at position 176, and/or other than S at position 252, and/or the NS viral segment has a nucleotide other than a at nucleotide position 39 or a nucleotide insertion after position 38, or any combination thereof; or optionally the M viral segment encodes a M1 polypeptide having a residue other than G at position 34, other than D at position 54, other than R at position 77, other than M at position 86, or other than I at position 97, or any combination thereof; or optionally the M viral segment encodes a BM2 polypeptide having a residue other than H at position 58, other than R at position 80, other than H at position 27, or other than G at position 26, or any combination thereof; or optionally the NP viral segment has a nucleotide other than g at nucleotide position 1795 or other than c at nucleotide position 50, or any combination thereof; or optionally the PA viral segment encodes a PA polypeptide having a residue other than Y at position 387, other than V at position 434, other than D at position 494, and/or other than T at position 524, and/or the PA viral segment has a nucleotide other than a at nucleotide 2272, other than a at position 1406, other than c at position 1445, or other than g at nucleotide 2213, or any combination thereof; or optionally the PB2 viral segment encodes a 2 polypeptide having a residue other than N at position 16; or any combination thereof, wherein the position in the NP polypeptide is relative to a NP polypeptide encoded by SEQ ID NO: 4, wherein the position in the NS polypeptide is relative to a NS polypeptide encoded by SEQ ID NO: 6, wherein the position in the M1 polypeptide is relative to a M1 polypeptide encoded by SEQ ID NO:5, wherein the position in the BM2 polypeptide is relative to a BM2 polypeptide encoded by SEQ ID NO:5, wherein the position in the PA polypeptide is relative to a PA polypeptide encoded by SEQ ID NO:3, or wherein the position in the PB2 polypeptide is relative to a BM2 polypeptide encoded by SEQ ID NO:1.

2. The isolated virus of claim 1 wherein the NP polypeptide has S at position 40 and optionally further has at least one of: T at position 28, Q at position 51, K at position 52, G at position 57, T at position 204, T at position 343, a at position 1795 or the NP viral segment has t at position 500.

3. The isolated virus of claim 1 wherein the M1 polypeptide has at least one of: V or N at position 34, G at position 54, K at position 77, T at position 86, or N at position 97.

4. The isolated virus of claim 1 wherein the BM2 polypeptide has at least one of: R at position 58, G at position 80, R at position 27 or R at position 26.

5. The isolated virus of claim 1 wherein the NS1 polypeptide has at least one of: N at position 42, Y at position 117, Q at position 176, T at position 252, or the NS segment has a nucleotide insertion of g after nucleotide position 38 or g at position 39.

6. The isolated virus of claim 1 wherein the PA viral segment has at least one of: H at position 387, A at position 434, N at position 494, A at position 524, g at position 1406, t at position 2272, t at position 1445, or any combination thereof.

7. The isolated virus of claim 1 wherein the NP polypeptide has S at position 40 and optionally further comprises one or more of: the NP vRNA has t at nucleotide 500, the M1 polypeptide has K at position 77, the NS1 polypeptide has Q at position 176 and the NS vRNA has g at nucleotide 39, or the PA vRNA has g at nucleotide 1406, t at nucleotide 1445, and t at nucleotide 2272.

8. The isolated virus of claim 1 wherein the NP polypeptide has S at position 40 and T at position 204 and optionally further comprises one or more of: the NP vRNA has t at nucleotide 500, the M1 polypeptide has T at position 86, the NS vRNA has an insertion of g after nucleotide 38, or the PA vRNA has g at nucleotide 1406, t at nucleotide 1445, and t at nucleotide 2272.

9. The isolated virus of claim 1 wherein the NA gene segment and the HA gene segment are from the same influenza virus isolate.

10. The isolated virus of claim 1 wherein the PA, PB1, PB2, NP, NS, and M viral segments comprise sequences encoding at least one of the following: a PB1 having the amino acid sequence encoded by SEQ ID NO:2 or PB1 with at least 80% amino acid sequence identity to the PB1 encoded by SEQ ID NO:2; a PB2 having the amino acid sequence encoded by SEQ ID NO:3 or PB2 with at least 80% amino acid sequence identity to the PB2 encoded by SEQ ID NO:3; a PA having the amino acid sequence encoded by SEQ ID NO:1 or PA with at least 80% amino acid sequence identity to the PA encoded by SEQ ID NO:1; a NP having the amino acid sequence encoded by SEQ ID NO:4 or NP with at least 80% amino acid sequence identity to the NP encoded by SEQ ID NO:4; a M having the amino acid sequence encoded by SEQ ID NO:5 or M with at least 80% amino acid sequence identity to the M encoded by SEQ ID NO:5; or a NS having the amino acid sequence encoded by SEQ ID NO: 6 or NS with at least 95% amino acid sequence identity to the NS encoded by SEQ ID NO:6.

11. The isolated virus of claim 1 which has a heterologous HA gene segment or a heterologous NA gene segment.

12. The isolated virus of claim 1 wherein the M1 polypeptide has V at position 34, N at position 97, or T at position 86, or any combination thereof: or the BM2 polypeptide has R at position 58 and/or G at position 80; or the NP polypeptide has S at position 40 or K at position 52.

13. A vaccine having the isolated recombinant virus of claim 1.

14. A method to prepare influenza virus, comprising: contacting a cell with:

a vector for vRNA or cRNA production comprising a promoter operably linked to an influenza virus PA DNA linked to a transcription termination sequence, a vector for vRNA or cRNA production comprising a promoter operably linked to an influenza virus PB1 DNA linked to a transcription termination sequence, a vector for vRNA or cRNA production comprising a promoter operably linked to an influenza virus PB2 DNA linked to a transcription termination sequence, a vector for vRNA or cRNA production comprising a promoter operably linked to an influenza virus HA DNA linked to a transcription termination sequence, a vector for vRNA or cRNA production comprising a promoter operably linked to an influenza virus NP DNA linked to a transcription termination sequence, a vector for vRNA or cRNA production comprising a promoter operably linked to an influenza virus NA DNA linked to a transcription termination sequence, a vector for vRNA or cRNA production comprising a promoter operably linked to an influenza virus M DNA linked to a transcription termination sequence, and a vector for vRNA or cRNA production comprising a promoter operably linked to an influenza virus NS DNA linked to a transcription termination sequence, wherein the PB1, PB2, PA, NP, NS, and M DNAs in the vectors for vRNA or cRNA production are from one or more influenza vaccine virus isolates, wherein the NA DNA in the vector for vRNA or cRNA production of NA has sequences for a heterologous or chimeric NA, and wherein the HA DNA in the vector for vRNA or cRNA production of HA has sequences for a heterologous or chimeric HA, wherein the NP vRNA or cRNA encodes a NP polypeptide having a serine at position 40, or a serine at position 40 and a threonine at position 204, wherein optionally the NS vRNA or cRNA encodes a NS1 polypeptide having a residue other than Y at position 42, other than M at position 117, other than K at position 176, and/or other than S at position 252, and/or a nucleotide other than an a at position 39 or a nucleotide insertion after position 38, or any combination thereof; or optionally the M vRNA or cRNA encodes a M1 polypeptide having a residue other than G at position 34, other than D at position 54, other than R at position 77, other than M at position 86, other than I at position 97, or any combination thereof; or optionally the M vRNA or cRNA encodes a BM2 polypeptide having a residue other than H at position 58, other than Rat position 80, other than H at position 27, other than G at position 26, or any combination thereof; or optionally the NP vRNA or cRNA has a nucleotide other than g at position 1795 or other than c at position 500, or any combination thereof; or optionally the PA vRNA or cRNA encodes a PA polypeptide having a residue other than Y at position 387, other than V at position 434, other than D at position 494, and/or other than T at position 524, and/or the PA vRNA or cRNA has a nucleotide other than a at nucleotide 2272, other than a at position 1406, other than c at position 1445, and/or other than g at nucleotide 2213, or any combination thereof; or optionally the PB2 vRNA or cRNA encodes a PB2 polypeptide has a residue other than N at position 16, wherein the position in the NS polypeptide is relative to a NS polypeptide encoded by SEQ ID NO: 6, wherein the position in the M1 polypeptide is relative to a M1 polypeptide encoded by SEQ ID NO:5, wherein the position in the BM2 polypeptide is relative to a BM2 polypeptide encoded by SEQ ID NO:5, wherein the position in the PA polypeptide is relative to a PA polypeptide encoded by SEQ ID NO:3, or wherein the position in the PB2 polypeptide is relative to a PB2 polypeptide encoded by SEQ ID NO:1;

or any combination thereof; and a vector for mRNA production comprising a promoter operably linked to a DNA segment encoding influenza virus PA, a vector for mRNA production comprising a promoter operably linked to a DNA segment encoding influenza virus PB1, a vector for mRNA production comprising a promoter operably linked to a DNA segment encoding influenza virus PB2, and a vector for mRNA production comprising a promoter operably linked to a DNA segment encoding influenza virus NP;

in an amount effective to yield infectious influenza virus.

15. The method of claim 14 wherein the cell is an avian cell or a mammalian cell.

16. The method of claim 15 wherein the cell is a Vero cell, a human cell or a MDCK cell.

17. The method of claim 14 wherein the NP polypeptide has S at position 40 and optionally the NP vRNA has t at nucleotide 500, the M1 polypeptide has K at position 77, the NS1 polypeptide has Q at position 176 and the NS vRNA has g at nucleotide 39, or the PA vRNA has g at nucleotide 1406, t at nucleotide 1445, and t at nucleotide 2272.

18. The method of claim 14 wherein the NP polypeptide has S at position 40 and T at position 204 and optionally the NP vRNA has t at nucleotide 500, the M1 polypeptide has T at position 86, the NS vRNA has an insertion of g after nucleotide 38, or the PA vRNA has g at nucleotide 1406, t at nucleotide 1445, and t at nucleotide 2272.

19. The method of claim 14 further comprising isolating the infectious influenza virus.

20. A vector for influenza B virus NP vRNA, cRNA or mRNA wherein the influenza B virus NP has at least 85% amino acid sequence identity to a polypeptide encoded by SEQ ID NO: 14 or 15 and has S at position 40, or S at position 40 and T at position 204, and optionally the NP vRNA has u at nucleotide 500.

* * * * *

SEQUENCE LISTING

```
<160> NUMBER OF SEQ ID NOS: 19

<210> SEQ ID NO 1
<211> LENGTH: 2396
<212> TYPE: DNA
<213> ORGANISM: Influenza B

<400> SEQUENCE: 1

agcagaagcg gagcgttttc aagatgacat tggctaaaat tgaattgtta aaacaactgt     60
taagggacaa cgaagccaaa acagtattga aacaaacaac ggtagaccaa tataacataa    120
taagaaaatt caatacatca agaattgaaa agaacccttc attaaggatg aagtgggcca    180
tgtgttctaa ttttcccttg gctctgacca agggtgatat ggcaaataga atccccttgg    240
aatacaaggg aatacaactt aaaacaaatg ctgaagacat aggaaccaaa ggccaaatgt    300
gctcaatagc agcagttacc tggtggaata catatggacc aataggagac actgaaggtt    360
tcgaaaaggt ctacgaaagc ttctttctca gaaagatgag acttgacaat gccacttggg    420
gccgaataac ttttggccca gttgaaagag taagaaaaag ggtactgcta aaccctctca    480
ccaaggaaat gcctccagat gaagcgagca atgtgataat ggaaatattg ttccctaagg    540
aagcaggaat accaagagaa tctacttgga tacataggga actgataaaa gaaaaaagag    600
aaaaattgaa aggaacgatg ataactccca ttgtactggc atacatgctt gagagagaat    660
tggttgcccg aagaaggttc ctgccagtgg caggagcaac atcagctgag ttcatagaaa    720
tgctacactg cttacaaggt gaaaattgga gacaaatata tcacccagga gggaataaac    780
taactgaatc taggtctcaa tcaatgattg tagcttgtag aaaaataatc agaagatcaa    840
tagtcgcatc aaacccacta gagctagctg tagaaattgc aaacaagact gtgatagata    900
ctgaaccttt aaaatcatgt ctggcagcca tagacggagg tgatgtagcc tgtgacataa    960
tgagagctgc attaggacta aagatcagac aaagacaaag atttggacgg cttgaactaa   1020
agagaatatc aggaagagga ttcaaaaatg atgaagaaat attgatcggg aacggaacaa   1080
tacagaagat tggaatatgg gacggagaag aggagttcca tgtaagatgt ggtgaatgca   1140
ggggaatatt aaaaaagagc aaaatgagaa tggaaaaact actaataaat tcagccaaaa   1200
aggaggacat gaaagattta ataatcttgt gcatggtatt ttctcaagac actaggatgt   1260
tccaaggagt gagaggagaa ataaattttc ttaatcgagc aggccaactt ttatctccaa   1320
tgtaccaact ccaaagatat tttttgaata ggagcaacga tctttttgat caatgggggt   1380
atgaggaatc acccaaagca agtgaactac atgggataaa tgaattaatg aatgcatctg   1440
attatacgtt gaaaggggtt gtagtaacaa aaaatgtgat tgatgacttt agttctactg   1500
aaacagaaaa agtatctata acaaaaaatc ttagtttaat aaaaagaact ggggaagtca   1560
taatgggggc taatgacgta agtgaattag aatcacaagc tcagctaatg ataacatatg   1620
atacacctaa gatgtgggag atgggaacaa ccaaagaact ggtgcaaaac acctaccaat   1680
gggtgctaaa aaatttggta acactgaagg ctcagtttct tctaggaaaa gaagacatgt   1740
tccaatggga tgcatttgaa gcatttgaaa gcataatccc ccagaagatg gctggccagt   1800
acagtggatt tgcaagggca gtgctcaaac aaatgagaga ccaagaggtt atgaaaactg   1860
accagttcat aaagttgttg cctttctgtt tctcaccacc aaaattaagg agcaatgggg   1920
```

-continued

```
agccttatca attcttgagg cttatattga agggaggagg agaaaatttc atcgaagtaa   1980

ggaaagggtc ccctctattc tcctacaatc cacaaacaga agtcctaact atatgcggca   2040

gaatgatgtc attaaaaggg aaaattgaag atgaagaaag gaatagatca atggggaatg   2100

cagtattggc aggctttctc gttagtggca agtatgaccc agatcttgga gatttcaaaa   2160

ctattgaaga acttgaaaag ctaaaaccgg gggagaaagc aaacatctta ctttatcaag   2220

gaaagcccgt taaagtagtt aaaaggaaaa gatatagtgc tttatccaat gacatttcac   2280

aaggaattaa gagacaaaga atgacagttg agtccatggg gtgggccttg agctaatata   2340

aatttatcca ttaattcaat aaacacaatt gagtgaaaaa tgctcgtgtt tctact       2396
```

<210> SEQ ID NO 2
<211> LENGTH: 2369
<212> TYPE: DNA
<213> ORGANISM: Influenza B

<400> SEQUENCE: 2

```
agcagaagcg gagcctttaa gatgaatata aatccttatt ttctcttcat agatgtaccc     60

atacaggcag caatttcaac aacattccca tacaccggtg ttcccctta ttcccatgga     120

acgggaacag gctacacaat agacaccgtg atcagaacac atgagtactc aaacaaggga    180

aaacagtaca tttctgatgt tacaggatgt acaatggtag atccaacaaa tgggccatta    240

cccgaagaca atgagccgag tgcctatgca caattagatt gcgttctgga ggctttggat    300

agaatggatg aagaacatcc aggtctgttt caagcagcct cacagaatgc catggaggca    360

ctaatggtca caactgtaga caaattaacc caggggagac agacttttga ttggacagta    420

tgcagaaacc aacctgctgc aacggcactg aacacaacaa taacctcttt taggttgaat    480

gatttgaatg gagccgacaa gggtggatta gtaccctttt gccaagatat cattgattca    540

ttggacagac ctgaaatgac tttcttctca gtaaagaata taaagaaaaa attgcctgct    600

aaaaacagaa agggtttcct cataaagaga ataccaatga aggtaaaaga cagaataacc    660

agagtggaat acatcaaaag agcattatca ttaaacacaa tgacaaaaga tgctgaaaga    720

ggcaaactaa aaagaagagc gattgccacc gctggaatac aaatcagagg gtttgtatta    780

gtagttgaaa acttggctaa aaatatctgt gaaaatctag aacaaagtgg tttgccagta    840

ggtggaaacg agaagaaggc caaactgtca aatgcagtgg ccaaaatgct cagtaactgc    900

ccaccaggag ggatcagcat gacagtaaca ggagacaata ccaaatggaa tgaatgctta    960

aatccaagaa tctttttggc tatgactgaa agaataacca gagacagccc aatttggttc   1020

cgggattttt gtagtatagc accggtcttg ttctccaata aaatagccag attgggaaaa   1080

gggtttatga taacaagcaa aacaaaaaga ctgaaggctc aaataccttg tcctgatctg   1140

tttagtatac cattagaaag atataatgaa gaaacaaggg caaaattgaa aaagctgaaa   1200

ccattcttca atgaagaagg aacggcatct ttgtcgcctg ggatgatgat gggaatgttt   1260

aatatgctat ctaccgtgtt gggagtagcc gcactaggta tcaaaaacat tggaaacaaa   1320

gaatacttat gggatggact gcaatcttct gatgattttg ctctgtttgt taatgcaaaa   1380

gatgaagaga catgtatgga aggaataaac gacttttacc gaacatgtaa actattggga   1440

ataaacatga gcaaaaagaa aagttactgt aatgaaactg gaatgtttga atttacaagc   1500

atgttctaca gagatggatt tgtatctaat tttgcaatgg aacttccttc atttggagtt   1560

gctggagtaa atgaatcagc agatatggca ataggaatga caataataaa gaacaatatg   1620

atcaacaatg ggatgggtcc agcaacagca caaacagcca tacaattatt catagctgat   1680
```

```
tatagataca cctacaaatg ccacagggga gattccaaag tggaaggaaa gagaatgaaa   1740
attataaagg agctatggga aaacactaaa ggaagagatg gtctgttagt agcagatggt   1800
gggcctaaca tttacaattt gagaaacttg catatcccag aaatagtatt aaagtacaac   1860
ctaatggacc ctgaatacaa agggcggtta cttcatcctc aaaatccctt tgtaggacat   1920
ttgtctattg agggcatcaa agaggcagat ataaccccag cacatggtcc agtaaagaaa   1980
atggactatg atgcggtgtc tggaactcat agttggagaa ccaaaaggaa cagatctata   2040
ctaaacactg atcagaggaa catgattctt gaggaacaat gctacgctaa gtgttgcaac   2100
ctttttgagg cctgttttaa cagtgcatca tacaggaaac cagtaggtca gcacagcatg   2160
cttgaggcta tggcccacag attaagaatg gatgcacgac tagattatga atcaggaaga   2220
atgtcaaagg atgattttga gaaagcaatg gctcaccttg gtgagattgg gtacatataa   2280
gcttcgaaga tgtctatggg gttattggtc atcattgaat acatgcggta cacaaatgat   2340
taaaatgaaa aaaggctcgt gtttctact                                     2369
```

<210> SEQ ID NO 3
<211> LENGTH: 2308
<212> TYPE: DNA
<213> ORGANISM: Influenza B

<400> SEQUENCE: 3

```
agcagaagcg gtgcgtttga tttgccataa tggatacttt tattacaaga aacttccaga     60
ctacaataat acaaaaggcc aaaaacacaa tggcagaatt tagtgaagat cctgaattac    120
aaccagcaat gctattcaac atctgcgtcc atctggaggt ctgctatgta ataagtgata    180
tgaattttct tgatgaagaa ggaaaagcat atacagcatt agaaggacaa ggaaaagaac    240
aaaacttgag accacaatat gaagtgattg agggaatgcc aagaaacata gcatggatgg    300
ttcaaagatc cttagcccaa gagcatggga tagagactcc aaggtatctg gctgatttgt    360
tcgattataa aactaagagg tttatagaag ttggaataac aaagggattg gctgatgatt    420
acttctggaa aaagaaagaa aagctgggga atagcatgga actgatgata ttcagctaca    480
atcaagacta ttcgttaagt aatgaatcct cattggatga ggaaggaaaa gggagagtgc    540
taagcagact cacagaactt caggctgagt taagtctgaa aaatctatgg caagttctca    600
taggagaaga agatattgaa aaaggaattg acttcaaact tggacaaaca atatctaaac    660
taagggatat atctgttcca gctggtttct ccaattttga aggaatgagg agctacatag    720
acaatataga tcctaaagga gcaatagaga gaaatctagc aaggatgtct cccttagtat    780
cagttacacc taaaaagttg aaatgggagg acctaagacc aatagggcct cacatttaca    840
accatgagct accagaagtt ccatataatg cctttcttct aatgtctgat gaattggggc    900
tggctaatat gactgaaggg aagtccaaga aaccgaagac cttagccaaa gagtgcctag    960
aaaagtactc aacactacgg gatcaaactg acccaatatt aataatgaaa agcgaaaaag   1020
ctaatgaaca cttcctatgg aaactgtgga gggactgtgt aaatacaata agtaatgagg   1080
aaacaagtaa cgaattacag aaaaccaatt atgccaagtg ggccacagga gatggattaa   1140
catatcagaa aataatgaaa gaagtagcaa tagatgacga aacaatgtac caagaagagc   1200
ccaaaatacc taacaaatgt agagtggctg cttgggttca aacagagatg aatctattga   1260
gcactctgac aagtaaaagg gccctggatc tgccagaaat agggccagac gtagcacccg   1320
tggagcatgt agggagtgaa agaaggaaat actttgttaa tgaaatcaac tactgtaagg   1380
```

-continued

```
cctctaccgt tatgatgaag tatgtacttt ttcacacttc attattaaat gaaagcaatg   1440

ccagcatggg aaaatataaa gtaataccaa taaccaacag agtagtaaat gaaaagggag   1500

aaagttttga catgctttat ggtctagcgg ttaaagggca atctcatctg aggggagata   1560

ctgatgttgt aacagttgtg actttcgaat ttagtagtac agatcccaga gtggactcag   1620

gaaagtggcc aaaatatact gtatttagaa ttggctcctt atttgtgagt gggagggaaa   1680

aatctgtata cctatattgc cgagtgaatg gtacaaataa gatccaaatg aaatggggaa   1740

tggaagctag aagatgtctg cttcaatcaa tgcaacaaat ggaagcaatt gttgaacaag   1800

aatcatcgat acaaggatat gacatgacca aagcttgttt caagggagac agagtgaata   1860

gtccaaaaac tttcagtatt gggactcaag aaggaaaact agtgaaagga tcctttggga   1920

aagcactaag agtaatattc accaaatgtt tgatgcacta tgtatttgga aatgcccaat   1980

tggaggggtt tagtgccgaa tctaggagac ttctactgtt aattcaggca ttaaaagaca   2040

gaaagggccc ttgggtattc gacttagagg gaatgtattc tggaatagaa gaatgtatta   2100

gtaacaaccc ttgggtaata cagagtgcat actggtttaa tgaatggttg ggctttgaaa   2160

aagaggggag taaagtatta gaatcagtag atgaaataat ggatgaatga aagaagggca   2220

tagtgctcaa tttggtacta ttttgttcat tatgtatcta aacatccaat aaaaagaatt   2280

gagaattaaa aatgcacgtg tttctact                                     2308


<210> SEQ ID NO 4
<211> LENGTH: 1840
<212> TYPE: DNA
<213> ORGANISM: Influenza B

<400> SEQUENCE: 4

agcagaagca cagcattttc ttgtgaactt caagtaccaa caaaaaactg aaaatcaaaa     60

tgtccaacat ggacattgac ggcatcaaca ctggaataat tgacaaaaca ccagaagaaa    120

taacttccgg aaccagtggg gcaaccagac caatcatcag accagcaacc cttgccccac    180

caagcaacaa acgaaccaga aacccatccc cggaaagggc aaccacaagc agtgaagctg    240

atgtcggaag gaaaacccaa aagaaacaaa ctccgacaga gataaagaag agcgtctaca    300

atatggtagt gaaactgggt gaattctaca accagatgat ggtcaaagct ggactcaacg    360

atgacatgga gagaaaccta atccaaaatg cacatgctgt ggaaagaatt ctattggctg    420

ctactgatga caagaaaact gaattccaaa agaaaaagaa tgccagagac gtcaaagaag    480

ggaaagaaga aatagaccac aacaaaacag gaggcacctt ttacaagatg gtaagagatg    540

ataaaaccat ctacttcagc cctataagaa ttaccttttt aaaagaagag gtgaaaacaa    600

tgtacaaaac caccatgggg agtgacggtt tcagtggact aaatcacatc atgattgggc    660

attcacagat gaacgatgtc tgtttccaaa gatcaaaggc actaaaaaga gttggacttg    720

acccttcatt aatcagtact tttgcaggaa gcacactccc cagaagatca ggtacaactg    780

gtgttgcgac caaaggaggt ggaactttag tggcagaagc cattcgattt ataggaagag    840

caatggcaga cagagggcta ttgagagaca tcagagccaa gacggcctat gaaaagattc    900

ttctgaatct gaaaaacaag tgctctgcgc cccaacaaaa ggctctggtt gatcaagtga    960

tcggaagtag aaatccaggg attgcagaca tagaagatct caccctgctt gctcgaagta   1020

tggtcgttgt taggccctct gtagcaagca aagtggtgct tcccataagc atctatgcta   1080

aaatacctca actggggttc aacgttgaag aatactctat ggttgggtat gaagccatgg   1140

ctctttataa tatggcaaca cctgtttcca tattaagaat gggagacgat gcaaaagata   1200
```

aatcacaatt attcttcatg tcttgctttg gagctgccta tgaagaccta agagttctgt 1260
ctgcactaac aggcacggaa ttcaagccta ggtcagcatt aaagtgcaaa ggtttccacg 1320
ttccagcaaa ggagcaagtg gaaggaatgg gggcagctct gatgtccatc aagctccagt 1380
tttgggctcc aatgaccaga tctgggggga atgaagtagg tggagacgga gggtctggtc 1440
aaataagttg cagccccgtg tttgcagtag aaagacctat tgctctaagc aagcaagctg 1500
taagaagaat gctgtcaatg aatattgagg gacgtgatgc agatgtcaaa ggaaatctac 1560
tcaagatgat gaatgattca atggctaaga aaaccaatgg aaatgctttc attgggaaga 1620
aaatgttcca aatatcagac aaaaacaaaa ccaatcccgt tgagattcca attaagcaga 1680
ccatccccag tttcttcttt gggagggaca cagcagagga ttatgatgac ctcgattatt 1740
aaagcaacaa aatagacact atggctgtga ttgtttcagt acgtttggaa tgtgggtgtt 1800
tactcttatt gaaataaatg taaaaaatgc tgttgtttct 1840

<210> SEQ ID NO 5
<211> LENGTH: 1190
<212> TYPE: DNA
<213> ORGANISM: Influenza B

<400> SEQUENCE: 5
agcagaagca cgcactttct taaaatgtcg ctgtttggag acacaattgc ctacctgctt 60
tcactaacag aagatggaga aggcaaagca gaactagcgg aaaaattaca ctgttggttc 120
ggtgggaaag aattcgatct agactctgct ttggaatgga taaaaaacaa aagatgccta 180
actgatatac aaaaagcact aattggtgcc tctatctgct tttgaaacc caaagaccaa 240 gaaagaaaaa gaagattcat cacagagccc ctgtcaggaa tgggaacaac agcaacaaaa 300
aagaaaggcc tgattctagc tgaaagaaaa atgagaagat gtgtgagttt tcatgaggca 360
tttgaaatag cagaaggcca tgaaagctca gcactactat attgtctcat ggtcatgtac 420
ctgaaccctg gaaattattc aatgcaagta aaactaggaa cgctctgtgc tttatgcgag 480
aaacaagcat cacattcaca cagagctcat agcagagcag caagatcttc agtgcctgga 540
gtgaggcgag aaatgcaaat ggtttcagct atgaacacag caaaaacaat gaatggaatg 600
gggaagggag aagacgtcca aaaactggca gaagagctgc aaagcaacat tggagtattg 660
agatctctgg gggcaagtca aaagaatgga gaaggaattg caaaggatgt aatggaagtg 720
ctaaagcaga gctccatggg aaattcagct cttgtgaaga aatacctata atgctcgagc 780
catttcagat tctttcaatt tgctctttca ttttatcggc tctccatttc atgggctgga 840
caatagggca tttaaatcaa ataaaaagag gagtaaacct aaaaatacga ataagaaatc 900
caaataaaga gacaataaat agagaggtat caattttgag acacagttac caaaaagaaa 960
tccaagccaa agaaacaata aaggaagtac tctctgacaa catggagaga ttgagtgacc 1020
acatagtaat tgaggggctt tctgctgaag agataataaa aatgggtgaa acagttttgg 1080
aggtagaaga attgcattaa acccaatttt caccgtattt cttactatgc atttaagcaa 1140
attgtaatca atgtcagcaa ataaactgga aaaagtgcgt tgtttctact 1190

<210> SEQ ID NO 6
<211> LENGTH: 1098
<212> TYPE: DNA
<213> ORGANISM: Influenza B

<400> SEQUENCE: 6

-continued

```
agcagaagca gaggatttgt ttagtcactg gcaaacggaa aaaaatggcg gacaacatga     60
ccacaacaca aattgaggtg ggtccgggag caaccaatgc cactataaac tttgaagcag    120
gaattttgga gtgctatgaa aggctttcat ggcaaagagc ccttgactac cctggtcaag    180
accgcctaaa cagactaaag agaaaattag aatcaagaat aaagactcac aacaaaagtg    240
agcctgaaag taaaaggatg tctcttgaag agagaaaagc aattggggta aaaatgatga    300
aagtgctcct atttatgaac ccatctgctg gaattgaagg gtttgagcca tactgtatga    360
aaaattcctc caatagcaac tgcccaaact gcaattgggc cgattaccct ccaacatcag    420
gaaagtgcct tgatgacata gaagaagaac cggagaatgt tgatgaccca actgaaatag    480
tattaaggga catgaacaac aaagatgcaa ggcaaaagat aaaagaggaa gtaaacactc    540
agaaagaagg gaagttccgt ttgacaataa aaagggatat acgtaatgtg ttgtccttga    600
gagtgttggt aaacggaaca ttcctcaagc accctaatgg atacaagtcc ttatcaactc    660
tgcatagatt gaatgcatat gaccagagtg gaaggcttgt tgctaaactt gttgctactg    720
atgatcttac agtggaggat gaagaagatg gccatcggat cctcaactca ctcttcgagc    780
gttttaatga aggacattca aagccaattc gagcagctga aactgcggtg ggagtcttat    840
cccaatttgg tcaagagcac cgattatcac cagaggaggg agacaattag actggttacg    900
gaagaacttt atcttttaag taaaagaatt gatgataaca tattgttcca caaaacagta    960
atagctaaca gctccataat agctgacatg attgtatcat tatcattatt ggaaacattg   1020
tatgagatga aggatgtggt tgaagtgtac agcaggcagt gcttgtgaat ttaaaataaa   1080
aatcctcttg ttactact                                                 1098
```

<210> SEQ ID NO 7
<211> LENGTH: 583
<212> TYPE: PRT
<213> ORGANISM: Influenza B

<400> SEQUENCE: 7

```
Met Lys Ala Ile Ile Val Leu Leu Met Val Val Thr Ser Asn Ala Asp
1               5                   10                  15

Arg Ile Cys Thr Gly Ile Thr Ser Ser Asn Ser Pro His Val Val Lys
            20                  25                  30

Thr Ala Thr Gln Gly Glu Val Asn Val Thr Gly Val Ile Pro Leu Thr
        35                  40                  45

Thr Thr Pro Thr Lys Ser His Phe Ala Asn Leu Lys Gly Thr Lys Thr
    50                  55                  60

Arg Gly Lys Leu Cys Pro Asn Cys Leu Asn Cys Thr Asp Leu Asp Val
65                  70                  75                  80

Ala Leu Gly Arg Pro Met Cys Met Gly Thr Ile Pro Ser Ala Lys Ala
                85                  90                  95

Ser Ile Leu His Glu Val Arg Pro Val Thr Ser Gly Cys Phe Pro Ile
            100                 105                 110

Met His Asp Arg Thr Lys Ile Arg Gln Leu Pro Asn Leu Leu Arg Gly
        115                 120                 125

Tyr Glu Asn Ile Arg Leu Ser Thr His Asn Val Ile Asn Ala Glu Arg
    130                 135                 140

Ala Pro Gly Gly Pro Tyr Arg Leu Gly Thr Ser Gly Ser Cys Pro Asn
145                 150                 155                 160

Val Thr Ser Arg Asn Gly Phe Phe Ala Thr Met Ala Trp Ala Val Pro
                165                 170                 175
```

-continued

```
Arg Asp Asn Lys Thr Ala Thr Asn Pro Leu Thr Val Glu Val Pro Tyr
            180                 185                 190

Ile Cys Thr Lys Gly Glu Asp Gln Ile Thr Val Trp Gly Phe His Ser
        195                 200                 205

Asp Asp Lys Thr Gln Met Lys Asn Leu Tyr Gly Asp Ser Asn Pro Gln
    210                 215                 220

Lys Phe Thr Ser Ser Ala Asn Gly Val Thr Thr His Tyr Val Ser Gln
225                 230                 235                 240

Ile Gly Asp Phe Pro Asn Gln Thr Glu Asp Gly Gly Leu Pro Gln Ser
                245                 250                 255

Gly Arg Ile Val Val Asp Tyr Met Val Gln Lys Pro Gly Lys Thr Gly
            260                 265                 270

Thr Ile Val Tyr Gln Arg Gly Val Leu Leu Pro Gln Lys Val Trp Cys
        275                 280                 285

Ala Ser Gly Arg Ser Lys Val Ile Lys Gly Ser Leu Pro Leu Ile Gly
    290                 295                 300

Glu Ala Asp Cys Leu His Glu Lys Tyr Gly Gly Leu Asn Lys Ser Lys
305                 310                 315                 320

Pro Tyr Tyr Thr Gly Glu His Ala Lys Ala Ile Gly Asn Cys Pro Ile
                325                 330                 335

Trp Val Lys Thr Pro Leu Lys Leu Ala Asn Gly Thr Lys Tyr Arg Pro
            340                 345                 350

Pro Ala Lys Leu Leu Lys Glu Arg Gly Phe Phe Gly Ala Ile Ala Gly
        355                 360                 365

Phe Leu Glu Gly Gly Trp Glu Gly Met Ile Ala Gly Trp His Gly Tyr
    370                 375                 380

Thr Ser His Gly Ala His Gly Val Ala Val Ala Ala Asp Leu Lys Ser
385                 390                 395                 400

Thr Gln Glu Ala Ile Asn Lys Ile Thr Lys Asn Leu Asn Ser Leu Ser
                405                 410                 415

Glu Leu Glu Val Lys Asn Leu Gln Arg Leu Ser Gly Ala Met Asp Glu
            420                 425                 430

Leu His Asn Glu Ile Leu Glu Leu Asp Glu Lys Val Asp Asp Leu Arg
        435                 440                 445

Ala Asp Thr Ile Ser Ser Gln Ile Glu Leu Ala Val Leu Leu Ser Asn
    450                 455                 460

Glu Gly Ile Ile Asn Ser Glu Asp Glu His Leu Leu Ala Leu Glu Arg
465                 470                 475                 480

Lys Leu Lys Lys Met Leu Gly Pro Ser Ala Val Asp Ile Gly Asn Gly
                485                 490                 495

Cys Phe Glu Thr Lys His Lys Cys Asn Gln Thr Cys Leu Asp Arg Ile
            500                 505                 510

Ala Ala Gly Thr Phe Asn Ala Gly Glu Phe Ser Leu Pro Thr Phe Asp
        515                 520                 525

Ser Leu Asn Ile Thr Ala Ala Ser Leu Asn Asp Asp Gly Leu Asp Asn
    530                 535                 540

His Thr Ile Leu Leu Tyr Tyr Ser Thr Ala Ala Ser Ser Leu Ala Val
545                 550                 555                 560

Thr Leu Met Ile Ala Ile Phe Ile Val Tyr Met Val Ser Arg Asp Asn
                565                 570                 575

Val Ser Cys Ser Ile Cys Leu
            580
```

```
<210> SEQ ID NO 8
<211> LENGTH: 466
<212> TYPE: PRT
<213> ORGANISM: Influenza B

<400> SEQUENCE: 8

Met Leu Pro Ser Thr Ile Gln Thr Leu Thr Leu Phe Leu Thr Ser Gly
1               5                   10                  15

Gly Val Leu Leu Ser Leu Tyr Val Ser Ala Ser Leu Ser Tyr Leu Leu
            20                  25                  30

Tyr Ser Asp Ile Leu Leu Lys Phe Ser Pro Thr Glu Ile Thr Ala Pro
        35                  40                  45

Lys Val Pro Leu Asp Cys Ala Asn Ala Ser Asn Val Gln Ala Val Asn
    50                  55                  60

Arg Ser Ala Thr Lys Gly Met Thr Leu Leu Leu Ser Glu Pro Glu Trp
65                  70                  75                  80

Thr Tyr Pro Arg Leu Ser Cys Gln Gly Ser Thr Phe Gln Lys Ala Leu
                85                  90                  95

Leu Ile Ser Pro His Arg Phe Gly Glu Thr Arg Gly Asn Ser Ala Pro
            100                 105                 110

Leu Ile Ile Arg Glu Pro Phe Ile Ala Cys Gly Pro Lys Glu Cys Lys
        115                 120                 125

His Phe Ala Leu Thr His Tyr Ala Ala Gln Pro Gly Gly Tyr Tyr Asn
    130                 135                 140

Gly Thr Arg Glu Asp Arg Asn Lys Leu Arg His Leu Ile Ser Val Lys
145                 150                 155                 160

Leu Gly Lys Ile Pro Thr Val Glu Asn Ser Ile Phe His Met Ala Ala
                165                 170                 175

Trp Ser Gly Ser Ala Cys His Asp Gly Arg Glu Trp Thr Tyr Ile Gly
            180                 185                 190

Val Asp Gly Pro Asp Ser Asn Ala Leu Ile Lys Ile Lys Tyr Gly Glu
        195                 200                 205

Ala Tyr Thr Asp Thr Tyr His Ser Tyr Ala Asn Asn Ile Leu Arg Thr
    210                 215                 220

Gln Glu Ser Ala Cys Asn Cys Ile Gly Gly Asp Cys Tyr Leu Met Ile
225                 230                 235                 240

Thr Asp Gly Ser Ala Ser Gly Ile Ser Lys Cys Arg Phe Leu Lys Ile
                245                 250                 255

Arg Glu Gly Arg Ile Ile Lys Glu Ile Phe Pro Thr Gly Arg Val Glu
            260                 265                 270

His Thr Glu Glu Cys Thr Cys Gly Phe Ala Ser Asn Lys Thr Ile Glu
        275                 280                 285

Cys Ala Cys Arg Asp Asn Ser Tyr Thr Ala Lys Arg Pro Phe Val Lys
    290                 295                 300

Leu Asn Val Glu Thr Asp Thr Ala Glu Ile Arg Leu Met Cys Thr Glu
305                 310                 315                 320

Thr Tyr Leu Asp Thr Pro Arg Pro Asp Asp Gly Ser Ile Thr Gly Pro
                325                 330                 335

Cys Glu Ser Asn Gly Asp Lys Gly Arg Gly Gly Ile Lys Gly Gly Phe
            340                 345                 350

Val His Gln Arg Met Ala Ser Lys Ile Gly Arg Trp Tyr Ser Arg Thr
        355                 360                 365

Met Ser Lys Thr Glu Arg Met Gly Met Glu Leu Tyr Val Lys Tyr Asp
    370                 375                 380
```

-continued

```
Gly Asp Pro Trp Thr Asp Ser Asp Ala Leu Ala Pro Ser Gly Val Met
385                 390                 395                 400

Val Ser Met Lys Glu Pro Gly Trp Tyr Ser Phe Gly Phe Glu Ile Lys
                405                 410                 415

Asp Lys Lys Cys Asp Val Pro Cys Ile Gly Ile Glu Met Val His Asp
            420                 425                 430

Gly Gly Lys Lys Thr Trp His Ser Ala Ala Thr Ala Ile Tyr Cys Leu
        435                 440                 445

Met Gly Ser Gly Gln Leu Leu Trp Asp Thr Val Thr Gly Val Asp Met
    450                 455                 460

Ala Leu
465


<210> SEQ ID NO 9
<211> LENGTH: 1843
<212> TYPE: DNA
<213> ORGANISM: Influenza B

<400> SEQUENCE: 9

tttctaatat ccacaaaatg aaggcaataa ttgtactact catggtagta acatccaacg     60

cagatcgaat ctgcactggg ataacatctt caaactcacc tcatgtggtc aaaacagcta    120

ctcaagggga agttaatgtg actggtgtga taccactgac aacaacacca acaaaatctc    180

attttgcaaa tctcaaagga acaaagacca gagggaaact atgcccaaac tgtctcaact    240

gcacagatct ggatgtggcc ttgggcagac caatgtgtat ggggaccata ccttcggcaa    300

aagcttcaat actccacgaa gtcagacctg ttacatccgg gtgctttcct ataatgcacg    360

acagaacaaa aatcagacag ctacccaatc ttctcagagg atatgaaaat atcagattat    420

caacccataa cgttatcaac gcagaaaggg caccaggagg accctacaga cttggaacct    480

caggatcttg ccctaacgtt accagtagaa acggattctt cgcaacaatg gcttgggctg    540

tcccaaggga caacaaaaca gcaacgaatc cactaacagt agaagtacca tacatttgca    600

caaaaggaga agaccaaatt actgtttggg ggttccattc tgatgacaaa acccaaatga    660

aaaacctcta tggagactca aatcctcaaa agttcacctc atctgccaat ggagtaacca    720

cacattatgt ttctcagatt ggtgacttcc caaatcaaac agaagacgga gggctaccac    780

aaagcggcag aattgttgtt gattacatgg tgcaaaaacc tgggaaaaca ggaacaattg    840

tctatcaaag aggtgttttg ttgcctcaaa aggtgtggtg cgcaagtggc aggagcaagg    900

taataaaagg gtccttgcct ttaattggtg aagcagattg ccttcacgaa aaatacggtg    960

gattaaacaa aagcaagcct tactacacag gagaacatgc aaaagccata ggaaattgcc   1020

caatatgggt gaaaacacct ttgaagcttg ccaatggaac caaatataga cctcctgcaa   1080

aactattaaa ggaaaggggt ttcttcggag ctattgctgg tttcttagag ggaggatggg   1140

aaggaatgat tgcaggttgg cacggataca catctcatgg agcacatgga gtggcagtgg   1200

cagcagacct taagagcacg caagaagcca taaacaagat aacaaaaaat ctcaattctt   1260

tgagtgagct agaagtaaag aatcttcaaa gactaagtgg tgccatggat gaactccaca   1320

acgaaatact cgagctggat gagaaagtgg atgatctcag agctgacaca ataagctcgc   1380

aaatagagct tgcagtcttg ctttccaacg aaggaataat aaacagtgaa gatgagcatc   1440

tattggcact tgagagaaaa ctaaagaaaa tgctgggtcc ctctgctgta gacataggga   1500

atggatgctt cgaaaccaaa cacaagtgca accagacctg cttagacagg atagctgctg   1560

gcacctttaa tgcaggagaa ttttctcttc ccacttttga ttcactgaat attactgctg   1620
```

catctttaaa tgatgatgga ttggataatc atactatact gctctactac tcaactgctg 1680
cttctagttt ggccgtaaca ttgatgatag ctatttttat tgtttatatg gtctccagag 1740
acaatgtttc ttgctccatc tgtctataag gaaaattaag ccctgtattt tcctttattg 1800
tagtgcttgt ttgcttgtta ccattacaaa gaaacgttat tga 1843

<210> SEQ ID NO 10
<211> LENGTH: 1504
<212> TYPE: DNA
<213> ORGANISM: Influenza B

<400> SEQUENCE: 10
aaactgaggc aaataggcca aaaatgaaca atgctacctt caactataca aacgttaacc 60
ctatttctca catcaggggg agtgttatta tcactatatg tgtcagcttc actgtcatac 120
ttactgtatt cggatatatt gctaaaattt tcaccaacag aaataactgc accaaaagtg 180
ccattggatt gtgcaaacgc atcaaatgtt caggctgtga accgttctgc aacaaaaggg 240
atgacacttc ttctctcaga accggagtgg acatacccct gtttatcttg ccagggctca 300
acctttcaga aagcactcct aattagccct catagattcg gagaaaccag aggaaactca 360
gctcccttga taataaggga accttttatt gcttgtggac caaaggaatg caaacacttt 420
gctctaaccc attatgcagc tcaaccaggg ggatactaca atggaacaag agaggacaga 480
aacaagctga ggcatctgat ttcagtcaaa ttgggcaaaa tcccaacagt agaaaactcc 540
attttccaca tggcagcttg gagcgggtcc gcatgccatg atggtagaga atggacatat 600
atcggagttg atggccctga cagtaatgca ttgatcaaaa taaaatatgg agaagcatat 660
actgacacat accattccta tgcaaacaac atcctaagaa cacaagaaag tgcctgcaat 720
tgcatcgggg gagattgtta tcttatgata actgatggct cagcttcagg aattagtaaa 780
tgcagatttc ttaagattcg agagggtcga ataataaaag aaatatttcc aacaggaaga 840
gtagaacata ctgaagaatg cacatgcgga tttgccagca ataaaaccat agaatgtgcc 900
tgtagagata acagttacac agcaaaaaga ccctttgtca aattaaatgt ggagactgat 960
acagctgaaa taagattgat gtgcacagag acttatttgg acacccccag accagatgat 1020
ggaagcataa cagggccttg cgaatctaat ggggacaaag ggcgtggagg catcaaggga 1080
ggatttgttc atcaaagaat ggcatccaag attggaagat ggtactctcg aacgatgtct 1140
aaaactgaaa gaatggggat ggaactgtat gtcaagtatg atggagaccc atggactgac 1200
agtgacgccc ttgctcctag tggagtaatg gtttcaatga aagaacctgg ttggtattcc 1260
tttggcttcg aaataaaaga taagaaatgt gatgtcccct gtattgggat agagatggta 1320
catgatggtg gaaaaaagac ttggcactca gcagcaacag ccatttactg tttaatgggc 1380
tcaggacaat tgctatggga cactgtcaca ggtgttgata tggctctgta atggaggaat 1440
ggttgagtct gttctaaacc ctttgttcct attttgtttg aacaattgtc cttactgaac 1500
ttaa 1504

<210> SEQ ID NO 11
<211> LENGTH: 2396
<212> TYPE: DNA
<213> ORGANISM: Influenza B

<400> SEQUENCE: 11
agcagaagcg gagcgttttc aagatgacat tggctaaaat tgaattgtta aaacaactgt 60

-continued

```
taagggacaa cgaagccaaa acagtattga aacaaacaac ggtagaccaa tataacataa    120
taagaaaatt caatacatca agaattgaaa agaacccttc attaaggatg aagtgggcca    180
tgtgttctaa ttttcccttg gctctgacca agggtgatat ggcaaataga atccccttgg    240
aatacaaggg aatacaactt aaaacaaatg ctgaagacat aggaaccaaa ggccaaatgt    300
gctcaatagc agcagttacc tggtggaata catatggacc aataggagac actgaaggtt    360
tcgaaaaggt ctacgaaagc ttctttctca gaaagatgag acttgacaat gccacttggg    420
gccgaataac ttttggccca gttgaaagag taagaaaaag ggtactgcta aaccctctca    480
ccaaggaaat gcctccagat gaagcgagca atgtgataat ggaaatattg ttccctaagg    540
aagcaggaat accaagagaa tctacttgga tacataggga actgataaaa gaaaaaagag    600
aaaaattgaa aggaacgatg ataactccca ttgtactggc atacatgctt gagagagaat    660
tggttgcccg aagaaggttc ctgccagtgg caggagcaac atcagctgag ttcatagaaa    720
tgctacactg cttacaaggt gaaaattgga gacaaatata tcacccagga gggaataaac    780
taactgaatc taggtctcaa tcaatgattg tagcttgtag aaaaataatc agaagatcaa    840
tagtcgcatc aaacccacta gagctagctg tagaaattgc aaacaagact gtgatagata    900
ctgaaccttt aaaatcatgt ctggcagcca tagacggagg tgatgtagcc tgtgacataa    960
tgagagctgc attaggacta aagatcagac aaagacaaag atttggacgg cttgaactaa   1020
agagaatatc aggaagagga ttcaaaaatg atgaagaaat attgatcggg aacggaacaa   1080
tacagaagat tggaatatgg gacggagaag aggagttcca tgtaagatgt ggtgaatgca   1140
ggggaatatt aaaaaagagc aaaatgagaa tggaaaaact actaataaat tcagccaaaa   1200
aggaggacat gaaagattta ataatcttgt gcatggtatt ttctcaagac actaggatgt   1260
tccaaggagt gagaggagaa ataaattttc ttaatcgagc aggccaactt ttatctccaa   1320
tgtaccaact ccaaagatat tttttgaata ggagcaacga tctttttgat caatgggggt   1380
atgaggaatc acccaaagca agtgaactac atgggataaa tgaattaatg aatgcatctg   1440
attatacgtt gaaaggggtt gtagtaacaa aaaatgtgat tgatgacttt agttctactg   1500
aaacagaaaa agtatctata acaaaaaatc ttagtttaat aaaaagaact ggggaagtca   1560
taatgggggc taatgacgta agtgaattag aatcacaagc tcagctaatg ataacatatg   1620
atacacctaa gatgtgggag atgggaacaa ccaaagaact ggtgcaaaac acctaccaat   1680
gggtgctaaa aaatttggta acactgaagg ctcagtttct tctaggaaaa gaagacatgt   1740
tccaatggga tgcatttgaa gcatttgaaa gcataatccc ccagaagatg gctggccagt   1800
acagtggatt tgcaagggca gtgctcaaac aaatgagaga ccaagaggtt atgaaaactg   1860
accagttcat aaagttgttg cctttctgtt tctcaccacc aaaattaagg agcaatgggg   1920
agccttatca attcttgagg cttatattga agggaggagg agaaaatttc atcgaagtaa   1980
ggaaagggtc ccctctattc tcctacaatc cacaaacaga agtcctaact atatgcggca   2040
gaatgatgtc attaaaaggg aaaattgaag atgaagaaag gaatagatca atggggaatg   2100
cagtattggc aggctttctc gttagtggca agtatgaccc agatcttgga gatttcaaaa   2160
ctattgaaga acttgaaaag ctaaaaccgg gggagaaagc aaacatctta ctttatcaag   2220
gaaagcccgt taaagtagtt aaaaggaaaa gatatagtgc tttatccaat gacatttcac   2280
aaggaattaa gagacaaaga atgacagttg agtccatggg gtgggccttg agctaatata   2340
aatttatcca ttaattcaat aaacacaatt gagtgaaaaa tgctcgtgtt tctact       2396
```

<210> SEQ ID NO 12
<211> LENGTH: 2369
<212> TYPE: DNA
<213> ORGANISM: Influenza B

<400> SEQUENCE: 12
agcagaagcg gagcctttaa gatgaatata aatccttatt ttctcttcat agatgtaccc 60
atacaggcag caatttcaac aacattccca tacaccggtg ttccccctta ttcccatgga 120
acgggaacag gctacacaat agacaccgtg atcagaacac atgagtactc aaacaaggga 180
aaacagtaca tttctgatgt tacaggatgt acaatggtag atccaacaaa tgggccatta 240
cccgaagaca atgagccgag tgcctatgca caattagatt gcgttctgga ggctttggat 300
agaatggatg aagaacatcc aggtctgttt caagcagcct cacagaatgc catggaggca 360
ctaatggtca caactgtaga caaattaacc caggggagac agacttttga ttggacagta 420
tgcagaaacc aacctgctgc aacggcactg aacacaacaa taacctcttt taggttgaat 480
gatttgaatg gagccgacaa gggtggatta gtaccctttt gccaagatat cattgattca 540
ttggacagac ctgaaatgac tttcttctca gtaaagaata taaagaaaaa attgcctgct 600
aaaaacagaa agggtttcct cataaagaga ataccaatga aggtaaaaga cagaataacc 660
agagtggaat acatcaaaag agcattatca ttaaacacaa tgacaaaaga tgctgaaaga 720
ggcaaactaa aaagaagagc gattgccacc gctggaatac aaatcagagg gtttgtatta 780
gtagttgaaa acttggctaa aaatatctgt gaaaatctag aacaaagtgg tttgccagta 840
ggtggaaacg agaagaaggc caaactgtca aatgcagtgg ccaaaatgct cagtaactgc 900
ccaccaggag ggatcagcat gacagtaaca ggagacaata ccaaatggaa tgaatgctta 960
aatccaagaa tctttttggc tatgactgaa agaataacca gagacagccc aatttggttc 1020
cgggattttt gtagtatagc accggtcttg ttctccaata aaatagccag attgggaaaa 1080
gggtttatga taacaagcaa aacaaaaaga ctgaaggctc aaataccttg tcctgatctg 1140
tttagtatac cattagaaag atataatgaa gaaacaaggg caaaattgaa aaagctgaaa 1200
ccattcttca atgaagaagg aacggcatct ttgtcgcctg ggatgatgat gggaatgttt 1260
aatatgctat ctaccgtgtt gggagtagcc gcactaggta tcaaaaacat tggaaacaaa 1320
gaatacttat gggatggact gcaatcttct gatgattttg ctctgtttgt taatgcaaaa 1380
gatgaagaga catgtatgga aggaataaac gacttttacc gaacatgtaa actattggga 1440
ataaacatga gcaaaaagaa aagttactgt aatgaaactg gaatgtttga atttacaagc 1500
atgttctaca gagatggatt tgtatctaat tttgcaatgg aacttccttc atttggagtt 1560
gctggagtaa atgaatcagc agatatggca ataggaatga caataataaa gaacaatatg 1620
atcaacaatg ggatgggtcc agcaacagca caaacagcca tacaattatt catagctgat 1680
tatagataca cctacaaatg ccacagggga gattccaaag tggaaggaaa gagaatgaaa 1740
attataaagg agctatggga aaacactaaa ggaagagatg gtctgttagt agcagatggt 1800
gggcctaaca tttacaattt gagaaacttg catatcccag aaatagtatt aaagtacaac 1860
ctaatggacc ctgaatacaa agggcggtta cttcatcctc aaaatccctt tgtaggacat 1920
ttgtctattg agggcatcaa agaggcagat ataaccccag cacatggtcc agtaaagaaa 1980
atggactatg atgcggtgtc tggaactcat agttggagaa ccaaaaggaa cagatctata 2040
ctaaacactg atcagaggaa catgattctt gaggaacaat gctacgctaa gtgttgcaac 2100
ctttttgagg cctgttttaa cagtgcatca tacaggaaac cagtaggtca gcacagcatg 2160

-continued

```
cttgaggcta tggcccacag attaagaatg gatgcacgac tagattatga atcaggaaga   2220

atgtcaaagg atgattttga gaaagcaatg gctcaccttg gtgagattgg gtacatataa   2280

gcttcgaaga tgtctatggg gttattggtc atcattgaat acatgcggta cacaaatgat   2340

taaaatgaaa aaaggctcgt gtttctact                                     2369


<210> SEQ ID NO 13
<211> LENGTH: 2308
<212> TYPE: DNA
<213> ORGANISM: Influenza B

<400> SEQUENCE: 13

agcagaagcg gtgcgtttga tttgccataa tggatacttt tattacaaga aacttccaga     60

ctacaataat acaaaaggcc aaaaacacaa tggcagaatt tagtgaagat cctgaattac    120

aaccagcaat gctattcaac atctgcgtcc atctggaggt ctgctatgta ataagtgata    180

tgaattttct tgatgaagaa ggaaaagcat atacagcatt agaaggacaa ggaaaagaac    240

aaaacttgag accacaatat gaagtgattg agggaatgcc aagaaacata gcatggatgg    300

ttcaaagatc cttagcccaa gagcatggga tagagactcc aaggtatctg gctgatttgt    360

tcgattataa aactaagagg tttatagaag ttggaataac aaagggattg gctgatgatt    420

acttctggaa aaagaaagaa aagctgggga atagcatgga actgatgata ttcagctaca    480

atcaagacta ttcgttaagt aatgaatcct cattggatga ggaaggaaaa gggagagtgc    540

taagcagact cacagaactt caggctgagt taagtctgaa aaatctatgg caagttctca    600

taggagaaga agatattgaa aaaggaattg acttcaaact tggacaaaca atatctaaac    660

taagggatat atctgttcca gctggtttct ccaattttga aggaatgagg agctacatag    720

acaatataga tcctaaagga gcaatagaga gaaatctagc aaggatgtct cccttagtat    780

cagttacacc taaaaagttg aaatgggagg acctaagacc aatagggcct cacatttaca    840

accatgagct accagaagtt ccatataatg cctttcttct aatgtctgat gaattggggc    900

tggctaatat gactgaaggg aagtccaaga aaccgaagac cttagccaaa gagtgcctag    960

aaaagtactc aacactacgg gatcaaactg acccaatatt aataatgaaa agcgaaaaag   1020

ctaatgaaca cttcctatgg aaactgtgga gggactgtgt aaatacaata agtaatgagg   1080

aaacaagtaa cgaattacag aaaaccaatt atgccaagtg ggccacagga gatggattaa   1140

catatcagaa aataatgaaa gaagtagcaa tagatgacga aacaatgtac caagaagagc   1200

ccaaaatacc taacaaatgt agagtggctg cttgggttca aacagagatg aatctattga   1260

gcactctgac aagtaaaagg gccctggatc tgccagaaat agggccagac gtagcacccg   1320

tggagcatgt agggagtgaa agaaggaaat actttgttaa tgaaatcaac tactgtaagg   1380

cctctaccgt tatgatgaag tatgtgcttt ttcacacttc attattaaat gaaagcaatg   1440

ccagtatggg aaaatataaa gtaataccaa taaccaacag agtagtaaat gaaaagggag   1500

aaagttttga catgctttat ggtctagcgg ttaaagggca atctcatctg aggggagata   1560

ctgatgttgt aacagttgtg actttcgaat ttagtagtac agatcccaga gtggactcag   1620

gaaagtggcc aaaatatact gtatttagaa ttggctcctt atttgtgagt gggagggaaa   1680

aatctgtata cctatattgc cgagtgaatg gtacaaataa gatccaaatg aaatggggaa   1740

tggaagctag aagatgtctg cttcaatcaa tgcaacaaat ggaagcaatt gttgaacaag   1800

aatcatcgat acaaggatat gacatgacca aagcttgttt caagggagac agagtgaata   1860

gtccaaaaac tttcagtatt gggactcaag aaggaaaact agtgaaagga tcctttggga   1920
```

-continued aagcactaag agtaatattc accaaatgtt tgatgcacta tgtatttgga aatgcccaat 1980
tggaggggtt tagtgccgaa tctaggagac ttctactgtt aattcaggca ttaaaagaca 2040
gaaagggccc ttgggtattc gacttagagg gaatgtattc tggaatagaa gaatgtatta 2100
gtaacaaccc ttgggtaata cagagtgcat actggtttaa tgaatggttg ggctttgaaa 2160
aagaggggag taaagtatta gaatcagtag atgaaataat ggatgaatga aagaagggca 2220
tagtgctcaa tttggtacta ttttgttcat tatgtatcta aacatccaat ataaagaatt 2280
gagaattaaa aatgcacgtg tttctact 2308

<210> SEQ ID NO 14
<211> LENGTH: 1843
<212> TYPE: DNA
<213> ORGANISM: Influenza B

<400> SEQUENCE: 14
agcagaagca cagcattttc ttgtgaactt caagtaccaa caaaaaactg aaaatcaaaa 60
tgtccaacat ggacattgac ggcatcaaca ctggaataat tgacaaaaca ccagaagaaa 120
taacttccgg aaccagtggg gcaaccagac caatcatcag accagcaacc cttgcctcac 180
caagcaacaa acgaaccaga aacccatccc cggaaagggc aaccacaagc agtgaagctg 240
atgtcggaag gaaaacccaa aagaaacaaa ctccgacaga gataaagaag agcgtctaca 300
atatggtagt gaaactgggt gaattctaca accagatgat ggtcaaagct ggactcaacg 360
atgacatgga gagaaaccta atccaaaatg cacatgctgt ggaaagaatt ctattggctg 420
ctactgatga caagaaaact gaattccaaa agaaaaagaa tgccagagac gtcaaagaag 480
ggaaagaaga aatagaccat aacaaaacag gaggcacctt ttacaagatg gtaagagatg 540
ataaaaccat ctacttcagc cctataagaa ttaccttttt aaaagaagag gtgaaaacaa 600
tgtacaaaac caccatgggg agtgacggtt tcagtggact aaatcacatc atgattgggc 660
attcacagat gaacgatgtc tgtttccaaa gatcaaaggc actaaaaaga gttggacttg 720
acccttcatt aatcagtact tttgcaggaa gcacactccc cagaagatca ggtacaactg 780
gtgttgcgac caaaggaggt ggaactttag tggcagaagc cattcgattt ataggaagag 840
caatggcaga cagagggcta ttgagagaca tcagagccaa gacggcctat gaaaagattc 900
ttctgaatct gaaaaacaag tgctctgcgc cccaacaaaa ggctctggtt gatcaagtga 960
tcggaagtag aaatccaggg attgcagaca tagaagatct caccctgctt gctcgaagta 1020
tggtcgttgt taggccctct gtagcaagca aagtggtgct tcccataagc atctatgcta 1080
aaatacctca actggggttc aacgttgaag aatactctat ggttgggtat gaagccatgg 1140
ctctttataa tatggcaaca cctgtttcca tattaagaat gggagacgat gcaaaagata 1200
aatcacaatt attcttcatg tcttgctttg gagctgccta tgaagaccta agagttctgt 1260
ctgcactaac aggcacggaa ttcaagccta ggtcagcatt aaagtgcaaa ggtttccacg 1320
ttccagcaaa ggagcaagtg gaaggaatgg gggcagctct gatgtccatc aagctccagt 1380
tttgggctcc aatgaccaga tctgggggga atgaagtagg tggagacgga gggtctggtc 1440
aaataagttg cagccccgtg tttgcagtag aaagacctat tgctctaagc aagcaagctg 1500
taagaagaat gctgtcaatg aatattgagg gacgtgatgc agatgtcaaa ggaaatctac 1560
tcaagatgat gaatgattca atggctaaga aaaccaatgg aaatgctttc attgggaaga 1620
aaatgttcca aatatcagac aaaaacaaaa ccaatcccgt tgagattcca attaagcaga 1680

```
ccatccccag tttcttcttt gggagggaca cagcagagga ttatgatgac ctcgattatt   1740

aaagcaacaa aatagacact atggctgtga ttgtttcagt acgtttggaa tgtgggtgtt   1800

tactcttatt gaaataaatg taaaaaatgc tgttgtttct act                     1843
```

<210> SEQ ID NO 15
<211> LENGTH: 1843
<212> TYPE: DNA
<213> ORGANISM: Influenza B

<400> SEQUENCE: 15

```
agcagaagca cagcattttc ttgtgaactt caagtaccaa caaaaaactg aaaatcaaaa     60

tgtccaacat ggacattgac ggcatcaaca ctggaataat tgacaaaaca ccagaagaaa    120

taacttccgg aaccagtggg gcaaccagac caatcatcag accagcaacc cttgcctcac    180

caagcaacaa acgaaccaga aacccatccc cggaaagggc aaccacaagc agtgaagctg    240

atgtcggaag gaaaacccaa aagaaacaaa ctccgacaga gataaagaag agcgtctaca    300

atatggtagt gaaactgggt gaattctaca accagatgat ggtcaaagct ggactcaacg    360

atgacatgga gagaaaccta atccaaaatg cacatgctgt ggaaagaatt ctattggctg    420

ctactgatga caagaaaact gaattccaaa agaaaaagaa tgccagagac gtcaaagaag    480

ggaaagaaga aatagaccat aacaaaacag gaggcacctt ttacaagatg gtaagagatg    540

ataaaaccat ctacttcagc cctataagaa ttaccttttt aaaagaagag gtgaaaacaa    600

tgtacaaaac caccatgggg agtgacggtt tcagtggact aaatcacatc atgattgggc    660

attcacagac gaacgatgtc tgtttccaaa gatcaaaggc actaaaaaga gttggacttg    720

acccttcatt aatcagtact tttgcaggaa gcacactccc cagaagatca ggtacaactg    780

gtgttgcgac caaaggaggt ggaactttag tggcagaagc cattcgattt ataggaagag    840

caatggcaga cagagggcta ttgagagaca tcagagccaa gacggcctat gaaaagattc    900

ttctgaatct gaaaaacaag tgctctgcgc cccaacaaaa ggctctggtt gatcaagtga    960

tcggaagtag aaatccaggg attgcagaca tagaagatct caccctgctt gctcgaagta   1020

tggtcgttgt taggccctct gtagcaagca aagtggtgct tcccataagc atctatgcta   1080

aaatacctca actggggttc aacgttgaag aatactctat ggttgggtat gaagccatgg   1140

ctctttataa tatggcaaca cctgtttcca tattaagaat gggagacgat gcaaaagata   1200

aatcacaatt attcttcatg tcttgctttg gagctgccta tgaagaccta agagttctgt   1260

ctgcactaac aggcacggaa ttcaagccta ggtcagcatt aaagtgcaaa ggtttccacg   1320

ttccagcaaa ggagcaagtg gaaggaatgg gggcagctct gatgtccatc aagctccagt   1380

tttgggctcc aatgaccaga tctgggggga atgaagtagg tggagacgga gggtctggtc   1440

aaataagttg cagccccgtg tttgcagtag aaagacctat tgctctaagc aagcaagctg   1500

taagaagaat gctgtcaatg aatattgagg gacgtgatgc agatgtcaaa ggaaatctac   1560

tcaagatgat gaatgattca atggctaaga aaaccaatgg aaatgctttc attgggaaga   1620

aaatgttcca aatatcagac aaaaacaaaa ccaatcccgt tgagattcca attaagcaga   1680

ccatccccag tttcttcttt gggagggaca cagcagagga ttatgatgac ctcgattatt   1740

aaagcaacaa aatagacact atggctgtga ttgtttcagt acgtttggaa tgtgggtgtt   1800

tactcttatt gaaataaatg taaaaaatgc tgttgtttct act                     1843
```

<210> SEQ ID NO 16
<211> LENGTH: 1190

-continued

<212> TYPE: DNA
<213> ORGANISM: Influenza B

<400> SEQUENCE: 16
agcagaagca cgcactttct taaaatgtcg ctgtttggag acacaattgc ctacctgctt 60
tcactaacag aagatggaga aggcaaagca gaactagcgg aaaaattaca ctgttggttc 120
ggtgggaaag aattcgatct agactctgct ttggaatgga taaaaaacaa aagatgccta 180
actgatatac aaaaagcact aattggtgcc tctatctgct tttgaaacc caaagaccaa 240 gaaagaaaaa gaaaattcat cacagagccc ctgtcaggaa tgggaacaac agcaacaaaa 300
aagaaaggcc tgattctagc tgaaagaaaa atgagaagat gtgtgagttt tcatgaggca 360
tttgaaatag cagaaggcca tgaaagctca gcactactat attgtctcat ggtcatgtac 420
ctgaaccctg gaaattattc aatgcaagta aaactaggaa cgctctgtgc tttatgcgag 480
aaacaagcat cacattcaca cagagctcat agcagagcag caagatcttc agtgcctgga 540
gtgaggcgag aaatgcaaat ggtttcagct atgaacacag caaaaacaat gaatggaatg 600
gggaagggag aagacgtcca aaaactggca gaagagctgc aaagcaacat tggagtattg 660
agatctctgg gggcaagtca aaagaatgga gaaggaattg caaaggatgt aatggaagtg 720
ctaaagcaga gctccatggg aaattcagct cttgtgaaga aatacctata atgctcgagc 780
catttcagat tctttcaatt tgctctttca ttttatcggc tctccatttc atgggctgga 840
caatagggca tttaaatcaa ataaaaagag gagtaaacct aaaaatacga ataagaaatc 900
caaataaaga gacaataaat agagaggtat caattttgag acacagttac caaaaagaaa 960
tccaagccaa agaaacaata aaggaagtac tctctgacaa catggagaga ttgagtgacc 1020
acatagtaat tgaggggctt tctgctgaag agataataaa aatgggtgaa acagttttgg 1080
aggtagaaga attgcattaa acccaatttt caccgtattt cttactatgc atttaagcaa 1140
attgtaatca atgtcagcaa ataaactgga aaaagtgcgt tgtttctact 1190

<210> SEQ ID NO 17
<211> LENGTH: 1190
<212> TYPE: DNA
<213> ORGANISM: Influenza B

<400> SEQUENCE: 17
agcagaagca cgcactttct taaaatgtcg ctgtttggag acacaattgc ctacctgctt 60
tcactaacag aagatggaga aggcaaagca gaactagcgg aaaaattaca ctgttggttc 120
ggtgggaaag aattcgatct agactctgct ttggaatgga taaaaaacaa aagatgccta 180
actgatatac aaaaagcact aattggtgcc tctatctgct tttgaaacc caaagaccaa 240 gaaagaaaaa gaagattcat cacagagccc ctgtcaggaa cgggaacaac agcaacaaaa 300
aagaaaggcc tgattctagc tgaaagaaaa atgagaagat gtgtgagttt tcatgaggca 360
tttgaaatag cagaaggcca tgaaagctca gcactactat attgtctcat ggtcatgtac 420
ctgaaccctg gaaattattc aatgcaagta aaactaggaa cgctctgtgc tttatgcgag 480
aaacaagcat cacattcaca cagagctcat agcagagcag caagatcttc agtgcctgga 540
gtgaggcgag aaatgcaaat ggtttcagct atgaacacag caaaaacaat gaatggaatg 600
gggaagggag aagacgtcca aaaactggca gaagagctgc aaagcaacat tggagtattg 660
agatctctgg gggcaagtca aaagaatgga gaaggaattg caaaggatgt aatggaagtg 720
ctaaagcaga gctccatggg aaattcagct cttgtgaaga aatacctata atgctcgagc 780

-continued

```
catttcagat tctttcaatt tgctctttca ttttatcggc tctccatttc atgggctgga    840

caatagggca tttaaatcaa ataaaaagag gagtaaacct aaaaatacga ataagaaatc    900

caaataaaga gacaataaat agagaggtat caattttgag acacagttac caaaaagaaa    960

tccaagccaa agaaacaata aaggaagtac tctctgacaa catggagaga ttgagtgacc   1020

acatagtaat tgaggggctt tctgctgaag agataataaa aatgggtgaa acagttttgg   1080

aggtagaaga attgcattaa acccaatttt caccgtattt cttactatgc atttaagcaa   1140

attgtaatca atgtcagcaa ataaactgga aaaagtgcgt tgtttctact              1190
```

<210> SEQ ID NO 18
<211> LENGTH: 1098
<212> TYPE: DNA
<213> ORGANISM: Influenza B

<400> SEQUENCE: 18

```
agcagaagca gaggatttgt ttagtcactg gcaaacggga aaaaatggcg gacaacatga     60

ccacaacaca aattgaggtg ggtccgggag caaccaatgc cactataaac tttgaagcag    120

gaattttgga gtgctatgaa aggctttcat ggcaaagagc ccttgactac cctggtcaag    180

accgcctaaa cagactaaag agaaaattag aatcaagaat aaagactcac aacaaaagtg    240

agcctgaaag taaaaggatg tctcttgaag agagaaaagc aattggggta aaaatgatga    300

aagtgctcct atttatgaac ccatctgctg gaattgaagg gtttgagcca tactgtatga    360

aaaattcctc caatagcaac tgcccaaact gcaattgggc cgattaccct ccaacatcag    420

gaaagtgcct tgatgacata gaagaagaac cggagaatgt tgatgaccca actgaaatag    480

tattaaggga catgaacaac aaagatgcaa ggcaaaagat aaaagaggaa gtaaacactc    540

agaaagaagg gaagttccgt ttgacaatac aaagggatat acgtaatgtg ttgtccttga    600

gagtgttggt aaacggaaca ttcctcaagc accctaatgg atacaagtcc ttatcaactc    660

tgcatagatt gaatgcatat gaccagagtg gaaggcttgt tgctaaactt gttgctactg    720

atgatcttac agtggaggat gaagaagatg gccatcggat cctcaactca ctcttcgagc    780

gttttaatga aggacattca aagccaattc gagcagctga aactgcggtg ggagtcttat    840

cccaatttgg tcaagagcac cgattatcac cagaggaggg agacaattag actggttacg    900

gaagaacttt atcttttaag taaaagaatt gatgataaca tattgttcca caaaacagta    960

atagctaaca gctccataat agctgacatg attgtatcat tatcattatt ggaaacattg   1020

tatgagatga aggatgtggt tgaagtgtac agcaggcagt gcttgtgaat ttaaaataaa   1080

aatcctcttg ttactact                                                1098
```

<210> SEQ ID NO 19
<211> LENGTH: 1099
<212> TYPE: DNA
<213> ORGANISM: Influenza B

<400> SEQUENCE: 19

```
agcagaagca gaggatttgt ttagtcactg gcaaacggga aaaaaatggc ggacaacatg     60

accacaacac aaattgaggt gggtccggga gcaaccaatg ccactataaa ctttgaagca    120

ggaattttgg agtgctatga aaggctttca tggcaaagag cccttgacta ccctggtcaa    180

gaccgcctaa acagactaaa gagaaaatta gaatcaagaa taaagactca caacaaaagt    240

gagcctgaaa gtaaaaggat gtctcttgaa gagagaaaag caattggggt aaaaatgatg    300

aaagtgctcc tatttatgaa cccatctgct ggaattgaag ggtttgagcc atactgtatg    360
```

-continued

```
aaaaattcct ccaatagcaa ctgcccaaac tgcaattggg ccgattaccc tccaacatca    420
ggaaagtgcc ttgatgacat agaagaagaa ccggagaatg ttgatgaccc aactgaaata    480
gtattaaggg acatgaacaa caaagatgca aggcaaaaga taaaagagga agtaaacact    540
cagaaagaag ggaagttccg tttgacaata aaaagggata tacgtaatgt gttgtccttg    600
agagtgttgg taaacggaac attcctcaag caccctaatg gatacaagtc cttatcaact    660
ctgcatagat tgaatgcata tgaccagagt ggaaggcttg ttgctaaact tgttgctact    720
gatgatctta cagtggagga tgaagaagat ggccatcgga tcctcaactc actcttcgag    780
cgttttaatg aaggacattc aaagccaatt cgagcagctg aaactgcggt gggagtctta    840
tcccaatttg gtcaagagca ccgattatca ccagaggagg gagacaatta gactggttac    900
ggaagaactt tatcttttaa gtaaaagaat tgatgataac atattgttcc acaaaacagt    960
aatagctaac agctccataa tagctgacat gattgtatca ttatcattat tggaaacatt   1020
gtatgagatg aaggatgtgg ttgaagtgta cagcaggcag tgcttgtgaa tttaaaataa   1080
aaatcctctt gttactact                                                1099
```